(12) United States Patent
Atobe et al.

(10) Patent No.: US 7,994,202 B2
(45) Date of Patent: Aug. 9, 2011

(54) BICYCLIC NITROGEN-CONTAINING HETEROCYCLIC COMPOUNDS

(75) Inventors: Masakazu Atobe, Tokyo (JP); Kenji Naganuma, Tokyo (JP); Akifumi Morimoto, Tokyo (JP)

(73) Assignee: Asahi Kasei Pharma Corporation, Tokyo (JP)

( * ) Notice: Subject to any disclaimer, the term of this patent is extended or adjusted under 35 U.S.C. 154(b) by 0 days.

(21) Appl. No.: 12/502,557

(22) Filed: Jul. 14, 2009

(65) Prior Publication Data

US 2010/0029733 A1 Feb. 4, 2010

Related U.S. Application Data

(60) Provisional application No. 61/081,498, filed on Jul. 17, 2008.

(51) Int. Cl.
| | |
|---|---|
| *A61K 31/5377* | (2006.01) |
| *A61K 31/506* | (2006.01) |
| *A61K 31/496* | (2006.01) |
| *A61K 31/4709* | (2006.01) |
| *A61K 31/4545* | (2006.01) |
| *A61K 31/454* | (2006.01) |
| *A61K 31/4439* | (2006.01) |
| *A61K 31/427* | (2006.01) |
| *C07D 471/04* | (2006.01) |
| *C07D 417/06* | (2006.01) |
| *C07D 417/14* | (2006.01) |
| *C07D 417/04* | (2006.01) |

(52) U.S. Cl. ........ 514/365; 514/338; 514/256; 514/333; 514/253.09; 514/234.5; 514/322; 514/303; 544/364; 544/133; 548/201; 546/269.7; 546/167; 546/199; 546/119

(58) Field of Classification Search ................ 514/365, 514/338, 256, 333, 253.09, 234.5, 322, 303; 544/364, 133; 548/201; 546/269.7, 167, 546/199, 119

See application file for complete search history.

(56) References Cited

U.S. PATENT DOCUMENTS

| | | | |
|---|---|---|---|
| 7,226,941 B2 | 6/2007 | Park et al. | |
| 7,241,791 B2 | 7/2007 | Steffan et al. | |
| 7,304,073 B2 | 12/2007 | Chadwick et al. | |
| 7,446,222 B2 | 11/2008 | Bit et al. | |
| 7,678,823 B2 | 3/2010 | Slade et al. | |
| 2002/0137746 A1 | 9/2002 | Carl et al. | |
| 2004/0167127 A1 | 8/2004 | Steffan et al. | |
| 2005/0020646 A1 | 1/2005 | Newgreen et al. | |
| 2005/0187276 A1 | 8/2005 | Park et al. | |
| 2006/0111421 A1 | 5/2006 | Chadwick et al. | |
| 2006/0205751 A1 | 9/2006 | Lee et al. | |
| 2006/0235057 A1 | 10/2006 | Bit et al. | |
| 2007/0225349 A1 | 9/2007 | Steffan et al. | |
| 2008/0207708 A1 | 8/2008 | Bit et al. | |
| 2008/0249135 A1 | 10/2008 | Slade et al. | |
| 2008/0275053 A1 | 11/2008 | Giblin et al. | |
| 2010/0120749 A1* | 5/2010 | Page et al. ................ 514/217.08 | |

FOREIGN PATENT DOCUMENTS

| | | |
|---|---|---|
| WO | 00/69465 A1 | 11/2000 |
| WO | 02/15902 A1 | 2/2002 |
| WO | 2004/031159 A1 | 4/2004 |
| WO | 2004/039753 A2 | 5/2004 |
| WO | 2004/083185 A2 | 9/2004 |
| WO | 2005/010534 A1 | 2/2005 |
| WO | 2005/030121 A2 | 4/2005 |
| WO | WO 2006041874 A2 * | 4/2006 |
| WO | WO 2007115306 A2 * | 10/2007 |
| WO | 2008/006790 A1 | 1/2008 |
| WO | 2008/006793 A1 | 1/2008 |
| WO | 2008/006794 A1 | 1/2008 |
| WO | 2008/006795 A2 | 1/2008 |
| WO | 2008/040753 A1 | 4/2008 |
| WO | 2008/054749 A1 | 5/2008 |
| WO | WO 2008049875 A1 * | 5/2008 |

OTHER PUBLICATIONS

Freeman et al. Best Practice & Research Clinical Obstetrics and Gynaecology, 2005, 19, 529-841.*

E. Ann Hallinan et al., "2,4-Disubstituted Oxazoles and Thiazoles as Latent Pharmacophores for Diacylhydrazine of SC-51089, a Potent $PGE_2$ Antagonist" Bioorganic & Medicinal Chemistry, vol. 9, pp. 1-6, 2001.

Adrian Hall et al., "Novel Methylene-Linked Heterocyclic $EP_1$ Receptor Antagonists" Bioorganic & Medicinal Chemistry Letters, vol. 18, pp. 1592-1597, 2008.

(Continued)

*Primary Examiner* — Joseph Kosack
*Assistant Examiner* — Matthew Coughlin
(74) *Attorney, Agent, or Firm* — Greenblum & Bernstein, PLC

(57) ABSTRACT

A nitrogen-containing bicyclic heterocyclic compound represented by the following formula (1) is provided. When the compound or a salt thereof is administered to a human being or an animal, the compound has a strong antagonistic action against EP1 receptors, and is useful, for example, as an active ingredient of a medicine for the prevention and/or treatment of overactive bladder. The compound is also useful as an active ingredient of a medicine for the prevention and/or treatment of symptoms such as frequency urinary, urinary urgency, or urinary incontinence.

(1)

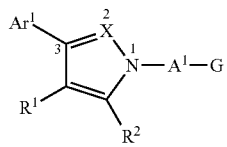

21 Claims, No Drawings

OTHER PUBLICATIONS

Adrian Hall et al., "Discovery of a Novel Indole Series of EP$_1$ Receptor Antagonists by Scaffold Hopping" Bioorganic & Medicinal Chemistry Letters, vol. 18, pp. 2684-2690, 2008.

A. Ziganshin et al., "Studying the Efficacy of a Series of Quinoxaline and Azolo[a(b)]quinoxaline Derivatives as P2X Receptor Antagonists" Eksp, Klin. Farmakol., vol. 68, No. 1, pp. 56-60, 2005, along with an English language abstract thereof.

U.S. Appl. No. 12/502,529 to Atobe et al., entitled "Nitrogen-Containing Heterocyclic Compounds," filed Jul. 14, 2009.

Li et al., "Design, Synthesis, and Biological Evaluation of Antiviral Agents Targeting Flavivirus Envelope Proteins," *J. Med. Chem.*, vol. 51, No. 15, pp. 4660-4671, 2008.

U.S. Office Action that issued with respect to U.S. Appl. No. 12/502,529, mailed Aug. 2, 2010.

U.S. Office Action that issued with respect to U.S. Appl. No. 12/502,529, mailed Jan. 6, 2011.

American Urogynecologic Society. Bladder Control Problems: Prevention. Published May 2008. Accessed Dec. 30, 2010. <http://www.mypelvichealth.org/TreatmentPrevention/BladderControlProblems/Prevention/tabid/115/Default.aspx>.

* cited by examiner

BICYCLIC NITROGEN-CONTAINING HETEROCYCLIC COMPOUNDS

CROSS REFERENCE TO RELATED APPLICATIONS

This application claims the benefit of U.S. Provisional Application No. 61/081,498, filed Jul. 17, 2008.

TECHNICAL FIELD

The present invention is relating to novel compounds that have an EP1 antagonistic activity and are useful as an effective component of a pharmaceutical agent.

DESCRIPTION OF THE RELATED ART

Overactive bladder is defined by The International Continence Society as a "disorder which includes urinary urgency with or without urge incontinence, urinary frequency, and nocturia" (Non-Patent Document 1). In addition, urinary incontinence is generally defined as an "involuntary loss of urine which can be objectively demonstrated and is a social or hygienic problem" and urinary urgency is generally understood as a "state at which strong and sudden desire to urinate occurs and the urge cannot be controlled." (Non-Patent Document 2).

Cause of an overactive bladder may include a change in bladder function due to aging, cerebral hemorrhage, cerebral infarction, Parkinson's disease, a neuronal disorder such as spinal cord injury, etc., lower urinary tract obstruction due to prostatic hyperplasia, etc. and a sensitive bladder due to expression of an irritative voiding symptom caused by hypersensitive bladder resulting from chronic cystitis, interstitial cystitis, etc. However, for most cases, the cause remains unknown.

Prostaglandin E2 (herein below, it can be sometimes abbreviated as PGE2) is one metabolite of an arachidonic acid cascade and is known to be involved with a cell protection activity, an oxytocic activity, a pain-generating activity, an activity of promoting peristaltic movement of a digestive tract, an analeptic activity, an activity of inhibiting secretion of gastric acid, an anti-hypertensive activity, a diuretic activity, etc.

It has been known that urothelium or smooth muscle of a bladder produces PGE2 and such production is increased by bladder disorder caused by various physiological irritation or inflammation, etc. (Non-Patent Documents 3 and 4). It is believed that PGE2 not only can contract smooth muscle of a bladder but also can increase voiding reflex by increasing afferent impulse as it acts on a sensory nerve of a bladder (Non-Patent Documents 5 and 6). According to recent studies, it was found that there are subtypes of PGE2 receptor which have a function different to each other. At the present moment, four subtypes including EP1, EP2, EP3 and EP4 are known (Non-Patent Document 7 and 8). Among these, EP1 receptor is mainly present in fiber C of the sensory nerves of a bladder. It was found that, by antagonizing this receptor, voiding reflex can be inhibited (Non-Patent Document 9). It was also known that in an overactive bladder which is caused by lower urinary tract obstruction due to spinal injury, prostatic hypertrophy, etc., a hyperactivity of afferent fiber C is confirmed and this detrusor overactivity can be inhibited by inhibiting this afferent route (Non-Patent Document 10).

For example, as a compound which has an antagonistic activity for EPI receptor, the compounds described in the following literatures have been known (Patent Document No. 1 to 5).

[Non-Patent Document 1] Abrams, P. et al., Neurourol. Urodyn. 21, p. 167-178 (2002)
[Non-Patent Document 2] Yamaguchi Osamu, Clinics and Drug Therapy, 21, p. 2-7 (2002)
[Non-Patent Document 3] Andersson, K E, Pharmacol. Rev. 45, 253-308 (1993)
[Non-Patent Document 4] Khan, M A. et al., Prostaglandins Leukot. Essent. Fatty Acids, 59, 415-422 (1998)
[Non-Patent Document 5] Palea, S. et al., Br. J. Pharmacol., 124p. 865-872 (1998)
[Non-Patent Document 6] Maggi, C A., Pharmacol. Res. 25, p. 13-20 (1992)
[Non-Patent Document 7] Negishi, M. et al., J. Lipid Mediators Cell Signaling 12, 379-391 (1995)
[Non-Patent Document 8] Narumiya, S. et al., Physiological Rev. 79, p. 1193-1226 (1999)
[Non-Patent Document 9] Ikeda, M. et al., Biomed. Res. 27, p. 49-54 (2006)
[Non-Patent Document 10] Yamaguchi Osamu, Folia) Pharmacologica Japonica, 121, p. 331-338 (2003)
[Patent Document No. 1] WO00/69465
[Patent Document No. 2] WO02/15902
[Patent Document No. 3] WO2004/039753
[Patent Document No. 4] WO2004/083185
[Patent Document No. 5] WO2005/010534

DISCLOSURE OF THE INVENTION

Problems to be Solved by the Invention

Object of the present invention is to provide compounds which have an antagonistic activity for EP1 receptor and are useful as an effective component of a pharmaceutical agent for prophylaxis and/or treatment of an overactive bladder, and the compounds which are useful as an effective component of a pharmaceutical agent for prophylaxis and/or treatment of symptoms including frequent urination, urinary urgency and urinary incontinence, etc.

Means for Solving the Problems

As a result of intensive study to solve the problems described above, inventors of the present invention found that the compounds represented by the following formula (1) have a significant antagonistic effect for EP1 receptor and are useful as an effective component of a pharmaceutical agent for prophylaxis and/or treatment of an overactive bladder. In addition, it was also found that they are useful as an effective component of a pharmaceutical agent for prophylaxis and/or treatment of symptoms including frequent urination, urinary urgency and urinary incontinence, etc. The present invention is completed based on these findings.

Specifically, the present invention includes the followings.

[1] Compounds represented by the formula (1) or salt thereof:

[Chemical Formula 1]

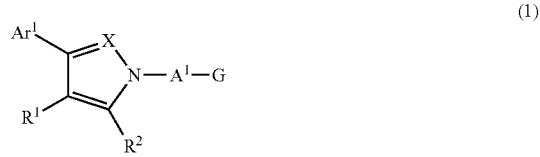

(1)

wherein in the formula (1), $Ar^1$ represents an aryl group which may be substituted, a saturated cyclic hydrocarbyl group which may be substituted, or a saturated heterocyclic group which may be substituted;

X represents a nitrogen atom, or $=C(R^{X1})$— [wherein $R^{X1}$ represents a hydrogen atom, or an alkyl group which may be substituted];

$R^1$ and $R^2$ together represent any of the following formulas $(Q^1)$ to $(Q^6)$

[Chemical Formula 2]

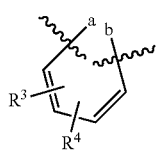
$(Q^1)$

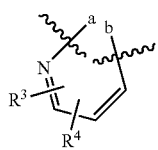
$(Q^2)$

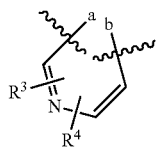
$(Q^3)$

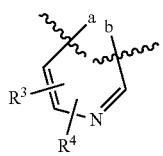
$(Q^4)$

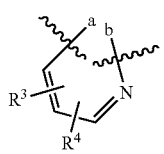
$(Q^5)$

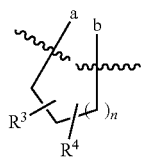
$(Q^6)$

[wherein in the formulas $(Q^1)$ to $(Q^6)$, $R^3$ and $R^4$, which may be same or different, each independently represent any of a hydrogen atom, a halogen atom, an alkyl group which may be substituted, an alkenyl group which may be substituted, an alkynyl group which may be substituted, an aryl group which may be substituted, an aralkyl group which may be substituted, a hydroxy group, an alkoxy group which may be substituted, an aryloxy group which may be substituted, an alkylthio group, an acyl group, an acyloxy group, an alkylsulfinyl group, an alkylsulfonyl group, an alkylcarbamoyl group, —$N(R^{Q1})(R^{Q2})$ {wherein $R^{Q1}$ and $R^{Q2}$ may be same or different, and each independently represent a hydrogen atom, an alkyl group which may be substituted, or an aryl group which may be substituted; or $R^{Q1}$ and $R^{Q2}$ together form a 3- to 7-membered ring to represent a cyclic amine in the form of $N(R^{Q1})(R^{Q2})$}, an acylamino group, an acyl(alkyl)amino group, an alkylsulfonylamino group, an alkylsulfonyl(alkyl)amino group, a carboxy group, —$CON(R^{Q3})(R^{Q4})$ {wherein $R^{Q3}$ and $R^{Q4}$ may be same or different, and each independently represent a hydrogen atom, an alkyl group which may be substituted, or an aryl group which may be substituted; or $R^{Q3}$ and $R^{Q4}$ together form a 3- to 7-membered ring to represent a cyclic amine in the form of $N(R^{Q3})(R^{Q4})$}, and —$COOR^{Q5}$ {wherein $R^{Q5}$ represents an alkyl group which may be substituted};

n represents an integer from 1 to 4; and $R^1$ and $R^2$ represent that they are bonded to each of the formulas $(Q^1)$ to $(Q^6)$ at the position of a and the position of b, respectively];

$A^1$ represents a single bond, an alkylene group which may be substituted, or an alkenylene group which may be substituted;

G represents any of the following formulas $(G^1)$, $(G^2$ or $(G^3)$:

[Chemical Formula 3]

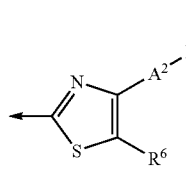
$(G^1)$

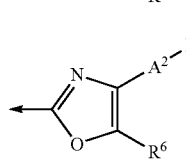
$(G^2)$

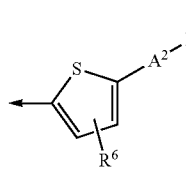
$(G^3)$

[wherein in the formulas $(G^1)$, $(G^2)$ and $(G^3)$, $A^2$ represents a single bond, an alkylene group which may be substituted, or an alkenylene group which may be substituted, $R^5$ represents a carboxy group, —$CON(R^{51})(R^{52})$ ($R^{51}$ and $R^{52}$ can be the same or different to each other, and each independently represent a hydrogen atom, an alkyl group which may be substituted, or an aryl group which may be substituted, or $R^{51}$ and $R^{52}$ together form a 3- to 7-membered ring to represent a cyclic amine of $N(R^{51})(R^{52})$.), —$COOR^{53}$ ($R^{53}$ represents an alkyl group which may be substituted.) or a tetrazol-5-yl group, and $R^6$ represents a hydrogen atom or an alkyl group which may be substituted].

[2] The compounds that are described above [1] or salt thereof in which G is the formula $(G^1)$.

[2-2] The compounds that are described above [1] or salt thereof in which G is the formula $(G^2)$.

[2-3] The compounds that are described above [1] or salt thereof in which G is the formula $(G^3)$.

[3] The compounds that are described in any one of the above [1] to [2-3] or salt thereof in which $R^5$ is a carboxy group. In addition, when the item numbers, that are referred to like [1] to [2-3] in the above, are described with a range and there is an additional item having branch number like [2-2], etc., an item having branch number like [2-2], etc. is also referred to, and it has the same meaning for the following descriptions.

[4] The compound or the salt thereof according to any one of [1] to [3] above, wherein X is a nitrogen atom.

[5] The compound or the salt thereof according to any one of [1] to [3] above, wherein X is =CH—.

[6] The compound or the salt thereof according to any one of [1] to [5] above, wherein $A^2$ is a single bond.

[7] The compound or the salt thereof according to any one of [1] to [6] above, wherein $A^1$ is a single bond, or a methylene group which may be substituted with a lower alkyl group.

[8] The compound or the salt thereof according to any one of [1] to [6] above, wherein $A^1$ is a single bond.

[9] The compound or the salt thereof according to any one of [1] to [6] above, wherein $A^1$ is a methylene group which may be substituted with a lower alkyl group.

[10] The compound or the salt thereof according to any one of [1] to [9] above, wherein $R^1$ and $R^2$ together represent the formula $(Q^1)$, $(Q^4)$, $(Q^5)$ or $(Q^6)$.

[11] The compound or the salt thereof according to any one of [1] to [9] above, wherein $R^1$ and $R^2$ together represent the formula $(Q^1)$

[12] The compound or the salt thereof according to any one of [1] to [9] above, wherein $R^1$ and $R^2$ together represent the formula $(Q^4)$ or $(Q^5)$.

[12-2] The compound or the salt thereof according to any one of [1] to [9] above, wherein $R^1$ and $R^2$ together represent the formula $(Q^5)$.

[13] The compound or the salt thereof according to any one of [1] to [9] above, wherein $R^1$ and $R^2$ together represent the formula $(Q^6)$.

[13-2] The compound or the salt thereof according to any one of [1] to [9] above, wherein $R^1$ and $R^2$ together represent the formula $(Q^6)$ [wherein in the formula $(Q^6)$, n represents 2 or 3].

[14] The compound or the salt thereof according to any one of [1] to [13-2] above, wherein $R^3$ and $R^4$ are groups that are each independently selected from the group consisting of a hydrogen atom, a halogen atom, an alkyl group which may be substituted, a hydroxy group, an alkoxy group which may be substituted, and —N($R^{Q1}$)($R^{Q2}$) [wherein $R^{Q1}$ and $R^{Q2}$ may be same or different, and each independently represent a hydrogen atom, an alkyl group which may be substituted, or an aryl group which may be substituted; or $R^{Q1}$ and $R^{Q2}$ together form a 3- to 7-membered ring to represent a cyclic amine in the form of N($R^{Q1}$)($R^{Q2}$)].

[14-2] The compound or the salt thereof according to any one of [1] to [13-2] above, wherein $R^3$ and $R^4$ are groups that are each independently selected from the group consisting of a hydrogen atom, a halogen atom, and an alkyl group which may be substituted.

[14-3] The compound or the salt thereof according to any one of [1] to [13-2] above, wherein $R^3$ and $R^4$ are groups that are each independently selected from the group consisting of a hydrogen atom, and —N($R^{Q1}$)($R^{Q2}$) [wherein $R^{Q1}$ and $R^{Q2}$ may be same or different, and each independently represent a hydrogen atom, an alkyl group which may be substituted, or an aryl group which may be substituted; or $R^{Q1}$ and $R^{Q2}$ together form a 3- to 7-membered ring to represent a cyclic amine in the form of N($R^{Q1}$)($R^{Q2}$)].

[15] The compound or the salt thereof according to any one of [1] to [14-3] above, wherein $Ar^1$ is an aryl group which may be substituted.

[16] The compound or the salt thereof according to any one of [1] to [14-3] above, wherein $Ar^1$ is a phenyl group which may be substituted.

[17] The compound or the salt thereof according to any one of [1] to [14-3] above, wherein $Ar^1$ is a phenyl group which may be substituted with one or a plurality of groups that are each independently selected from the group consisting of a halogen atom, an alkyl group which may be substituted, a hydroxy group, and an alkoxy group which may be substituted.

[17-2] The compound or the salt thereof according to any one of [1] to [14-3] above, wherein $Ar^1$ is a phenyl group which may be substituted with one or a plurality of groups that are each independently selected from the group consisting of a halogen atom, and an alkyl group which may be substituted.

[18] The compound or the salt thereof according to any one of [1] to [14-3] above, wherein $Ar^1$ is a saturated heterocyclic group which may be substituted.

[18-2] The compound or the salt thereof according to any one of [1] to [14-3] above, wherein $Ar^1$ is a saturated cyclic hydrocarbyl group which may be substituted.

[18-3] The compound or the salt thereof according to any one of [1] to [14-3] above, wherein $Ar^1$ is a partially unsaturated carbocyclic group or heterocyclic group.

[18-4] The compound or the salt thereof according to any one of [1] to [14-3] above, wherein $Ar^1$ is a partially unsaturated carbocyclic group.

[18-5] The compound or the salt thereof according to any one of [1] to [14-3] above, wherein $Ar^1$ is a partially unsaturated heterocyclic group.

[18-6] The compound or the salt thereof according to [1] above, wherein G is the formula $(G^1)$; $A^1$ and $A^2$ are each a single bond; X is a nitrogen atom; $R^1$ and $R^2$ together represent the formula $(Q^1)$ or $(Q^5)$; $Ar^1$ is a phenyl group, a 4-fluorophenyl group or a 4-methoxyphenyl group; $R^3$ is a trifluoromethyl group or a halogen atom; $R^4$ is a hydrogen atom; $R^5$ is a carboxy group; and $R^6$ is a hydrogen atom.

[18-7] The compound or the salt thereof according to [1] above, wherein G is the formula (G1); $A^1$ and $A^2$ are each a single bond; X is a nitrogen atom; $R^1$ and $R^2$ together represent the formula $(Q^1)$ or $(Q^5)$; $Ar^1$ is a phenyl group, a 4-fluorophenyl group or a 4-methoxyphenyl group; $R^3$ is a trifluoromethyl group; $R^4$ is a hydrogen atom; $R^5$ is a carboxy group; and $R^6$ is a hydrogen atom.

[18-8] The compound or the salt thereof according to [1] above, wherein G is the formula $(G^1)$; $A^1$ and $A^2$ are each a single bond; X is a nitrogen atom; $R^1$ and $R^2$ together represent the formula $(Q^1)$ or $(Q^5)$; $Ar^1$ is a phenyl group, a 4-fluorophenyl group or a 4-methoxyphenyl group; $R^3$ is a 6-trifluoromethyl group; $R^4$ is a hydrogen atom; $R^5$ is a carboxy group; and $R^6$ is a hydrogen atom.

[18-9] The compound or the salt thereof according to [1] above, wherein G is the formula $(G^1)$; $A^1$ and $A^2$ are each a single bond; X is a nitrogen atom; $R^1$ and $R^2$ together represent the formula $(Q^1)$ or $(Q^5)$; $Ar^1$ is a phenyl group, a 4-fluorophenyl group or a 4-methoxyphenyl group; $R^3$ is a 6-chlorine atom; $R^4$ is a hydrogen atom; $R^5$ is a carboxy group; and $R^6$ is a hydrogen atom.

[18-10] The compound or the salt thereof according to [1] above, wherein G is the formula $(G^1)$; $A^1$ and $A^2$ are each a single bond; X is a nitrogen atom; $R^1$ and $R^2$ together represent the formula $(Q^1)$; $Ar^1$ is a phenyl group, a 4-fluorophenyl group or a 4-methoxyphenyl group; $R^3$ is a 6-bromine atom; $R^4$ is a hydrogen atom; $R^5$ is a carboxy group; and $R^6$ is a hydrogen atom.

[18-11] The compound or the salt thereof according to [1] above, wherein G is the formula $(G^1)$; $A^1$ and $A^2$ are each a single bond; X is a nitrogen atom; $R^1$ and $R^2$ together represent the formula $(Q^5)$; $Ar^1$ is a phenyl group, a 4-fluorophenyl group or a 4-methoxyphenyl group; $R^3$ is a 6-iodine atom; $R^4$ is a hydrogen atom; $R^5$ is a carboxyl group; and $R^6$ is a hydrogen atom.

[18-12] The compound or the salt thereof according to [1] above, wherein the compound represented by the formula (1) is a compound selected from the group consisting of 2-{3-phenyl-6-(trifluoromethyl)-1H-indazol-1-yl}thiazole-4-carboxylic acid; 2-{3-(3,4-dihydro-2H-pyran-6-yl)-6-(trifluoromethyl)-1H-indazol-1-yl}thiazole-4-carboxylic acid; 2-{3-phenyl-6-(trifluoromethyl)-1H-pyrazolo[3,4-b]pyridin-1-yl}thiazole-4-carboxylic acid; 2-(6-chloro-3-phenyl-1H-indazol-1-yl)thiazole-4-carboxylic acid; 2-(6-bromo-3-phenyl-1H-indazol-1-yl)thiazole-4-carboxylic acid; and 2-(6-iodo-3-phenyl-1H-indazol-1-yl)thiazole-4-carboxylic acid.

[19] A pharmaceutical agent which includes as an effective component the compounds that are described in any one of the above [1] to [18-12] or pharmaceutically acceptable salt thereof.

[19-2] A prodrug of the compounds that are described in any one of the above [1] to [18-12] or pharmaceutically acceptable salt thereof.

[20] The pharmaceutical agent that is described above [19], which is used for prophylaxis and/or treatment of an overactive bladder.

[20-2] The pharmaceutical agent that is described above [19], which is used for prophylaxis and/or treatment of symptoms including frequent urination, urinary urgency and urinary incontinence.

[21] An EP1 antagonist which includes as an effective component the compounds that are described in any one of the above [1] to [18-12] or pharmaceutically acceptable salt thereof.

[22] Use of the compounds that are described in any one of the above [1] to [18-12] or pharmaceutically acceptable salt thereof for the preparation of a pharmaceutical agent which is used for prophylaxis and/or treatment of an overactive bladder.

[22-2] Use of the compounds that are described in any one of the above [1] to [18-12] or pharmaceutically acceptable salt thereof for the preparation of a pharmaceutical agent which is used for prophylaxis and/or treatment of symptoms including frequent urination, urinary urgency and urinary incontinence.

[23] A method for the prophylaxis and/or treatment of an overactive bladder in mammal, including administering to the mammal the compounds that are described in any one of the above [1] to [18-12] or pharmaceutically acceptable salt thereof in an amount which is effective for the prophylaxis and/or treatment of an overactive bladder.

[23-2] A method for the prophylaxis and/or treatment of frequency urinary, urinary urgency or urinary incontinence in mammal, including administering to the mammal the compounds that are described in any one of the above [1] to [18-12] or pharmaceutically acceptable salt thereof in an amount which is effective for the prophylaxis and/or treatment of said symptoms.

Effect of the Invention

The "compounds represented by the formula (1) or salt thereof" (hereinafter, they can be sometimes abbreviated as the "compounds of the present invention") have a potent antagonistic activity for EP1 receptor when they are administered to a human or an animal, and they are useful as an effective component of a pharmaceutical agent for the prophylaxis and/or treatment of an overactive bladder, for example. Furthermore, they are useful as an effective component of a pharmaceutical agent for the prophylaxis and/or treatment of symptoms including frequency urinary, urinary urgency and urinary incontinence.

BEST MODE TO CARRY OUT THE INVENTION

Hereinafter, the present invention will be described in more detail.

In the present specification, a fluorine atom, a chlorine atom, a bromine atom or an iodine atom is exemplified as a halogen atom.

As for the "lower" substituent described in the present specification, a substituent having at most ten carbon atoms, which constitute the substituent, can be mentioned. Specifically, substituents having 1 to 6 carbon atoms can be mentioned. Substituents having 1 to 3 carbon atoms can be mentioned as a preferred example.

Examples of an alkyl group described in the present specification include a linear, branched, or cyclic saturated hydrocarbon group, or a combination thereof. A lower alkyl group is preferred. Preferred examples thereof include an alkyl group having 1 to 6 carbon atoms, and particularly preferred examples thereof include an alkyl group having 1 to 3 carbon atoms. Preferred examples of an alkyl group having 1 to 3 carbon atoms include a methyl group, an ethyl group, an n-propyl group, an isopropyl group, or a cyclopropyl group and the like. In addition, preferred examples of an alkyl group having 4 to 6 carbon atoms include an n-butyl group, an isobutyl group, a s-butyl group, a t-butyl group, a cyclobutyl group, a cyclopropylmethyl group, an n-pentyl group, a cyclopentyl group, a cyclopropylethyl group, a cyclobutylmethyl group, an n-hexyl group, a cyclohexyl group, a cyclopropylpropyl group, a cyclobutylethyl group, or a cyclopentylmethyl group and the like. As an alkyl group, a methyl group, an ethyl group, an n-propyl group, or an isopropyl group is particularly preferred.

Examples of an alkenyl group described in the present specification include a lower alkenyl group which has one or two or more double bonds. A lower alkenyl group including one double bond is preferred. An alkenyl group having 2 to 5 carbon atoms is preferred as a lower alkenyl group. An alkenyl group having 2 to 4 carbon atoms is particularly preferred. Preferred examples of an alkenyl group having 2 to 4 carbon atoms include a vinyl group, an allyl group, a propenyl group, a butylidene group, a but-1-enyl group, a but-2-enyl group, a but-3-enyl group and the like. In addition, preferred examples of an alkenyl group having 5 carbon atoms include a pentylidene group, a pent-1-enyl group, a pent-2-enyl group, a pent-3-enyl group, a pent-4-enyl and the like. Particularly preferred examples of an alkenyl group include a vinyl group, an allyl group, or a propenyl group.

Examples of an alkynyl group of the present specification include a lower alkynyl group which has one or two or more triple bonds. A lower alkynyl group including one triple bond is preferred. The alkynyl group including 2 to 5 carbon atoms is preferred as a lower alkynyl group. Specifically, preferred examples include an ethynyl group, a prop-1-ynyl group, a prop-2-ynyl group, a but-1-ynyl group, a but-2-ynyl group, a but-3-ynyl group, a pent-1-ynyl group, a pent-2-ynyl group, a pent-3-ynyl group, or a pent-4-ynyl group and the like. An ethynyl group, a prop-2-ynyl group, or a but-3-ynyl group is particularly preferred.

As for the alkylene group of the present specification, a divalent residue which is formed by removal of any single hydrogen atom from the alkyl group described above can be exemplified and it includes a linear, branched, or cyclic saturated divalent hydrocarbon group, or a combination thereof. A lower alkylene group is preferred. As for the lower alkylene group, an alkylene group having 1 to 6 carbon atoms is preferred. An alkylene group having 1 to 3 carbon atoms is particularly preferred. Preferred examples of an alkylene group having 1 to 3 carbon atoms include a methylene group, an ethylene group, an n-propylene GROUP, an isopropylene group or a cyclopropylene group. In addition, preferred examples of an alkylene group having 4 to 6 carbon atoms include a divalent residue which is formed by removal of any single hydrogen atom from the group which is described above as a preferred example of the alkyl group having 4 to 6 carbon atoms. As an alkylene group, a methylene group, an ethylene group, an n-propylene group or an isopropylene group is particularly preferred. A methylene group can be mentioned as the most preferred example of an alkylene group. There is other embodiment in which an ethylene group is the most preferred example of an alkylene group.

As for an alkenylene group of the present specification, a divalent residue, which is formed by removal of any single hydrogen atom from the alkenyl group described above, can be exemplified and it includes a lower alkenylene group including one or two or more double bonds. A lower alkenylene group including one double bond is preferred. An alkenylene group having 2 to 5 carbon atoms is preferred as a lower alkenylene group. An alkenylene group having 2 to 4 carbon atoms is particularly preferred. Preferred examples of an alkenylene group having 2 to 4 carbon atoms include a vinylene group, a propenylene group, a but-1-enylene group, a but-2-enylene group, a but-3-enylene group and the like. As for an alkenylene group having 5 carbon atoms, a divalent residue which is formed by removal of any single hydrogen atom from the group which is described above as a preferred example of the alkenyl group having 5 carbon atoms can be mentioned. As an alkenylene group, a vinylene group or a propenylene group is more preferred. A vinylene group is particularly preferred.

With respect to stereochemistry relating to a double bond, any of cis and trans is acceptable. Preferred stereochemistry is trans.

As for an alkoxy group of the present specification, a linear, branched, cyclic saturated alkyl ether group, or a saturated alkyl ether group having combination thereof can be mentioned. A lower alkoxy group is preferred. As a lower alkoxy group, an alkoxy group including 1 to 6 carbon atoms is preferred. An alkoxy group including 1 to 4 carbon atoms is particularly preferred. Preferred examples of an alkoxy group including 1 to 4 carbon atoms include a methoxy group, an ethoxy group, an n-propoxy group, an isopropoxy group, a cyclopropoxy group, an n-butoxy group, an isobutoxy group, a s-butoxy group, a t-butoxy group, a cyclobutoxy group, or a cyclopropylmethoxy group and the like. In addition, preferred examples of an alkoxy group including 5 or 6 carbon atoms include an n-pentyloxy group, a cyclopentyloxy group, a cyclopropylethyloxy group, a cyclobutylmethyloxy group, an n-hexyloxy group, a cyclohexyloxy group, a cyclopropylpropyloxy group, a cyclobutylethyloxy group, and a cyclopentylmethyloxy group and the like.

As for the aryl ring of the present specification, a monocyclic aromatic ring or a fused polycyclic aromatic ring and the like can be mentioned. The monocyclic aromatic ring or the fused polycyclic aromatic ring defined herein includes a partially unsaturated monocyclic ring or a fused bicyclic carbon ring or a fused bicyclic heterocyclic ring. The aryl ring can be a hydrocarbon ring or, as a ring-constituting atom other than a carbon atom, it may include one or more, for example 1 to 3, of one or two or more kinds of heteroatoms that are selected from a group consisting of a nitrogen atom, a sulfur atom and an oxygen atom.

Examples of a monocyclic aromatic ring include a monocyclic aromatic hydrocarbon or a monocyclic aromatic heterocycle which includes one or two or more heteroatoms. As a monocyclic aromatic hydrocarbon, a benzene ring, a cyclopentene ring or a cyclohexene ring can be mentioned as a preferred example. As a monocyclic aromatic heterocycle, a 5- or 6-membered aromatic heterocycle, which includes one or two or more heteroatoms, can be mentioned. Specific examples of the preferred 5- or 6-membered aromatic heterocycle include thiophene, pyridine, furan, thiazole, oxazole, pyrazole, pyrazine, pyrimidine, pyrrole, imidazole, pyridazine, isothiazole, isoxazole, 1,2,4-oxadiazole, 1,3,4-oxadiazole, 1,2,4-thiadiazole, 1,3,4-thiadiazole, furazane, 2,3-dihydrofuran, 3,4-dihydro-2H-pyran and the like.

Further, as a partially unsaturated monocycle which is included in the monocyclic aromatic ring, a partially unsaturated monocyclic carbon ring, or a monocyclic hetero ring can be mentioned. Specific example of a partially unsaturated monocyclic carbon ring include a cyclopentene ring, a cyclopenta-1,3-diene ring, a cyclohexene ring and a cyclohexa-1,3-diene ring.

Further, as a partially unsaturated monocyclic hetero ring, specific examples include a 2,3-dihydrofuran ring, a 2,5-dihydrofuran ring, a 2,3-dihydrothiophene ring, a 3,4-dihydro-2H-pyrane ring, a 3,6-dihydro-2H-pyrane ring and a 3,4-dihydro-2H-thiopyrane ring.

Examples of a fused polycyclic aromatic ring include a fused polycyclic aromatic hydrocarbon or a fused polycyclic aromatic heterocycle which includes one or two or more heteroatoms. As a fused polycyclic aromatic hydrocarbon, for example, a fused polycyclic aromatic hydrocarbon including 9 to 14 carbon atoms, i.e., bi- or tri-cyclic aromatic hydrocarbon can be mentioned. Specifically, preferred examples include naphthalene, indene, fluorene, anthracene and the like. As a fused polycyclic aromatic heterocycle, a 9- to 14-membered, preferably 9- or 10-membered, fused polycyclic aromatic heterocycle including one or more heteroatom, for example one to four heteroatoms, can be mentioned. Specifically, preferred examples include benzofuran, benzothiophene, benzimidazole, benzoxazole, benzothiazole, benzisothiazole, naphtho[2,3-b]thiophene, quinoline, isoquinoline, indole, quinoxaline, phenanthridine, phenothiazine, phenoxazine, phthalazine, naphthyridine, quinazoline, cinnoline, carbazole, β-carboline, acridine, phenazine, phthalimide, thioxanthen and the like.

As for an aryl group of the present specification, a monocyclic aromatic group or a fused polycyclic aromatic group and the like can be mentioned, for example. In addition, a monovalent residue that is produced by removing any single hydrogen atom from the above-described aryl ring can be exemplified. Further, the monocyclic aromatic group includes a partially unsaturated monocyclic group, a fused bicyclic hydrocarbon group or heterocyclic group.

As the monocyclic aromatic group, a monovalent residue that is produced by removing any single hydrogen atom from a monocyclic aromatic ring can be exemplified. More specific and preferred examples of a monocyclic aromatic group include a phenyl group, a cyclopentenyl group (1-, 3- or 4-cyclopentenyl group), a cyclohexenyl group (1-, 3- or 4-cyclohexenyl group), a thienyl group (2- or 3-thienyl group), a pyridyl group (2-, 3- or 4-pyridyl group), a furyl group (2- or 3-furyl group), a thiazolyl group (2-, 4- or 5-thiazolyl group), an oxazolyl group (2-, 4- or 5-oxazolyl group), a pyrazolyl group (1-, 3- or 4-pyrazolyl group), a 2-pyrazinyl group, a pyrimidinyl group (2-, 4- or 5-pyrimidinyl group), a pyrrolyl group (1-, 2- or 3-pyrrolyl group), an imidazolyl group (1-, 2- or 4-imidazolyl group), a pyridazinyl group (3- or 4-pyridazinyl group), a 3-isothiazolyl group, a 3-isoxazolyl group, a 1,2,4-oxadiazol-5-yl group, a 1,2,4-oxadiazol-3-yl group, a 2,3-dihydrofuran-2-yl group, a 2,3-dihydrofuran-3-yl group, a 2,3-dihydrofuran-4-yl group, a 2,3-dihydrofuran-5-yl group, a 2,5-dihydrofuran-2-yl group, a 2,5-dihydrofuran-3-yl group, a 2,3-dihydrothiophen-5-yl group, a 3,4-dihydro-2H-pyran-2-yl group, a 3,4-dihydro-2H-pyran-3-yl group, a 3,4-dihydro-2H-pyran-4-yl group, a 3,4-dihydro-2H-pyran-5-yl group, a 3,4-dihydro-2H-pyran-6-yl group, a 3,6-dihydro-2H-pyran-2-yl group, a 3,6-dihydro-2H-pyran-3-yl group, a 3,6-dihydro-2H-pyran-4-yl group, a 3,6-dihydro-2H-pyran-5-yl group, a 3,6-dihydro-2H-pyran-6-yl group, a 3,4-dihydro-2H-thiopyran-6-yl group and the like.

As for the a fused polycyclic aromatic group, a monovalent residue that is produced by removing any single hydrogen atom from a fused polycyclic aromatic group including 2 to 4, preferably 2 or 3, rings can be exemplified.

Specifically, preferred examples of a fused polycyclic aromatic group include a 1-naphthyl group, a 2-naphthyl group, a 2-indenyl group, a 2-anthryl group, a quinolyl group (2-, 3-, 4-, 5-, 6-, 7- or 8-quinolyl group), an isoquinolyl group (1-, 3-, 4-, 5-, 6-, 7- or 8-isoquinolyl group), an indolyl group (1-, 2-, 3-, 4-, 5-, 6- or 7-indolyl group), an isoindolyl group (1-, 2-, 4- or 5-isoindolyl group), a phthalazinyl group (1-, 5- or 6-phthalazinyl group), a quinoxalinyl group (2-, 3- or 5-quinoxalinyl group), a benzofuranyl group (2-, 3-, 4-, 5- or 6-benzofuranyl group), a benzothiazolyl group (2-, 4-, 5- or 6-benzothiazolyl group), a benzimidazolyl group (1-, 2-, 4-, 5- or 6-benzimidazolyl group), a 2,1,3-benzoxadiazol-4-yl group, a 2,1,3-benzoxadiazol-5-yl group, a 2,1,3-benzoxadiazol-6-yl group, a fluorenyl group (1-, 2-, 3- or 4-fluorenyl group), a thioxanthenyl group and the like.

As for a partially unsaturated monocyclic group, a monovalent residue that is produced by removing any single hydrogen atom from the partially unsaturated monocycle can be exemplified, and it includes a partially unsaturated monocyclic carbon ring group or a monocyclic heterocyclic group. Specific examples a partially unsaturated monocyclic carbon ring group include a cyclopentenyl group (1-, 3- or 4-cyclopentenyl group), a cyclopenta-1,3-dienyl group (1-cyclopenta-1,3-dienyl group, a 2-cyclopenta-1,3-dienyl group or 5-cyclopenta-1,3-dienyl group), a cyclohexenyl group (1-, 3- or 4-cyclohexenyl group) or a cyclohexa-1,3-dienyl group (1-cyclohexa-1,3-dienyl group, a 2-cyclohexa-1,3-dienyl group and a 5-cyclohexa-1,3-dienyl group). A 1-cyclopentenyl group or 1-cyclohexenyl group is more preferred. A 1-cyclohexenyl group is more preferred.

Further, specific examples of a partially unsaturated monocyclic heterocyclic group include a 2,3-dihydrofuran-2-yl group, a 2,3-dihydrofuran-3-yl group, a 2,3-dihydrofuran-4-yl group, a 2,3-dihydrofuran-5-yl group, a 2,5-dihydrofuran-2-yl group, a 2,5-dihydrofuran-3-yl group, a 2,3-dihydrothiophen-5-yl group, a 3,4-dihydro-2H-pyran-2-yl group, a 3,4-dihydro-2H-pyran-3-yl group, a 3,4-dihydro-2H-pyran-4-yl group, a 3,4-dihydro-2H-pyran-5-yl group, a 3,4-dihydro-2H-pyran-6-yl group, a 3,6-dihydro-2H-pyran-2-yl group, a 3,6-dihydro-2H-pyran-3-yl group, a 3,6-dihydro-2H-pyran-4-yl group, a 3,6-dihydro-2H-pyran-5-yl group, a 3,6-dihydro-2H-pyran-6-yl group and a 3,4-dihydro-2H-thiopyran-6-yl group. A 2,3-dihydrofuran-5-yl group or 3,4-dihydro-2H-pyran-6-yl group is more preferred. A 3,4-dihydro-2H-pyran-6-yl group is more preferred.

As for the cyclic saturated hydrocarbon of the present specification, a fully saturated monocyclic ring structure can be mentioned, for example. The ring consists only of a carbon atom and a 5- or 6-membered ring is particularly preferred. Specific examples include cyclopentane and cyclohexane.

As for the cyclic saturated hydrocarbon group of the present specification, a monovalent residue that is produced by removing any single hydrogen atom from the cyclic saturated hydrocarbon group described above can be mentioned, for example.

Examples of a saturated heterocycle of the present specification include a fully saturated monocyclic ring structure, for example. The ring can be a 3- to 7-membered ring which includes one or more, for example 1 to 3, preferably 1 of one or two or more kinds of heteroatoms that are selected from a group consisting of a nitrogen atom, a sulfur atom and an oxygen atom as a ring-constituting atom other than a carbon atom, for example. A 5- or 6-membered ring is particularly preferred. Specifically preferred examples include tetrahydropyran, tetrahydrofuran, piperidine, pyrrolidine, tetrahydrothiopyran, tetrahydrothiophene, morpholine, piperazine and the like. Piperidine, pyrrolidine or tetrahydropyran is a particularly preferred example.

As for the saturated heterocyclic group of the present specification, a monovalent residue that is produced by removing any single hydrogen atom from the saturated heterocyclic group described above can be mentioned, for example. Specific examples of a monocyclic aromatic group include a tetrahydropyranyl group (2,3- or 4-tetrahydropyranyl group), a tetrahydrofuryl group (2- or 3-tetrahydrofuryl group), a piperidinyl group (1-, 2-, 3- or 4-piperidinyl group), a pyrrolidinyl group (1-, 2- or 3-pyrrolidinyl group), a tetrahydrothiopyranyl group (2-, 3- or 4-tetrahydrothiopyranyl group), a tetrahydrothiophenyl group (2- or 4-tetrahydrothiophenyl group), a morpholinyl group (2-, 3- or 4-morpholinyl group), a piperidinyl group (1-, 2- or 3-piperidinyl group) and the like. A piperidinyl group, a pyrrolidinyl group or tetrahydropyranyl group can be mentioned as a particularly preferred example.

As for the aryloxy group of the present specification, it indicates an aryl group which is bonded to an oxygen atom. The aryl moiety of an aryloxy group is the same as the aryl group described above. The aryl moiety of an aryloxy group is preferably a monocyclic aromatic group, and the examples of an aryloxy group include a phenoxy group, a 2-thienyloxy group, a 3-thienyloxy group, a 2-pyridyloxy group, a 3-pyridyloxy group, a 4-pyridyloxy group, a 2-furyloxy group, a 3-furyloxy group, a 2-thiazolyloxy group, a 4-thiazolyloxy group, a 5-thiazolyloxy group, a 2-oxazolyloxy group, a 4-oxazolyloxy group, a 5-oxazolyloxy group, a 3-pyrazolyloxy group, a 4-pyrazolyloxy group, a 2-pyrazinyloxy group, a 2-pyrimidinyloxy group, a 4-pyrimidinyloxy group, a 5-pyrimidinyloxy group, a 2-pyrrolyloxy group, a 3-pyrrolyloxy group, a 2-imidazolyloxy group, a 4-imidazolyloxy group, a 3-pyridazinyloxy group, a 4-pyridazinyloxy group, a 3-isothiazolyloxy group, a 3-isoxazolyloxy group, a 1,2,4-oxadiazol-5-yloxy group, a 1,2,4-oxadiazol-3-yloxy group or a 3,4-dihydro-2H-pyran-6-yloxy group and the like. A phenoxy group, a 2-thienyloxy group, a 3-thienyloxy group, a 2-furyloxy group, a 3-furyloxy group, a 2-pyrrolyloxy group, a 3-pyrrolyloxy group and the like are preferred. A phenoxy group is particularly preferred.

As for the aralkyl group of the present specification, an alkyl group described above of which one hydrogen atom is substituted with the aryl group defined in the present specification can be mentioned. Specific examples include a benzyl group, a phenethyl group, a 1-(phenyl)ethyl group, a phenylpropyl group, a 1-naphthylmethyl group, a 2-naphthylmethyl group, a 2-pyridylmethyl group, a 3-pyridylmethyl group, a 4-pyridylmethyl group, a 2-furylmethyl group, a 3-furylmethyl group, a 2-thienylmethyl group, a 3-thienylmethyl group and the like, and a benzyl group and a phenethyl group are preferred.

As for the alkylthio group of the present specification, a saturated alkylthio ether group having 1 to 6 carbon atoms can be mentioned, and the alkyl group described above to which a sulfur atom is added can be mentioned, for example. Specific examples include a methylthio group, an ethylthio group, an n-propylthio group, an isopropylthio group, a cyclopropylthio group, an n-butylthio group, an isobutylthio group, a s-butylthio group, a t-butylthio group, a cyclobutylthio group, a cyclopropylmethylthio group and the like.

As for the acyl group of the present specification, an alkanoyl group or an arylcarbonyl group can be mentioned. As for an alkanoyl group, a saturated alkylcarbonyl group having 2 to 6 carbon atoms can be mentioned. Specific examples include an acetyl group, a propanoyl group, a butanoyl group, a 2-methylpropanoyl group, a cyclopropylcarbonyl group, a pentanoyl group, a 3-methylbutanoyl group, a 2,2-dimethylpropanoyl group, a cyclobutylcarbonyl group and the like.

As for the acyloxy group of the present specification, an alkanoyloxy group (alkylcarbonyloxy group) or an arylcarbonyloxy group can be mentioned, for example. As for an alkanoyloxy group, a saturated alkylcarbonyloxy group having 2 to 6 carbon atoms can be mentioned. Specific examples include an acetoxy group, a propanoyloxy group, a butanoyloxy group, a 2-methylpropanoyloxy group, a cyclopropylcarbonyloxy group, a pentanoyloxy group, a 3-methylbutanoyloxy group, a 2,2-dimethylpropanoyloxy group, a cyclobutylcarbonyloxy group and the like.

As for the alkylsulfinyl group of the present specification, a saturated alkylsulfinyl group having 1 to 6 carbon atoms can be mentioned. Specific examples include a methylsulfinyl group, an ethylsulfinyl group, an n-propylsulfinyl group, an isopropylsulfinyl group, a cyclopropylsulfinyl group, an n-butylsulfinyl group, an isobutylsulfinyl group, a s-butylsulfinyl group, a t-butylsulfinyl group, a cyclobutylsulfinyl group, a cyclopropylmethylsulfinyl group and the like.

As for the alkylsulfonyl group of the present specification, a saturated alkylsulfonyl group having 1 to 6 carbon atoms can be mentioned. Specific examples include a methylsulfonyl group, an ethylsulfonyl group, an n-propylsulfonyl group, an isopropylsulfonyl group, a cyclopropylsulfonyl group, an n-butylsulfonyl group, an isobutylsulfonyl group, a s-butylsulfonyl group, a t-butylsulfonyl group, a cyclobutylsulfonyl group, a cyclopropylmethylsulfonyl group and the like.

As for the alkylcarbamyl group of the present specification, a saturated alkylcarbamyl group having 2 to 6 carbon atoms can be mentioned. Specific examples include a methylcarbamyl group, an ethylcarbamyl group, an n-propylcarbamyl group, an isopropylcarbamyl group, a cyclopropylcarbamyl group, an n-butylcarbamyl group, an isobutylcarbamyl group, a s-butylcarbamyl group, a t-butylcarbamyl group, a cyclobutylcarbamyl group, a cyclopropylmethylcarbamyl group and the like.

As for the alkylamino group of the present specification, a saturated alkylamino group having 1 to 6 carbon atoms can be mentioned. Specific examples include a methylamino group, an ethylamino group, an n-propylamino group, an isopropylamino group, a cyclopropylamino group, an n-butylamino group, an isobutylamino group, a s-butylamino group, a t-butylamino group, a cyclobutylamino group, a cyclopropylmethylamino group and the like.

As for the dialkylamino group of the present specification, an amino group substituted with 1 to 6 same or different alkyl groups can be mentioned. Specific examples include a dimethylamino group, an ethyl(methyl)amino group, a diethylamino group, a methyl(n-propyl)amino group, an isopropyl(methyl)amino group, a cyclopropyl(methyl)amino group, an n-butyl(methyl)amino group, an isobutyl(methyl)amino group, a s-butyl(methyl)amino group, a t-butyl(methyl)amino group, a cyclobutyl(methyl)amino group, a cyclopropylmethyl(methyl)amino group and the like. Further, two substituents on the nitrogen may together form a 3- to 7-membered ring to yield a cyclic amine, and in such case, as a dialkylamino group, a 3- to 7-membered cyclic amine can be mentioned. Specific examples include a pyrrolidino group, a piperidine group and the like.

As for the acylamino group of the present specification, an amino group, which is substituted with the acyl group described above, can be mentioned. Specific examples include an acetylamino group, a propanoylamino group, a butanoylamino group, a 2-methylpropanoylamino group, a cyclopropylcarbonylamino group, a pentanoylamino group, a 3-methylbutanoylamino group, a 2,2-dimethylpropanoylamino group, a cyclobutylcarbonylamino group and the like.

As for the acyl(alkyl)carbamyl group of the present specification, an amino group which is substituted simultaneously with one acyl group described above and one alkyl group described above can be mentioned. Specific examples include an acetyl(methyl)amino group, a methyl(propanoyl)amino group, a butanoyl(methyl)amino group, a methyl(2-methylpropanoyl)amino group, a cyclopropylcarbonyl(methyl)amino group, a methyl(pentanoyl)amino group, a methyl(3-methylbutanoyl)amino group, a 2,2-dimethylpropanoyl(methyl)amino group, a cyclobutylcarbonyl(methyl)amino group and the like.

As for the alkylsulfonylamino group of the present specification, an amino group, which is substituted with the alkylsulfonyl group described above, can be mentioned. Specific examples include a methylsulfonylamino group, an ethylsulfonylamino group, an n-propylsulfonylamino group, an isopropylsulfonylamino group, a cyclopropylsulfonylamino group, an n-butylsulfonylamino group, an isobutylsulfonylamino group, a s-butylsulfonylamino group, a t-butylsulfonylamino group, a cyclobutylsulfonylamino group, a cyclopropylmethylsulfonylamino group and the like.

As for the alkylsulfonyl(alkyl)amino group of the present specification, an amino group which is substituted simultaneously with one alkylsulfonyl group described above and one alkyl group described above can be mentioned. Specific examples include a methyl(methylsulfonyl)amino group, an ethylsulfonyl(methyl)amino group, a methyl(n-propylsulfonyl)amino group, an isopropylsulfonyl(methyl)amino group, a cyclopropylsulfonyl(methyl)amino group, an n-butylsulfonyl(methyl)amino group, an isobutylsulfonyl(methyl)amino group, a s-butylsulfonyl(methyl)amino group, a t-butylsulfonyl(methyl)amino group, a cyclobutylsulfonyl(methyl)amino group, a cyclopropylmethylsulfonyl(methyl)amino group and the like.

As for a group which may be substituted as described in the present specification (i.e., an alkyl group, an alkenyl group, an alkynyl group, an aryl group, an aralkyl group, an alkoxy group, an aryloxy group, a phenyl group, an alkylene group, a methylene group, an alkenylene group and the like), an unsubstituted group or a group which is substituted generally with one to several substituents within the upper limit, that is the maximum number of allowed substitution, can be mentioned.

As for a substituent for the alkyl group which may be substituted as described in the present specification, a hydroxy group, a cyano group, a halogen atom, an aryl group, an aryloxy group, an alkoxy group, an alkylthio group, an acyl group, an acyloxy group, an alkylsulfinyl group, an alkylsulfonyl group, an alkylcarbamyl group, an amino group, an alkylamino group, a dialkylamino group, an acylamino group, an acyl(alkyl)amino group, an alkylsulfonylamino group, an alkylsulfonyl(alkyl)amino group and the like can be mentioned.

As for a substituent for the alkylene group which may be substituted as described in the present specification, the substituent described for the alkyl group which may be substituted as described above can be also mentioned.

As for a substituent for the methylene group which may be substituted with a lower alkyl group as described in the present specification, an alkyl group having 1 to 6 carbon atoms is preferred. An alkyl group having 1 to 3 carbon atoms is particularly preferred. Preferred examples of an alkyl group having 1 to 3 carbon atoms include a methyl group, an ethyl group, an n-propyl group, an isopropyl group, a cyclopropyl group and the like. Examples of an alkyl group having 4 to 6 carbon atoms include an n-butyl group, an isobutyl group, a s-butyl group, a t-butyl group, a cyclobutyl group, a cyclopropylmethyl group, an n-pentyl group, a cyclopentyl group, a cyclopropylethyl group, a cyclobutylmethyl group, an n-hexyl group, a cyclohexyl group, a cyclopropylpropyl group, a cyclobutylethyl group, a cyclopentylmethyl group and the like.

As for a substituent for the alkenyl group which may be substituted as described in the present specification, the substituent described for the alkyl group which may be substituted as described above can be also mentioned.

As for a substituent for the alkenylene group which may be substituted as described in the present specification, the substituent described for the alkyl group which may be substituted as described above can be also mentioned.

As for a substituent for the alkynyl group which may be substituted as described in the present specification, the substituent described for the alkyl group which may be substituted as described above can be also mentioned.

As for a substituent for the aryl ring which may be substituted and a substituent for the aryl group which may be substituted as described in the present specification, a hydroxy group, a halogen atom, an alkyl group which may be substituted, an alkenyl group which may be substituted, an alkynyl group which may be substituted, an aryl group, an alkoxy group which may be substituted, an alkylthio group, an acyl group, an acyloxy group, an alkylsulfinyl group, an alkylsulfonyl group, an alkylcarbamyl group, —N($R^{411}$)($R^{412}$) ($R^{411}$ and $R^{412}$ may be same or different to each other, and each independently represent a hydrogen atom, an alkyl group which may be substituted or an aryl group which may be substituted, or $R^{411}$ and $R^{412}$ together form a 3- to 7-membered ring to represent a cyclic amine of N($R^{411}$)($R^{412}$).), an acylamino group, an acyl(alkyl)amino group, an alkylsulfonylamino group, an alkylsulfonyl(alkyl)amino group, a carboxy group, —CON($R^{413}$)($R^{414}$) ($R^{413}$ and $R^{414}$ may be same or different to each other, and each independently represent a hydrogen atom, an alkyl group which may be substituted or an aryl group which may be substituted, or $R^{413}$ and $R^{414}$ together form a 3- to 7-membered ring to represent a cyclic amine of N($R^{413}$)($R^{414}$).) or —COO$R^{415}$ ($R^{415}$ represents an alkyl group which may be substituted.), and the number of substituent is not specifically limited, if it is an allowed number of substitution. Preferably, it is between 1 and 3. When two or more substituents are present, they may be same or different to each other.

In the present specification, the substituent for the cyclic saturated hydrocarbon which may be substituted, and the substituent for the saturated cyclic hydrocarbyl group which may be substituted are similar to the substituent for the aryl ring which may be substituted or the aryl group which may be substituted.

In the present specification, the substituent for the saturated heterocyclic ring which may be substituted, and the substituent for the saturated heterocyclic group which may be substituted are similar to the substituent for the aryl ring which may be substituted or the aryl group which may be substituted.

As for an aralkyl group which may be substituted, the alkyl group which may be substituted as described above of which one hydrogen atom is substituted with an aryl group which may be substituted as described in the present specification can be mentioned.

As for a substituent for the alkoxy group which may be substituted as described in the present specification, the substituent described for the alkyl group which may be substituted as described above can be also mentioned.

As for a substituent for the aryloxy group which may be substituted as described in the present specification, the substituent described for the alkyl group which may be substituted as described above can be also mentioned.

Next, each substituent for the compounds of the present invention will be described more specifically.

$Ar^1$ represents an aryl group which may be substituted, a saturated cyclic hydrocarbyl group which may be substituted, or a saturated heterocyclic group which may be substituted. $Ar^1$ is preferably an aryl group which may be substituted. In other embodiments, a saturated heterocyclic group may also be preferred.

When $Ar^1$ represents an aryl group which may be substituted, the aryl group of the aryl group which may be substituted is preferably a phenyl group, a cyclopentenyl group (1-, 3- or 4-cyclopentenyl group), a cyclohexenyl group (1-, 3- or 4-cyclohexenyl group), a thienyl group (2- or 3-thienyl group), a pyridyl group (2-, 3- or 4-pyridyl group), a furyl group (2- or 3-furyl group), a thiazolyl group (2-, 4- or 5-thiazolyl group), an oxazolyl group (2-, 4- or 5-oxazolyl group), a pyrazolyl group (1-, 3- or 4-pyrazolyl group), a 2-pyrazinyl group, a pyrimidinyl group (2-, 4- or 5-pyrimidinyl group), a pyrrolyl group (1-, 2- or 3-pyrrolyl group), an imidazolyl group (1-, 2- or 4-imidazolyl group), a pyridazinyl group (3- or 4-pyridazinyl group), a 3-isothiazolyl group, a 3-isoxazolyl group, a 1,2,4-oxadiazol-5-yl group, a 1,2,4-oxadiazol-3-yl group, a 2,3-dihydrofuran-2-yl group, a 2,3-dihydrofuran-3-yl group, a 2,3-dihydrofuran-4-yl group, a 2,3-dihydrofuran-5-yl group, a 2,5-dihydrofuran-2-yl group, a 2,5-dihydrofuran-3-yl group, a 2,3-dihydrothiophen-5-yl group, a 3,4-dihydro-2H-pyran-2-yl group, a 3,4-dihydro-2H-pyran-3-yl group, a 3,4-dihydro-2H-pyran-4-yl group, a 3,4-dihydro-2H-pyran-5-yl group, a 3,4-dihydro-2H-pyran-6-yl group, a 3,6-dihydro-2H-pyran-2-yl group, a 3,6-dihydro-2H-pyran-3-yl group, a 3,6-dihydro-2H-pyarn-4-yl group, a 3,6-dihydro-2H-pyran-5-yl group, a 3,6-dihydro-2H-pyran-6-yl group, a 3,4-dihydro-2H-thiopyran-6-yl group, a 1-naphthyl group, a 2-naphthyl group, a 2-indenyl group, a 2-anthryl group, a quinolyl group (2-, 3-, 4-, 5-, 6-, 7- or 8-quinolyl group), an isoquinolyl group (1-, 3-, 4-, 5-, 6-, 7- or 8-isoquinolyl group), an indolyl group (1-, 2-, 3-, 4-, 5-, 6- or 7-indolyl group), an isoindolyl group (1-, 2-, 4- or 5-isoindolyl group), a phthalazinyl group (1-, 5- or 6-phthalazinyl group), a quinoxalinyl group (2-, 3- or 5-quinoxalinyl group), a benzofuranyl group (2-, 3-, 4-, 5- or 6-benzofuranyl group), a benzothiazolyl group (2-, 4-, 5- or 6-benzothiazolyl group), a benzimidazolyl group (1-, 2-, 4-, 5- or 6-benzimidazolyl group), 2,1,3-benzoxadiazol-4-yl group, a 2,1,3-benzoxadiazol-5-yl group, a 2,1,3-benzoxadiazol-6-yl group, a fluorenyl group (1-, 2-, 3- or 4-fluorenyl group), or a thioxanthenyl group. The aryl group is more preferably a phenyl group, a 1-cyclopentenyl group, a 1-cyclohexenyl group, a 2-thienyl group, a 3-thienyl group, a 3-pyridyl group, a 2-furyl group, a 3-furyl group, a 4-pyrazolyl group, a 5-pyrimidinyl group, a 3,4-dihydro-2H-pyran-6-yl group, a 2-naphthyl group, a 3-quinolyl group, a 8-quinolyl group, a 6-indolyl group, a 2-benzofuranyl group, or a 3-benzothiazolyl group; even more preferably a phenyl group, a 1-cyclopentenyl group, a 1-cyclohexenyl group, a 2-thienyl group, a 3-thienyl group, a 3-pyridyl group, a 2-furyl group, a 3-furyl group, a 3,4-dihydro-2H-pyran-6-yl group, or a 2-benzofuranyl group; particularly preferably a phenyl group, a 1-cyclohexenyl group, or a 3-thienyl group; and most preferably a phenyl group.

Furthermore, in other embodiments, when $Ar^1$ represents an aryl group which may be substituted, a partially unsaturated monocyclic carbocyclic group or a monocyclic heterocyclic group may be preferred as the aryl group of the aryl group which may be substituted. Specifically, as a partially unsaturated monocyclic carbon ring group, a cyclopentenyl group (1-, 3- or 4-cyclopentenyl group) or a cyclohexenyl group (1-, 3- or 4-cyclohexenyl group) is exemplified and a 1-cyclopentenyl group or a 1-cyclohexenyl group is preferred. A 1-cyclohexenyl group is more preferred.

Further, as a partially unsaturated monocyclic heterocycle group, specific examples include a 2,3-dihydrofuran-2-yl group, a 2,3-dihydrofuran-3-yl group, a 2,3-dihydrofuran-4-yl group, a 2,3-dihydrofuran-5-yl group, a 2,5-dihydrofuran-2-yl group, a 2,5-dihydrofuran-3-yl group, a 2,3-dihydrothiophen-5-yl group, a 3,4-dihydro-2H-pyran-2-yl group, a 3,4-dihydro-2H-pyran-3-yl group, a 3,4-dihydro-2H-pyran-4-yl group, a 3,4-dihydro-2H-pyran-5-yl group, a 3,4-dihydro-2H-pyran-6-yl group, a 3,6-dihydro-2H-pyran-2-yl group, a 3,6-dihydro-2H-pyran-3-yl group, a 3,6-dihydro-2H-pyran-4-yl group, a 3,6-dihydro-2H-pyran-5-yl group, a 3,6-dihydro-2H-pyran-6-yl group and a 3,4-dihydro-2H-thiopyran-6-yl group. A 2,3-dihydrofuran-5-yl group and a 3,4-dihydro-2H-pyran-6-yl group are preferred. A 3,4-dihydro-2H-pyran-6-yl group is more preferred.

The substituent for the aryl group which may be substituted as represented by $Ar^1$ is not particularly limited as long as it is the above-mentioned substituent for the aryl group which may be substituted, but is preferably a hydroxy group, a halogen atom, an alkyl group which may be substituted, an alkenyl group which may be substituted, or an alkoxy group which may be substituted. The substituent is preferably a hydroxy group, a halogen atom, an alkyl group which may be substituted, or an alkoxy group which may be substituted; more preferably a halogen atom, an alkyl group which may be substituted, or an alkoxy group which may be substituted; and particularly preferably a halogen atom. The number of substituents is preferably 1 to 2. In other embodiments, an unsubstituted aryl group may also be preferred.

When $Ar^1$ represents a saturated cyclic hydrocarbyl group which may be substituted, the saturated cyclic hydrocarbyl group of the saturated cyclic hydrocarbyl group which may be substituted is preferably a cyclopentyl group or a cyclohexyl group. The substituent for the saturated cyclic hydrocarbyl group which may be substituted is not particularly limited as long as it is the above-mentioned substituent for the saturated cyclic hydrocarbyl group which may be substituted, but s preferably a hydroxy group, a halogen atom, an alkyl group which may be substituted, or an alkoxy group which may be substituted; and more preferably an alkyl group which may be substituted, or an alkoxy group which may be substituted. The number of substituents is preferably 1 to 2. In other embodiments, an unsubstituted saturated cyclic hydrocarbyl group may also be preferred.

When $Ar^1$ represents a saturated heterocyclic group which may be substituted, the saturated heterocyclic group of the saturated heterocyclic group which may be substituted, is preferably a tetrahydropyranyl group (2-, 3- or 4-tetrahydropyranyl group), a tetrahydrofuryl group (2- or 3-tetrahydrofuryl group), a piperidinyl group (1-, 2-, 3- or 4-piperidinyl group), a pyrrolidinyl group (1-, 2- or 3-pyrrolidinyl group), a tetrahydrothiopyranyl group (2-, 3- or 4-tetrahydrothiopyranyl group), a tetrahydrothiophenyl group (2- or 4-tetrahydrothiophenyl group), a morpholinyl group (2-, 3- or 4-morpholinyl group), or a piperidinyl group (1-, 2- or 3-piperidinyl group); more preferably a 1-pyrrolidinyl group or a 1-piperidinyl group; and particularly preferably a 1-piperidinyl group. The substituent for the saturated heterocyclic group which may be substituted is not particularly limited as long as it is the above-mentioned substituent for the saturated heterocyclic group which may be substituted, but is preferably a hydroxy group, a halogen atom, an alkyl group which may be substituted, or an alkoxy group which may be substituted; and more preferably an alkyl group which may be substituted, or an alkoxy group which may be substituted. The number of substituents is preferably 1 to 2. In other embodiments, an unsubstituted saturated heterocyclic group may also be preferred.

X represents a nitrogen atom or $=C(R^{X1})-$ [wherein $R^{X1}$ represents a hydrogen atom, or an alkyl group which may be substituted]. X is preferably a nitrogen atom or $=CH-$, and more preferably a nitrogen atom. When $R^{X1}$ represents an alkyl group which may be substituted, the alkyl group is not particularly limited as long as it is the above-mentioned alkyl group which may be substituted, but is more preferably a lower alkyl group, and particularly preferably a methyl group or an ethyl group.

$R^1$ and $R^2$ together represent any of the following formulas $(Q^1)$ to $(Q^6)$

[Chemical Formula 4]

(Q¹)

(Q²)

(Q³)

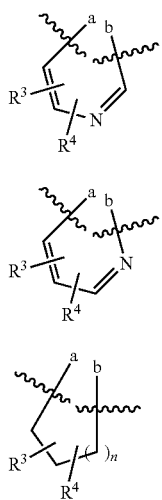

(Q⁴)

(Q⁵)

(Q⁶)

wherein in the formulas (Q¹) to (Q⁶), R³ and R⁴, which may be same or different, each independently represent any of a hydrogen atom, a halogen atom, an alkyl group which may be substituted, an alkenyl group which may be substituted, an alkynyl group which may be substituted, an aryl group which may be substituted, an aralkyl group which may be substituted, a hydroxy group, an alkoxy group which may be substituted, an aryloxy group which may be substituted, an alkylthio group, an acyl group, an acyloxy group, an alkylsulfinyl group, an alkylsulfonyl group, an alkylcarbamoyl group, —N(R^{Q1})(R^{Q2}) [wherein R^{Q1} and R^{Q2} may be same or different, and each independently represent a hydrogen atom, an alkyl group which may be substituted, or an aryl group which may be substituted; or R^{Q1} and R^{Q2} together form a 3- to 7-membered ring to represent a cyclic amine in the form of N(R^{Q1})(R^{Q2})], an acylamino group, an acyl(alkyl)amino group, an alkylsulfonylamino group, an alkylsulfonyl(alkyl)amino group, a carboxy group, —CON(R^{Q3})(R^{Q4}) [wherein R^{Q3} and R^{Q4} may be same or different, and each independently represent a hydrogen atom, an alkyl group which may be substituted, or an aryl group which may be substituted; or R^{Q3} and R^{Q4} together form a 3- to 7-membered to represent a cyclic amine in the form of N(R^{Q3})(R^{Q4})], or —COOR^{Q5} [wherein R^{Q5} represents an alkyl group which may be substituted];

n represents an integer from 1 to 4; and

R¹ and R² represent that they are bonded to each of the formulas (Q¹) to (Q⁶) at the position of a and the position of b, respectively.

When R¹ and R² together represent one of the formulas (Q¹) to (Q⁶), the formula (1) adopts a structure represented by each of the following formulas (1-1) to (1-6):

[Chemical Formula 5]

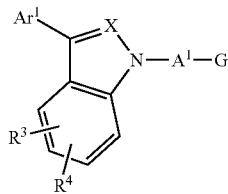

(1-1)

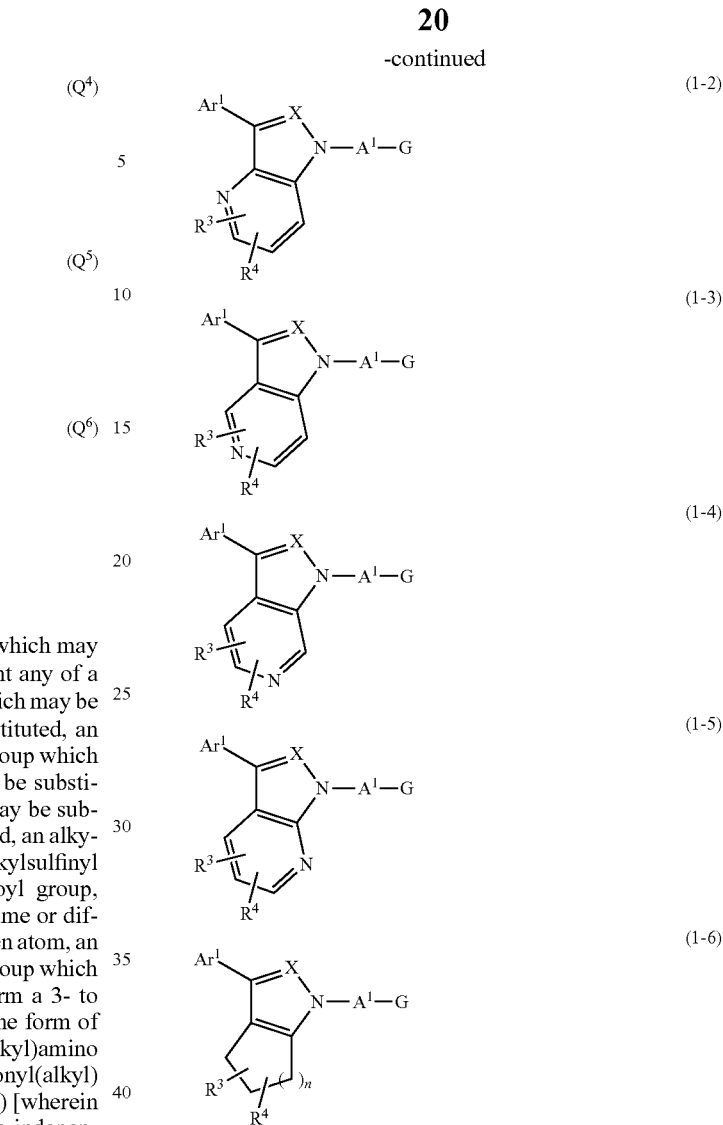

wherein in the formulas (1-1) to (1-5), Ar¹, X, R³, R⁴, A¹, G and n have the same meanings as defined above.

It is preferred that R¹ and R² together represent the formula (Q¹), (Q⁴), (Q⁵) or (Q⁶); it is particularly preferred that they together represent the formula (Q¹), (Q⁴) or (Q⁵); and it is particularly preferred that they represent the formula (Q¹). In other embodiments, it is particularly preferred that they represent the formula (Q⁴) or (Q⁵). In still other embodiments, R¹ and R² representing the formula (Q⁶) may also be preferred.

R³ and R⁴, which may be same or different, each independently represent a hydrogen atom, a halogen atom, an alkyl group which may be substituted, an alkenyl group which may be substituted, an alkynyl group which may be substituted, an aryl group which may be substituted, an aralkyl group which may be substituted, a hydroxy group, an alkoxy group which may be substituted, an aryloxy group which may be substituted, an alkylthio group, an acyl group, an acyloxy group, an alkylsulfinyl group, an alkylsulfonyl group, an alkylcarbamoyl group, —N(R^{Q1})(R^{Q2}) [wherein R^{Q1} and R^{Q2} may be same or different, and each independently represent a hydrogen atom, an alkyl group which may be substituted, or an aryl group which may be substituted; or R^{Q1} and R^{Q2} together form a 3- to 7-membered ring to represent a cyclic amine in the form of N(R^{Q1})(R^{Q2})], an acylamino group, an acyl(alkyl)

amino group, an alkylsulfonylamino group, an alkylsulfonyl(alkyl)amino group, a carboxy group, —CON($R^{Q3}$)($R^{Q4}$) [wherein $R^{Q3}$ and $R^{Q4}$ may be same or different, and each independently represent a hydrogen atom, an alkyl group which may be substituted, or an aryl group which may be substituted; or $R^{Q3}$ and $R^{Q4}$ together form a 3- to 7-membered ring to represent a cyclic amine in the form of N($R^{Q3}$)($R^{Q4}$)], or —COOR$^{Q5}$ [wherein $R^{Q5}$ represents an alkyl group which may be substituted]. The group represented by $R^3$ and $R^4$ is preferably a hydrogen atom, a halogen atom, an alkyl group which may be substituted, an alkoxy group which may be substituted, or —N($R^{Q1}$)($R^{Q2}$) [wherein $R^{Q1}$ and $R^{Q2}$ have the same meanings as defined above]; even more preferably a hydrogen atom, a halogen atom, or an alkyl group which may be substituted; and particularly preferably a hydrogen atom or a halogen atom. In other embodiments, a hydrogen atom or an alkyl group, which may be substituted, may be particularly preferred. In still other embodiments, a hydrogen atom or —N($R^{Q1}$)($R^{Q2}$) [wherein $R^{Q1}$ and $R^{Q2}$ have the same meanings as defined above] may be particularly preferred.

$R^{Q1}$ and $R^{Q2}$ are each preferably a hydrogen atom, or an alkyl group which may be substituted. Suitable examples of the alkyl group of the alkyl group which may be substituted as represented by $R^{Q1}$ and $R^2$, include a methyl group, an ethyl group, an n-propyl group, an isopropyl group, a cyclopropyl group and the like, and a methyl group or an ethyl group is particularly preferred. The substituent for the alkyl group which may be substituted is preferably a hydroxy group, a cyano group, a halogen atom, an aryl group, an aryloxy group, an alkoxy group, an amino group, an alkylamino group, or a dialkylamino group; and particularly preferably an aryl group, an aryloxy group or an alkoxy group.

The positions of substitution for $R^3$ and $R^4$ are not particularly limited as long as they are substitutable positions on the formulas ($Q^1$) to ($Q^6$), and may be present at any positions.

Preferred examples representing the position and number of the substituents other than hydrogen atom among $R^3$ and $R^4$ in the case where $R^1$ and $R^2$ together represent the formula ($Q^1$), will be described below. However, in the following formulas, a and b have the same meanings as defined above, and $W^1$ and/or $W^2$ represents the bonding position for a substituent.

[Chemical Formula 6]

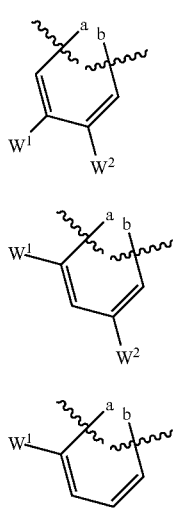

($Q^{1A}$)

($Q^{1B}$)

($Q^{1C}$)

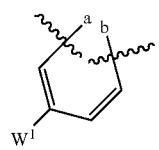

($Q^{1D}$)

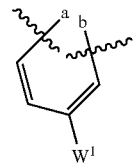

($Q^{1E}$)

are preferred;

[Chemical Formula 7]

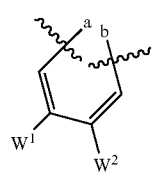

($Q^{1A}$)

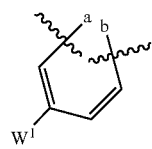

($Q^{1D}$)

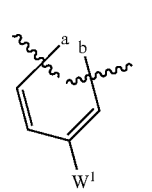

($Q^{1E}$)

are particularly preferred; and

[Chemical Formula 8]

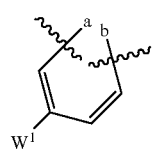

($Q^{1D}$)

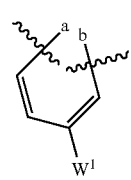

($Q^{1E}$)

are even more preferred; and

[Chemical Formula 9]

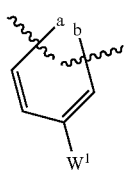
(Q$^{1E}$)

is particularly preferred.

Preferred examples representing the position and number of the substituents other than hydrogen atom among R$^3$ and R$^4$ in the case where R$^1$ and R$^2$ together represent the formula (Q$^2$), will be described below. However, in the following formulas, a and b have the same meanings as defined above, and W$^1$ and/or W$^2$ represents the bonding position for a substituent.

[Chemical Formula 10]

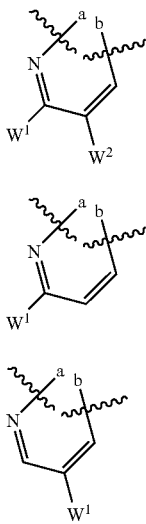
(Q$^{2A}$)
(Q$^{2B}$)
(Q$^{2C}$)

are preferred;

[Chemical Formula 11]

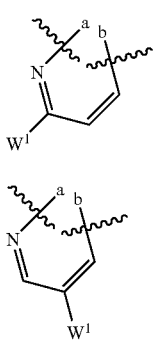
(Q$^{2B}$)
(Q$^{2C}$)

are more preferred; and

[Chemical Formula 12]

(Q$^{2C}$)

is particularly preferred.

Preferred examples representing the position and number of the substituents other than hydrogen atom among R$^3$ and R$^4$ in the case where R$^1$ and R$^2$ together represent the formula (Q$^3$), will be described below. However, in the following formulas, a and b have the same meanings as defined above, and W$^1$ and/or W$^2$ represents the bonding position for a substituent.

[Chemical Formula 13]

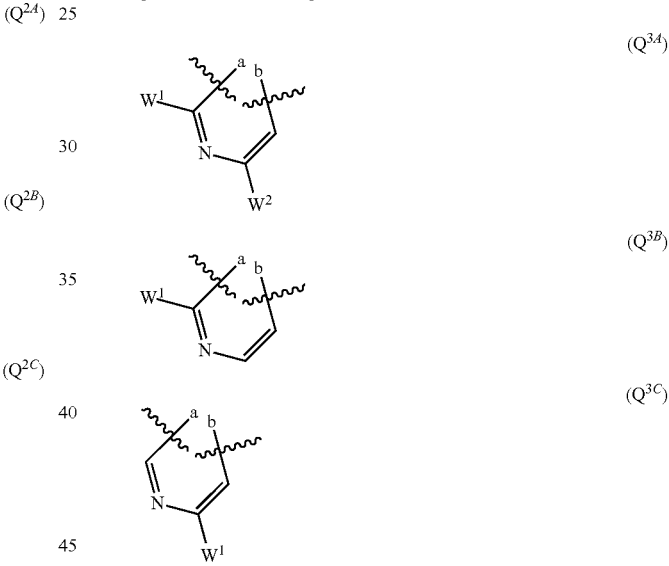
(Q$^{3A}$)
(Q$^{3B}$)
(Q$^{3C}$)

are preferred;

[Chemical Formula 14]

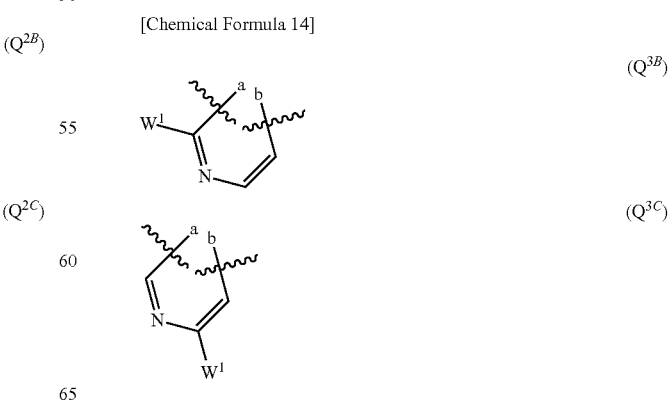
(Q$^{3B}$)
(Q$^{3C}$)

are more preferred; and

[Chemical Formula 15]

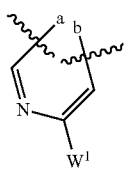

is particularly preferred.

Preferred examples representing the position and number of the substituents other than hydrogen atom among $R^3$ and $R^4$ in the case where $R^1$ and $R^2$ together represent the formula ($Q^4$), will be described below. However, in the following formulas, a and b have the same meanings as defined above, and $W^1$ and/or $W^2$ represents the bonding position for a substituent.

[Chemical Formula 16]

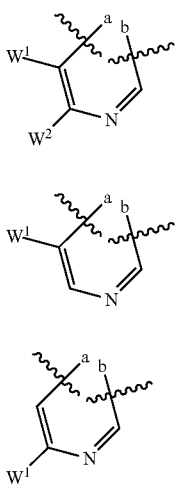

are preferred;

[Chemical Formula 17]

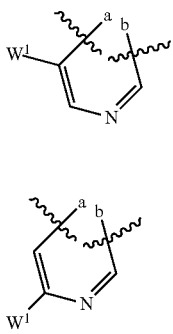

are more preferred; and

[Chemical Formula 18]

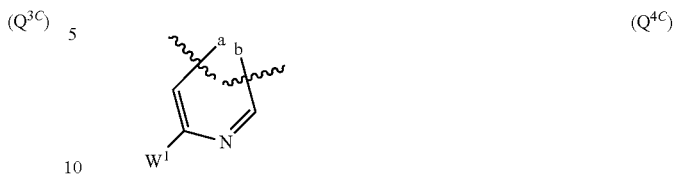

is particularly preferred.

Preferred examples representing the position and number of the substituents other than hydrogen atom between $R^3$ and $R^4$ in the case where $R^1$ and $R^2$ together represent the formula ($Q^5$), will be described below. However, in the following formulas, a and b have the same meanings as defined above, and $W^1$ and/or $W^2$ represents the bonding position for a substituent.

[Chemical Formula 19]

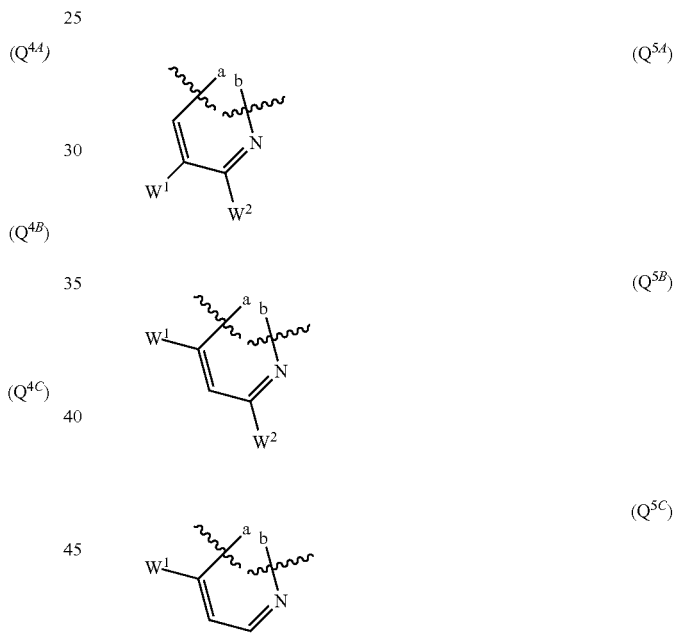

are preferred;

[Chemical Formula 20]

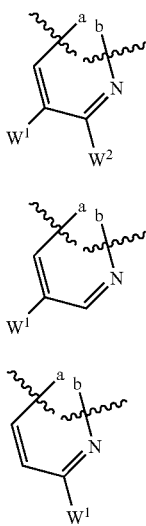

(Q$^{5A}$)

(Q$^{5D}$)

(Q$^{5E}$)

are more preferred;

[Chemical Formula 21]

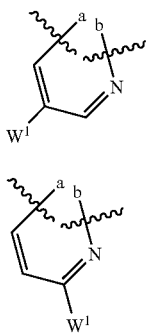

(Q$^{5D}$)

(Q$^{5E}$)

are even more preferred; and

[Chemical Formula 22]

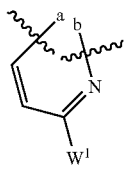

(Q$^{5E}$)

is particularly preferred.

n represents an integer from 1 to 4. The integer represented by n is preferably 2 or 3, and 2 is particularly preferred.

A$^1$ represents a single bond, an alkylene group which may be substituted, or an alkenylene group which may be substituted. A$^1$ is preferably a single bond or an alkylene group; even more preferably a single bond, or a methylene group which may be substituted with a lower alkyl group; and particularly preferably a single bond. In other embodiments, a methylene group may be particularly preferred.

G represents the following formula (G$^1$), (G$^2$) or (G$^3$)

[Chemical Formula 23]

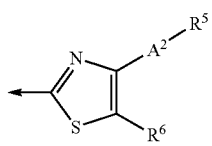

(G$^1$)

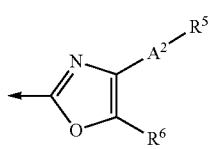

(G$^2$)

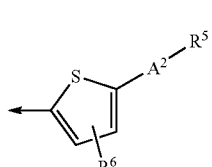

(G$^3$)

wherein in the formulas (G$^1$), (G$^2$) and (G$^3$), A$^2$ represents a single bond, an alkylene group which may be substituted, or an alkenylene group which may be substituted; R$^5$ represents a carboxy group, —CON(R$^{51}$)(R$^{52}$) [wherein R$^{51}$ and R$^{52}$ may be same or different, and each independently represent a hydrogen atom, an alkyl group which may be substituted, or an aryl group which may be substituted; or R$^{51}$ and R$^{52}$ together form a 3- to 7-membered ring to represent a cyclic amine in the form of N(R$^{51}$)(R$^{52}$)], —COOR$^{53}$ [wherein R$^{53}$ represents an alkyl group which may be substituted], or a tetrazol-5-yl group; and R$^6$ represents a hydrogen atom, or an alkyl group which may be substituted. Here, in the formulas (G$^1$), (G$^2$) and (G$^3$), the arrow represents the position of bonding with A$^1$.

It is preferred that G represent the formula (G$^1$) or (G$^3$), and it is particularly preferred that G represents the formula (G$^1$). In other embodiments, G representing the formula (G$^3$) may be particularly preferred.

A$^2$ represents a single bond, an alkylene group which may be substituted, or an alkenylene group which may be substituted. A$^2$ is preferably a single bond.

R$^5$ represents a carboxy group, —CON(R$^{51}$)(R$^{52}$) [wherein R$^{51}$ and R$^{52}$ may be same or different, and each independently represent a hydrogen atom, an alkyl group which may be substituted, or an aryl group which may be substituted; or R$^{51}$ and R$^{52}$ together form a 3- to 7-membered ring to represent a cyclic amine in the form of N(R$^{51}$)(R$^{52}$)], —COOR$^{53}$ [wherein R$^{53}$ represents an alkyl group which may be substituted], or a tetrazol-5-yl group. R$^5$ is preferably a carboxy group, or —COOR$^{53}$ [wherein R$^{53}$ has the same meaning as defined above], and is particularly preferably a carboxy group. R$^{53}$ is not particularly limited as long as it is the above-mentioned alkyl group which may be substituted, but is more preferably a lower alkyl group, and is particularly preferably a methyl group or an ethyl group.

R$^6$ represents a hydrogen atom, or an alkyl group which may be substituted. R$^6$ is preferably a hydrogen atom. R$^6$ indicates its presence at the 5-position of the thiazole ring for the formula (G$^1$), and at the 5-position of the oxazole ring for the formula ($G^2$). $R^6$ can be present on any arbitrary carbon atom for the formula ($G^3$), excluding the positions of bonding with $A^1$ and $A^2$.

The combination of various substituents in the compound of the present invention is not particularly limited, but for example, the following are preferred:

<A1> A compound in which G represents the formula ($G^1$);

<A2> A compound in which G represents the formula ($G^2$);

<A3> A compound in which G represents the formula ($G^3$);

<B1> A compound in which $R^5$ is a carboxy group;

<B2> A compound in which $R^5$ is —$COOR^{83}$;

<B3> A compound in which $R^5$ is a tetrazol-5-yl group;

<C1> A compound according to any one of <A1> to <A3> above, in which <B1> applies;

<C2> A compound according to any one of <A1> to <A3> above, in which <B2> applies;

<C3> A compound according to any one of <A1> to <A3> above, in which <B3> applies;

<D1> A compound in which X is a nitrogen atom;

<D2> A compound in which X is =CH—;

<E1> A compound according to any one of <A1> to <C3> above, in which <D1> applies;

<E2> A compound according to any one of <A1> to <C3> above, in which <D2> applies;

<F1> A compound in which $A^2$ is a single bond;

<F2> A compound in which $A^2$ is an ethylene group;

<F3> A compound in which $A^2$ is a methylene group;

<F4> A compound in which $A^2$ is an ethenylene group;

<G1> A compound according to any one of <A1> to <E2> above, in which <F1> applies;

<G2> A compound according to any one of <A1> to <E2> above, in which <F2> applies;

<G3> A compound according to any one of <A1> to <E2> above, in which <F3> applies;

<G4> A compound according to any one of <A1> to <E2> above, in which <F4> applies;

<H1> A compound in which $A^1$ is a single bond;

<H2> A compound in which $A^1$ is an alkylene group;

<H3> A compound in which $A^1$ is an alkylene group having 2 or fewer carbon atoms, which may be substituted with a lower alkyl group;

<H4> A compound in which $A^1$ is an ethylene group;

<H5> A compound in which $A^1$ is a methylene group;

<H6> A compound in which $A^1$ is an alkenylene group;

<H7> A compound in which $A^1$ is an ethenylene group which may be substituted with a lower alkyl group;

<H8> A compound in which $A^1$ is an ethenylene group;

<I1> A compound according to any one of <A1> to <G4> above, in which <H1> applies;

<I2> A compound according to any one of <A1> to <G4> above, in which <H2> applies;

<I3> A compound according to any one of <A1> to <G4> above, in which <H3> applies;

<I4> A compound according to any one of <A1> to <G4> above, in which <H4> applies;

<I5> A compound according to any one of <A1> to <G4> above, in which <H5> applies;

<I6> A compound according to any one of <A1> to <G4> above, in which <H6> applies;

<I7> A compound according to any one of <A1> to <G4> above, in which <H7> applies;

<I8> A compound according to any one of <A1> to <G4> above, in which <H8> applies;

<J1> A compound in which $R^1$ and $R^2$ together represent the formula ($Q^1$);

<J2> A compound in which $R^1$ and $R^2$ together represent the formula ($Q^1$), and the position and number of the substituents other than hydrogen among $R^3$ and $R^4$ are represented by the formula ($Q^{1D}$);

<J3> A compound in which $R^1$ and $R^2$ together represent the formula ($Q^1$), and the position and number of the substituents other than hydrogen among $R^3$ and $R^4$ are represented by the formula ($Q^{1E}$);

<J4> A compound in which $R^1$ and $R^2$ together represent the formula ($Q^2$);

<J5> A compound in which $R^1$ and $R^2$ together represent the formula ($Q^2$), and the position and number of the substituents other than hydrogen among $R^3$ and $R^4$ are represented by the formula ($Q^{2B}$);

<J6> A compound in which $R^1$ and $R^2$ together represent the formula ($Q^2$), and the position and number of the substituents other than hydrogen among $R^3$ and $R^4$ are represented by the formula ($Q^{2C}$);

<J7> A compound in which $R^1$ and $R^2$ together represent the formula ($Q^3$);

<J8> A compound in which $R^1$ and $R^2$ together represent the formula ($Q^3$), and the position and number of the substituents other than hydrogen among $R^3$ and $R^4$ are represented by the formula ($Q^{3B}$);

<J9> A compound in which $R^1$ and $R^2$ together represent the formula ($Q^3$), and the position and number of the substituents other than hydrogen among $R^3$ and $R^4$ are represented by the formula ($Q^{3C}$)

<J10> A compound in which $R^1$ and $R^2$ together represent the formula ($Q^4$);

<J11> A compound in which $R^1$ and $R^2$ together represent the formula ($Q^4$), and the position and number of the substituents other than hydrogen among $R^3$ and $R^4$ are represented by the formula ($Q^{4B}$);

<J12> A compound in which $R^1$ and $R^2$ together represent the formula ($Q^4$), and the position and number of the substituents other than hydrogen among $R^3$ and $R^4$ are represented by the formula ($Q^{4C}$);

<J13> A compound in which $R^1$ and $R^2$ together represent the formula ($Q^5$);

<J14> A compound in which $R^1$ and $R^2$ together represent the formula ($Q^5$), and the position and number of the substituents other than hydrogen among $R^3$ and $R^4$ are represented by the formula ($Q^{5D}$);

<J15> A compound in which $R^1$ and $R^2$ together represent the formula ($Q^5$), and the position and number of the substituents other than hydrogen among $R^3$ and $R^4$ are represented by the formula ($Q^{5E}$);

<J16> A compound in which $R^1$ and $R^2$ together represent the formula ($Q^6$), and n is 2;

<J17> A compound in which $R^1$ and $R^2$ together represent the formula ($Q^6$), and n is 3;

<K1> A compound according to any one of <A1> to <I8> above, in which <J1> applies;

<K2> A compound according to any one of <A1> to <I8> above, in which <J2> applies;

<K3> A compound according to any one of <A1> to <I8> above, in which <J3> applies;

<K4> A compound according to any one of <A1> to <I8> above, in which <J4> applies;

<K5> A compound according to any one of <A1> to <I8> above, in which <J5> applies;

<K6> A compound according to any one of <A1> to <I8> above, in which <J6> applies;

<K7> A compound according to any one of <A1> to <I8> above, in which <J7> applies;
<K8> A compound according to any one of <A1> to <I8> above, in which <J8> applies;
<K9> A compound according to any one of <A1> to <I8> above, in which <J9> applies;
<K10> A compound according to any one of <A1> to <I8> above, in which <J10> applies;
<K11> A compound according to any one of <A1> to <I8> above, in which <J11> applies;
<K12> A compound according to any one of <A1> to <I8> above, in which <J12> applies;
<K13> A compound according to any one of <A1> to <I8> above, in which <J13> applies;
<K14> A compound according to any one of <A1> to <I8> above, in which <J14> applies;
<K15> A compound according to any one of <A1> to <I8> above, in which <J15> applies;
<K16> A compound according to any one of <A1> to <I8> above, in which <J16> applies;
<K17> A compound according to any one of <A1> to <I8> above, in which <J17> applies;
<L1> A compound in which $R^3$ is a hydrogen atom;
<L2> A compound in which $R^3$ is a fluorine atom;
<L3> A compound in which $R^3$ is a chlorine atom;
<L4> A compound in which $R^3$ is a bromine atom;
<L5> A compound in which $R^3$ is a iodine atom;
<L6> A compound in which $R^3$ is a methyl group;
<L7> A compound in which $R^3$ is an ethyl group;
<L8> A compound in which $R^3$ is an n-propyl group;
<L9> A compound in which $R^3$ is an isopropyl group;
<L10> A compound in which $R^3$ is a trifluoromethyl group;
<L11> A compound in which $R^3$ is —N($R^{Q1}$)($R^{Q2}$);
<M1> A compound according to any one of <A1> to <K17> above, in which <L1> applies;
<M2> A compound according to any one of <A1> to <K17> above, in which <L2> applies;
<M3> A compound according to any one of <A1> to <K17> above, in which <L3> applies;
<M4> A compound according to any one of <A1> to <K17> above, in which <L4> applies;
<M5> A compound according to any one of <A1> to <K17> above, in which <L5> applies;
<M6> A compound according to any one of <A1> to <K17> above, in which <L6> applies;
<M7> A compound according to any one of <A1> to <K17> above, in which <L7> applies;
<M8> A compound according to any one of <A1> to <K17> above, in which <L8> applies;
<M9> A compound according to any one of <A1> to <K17> above, in which <L9> applies;
<M10> A compound according to any one of <A1> to <K17> above, in which <L10> applies;
<N1> A compound in which $R^4$ is a hydrogen atom;
<N2> A compound in which $R^4$ is a fluorine atom;
<N3> A compound in which $R^4$ is a chlorine atom;
<N4> A compound in which $R^4$ is a bromine atom;
<N5> A compound in which $R^4$ is a iodine atom;
<N6> A compound in which $R^4$ is a methyl group;
<N7> A compound in which $R^4$ is an ethyl group;
<N8> A compound in which $R^4$ is an n-propyl group;
<N9> A compound in which $R^4$ is an isopropyl group;
<N10> A compound in which $R^4$ is a trifluoromethyl group;
<N11> A compound in which $R^4$ is —N($R^{Q1}$)($R^{Q2}$);
<O1> A compound according to any one of <A1> to <M11> above, in which <N1> applies;
<O2> A compound according to any one of <A1> to <M11> above, in which <N2> applies;
<O3> A compound according to any one of <A1> to <M11> above, in which <N3> applies;
<O4> A compound according to any one of <A1> to <M11> above, in which <N4> applies;
<O5> A compound according to any one of <A1> to <M11> above, in which <N5> applies;
<O6> A compound according to any one of <A1> to <M11> above, in which <N6> applies;
<O7> A compound according to any one of <A1> to <M11> above, in which <N7> applies;
<O8> A compound according to any one of <A1> to <M11> above, in which <N8> applies;
<O9> A compound according to any one of <A1> to <M11> above, in which <N9> applies;
<O10> A compound according to any one of <A1> to <M11> above, in which <N10> applies;
<O11> A compound according to any one of <A1> to <M11> above, in which <N11> applies;
<P1> A compound in which $Ar^1$ is a phenyl group;
<P2> A compound in which $Ar^1$ is a 1-cyclopentenyl group;
<P3> A compound in which $Ar^1$ is a 1-cyclohexenyl group;
<P4> A compound in which $Ar^1$ is a 2-thienyl group;
<P5> A compound in which $Ar^1$ is a 3-thienyl group;
<P6> A compound in which $Ar^1$ is a 3-pyridyl group;
<P7> A compound in which $Ar^1$ is a 2-furyl group;
<P8> A compound in which $Ar^1$ is a 3-furyl group;
<P9> A compound in which $Ar^1$ is a 3,4-dihydro-2H-pyran-6-yl group;
<P10> A compound in which $Ar^1$ is a 2-benzofuranyl group;
<P11> A compound in which $Ar^1$ is a cyclopentyl group;
<P12> A compound in which $Ar^1$ is a cyclohexyl group;
<P13> A compound in which $Ar^1$ is a 1-piperidinyl group;
<Q1> A compound according to any one of <A1> to <O11> above, in which <P1> applies;
<Q2> A compound according to any one of <A1> to <O11> above, in which <P2> applies;
<Q3> A compound according to any one of <A1> to <O11> above, in which <P3> applies;
<Q4> A compound according to any one of <A1> to <O11> above, in which <P4> applies;
<Q5> A compound according to any one of <A1> to <O11> above, in which <P5> applies;
<Q6> A compound according to any one of <A1> to <O11> above, in which <P6> applies;
<Q7> A compound according to any one of <A1> to <O11> above, in which <P7> applies;
<Q8> A compound according to any one of <A1> to <O11> above, in which <P8> applies;
<Q9> A compound according to any one of <A1> to <O11> above, in which <P9> applies;
<Q10> A compound according to any one of <A1> to <O11> above, in which <P10> applies;
<Q11> A compound according to any one of <A1> to <O11> above, in which <P11> applies;
<Q12> A compound according to any one of <A1> to <O11> above, in which <P12> applies;
<Q13> A compound according to any one of <A1> to <O11> above, in which <P13> applies;
<R1> A compound in which $Ar^1$ is unsubstituted;
<R1> A compound in which $Ar^1$ is substituted with one hydroxy group;
<R2> A compound in which $Ar^1$ is substituted with one fluorine atom;

<R3> A compound in which Ar¹ is substituted with one chlorine atom;

<R4> A compound in which Ar¹ is substituted with one bromine atom;

<R5> A compound in which Ar¹ is substituted with one methyl group;

<R6> A compound in which Ar¹ is substituted with one ethyl group;

<R7> A compound in which Ar¹ is substituted with one n-propyl group;

<R8> A compound in which Ar¹ is substituted with one isopropyl group;

<R9> A compound in which Ar¹ is substituted with one trifluoromethyl group;

<R10> A compound in which Ar¹ is substituted with one methoxy group;

<R11> A compound in which Ar¹ is substituted with one ethoxy group;

<R12> A compound in which Ar¹ is substituted with one n-propoxy group;

<R13> A compound in which Ar¹ is substituted with one isopropoxy group;

<R14> A compound in which Ar¹ is substituted with one trifluoromethyloxy group;

<R15> A compound in which Ar¹ is substituted with two substituents other than hydrogen;

<R16> A compound in which the two substituents other than hydrogen of Ar¹ are all fluorine atoms;

<R17> A compound in which the two substituents other than hydrogen of Ar¹ are all chlorine atoms;

<R18> A compound in which the two substituents other than hydrogen of Ar¹ are all methyl groups;

<R19> A compound in which the two substituents other than hydrogen of Ar¹ are all methoxy groups;

<R20> A compound in which the two substituents other than hydrogen of Ar¹ are all trifluoromethyl groups;

<R21> A compound in which the two substituents other than hydrogen of Ar¹ are a fluorine atom and a chlorine atom, respectively;

<R22> A compound in which the two substituents other than hydrogen of Ar¹ are a fluorine atom and a methyl group, respectively;

<R23> A compound in which the two substituents other than hydrogen of Ar¹ are a fluorine atom and a methoxy group, respectively;

<R24> A compound in which the two substituents other than hydrogen of Ar¹ are a fluorine atom and a trifluoromethyl group, respectively;

<R25> A compound in which the two substituents other than hydrogen of Ar¹ are a chlorine atom and a methyl group, respectively;

<R26> A compound in which the two substituents other than hydrogen of Ar¹ are a chlorine atom and a methoxy group, respectively;

<R27> A compound in which the two substituents other than hydrogen of Ar¹ are a chlorine atom and a trifluoromethyl group, respectively;

<R28> A compound in which the two substituents other than hydrogen of Ar¹ are a methyl group and a methoxy group, respectively;

<R29> A compound in which the two substituents other than hydrogen of Ar¹ are a methyl group and a trifluoromethyl group, respectively;

<R30> A compound in which the two substituents other than hydrogen of Ar¹ are a methoxy group and a trifluoromethyl group, respectively;

<S1> A compound according to any one of <A1> to <Q13> above, in which <R1> applies;

<S2> A compound according to any one of <A1> to <Q13> above, in which <R2> applies;

<S3> A compound according to any one of <A1> to <Q13> above, in which <R3> applies;

<S4> A compound according to any one of <A1> to <Q13> above, in which <R4> applies;

<S5> A compound according to any one of <A1> to <Q13> above, in which <R5> applies;

<S6> A compound according to any one of <A1> to <Q13> above, in which <R6> applies;

<S7> A compound according to any one of <A1> to <Q13> above, in which <R7> applies;

<S8> A compound according to any one of <A1> to <Q13> above, in which <R8> applies;

<S9> A compound according to any one of <A1> to <Q13> above, in which <R9> applies;

<S10> A compound according to any one of <A1> to <Q13> above, in which <R10> applies;

<S11> A compound according to any one of <A1> to <Q13> above, in which <R11> applies;

<S12> A compound according to any one of <A1> to <Q13> above, in which <R12> applies;

<S13> A compound according to any one of <A1> to <Q13> above, in which <R13> applies;

<S14> A compound according to any one of <A1> to <Q13> above, in which <R14> applies;

<S15> A compound according to any one of <A1> to <Q13> above, in which <R15> applies;

<S16> A compound according to any one of <A1> to <Q13> above, in which <R16> applies;

<S17> A compound according to any one of <A1> to <Q13> above, in which <R17> applies;

<S18> A compound according to any one of <A1> to <Q13> above, in which <R18> applies;

<S19> A compound according to any one of <A1> to <Q13> above, in which <R19> applies;

<S20> A compound according to any one of <A1> to <Q13> above, in which <R20> applies;

<S21> A compound according to any one of <A1> to <Q13> above, in which <R21> applies;

<S22> A compound according to any one of <A1> to <Q13> above, in which <R22> applies;

<S23> A compound according to any one of <A1> to <Q13> above, in which <R23> applies;

<S24> A compound according to any one of <A1> to <Q13> above, in which <R24> applies;

<S25> A compound according to any one of <A1> to <Q13> above, in which <R25> applies;

<S26> A compound according to any one of <A1> to <Q13> above, in which <R26> applies;

<S27> A compound according to any one of <A1> to <Q13> above, in which <R27> applies;

<S28> A compound according to any one of <A1> to <Q13> above, in which <R28> applies;

<S29> A compound according to any one of <A1> to <Q13> above, in which <R29> applies;

<S30> A compound according to any one of <A1> to <Q13> above, in which <R30> applies;

<T1> A compound in which $R^6$ is a hydrogen atom;

<T2> A compound in which $R^6$ is a methyl group;

<T3> A compound in which $R^6$ is an ethyl group;

<U1> A compound according to any one of <A1> to <S30> above, in which <T1> applies;

<U2> A compound according to any one of <A1> to <S30> above, in which <T2> applies; and <U3> A compound according to any one of <A1> to <S30> above, in which <T3> applies.

Compounds of the present invention are novel compound that have never been disclosed in any literature. Although the compounds of the present invention can be produced according to the method described below, for example, a method of preparing the compounds of the present invention is not limited thereto.

For each reaction, reaction time is not specifically limited. Since the progress of a reaction can be easily monitored using an analytical means that is described below, each reaction may be terminated when the amount of a target compound is highest. Further, each reaction may be carried out under inert gas atmosphere such as nitrogen stream or argon stream, etc., if required. Further, for each reaction, when protection using a protective group or subsequent deprotection is required, it can be appropriately carried out by using the methods described below.

Examples of a protective group which can be used for the present invention include a protective group for a carboxyl group (—COOH), a protective group for a hydroxy group (—OH), a protective group for a formyl group (—CHO—), a protective group for an amino group (—NH$_2$), and the like.

As for a protective group for a carboxyl group, an alkyl group having 1 to 4 carbon atoms, an alkenyl group having 2 to 4 carbon atoms, an alkyl group having 1 to 4 carbon atoms that is substituted with an alkoxy group having 1 to 4 carbon atoms, an alkyl group having 1 to 4 carbon atoms that is substituted with 1 to 3 halogen atoms, etc. are mentioned. Specific examples include a methyl group, an ethyl group, a t-butyl group, an allyl group, a methoxyethyl group, or trichloroethyl group, and the like.

As for a protective group for a hydroxy group, an alkyl group having 1 to 4 carbon atoms, an alkenyl group having 2 to 4 carbon atoms, an alkyl group having 1 to 4 carbon atoms that is substituted with an alkoxy group having 1 to 4 carbon atoms, an alkyl group having 1 to 4 carbon atoms that is substituted with 1 to 3 halogen atoms, a silyl group which is substituted with three different or the same phenyl groups or alkyl groups having 1 to 4 carbon atoms, a tetrahydropyranyl group, a tetrahydrofuryl group, a propargyl group, a trimethylsilylethyl group and the like can be mentioned. Specific examples include a methyl group, an ethyl group, a t-butyl group, an allyl group, a methoxymethyl (MOM) group, a methoxyethyl (MEM) group, a trichloroethyl group, a phenyl group, a methylphenyl group, a chlorophenyl group, a benzyl group, a methylbenzyl group, a chlorobenzyl group, a dichlorobenzyl group, a fluorobenzyl group, a trifluoromethylbenzyl group, a nitrobenzyl group, a methoxyphenyl group, an N-methylaminobenzyl group, an N,N-dimethylaminobenzyl group, a phenacyl group, a trityl group, a 1-ethoxyethyl (EE) group, a tetrahydropyranyl (THP) group, a tetrahydrofuryl group, a propargyl group, a trimethylsilyl (TMS) group, a triethylsilyl (TES) group, a t-butyldimethylsilyl (TBDMS) group, a t-butyldiphenylsilyl (TBDPS) group, an acetyl (Ac) group, a pyvaloyl group, a benzoyl group, an aryloxycarbonyl (Alloc) group, a 2,2,2-trichloroethoxycarbonyl (Troc) group and the like.

As for a protective group for a formyl group, an acetal group and the like can be mentioned, for example. Specifically, dimethylacetal and the like can be mentioned.

As for a protective group for an amino group, a benzyl group, a methylbenzyl group, a chlorobenzyl group, a dichlorobenzyl group, a fluorobenzyl group, a trifluoromethylbenzyl group, a nitrobenzyl group, a methoxyphenyl group, an N-methylaminobenzyl group, an N,N-dimethylaminobenzyl group, a phenacyl group, an acetyl group, a trifluoroacetyl group, a pivaloyl group, a benzoyl group, an allyloxycarbonyl group, a 2,2,2-trichloroethoxycarbonyl group, a benzyloxycarbonyl group, a t-butoxycarbonyl (Boc) group, a 1-methyl-1-(4-biphenyl)ethoxycarbonyl (Bpoc) group, a 9-fluorenylmethoxycarbonyl group, a benzyloxymethyl (BOM) group, and a 2-(trimethylsilyl)ethoxymethyl (SEM) group, etc. can be mentioned.

A protective group can be deprotected simultaneously or sequentially during an intermediate step or a final step of a production process, and can be converted accordingly to a desired product. A process for protection and deprotection can be carried out according to a known method, for example, a method described in "Protective Groups in Organic Synthesis, 2007, John Wiley & Sons, Inc." It can be carried out according to the methods (1) to (6) described below, for example.

(1) Deprotection method based on alkali hydrolysis is carried out, for example, by the reaction with a base in a polar solvent. Examples of a base include, for example, an alkali metal base such as sodium hydroxide, potassium hydroxide, lithium hydroxide, barium hydroxide, calcium hydroxide, sodium carbonate, potassium carbonate, sodium methoxide, potassium t-butoxide, etc., and an organic base such as triethyl amine, etc. Use amount of these bases is 1 to 20 times, preferably 1 to 10 times the molar amount of a reaction compound for an alkali metal base, and 1 mole to excess molar amount for an organic base. The reaction solvent is generally an inert medium which does not interfere a reaction. Preferably, the reaction is carried out in a polar solvent. Examples of the polar solvent include water, methanol, ethanol, tetrahydrofuran, dioxane and the like. A mixture thereof can be also used, if necessary. The reaction temperature is appropriately chosen between −10° C. to reflux temperature of a solvent, for example. The reaction time is generally between 0.5 to 72 hours, preferably 1 to 48 hours when an alkali metal base is used. When an organic base is used, it is generally 5 hours to 14 days. Since the progress of reaction can be monitored by thin layer chromatography (TLC), high performance liquid chromatography (HPLC), etc., the reaction can be generally terminated when the amount of a target compound is highest.

(2) Deprotection reaction under acidic condition is carried out, for example, in an organic solvent such as dichloromethane, chloroform, dioxane, ethyl acetate, anisole, etc. in the presence of an organic acid such as acetic acid, trifluoroacetic acid, methanesulfonic acid, or p-toluenesulfonic acid, etc., Lewis acid such as boron tribromide, boron trifluoride, aluminum bromide, aluminum chloride and the like, or an inorganic acid such as hydrochloric acid, sulfuric acid and the like or a mixture thereof (hydrobromic acid, acetic acid, etc.) at the temperature of −10 to 100° C. In addition, there is another method in which ethanethiol, 1,2-ethanedithiol, etc. are added as an additive.

(3) Deprotection reaction based on hydrogenation can be carried out, for example, in an ether-based solvent such as tetrahydrofuran, dioxane, dimethoxy ethane, diethyl ether, and the like, an alcohol-based solvent such as methanol, ethanol, and the like, a benzene type solvent such as benzene, toluene and the like, a ketone-based solvent such as acetone, methyl ethyl ketone and the like, a nitrile-based solvent such as acetonitrile and the like, an amide-based solvent such as dimethylformamide, and the like, an ester-based solvent such as ethyl acetate and the like, water, acetic acid, or a mixed solvent including two or more of them in the presence of a catalyst such as carbon palladium powder, platinum oxide ($PtO_2$), activated nickel and the like and a hydrogen source such as atmospheric or pressurized hydrogen gas, ammonium formic acid, hydrazine hydrate and the like at the temperature of −10 to 60° C.

(4) Deprotection reaction of a silyl group is carried out, for example, by using tetra-n-butyl ammonium fluoride and the like in an organic solvent which is miscible with water (e.g., tetrahydrofuran, acetonitrile and the like) at the temperature of −10 to 60° C.

(5) Deprotection reaction using a metal is carried out in an acidic solvent, for example, in acetic acid, a buffer solution having pH 4.2 to 7.2, or a mixed solvent including them and an organic solvent such as tetrahydrofuran and the like, in the presence of zinc powder with or without ultrasonication at the temperature of −10 to 60° C.

(6) Deprotection reaction using a metal complex is carried out, for example, in an organic solvent such as dichloromethane, dimethylformamide, tetrahydrofuran, ethyl acetate, acetonitrile, dioxane, ethanol and the like, water, or a mixed solvent thereof, in the presence of a trapping agent such as tributyl tin hydride, triethyl silane, dimedone, morpholine, diethylamine, pyrrolidine and the like, an organic acid such as acetic acid, formic acid, 2-ethyl hexanoic acid and the like and/or an organic acid salt such as sodium 2-ethyl hexanoate, potassium 2-ethyl hexanoate, and the like, with or without a phosphine-based reagent such as triphenyl phosphine and the like by using a metal complex such as tetrakis triphenyl phosphine palladium (0), dichlorobis(triphenylphosphine)palladium (II), palladium (II) acetate, chlorotris(triphenylphosphine)rhodium (I) and the like, at the temperature of −10 to 60° C.

The compounds represented by the formula (1) can be prepared according to a retrosynthetic pathway according to the following reaction, for example.

[Chemical Formula 24]

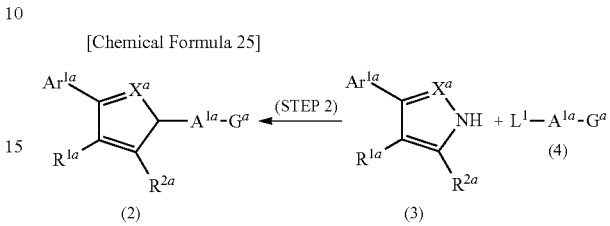

(1)                          (2)

For example, the compound represented by the formula (1) can be produced by simultaneously or successively removing all protective groups from a compound represented by formula (2) [wherein $Ar^{1a}$, $X^a$, $R^{1a}$, $R^{2a}$, $A^{1a}$ and $G^a$ have the same meanings as $Ar^1$, X, $R^1$, $R^2$, $A^1$ and G described above, respectively {provided that the formulas represented by $R^{1a}$ and $R^{2a}$ together, which correspond to the formulas ($Q^1$) to ($Q^6$) represented by $R^1$ and $R^2$ together, are designated as ($Q^{1a}$) to ($Q^{6a}$), respectively. In the formulas ($Q^{1a}$) to ($Q^{6a}$), the symbols corresponding to $R^3$ and $R^4$ in the formulas ($Q^1$) to ($Q^6$) are designated as $R^{3a}$ and $R^{4a}$, respectively. n has the same meaning as defined above. The formulas represented by $G^3$, which correspond to the formulas ($G^1$) to ($G^3$) represented by G, are designated as ($G^{1a}$) to ($G^{3a}$), respectively. In the formulas ($G^{1a}$) to ($G^{3a}$), the symbols corresponding to $A^2$, $R^5$ and $R^6$ in the formulas ($G^1$) to ($G^3$) are designated as $A^{2a}$, $R^{5a}$ and $R^{6a}$, respectively), or one or more groups among them may also be protected]. The deprotection reaction may be carried out according to known methods, for example, the methods described in Protective Groups in Organic Synthesis, published by John Wiley and Sons (2007 edition).

Furthermore, if $Ar^{1a}$, $X^a$, $R^{1a}$, $R^{2a}$, $A^{1a}$ and $G^a$ in the formula (2) have the same meanings as defined for $Ar^1$, X, $R^1$, $R^2$, $A^1$ and G, respectively, the compound represented by the formula (2) is directly equal to the compound represented by the formula (1), without undergoing deprotection.

The compound represented by the formula (2) can be produced according to, for example, the retrosynthetic pathway of the following reaction pathway.

[Chemical Formula 25]

In the compound represented by the formula (2), when $A^{1a}$ represents a single bond or an alkenylene group which may be substituted, the compound represented by the formula (2) can be produced by reacting a compound represented by formula (3) [wherein $Ar^{1a}$, $X^a$, $R^{1a}$ and $R^{2a}$ have the same meanings as defined above] with a compound represented by formula (4) [wherein $A^{1a}$ and $G^a$ have the same meanings as defined above; and $L^1$ represents a chlorine atom, a bromine atom or an iodine atom] in the presence of a base, using a commercially available copper catalyst, or a catalyst prepared from a copper powder or a copper salt and a ligand. In regard to the reaction between the compound represented by the formula (3) and the compound represented by the formula (4), the amount of use of the compound represented by the formula (4) may be ⅕ to 20 equivalents based on the compound represented by the formula (3), and the amount of use is, for example, ½ equivalents to 10 equivalents, and preferably 1 equivalent to 5 equivalents. However, the amount of use may be appropriately designed while taking into consideration of the purity of the compound represented by the formula (2), yield, purification efficiency, and the like. As for the copper catalyst, for example, a commercially available catalyst such as bis(acetylacetonato)copper(II) may be purchased and directly added to the reaction system, or catalysts separately prepared by mixing copper powder, copper(I) chloride, copper(I) bromide, copper(I) iodide, copper(I) cyanide, copper (I) oxide, copper(II) chloride, copper(II) bromide, copper(II) acetate, copper(II) sulfate, copper(II) oxide or the like with an arbitrary ligand, may also be used. Examples of the ligand include (1S,2S)-(+)-N,N-dimethylcycloexane-1,2-diamine, (1R,2R)-(−)-N,N-dimethylcyclohexane-1,2-diamine, (1S, 2S)-(+)-1,2-cyclohexanediamine, (1R,2R)-(−)-1,2-cyclohexanediamine, 1,10-phenanthroline, 2,9-dimethyl-1,10-phenanthroline, 4,7-dimethyl-1,10-phenanthroline, 3,4,7,8-tetramethyl-1,10-phenanthroline, 2,2,6,6-tetramethyl-3,5-heptanedione, 2-acetylcyclohexanone, 2-propionylcyclohexanone, N,N-diethylsalicylamide, N-methylethylenediamine, N,N-dimethylethylenediamine, N,N'-dimethylethylenediamine, N,N,N',N'-tetramethylethylenediamine, 8-quinolinol, 1,1'-binaphthyl-2,2'-diol, 2,2'-dihydroxybiphenyl, catechol, ethylene glycol, 9,10-phenanthrenequinone, L-(−)-proline, D-(+)-proline, glycine, and the like. Preferably, copper(I) iodide is used together with (1S,2S)-(+)-N,N-dimethylcyclohexane-1,2-diamine as the ligand to be mixed. The amount of use of the copper catalyst may be 1/1000 to 1 equivalent based on the compound represented by the formula (3), and the amount of use is, for example, 1/500 equivalents to ½ equivalents, and preferably ¹⁄₁₀₀ equivalents to ⅕ equivalents. As for the base, for example, lithium hydroxide, sodium hydroxide, potassium hydroxide, sodium carbonate, potassium carbonate, cesium carbonate, cesium fluoride, potassium fluoride, potassium phosphate, potassium acetate, or the like can be used, and preferred are potassium phosphate or cesium carbonate. The amount of use of the base may be ¹⁄₂₀ to 20 equivalents based on the compound represented by the formula (3), and the amount of use is, for example, ¹⁄₁₀ equivalents to 10 equivalents, and preferably ½ equivalents to 5 equivalents. As for the solvent used in the reaction, for example, N,N-dimethylformamide, N,N-dimethylacetamide, N-methyl-2-pyrrolidone, toluene, xylene, mesitylene, 1,4-dioxane, tetrahydrofuran, dimethylsulfoxide or the like may be mentioned, and N,N-dimethylacetamide and mesitylene are preferred examples. These solvents can also be used as mixtures of two or more kinds, or these solvents can also be mixed with water and used. The reaction can be carried out at a temperature of usually 20° C. to 250° C., and preferably 80° C. to 200° C. The reaction time is not particularly limited, but usually, the reaction time, for example, from 4 hours to 72 hours, and preferably from 8 hours to 48 hours.

Among the compounds represented by the formula (2), the compound in which $A^{1a}$ in the formula (2) represents an alkylene group which may be substituted, can be produced by reacting the compound represented by the formula (3) [wherein $Ar^{1a}$, $X^a$, $R^{1a}$ and $R^{2a}$ have the same meanings as defined above], with the compound represented by the formula (4) [wherein $A^{1a}$, $G^a$ and $L^1$ have the same meanings as defined above], in the presence of a base. In regard to the reaction between the compound represented by the formula (3) and the compound represented by the formula (4), the amount of use of the compound represented by the formula (4) may be ⅕ to 20 equivalents based on the compound represented by the formula (3), and the amount of use is preferably ½ equivalents to 10 equivalents, and more preferably 1 equivalent to 5 equivalents. However, the amount of use may be appropriately designed while taking into consideration of the purity of the compound represented by the formula (2), yield, purification efficiency and the like. As for the base, for example, sodium hydride, potassium hydride, sodium ethoxide, potassium t-butoxide, sodium carbonate, potassium carbonate and the like can be used, and preferred is sodium hydride. The amount of use of the base may be an equivalent amount or an excess amount relative to the amount of the compound (3) used as a raw material, and the amount of use is, for example, 1 equivalent to 10 equivalents, and preferably 1 equivalent to 5 equivalents. As for the solvent used in the reaction, for example, N,N-dimethylformamide, N,N-dimethylacetamide, xylene, toluene, 1,4-dioxane, tetrahydrofuran and the like may be mentioned, and N,N-dimethylformamide and N,N-dimethylacetamide are preferred examples. These solvents can also be used as mixtures of two or more kinds. The reaction can be carried out at a temperature of usually −40° C. to 100° C., and preferably −20° C. to 60° C. The reaction time is not particularly limited, but the reaction time is, for example, usually from 0.5 hours to 48 hours, and preferably from 1 hour to 24 hours.

Among the compounds represented by the formula (2), a compound in which $R^{3a}$ and/or $R^{4a}$ in the formula (2) is an alkoxy group which may be substituted or an alkoxy group which is substituted with a substituent having one or more protective groups, can be produced by reacting a compound in which $R^{3a}$ and/or $R^{4a}$ in the formula (2) is a hydroxy group, with an alkylating agent corresponding to the alkyl group which may be substituted or the alkyl group which is substituted with a substituent having one or more protective groups, in the presence of a base as necessary. As for the alkylating agent, for example, halides of an alkyl group which may be substituted or an alkyl group which is substituted with a substituent having one or more protective groups, and the like can be used, and examples thereof include alkyl iodide, alkyl bromide, alkyl chloride, and the like. Furthermore, alkylating agents having other leaving groups such as mesylate, tosylate and triflate instead of the halides, are also useful. The amount of use of the alkylating agent may be an equivalent amount or an excess amount relative to the amount of the compound in which $R^{3a}$ and/or $R^{4a}$ in the formula (2) is a hydroxy group, and the amount of use is, for example, 1 equivalent to 10 equivalents, and preferably 1 equivalent to 5 equivalents. During the reaction, a base can be used if necessary, and the base may be either an organic base or an inorganic base. Examples thereof include sodium hydride, potassium hydride, sodium hydroxide, potassium hydroxide, potassium carbonate, sodium carbonate, triethylamine, diisopropylethylamine, N-methylmorpholine, pyridine and the like. The amount of use of the base may be an equivalent amount or an excess amount relative to the amount of the compound in which $R^{3a}$ and/or $R^{4a}$ in the formula (2) is a hydroxy group, and the amount of use is, for example, 1 equivalent to 100 equivalents, and preferably 1 equivalent to 30 equivalents. As for the solvent used in the reaction, an inert solvent can be used. Examples of the inert solvent include dichloromethane, chloroform, 1,2-dichloroethane, tetrahydrofuran, 1,4-dioxane, dimethoxyethane, N,N-dimethylformamide, N,N-dimethylacetamide, and the like. Tetrahydrofuran or N,N-dimethylformamide is preferred. These may also be suitably used as mixtures of two or more kinds. The reaction can be carried out at a temperature of usually −20° C. to 100° C., and preferably −10° C. to 50° C. The reaction time is not particularly limited, but is, for example, usually from 0.2 hours to 24 hours, and preferably from 1 hour to 5 hours. In another embodiment, for the compound in which $R^{3a}$ and/or $R^{4a}$ is a hydroxy group among the compounds represented by the formula (2), a method of allowing an alkyl alcohol to react in an inert solvent, in the presence of a phosphorus reagent and an azo compound, may be mentioned (see Chem. Lett., 539-542 (1994); Synthesis, 1 (1981), or the like). The inert solvent may be tetrahydrofuran, dioxane, toluene, dichloromethane or the like, and tetrahydrofuran or dichloromethane is preferred. These solvents may also be suitably used as mixtures of two or more. Examples of the phosphorus reagent include triphenylphosphine, tributylphosphine, and the like. Examples of the azo compound include diethyl azodicarboxylate, diisopropyl azodicarboxylate, N,N,N',N'-tetramethylazodicarbonamide, and the like.

Among the compounds represented by the formula (2), a compound in which $R^{3a}$ and/or $R^{4a}$ in the formula (2) is —N($R^{Q1}$)($R^{Q2}$) [wherein $R^{Q1}$ and $R^{Q2}$ have the same meanings as defined above, or may be substituted with a substituent having one or more protective groups], can be produced by subjecting the compound in which $R^{3a}$ and/or $R^{4a}$ in the formula (2) is —N($R^{Q1}$)($R^{Q2}$) [wherein $R^{Q1}$ and $R^{Q2}$ have the same meanings as defined above, or may be substituted with a substituent having one or more protective groups, provided that one or more groups of $R^{Q1}$ and $R^{Q2}$ are hydrogen atoms], to coupling with an aldehyde or ketone corresponding to the substituent to be introduced, through a reductive amination reaction. As for the reductive amination, there may be mentioned, for example, the methods described in the article ["Reductive Amination Reaction" described in New Lectures on Experimental Chemistry (edited by The Chemical Society of Japan, published by Maruzen, Inc.), Vol. 20, page 300], or methods according to the reference materials described in the aforementioned article. The amount of use of the corresponding aldehyde or ketone may be ⅕ to 20 equivalents based on the compound in which $R^{3a}$ and/or $R^{4a}$ in the formula (2) is —$N(R^{Q1})(R^{Q2})$ [wherein $R^{Q1}$ and $R^{Q2}$ have the same meanings as defined above, or may be substituted with a substituent having one or more protective groups, provided that one or more groups of $R^{Q1}$ and $R^{Q2}$ are hydrogen atoms], and the amount of use is preferably ½ equivalents to 10 equivalents, and more preferably 1 equivalent to 5 equivalents. As for the reducing agent, for example, metal hydride reducing agents such as sodium borohydride, sodium borocyanohydride, sodium borohydride triacetate, borane-dimethylsulfide complexes, borane-pyridine complexes, borane-triethylamine complexes, borane-tetrahydrofuran complexes and lithium triethylboron hydride, may be mentioned. Preferably, sodium borocyanohydride or sodium borohydride triacetate may be mentioned. The reducing agent may be used in an amount of ¹⁄₁₀ equivalents or more, and preferably 1 to 20 equivalents, based on the compound in which $R^{3a}$ and/or $R^{4a}$ in the formula (2) is —$N(R^{Q1})(R^{Q2})$ [wherein $R^{Q1}$ and $R^{Q2}$ have the same meanings as defined above, or may be substituted with a substituent having one or more protective groups, provided that one or more groups of $R^{Q1}$ and $R^{Q2}$ are hydrogen atoms]. The acid to be added may be acetic acid or trifluoroacetic acid, and acetic acid is preferred. The amount of use of the acid may be ¹⁄₁₀ to 20 equivalents, and preferably ⅕ equivalents to 10 equivalents, based on the compound in which $R^{3a}$ and/or $R^{4a}$ in the formula (2) is —$N(R^{Q1})(R^{Q2})$ [wherein $R^{Q1}$ and $R^{Q2}$ have the same meanings as defined above, or may be substituted with a substituent having one or more protective groups, provided that one or more groups of $R^{Q1}$ and $R^{Q2}$ are hydrogen atoms]. As for the solvent, for example, methanol, ethanol, isopropanol, tetrahydrofuran, 1,2-dimethoxyethane, 1,4-dioxane, dichloromethane, chloroform, 1,2-dichloroethane, N,N-dimethylformamide and the like may be mentioned, and preferably methanol, tetrahydrofuran or dichloromethane may be mentioned. The reaction temperature may be 0° C. or higher, and preferably from 10° C. to the reflux temperature of the solvent. The reaction time may be 0.1 hours or longer, and preferably from 0.5 to 30 hours.

Among the compounds represented by the formula (2), a compound in which $R^{3a}$ and/or $R^{4a}$ in the formula (2) is an amino group can be produced by subjecting a compound in which $R^{3a}$ and/or $R^{4a}$ in the formula (2) is a nitro group, to a reduction reaction. As for the reduction reaction, a method based on catalytic hydrogen reduction may be mentioned, and the catalytic hydrogen reduction can be carried out in a solvent and under a hydrogen atmosphere, using a catalyst. Examples of the catalyst include palladium-carbon, platinum oxide, platinum-carbon, palladium hydroxide, and the like. As for the solvent used in the reaction, for example, dichloromethane, chloroform, carbon tetrachloride, diethyl ether, tetrahydrofuran, dioxane, 1,2-dimethoxyethane, methanol, ethanol and the like may be mentioned. Preferably, tetrahydrofuran or methanol may be mentioned. These solvents may also be suitably used as mixtures of two or more kinds. The reaction can be carried out at a temperature of usually −80° C. to 100° C., and preferably 0° C. to 50° C. The reaction time is not particularly limited, but may be usually from 1 hour to 96 hours, for example, and preferably from 3 hours to 48 hours.

Among the compounds represented by the formula (2), a compound in which $R^{3a}$ and/or $R^{4a}$ in the formula (2) is an alkylsulfonylamino group or an alkylsulfonyl(alkyl)amino group, can be produced by subjecting a compound in which $R^{3a}$ and/or $R^{4a}$ in the formula (2) is an amino group, to coupling with a sulfonyl halide corresponding to the substituent to be introduced. Such a sulfonylation reaction may be carried out in the presence of a base if necessary, and examples of the base that is used as necessary include organic amines such as triethylamine, diisopropylamine and pyridine; inorganic amines such as potassium carbonate and sodium carbonate; and the like. A preferred base is triethylamine or pyridine. The amount of use of these bases may be ¹⁄₁₀ to 20 equivalents, and preferably ⅕ equivalents to 10 equivalents, based on the compound in which $R^{3a}$ and/or $R^{4a}$ in the formula (2) is —$N(R^{Q1})(R^{Q2})$ [wherein $R^{Q1}$ and $R^{Q2}$ have the same meanings as defined above, or may be substituted with a substituent having one or more protective groups; provided that one or more groups of $R^{Q1}$ and $R^{Q2}$ are hydrogen atoms]. As for the solvent that is used in the reaction, for example, dichloromethane, chloroform, carbon tetrachloride, diethyl ether, tetrahydrofuran, dioxane, 1,2-dimethoxyethane or the like may be mentioned, and a preferred solvent is dichloromethane. Furthermore, these solvents may also be suitably used as mixtures of two or more species. The reaction can be carried out at a temperature of usually −80° C. to 100° C., and preferably 0° C. to 50° C. The reaction time is not particularly limited, but for example, the reaction time is usually from 1 hour to 96 hours, and preferably from 3 hours to 48 hours.

Among the compounds represented by the formula (2), a compound in which $R^{3a}$ and/or $R^{4a}$ in the formula (2) is an acylamino group or an acyl(alkyl)amino group can be produced by subjecting a compound in which $R^{3a}$ and/or $R^{4a}$ in the formula (2) is an amino group, to coupling with an acyl halide corresponding to the substituent to be introduced. Such an acylation reaction may be carried out in the presence of a base, if necessary, and examples of the base that is used as necessary include organic amines such as triethylamine, diisopropylethylamine and pyridine; inorganic amines such as potassium carbonate and sodium carbonate; and the like. A preferred base is triethylamine or pyridine. The amount of use of these bases may be ¹⁄₁₀ to 20 equivalents, and preferably ⅕ equivalents to 10 equivalents, based on the compound in which $R^{3a}$ and/or $R^{4a}$ in the formula (2) is —$N(R^{Q1})(R^{Q2})$ [wherein $R^{Q1}$ and $R^{Q2}$ have the same meanings as defined above, or may be substituted with a substituent having one or more protective groups; provided that one or more groups of $R^{Q1}$ and $R^{Q2}$ are hydrogen atoms]. As for the solvent that is used in the reaction, for example, dichloromethane, chloroform, carbon tetrachloride, diethyl ether, tetrahydrofuran, dioxane, 1,2-dimethoxyethane or the like may be mentioned, and a preferred solvent is dichloromethane. Furthermore, these solvents may also be suitably used as mixtures of two or more species. The reaction can be carried out at a temperature of usually −80° C. to 100° C., and preferably 0° C. to 50° C. The reaction time is not particularly limited, but for example, the reaction time is usually from 1 hour to 96 hours, and preferably from 3 hours to 48 hours.

Among the compounds represented by the formula (2), a compound in which $R^{3a}$ and/or $R^{4a}$ in the formula (2) is an acylamino group or an acyl(alkyl)amino group can be produced by subjecting a compound in which $R^{3a}$ and/or $R^{4a}$ in the formula (2) is an amino group, to a condensation reaction with a carboxylic acid corresponding to the substituent to be introduced. The amount of use of the carboxylic acid corresponding to the substituent to be introduced may be, for example, 0.5- to 10-fold, and preferably 1- to 5-fold, the molar amount of the compound in which $R^{3a}$ and/or $R^{4a}$ in the formula (2) is an acylamino group or an acyl(alkyl)amino group. As for the dehydrating condensation agent, a carbodiimide-based condensation agent such as dicyclohexylcarbodiimide (DCC) or 1-ethyl-3-(3-dimethylaminopropyl)carbodiimide hydrochloride (WSC); a uronium/guanidium salt type condensation agent such as O-(benzotriazol-1-yl)-N,N, N,N-tetramethyluronium hexafluorophosphate (HBTU), O-(benzotriazol-1-yl)-N,N,N,N-tetramethyluronium tetrafluoroborate (TBTU), or O-(7-azabenzotriazol-1-yl)-N,N,N,N-tetramethyluronium hexafluorophosphate (HATU); a phosphonium salt type condensation agent such as (benzotriazol-1-yloxy)tris(dimethylamino)phosphonium hexafluorophosphate (BOP), (benzotriazol-1-yloxy)tripyrrolidinophosphonium hexafluorophosphate (PyBOP), or bromotripyrrolidinophosphonium hexafluorophosphate (PyBroP); or the like may be mentioned, but a carbodiimide type condensation agent such as WSC is preferred. The amount of use of the dehydrating condensation agent that is used in the condensation reaction is 0.1- to 10-fold, and preferably 0.5- to 5-fold, the molar amount of the compound in which $R^{3a}$ and/or $R^{4a}$ in the formula (2) is an acylamino group or an acyl(alkyl)amino group. Such a condensation reaction may be carried out in the presence of a base if necessary, and examples of the base that is used as necessary include organic amine bases such as triethylamine, diisopropylethylamine, N-methylmorpholine, pyridine, 4-dimethylaminopyridine, imidazole and 2,6-lutidine, while preferred bases are triethylamine and diisopropylethylamine. The amount of use of the base that is used in the condensation reaction is 0.5- to 10-fold, and preferably 1- to 5-fold, the molar amount of the compound in which $R^{3a}$ and/or $R^4$, in the formula (2) is an acylamino group or an acyl(alkyl)amino group. As for the solvent that is used in the reaction, for example, dichloromethane, chloroform, ethyl acetate, acetonitrile, N,N-dimethylformamide, tetrahydrofuran, 1,4-dioxane or the like may be mentioned, and a preferred solvent is N,N-dimethylformamide. Furthermore, these solvents can also be used as mixtures of two or more species.

The reaction temperature may vary depending on the raw material compound, the type of the dehydrating condensation agent, the base or the solvent, or the like, but for example, the reaction temperature may be usually 0° C. to the reflux temperature of the solvent, and preferably the ambient temperature to the reflux temperature of the solvent.

Upon performing the condensation reaction using a carbodiimide type condensation agent, a condensation aid such as 1-hydroxybenzotriazole (HOBt) or 1-hydroxy-7-azabenzotriazole (HOAt) may be added, and the amount of use is 0.1- to 10-fold, and preferably 1- to 5-fold, the molar amount of the compound represented by the formula (9).

A compound in which $R^{3a}$ and/or $R^{4a}$ in the formula (2) is halogen can be produced from a compound in which $R^{3a}$ and/or $R^{4a}$ in the formula (2) is an amino group, by the Sandmeyer reaction. The Sandmeyer reaction can be carried out by sequentially or simultaneously subjecting the compound to the action of a diazotizing agent such as sodium nitrite, t-butyl nitrite or amyl nitrite, and of a halogenating agent such as copper bromide. The amount of use of each of the reaction agents can be 1 equivalent to 10 equivalents, and preferably 1 equivalent to 5 equivalents, based on the compound in which $R^{3a}$ and/or $R^{4a}$ in the formula (2) is an amino group. As for the solvent that is used in the reaction, for example, water, ethanol, methanol, propanol, isopropanol, acetonitrile or the like may be mentioned, and a preferred solvent is water or acetonitrile. Furthermore, these solvents can also be used as mixtures of two or more species. The reaction can be carried out at a temperature of usually −30° C. to 150° C., and preferably 0° C. to 100° C. The reaction time is not particularly limited, but for example, the reaction time is usually from 1 hour to 96 hours, and preferably from 3 hours to 36 hours.

A compound in which $R^{3a}$ and/or $R^{4a}$ in the formula (2) is an alkenyl group which may be substituted, can be produced from a compound in which $R^{3a}$ and/or $R^{4a}$ in the formula (2) is halogen, by the Suzuki-Miyaura reaction. For example, there may be mentioned the methods described in Organometallics in Synthesis a manual (published by Willy Co., Ltd.), $2^{nd}$ Edition, Chapter 10, or methods equivalent to the Reference Documents described in the literature. As for the solvent that is used in the reaction, for example, diethyl ether, tetrahydrofuran, 1,2-dimethoxyethane, acetonitrile, N,N-dimethylformamide, water or mixed solvents thereof may be mentioned. Alkylation, alkenylation, alkynylation or arylation can be suitably carried out, for example, by allowing the reaction to proceed in the presence of any of palladium catalysts, using a Grignard reagent, an organozinc reagent, an organic boronic acid reagent, an organic boronic acid ester reagent, an organolithium reagent, an organocopper reagent, or an organotin reagent, each of which has been purchased as a commercially available product or produced according to an ordinary method. As for the palladium catalyst, for example, a commercially available catalyst such as tetrakis(triphenylphosphine)palladium, tetrakis(methyldiphenylphosphine)palladium, dichlorobis(triphenylphosphine)palladium, dichlorobis(tri-o-tolylphosphine)palladium, dichlorobis(tricyclohexylphosphine)palladium, dichlorobis(triethylphosphine)palladium, palladium acetate, palladium chloride, bis(acetonitrile)palladium chloride, tris(dibenzylideneacetone)dipalladium, or bis(diphenylphosphinoferrocene)palladium chloride may be purchased and directly added to the reaction system, or a catalyst which has been separately prepared from palladium acetate, tris(dibenzylideneacetone)dipalladium or the like and an arbitrary ligand and isolated, may also be added. Furthermore, a catalyst which is assumed to actually participate in the reaction system, may also be prepared by mixing palladium acetate, tris(dibenzylideneacetone)dipalladium or the like and an arbitrary ligand. The valency of palladium may be either 0 or +2. As for the ligand, there may be mentioned trifurylphosphine, tri(p-tolyl)phosphine, tri(cyclohexyl)phosphine, tri(t-butyl)phosphine, dicyclohexylphenylphosphine, 1,1'-bis(di-t-butylphosphino)ferrocene, 2-dicyclohexylphosphino-2'-dimethylamino-1,1'-biphenyl, 2-(di-t-butylphosphino)biphenyl, imidazol-2-ylidenecarbene and the like. Other examples include 2-dicyclohexylphosphino-2',6'-dimethoxybiphenyl, 2-dicyclohexyl-2',4',6'-triisopropylbiphenyl, 1,2,3,4,5-pentamethyl-1'-(di-t-butylphosphino)ferrocene, and the like. The equivalent number of the palladium catalyst that is used may be an equivalent amount or a catalytic amount, but is preferably 0.01 to 20.0 mol %, and in particular, more preferably 0.10 to 10.0 mol %. As for the base that is used in the aforementioned reaction, there may be mentioned sodium carbonate, potassium carbonate, cesium carbonate, cesium fluoride, potassium fluoride, potassium phosphate, potassium acetate, triethylamine, potassium hydroxide, sodium hydroxide, sodium methoxide, lithium methoxide and the like. The reaction temperature may be preferably between 20° C. and 150° C., and particularly preferably between 20° C. and 120° C.

Among the compounds represented by the formula (4), in the case of a compound in which Ala represents a single bond, for example, commercially available ethyl 2-bromothiazole-4-carboxylate (manufactured by Combi-Blocks, Inc.), methyl 2-bromothiazole-4-carboxylate (manufactured by Combi-Blocks, Inc.), ethyl 2-chloroxazole-4-carboxylate (manufactured by Combi-Blocks, Inc.), ethyl 2-bromothiophenecarboxylate (manufactured by Alfa Aesar GmbH & Co. KG), or the like may be used. Alternatively, a compound produced by reacting a compound in which L1 is an amino group, with a nitrous acid ester in an organic solvent according to a known method (see J. Org. Chem., 61, 4623-4633 (1996); Tetrahedron: Asymmetry, 9, 1395-1408 (1998); or the like), and then subjecting the reaction product to the action of a metal halide, can also be used.

Among the compounds represented by the formula (4), in the case of a compound in which Ala represents a methylene group which may be substituted, for example, a compound produced according to a known method (see Liebigs. Ann. Chem., 4, 623-632 (1981) or the like) can be used.

The compound represented by the formula (3) can be produced according to, for example, a retrosynthetic pathway of the following reaction pathway.

[Chemical Formula 26]

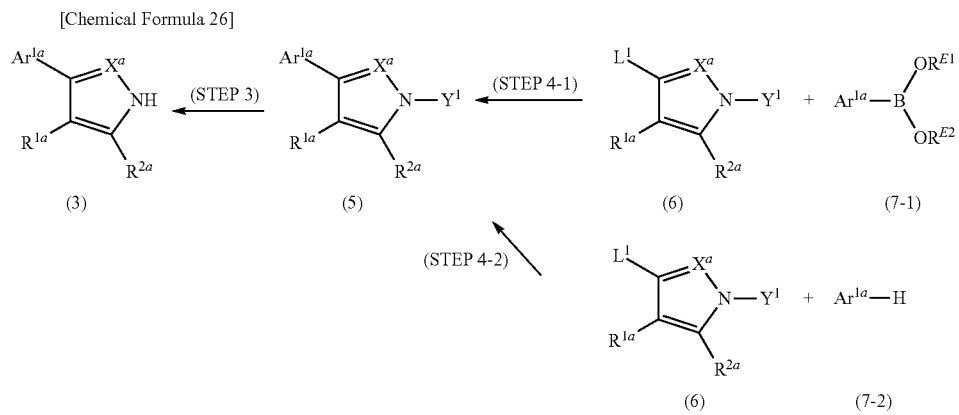

For example, the compound represented by the formula (3) can be produced from a compound represented by formula (5) [wherein $Ar^{1a}$, $X^a$, $R^{1a}$ and $R^{2a}$ have the same meanings as defined above; and $Y^1$ represents a hydrogen atom, or a protective group for amino group]. That is, $Y^1$ in the formula (5) may be removed according to the methods described in the previously described "Protective Groups in Organic Synthesis, published by John Wiley and Sons (2007 edition). Furthermore, when $Y^1$ in the formula (5) is a hydrogen atom, the compound represented by the formula (5) is directly equal to the compound represented by the formula (3), without undergoing deprotection.

Among the compounds represented by the formula (5), a compound in which $Ar^{1a}$ is an aryl group which may be substituted, and the aryl group is bonded to a pyrazole ring or a pyrrole ring at a carbon atom, can be produced by reacting a compound represented by formula (6) [wherein $R^{1a}$, $R^{2a}$, $X^a$ and $Y^1$ have the same meanings; and $L^1$ represents a bromine atom or an iodine atom], with a compound represented by formula (7-1) [wherein $Ar^{1a}$ has the same meaning as defined above; and $R^{E1}$ and $R^{E2}$, which may be same or different, each independently represent a hydrogen atom, or a lower alkyl group, or $R^{E1}$ and $R^{E2}$ together form a 5- to 6-membered ring to represent a cyclic boronic acid ester in the form of $B(OR^{E1})(OR^{E2})$], in the presence of a base, using a commercially available palladium catalyst or a catalyst prepared from a palladium complex and a ligand. In regard to this reaction, $Y^1$ may be hydrogen or may be a protective group for amino group, and whichever may be selected according to necessity. In that case, the protection and deprotection of before and after the reaction may be carried out according to the methods described in the Protective Groups in Organic Synthesis, published by John Wiley and Sons (2007 edition). In regard to the reaction between the compound represented by the formula (6) and the compound represented by the formula (7-1), the amount of use of the compound represented by the formula (7-1) may be ⅕ to 20 equivalents based on the compound represented by the formula (6), and the amount of use is preferably ½ equivalents to 10 equivalents, and more preferably 1 equivalent to 5 equivalents. However, the amount of use may be appropriately designed while taking into consideration of the purity of the compound represented by the formula (5), yield, purification efficiency, and the like. As for the palladium catalyst, for example, a commercially available catalyst such as tris(dibenzylideneacetone)dipalladium, (dibenzylideneacetone)palladium, tetrakis(triphenylphosphine)palladium, dichlorobis(triphenylphosphine)palladium, palladium acetate or palladium chloride, may be purchased and directly added into the reaction system, or a catalyst separately prepared by mixing palladium acetate, (dibenzylideneacetone)palladium or the like with an arbitrary ligand, may also be used. Examples of the ligand include triphenylphosphine, tri-o-tolylphosphine, tri-t-butylphosphine, tricyclohexylphosphine, tricyclohexylphosphine tetrafluoroborate, 2-(di-t-butylphosphino)biphenyl, and the like. Preferably, (dibenzylideneacetone)palladium is used together with tri-o-tolylphosphine as the ligand to be mixed, or palladium acetate is used together with tricyclohexylphosphine tetrafluoroborate as a ligand to be mixed. The amount of use of the palladium catalyst may be 1/1000 to 1 equivalent based on the compound represented by the formula (6), and the amount of use is, for example, 1/100 equivalents to ½ equivalents, and preferably 1/100 equivalents to ⅕ equivalents. As for the base, for example, sodium carbonate, potassium carbonate, cesium carbonate, cesium fluoride, potassium fluoride, potassium phosphate, potassium acetate or the like can be used, and preferably, sodium carbonate or potassium carbonate may be mentioned. The amount of use of the base may be 1/10 equivalents to 10 equivalents, and preferably ⅕ equivalents to 5 equivalents, based on the compound represented by the formula (6). Examples of the solvent used in the reaction include N,N-dimethylformamide, N,N-dimethylacetamide, xylene, toluene, 1,4-dioxane, tetrahydrofuran, ethanol, methanol, and the like, and preferred examples are N,N-dimethylformamide and 1,4-dioxane. These solvents can also be used as mixtures of two or more kinds, and these solvents can also be used as mixtures with water. The reaction can be carried out at a temperature of usually 0° C. to 150° C., and preferably 40° C. to 120° C. The reaction time is not particularly limited, but for example, the reaction time is usually from 1 hour to 72 hours, and preferably from 2 hours to 24 hours.

Among the compounds represented by the formula (5), the compound in which $Ar^{1a}$ is an aryl group which may be substituted or a saturated heterocyclic ring which may be substituted, and the ring is bonded to the pyrazole ring or pyrrole ring at the nitrogen atom, can be produced by reacting a compound represented by formula (6) [wherein $R^{1a}$, $R^{2a}$, $X^2$, $Y^1$ and $L^1$ have the same meanings as defined above], with a compound represented by formula (7-2) [wherein $Ar^{1a}$ has the same meaning as defined above], in the presence of a base, using a commercially available palladium catalyst or a catalyst prepared from a palladium complex and a ligand. In this reaction, $Y^1$ may be hydrogen, or a protective for amino group, and whichever may be selected according to necessity. In that case, the protection and deprotection of before and after the reaction may be carried out according to the methods described in the previously mentioned Protective Groups in Organic Synthesis, published by John Wiley and Sons (2007 edition), or the like. In regard to the reaction between the compound represented by the formula (6) and the compound represented by the formula (7-2), the amount of use of the compound represented by the formula (7-2) may be 1/5 to 20 equivalents based on the compound represented by the formula (6), and the amount of use is preferably 1/2 equivalents to 10 equivalents, and more preferably 1 equivalent to 5 equivalents. However, the amount of use may be appropriately designed while taking into consideration of the purity of the compound represented by the formula (5), yield, purification efficiency and the like. As for the palladium catalyst, for example, the palladium catalysts described above or the like may be mentioned, but tris(dibenzylideneacetone)dipalladium, (dibenzylideneacetone)palladium, palladium(II) acetate and the like may be mentioned as examples. Examples of the ligand include 2-(di-t-butylphosphino)biphenyl, 2-(dicyclohexylphosphino)biphenyl, 2,2'-bis(diphenylphosphino)-1,1'-binaphthyl, xantphos, and tri-t-butylphosphine. Preferably, palladium(II) acetate is used together with xantphos as the ligand to be mixed. The amount of use of the palladium catalyst is preferably 1/1000 to 1 equivalent based on the compound represented by the formula (6), and the amount of use is, for example, 1/100 equivalents to 1/2 equivalents, and preferably 1/100 equivalents to 1/5 equivalents. As for the base, for example, potassium carbonate, cesium carbonate, potassium phosphate, sodium t-butoxide, or the like can be used, and preferably, cesium carbonate or potassium phosphate is used. The amount of use of the base is preferably 1/20 to 20 equivalents based on the compound represented by the formula (6), and the amount of use is, for example, 1/10 equivalents to 10 equivalents, and preferably 1/2 equivalents to 5 equivalents. Examples of the solvent used in the reaction include N,N-dimethylformamide, N,N-dimethylacetamide, toluene, xylene, 1,4-dioxane, tetrahydrofuran, 1,2-dimethoxyethane, and the like, and 1,4-dioxane may be mentioned as a preferred example. These solvents can also be used as mixtures of two or more kinds, and these solvents can also be used as mixtures with water. The reaction can be carried out at a temperature of usually 20° C. to 200° C., and preferably 60° C. to 150° C. The reaction time is not particularly limited, but the reaction time is, for example, usually from 4 hours to 72 hours, and preferably from 8 hours to 48 hours.

Among the compounds represented by the formula (5), as for a compound in which $X^a$ is a carbon atom, a compound produced according to a known method (see J. Heterocyclic Chem., 37, 1281-1288 (2007) or the like) can be used.

Among the compounds represented by the formula (5), the compound in which $R^{3a}$ and/or $R^{4a}$ in the formula (5) is an aryl group which may be substituted, can be synthesized by subjecting a compound in which $R^{3a}$ and/or $R^{4a}$ in the formula (5) is a chlorine atom, a bromine atom, an iodine atom, a p-toluenesulfonyloxy group (TsO—), a methanesulfonyloxy group (MsO—) or a trifluoromethanesulfonyloxy group (TfO—), to the action of commercially available arylboronic acid and arylboronic acid ester reagents, according to the synthesis method for the compound in which $Ar^1$ is an aryl group which may be substituted, and the aryl group is bonded to the pyrazole ring or pyrrole ring at a carbon atom, among the compounds represented by the formula (5).

Among the compounds represented by the formula (5), a compound in which $R^{3a}$ and/or $R^{4a}$ in the formula (5) is a p-toluenesulfonyloxy group (TsO—), a methanesulfonyloxy group (MsO—) or a trifluoromethanesulfonyloxy group (TfO—), can be produced from the compound in which $R^{3a}$ and/or $R^{4a}$ in the formula (5) is a hydroxy group, among the compounds represented by the formula (5). That is, a known method of allowing p-toluenesulfonic acid chloride, methanesulfonic acid chloride, trifluoromethanesulfonyl chloride, methanesulfonic anhydride, trifluoromethanesulfonic anhydride, N-phenyltrifluoromethanesulfonimide or the like in the presence of an appropriate base such as triethylamine, N,N-diisopropylethylamine, pyridine, sodium carbonate, potassium carbonate, or sodium hydrogen carbonate, may be mentioned as an adequate example.

Among the compounds represented by the formula (6), as for the compound in which $Y^1$ is a protective group for amino group, a compound produced by selecting an appropriate protective group for a compound in which $Y^1$ represents a hydrogen atom among the compounds represented by the formula (6), and performing protection according to the methods described in the previously mentioned Protective Groups in Organic Synthesis, published by John Wiley and Sons (2007 edition) or the like, can also be used.

Among the compounds represented by the formula (6), the compound in which $Y^1$ represents a hydrogen atom, can be produced by subjecting a compound in which $Y^1$ represents a hydrogen atom and $L^1$ represents a hydrogen atom, among the compounds represented by the formula (6), to the action of bromine molecules or iodine molecules in the presence of a base. As for the base, for example, sodium hydroxide, potassium hydroxide, potassium carbonate, cesium carbonate, potassium phosphate, potassium t-butoxide, or the like can be used, and preferably, potassium hydroxide or potassium t-butoxide may be used. The amount of use of the base that can be used is preferably 1/20 to 20 equivalents based on the compound in which $Y^1$ is a hydrogen atom, and L1 is a hydrogen atom, among the compounds represented by the formula (6), and the amount of use is, for example, 1/10 equivalents to 10 equivalents, and preferably 1/2 equivalents to 5 equivalents. The amount of use of the bromine molecules or iodine molecules used may be 1/5 to 20 equivalents, and preferably, the amount of use is, for example, 1/2 equivalents to 10 equivalents, and more preferably 1 equivalent to 5 equivalents. Examples of the solvent used in the reaction include N,N-dimethylformamide, toluene, xylene, 1,4-dioxane, tetrahydrofuran, and the like, and N,N-dimethylformamide and tetrahydrofuran may be mentioned as preferred examples. These solvents can also be used as mixtures of two or more kinds. In regard to the reaction temperature, an appropriate temperature is selected usually from 0° C. to the reflux temperature of the solvent. The reaction time is not particularly limited, but the reaction time is, for example, usually from 0.2 hours to 24 hours, and preferably from 0.5 hours to 12 hours.

Among the compounds represented by the formula (6), as for the compound in which $Y^1$ represents a hydrogen atom, and $L^1$ represents a hydrogen atom, for example, commercially available indole (manufactured by Kanto Chemical Co., Inc.), indazole (manufactured by Wako Pure Chemical Industries, Ltd.), 5-nitroindazole (manufactured by Tokyo Chemical Industry Co., Ltd.), 6-nitroindazole (manufactured by Tokyo Chemical Industry Co., Ltd.), 7-nitroindazole (manufactured by Alfa Aesar GmbH & Co. KG), 6-fluoroindazole (manufactured by J&W PharmLab, LLC), or the like may be used, or a compound produced according to a known method (see Bioorg. Med. Chem. Lett., 11, 1153-1156 (2001); Synthesis, 588-592 (1999); J. Org. Chem., 71, 8166-8172 (2006); or the like) can also be used.

As for the compound represented by the formula (7-1), for example, commercially available benzeneboronic acid (manufactured by Tokyo Chemical Industry Co., Ltd.), thiophene-2-boronic acid (manufactured by Sigma-Aldrich Corp.), thiophene-3-boronic acid (manufactured by Sigma-Aldrich Corp.), 3-pyridineboronic acid (manufactured by Wako Pure Chemical Industries, Ltd.), or the like may be used, or a compound produced according to known methods (see Chem. Rev., 95, 2457-2483 (1995); J. Organomet. Chem., 576, 147-168 (1999); or the like) can also be used.

As for the compound represented by the formula (7-2), for example, commercially available pyrrolidine (manufactured by Tokyo Chemical Industry Co., Ltd.), piperidine (manufactured by Tokyo Chemical Industry Co., Ltd.), morpholine (manufactured by Tokyo Chemical Industry Co., Ltd.), 1-methylpiperazine (manufactured by Tokyo Chemical Industry Co., Ltd.), pyrrole (manufactured by Tokyo Chemical Industry Co., Ltd.), imidazole (manufactured by Tokyo Chemical Industry Co., Ltd.), pyrazole (manufactured by Tokyo Chemical Industry Co., Ltd.) or the like can be used.

Among the compounds represented by the formula (3), a compound represented by the formula (3A) [wherein $Ar^{1a}$ has the same meaning as defined above] in which $X^a$ represents a nitrogen atom, and $R^{1a}$ and $R^{2a}$ together represent any of the formulas $(Q^{1a})$ to $(Q^{5a})$, can be produced according to, for example, the retrosynthetic pathway of the following reaction pathway.

example, ½ equivalents to 10 equivalents, and preferably 1 equivalent to 5 equivalents. However, the amount of use may be appropriately designed while taking into consideration of the purity of the compound represented by the formula (3A), yield, purification efficiency, or the like. As the copper catalyst, for example, copper powder, copper(I) chloride, copper (I) bromide, copper(I) iodide, copper(I) cyanide, copper(I) oxide, copper(II) chloride, copper(II) bromide, copper(II) acetate, copper(II) sulfate, copper(II) oxide, and the like can be used, and copper(II) oxide is preferred. The amount of use of the copper catalyst may be 1/1000 to 1 equivalent based on the compound represented by the formula (8A), and the amount of use is, for example, 1/500 equivalents to ½ equivalents, and preferably 1/100 equivalents to ⅕ equivalents. As the base, for example, potassium carbonate, cesium carbonate, potassium phosphate, sodium t-butoxide or the like can be used, and potassium carbonate is preferred. The amount of use of the base is preferably 1/20 equivalents to 20 equivalents based on the compound represented by the formula (8A), and the amount of use is, for example, 1/10 equivalents to 10 equivalents, and preferably ½ equivalents to 5 equivalents. As the solvent used in the reaction, for example, N,N-dimethylformamide, toluene, xylene, 1,4-dioxane, tetrahydrofuran, or the like may be mentioned, and xylene may be mentioned as a preferred example. These solvents can also be used as mixtures of two or more kinds. As for the reaction temperature, an appropriate temperature is selected usually from 0° C. to the reflux temperature of the solvent. The reaction time is not particularly limited, but the reaction time is, for example, usually from 0.2 hours to 24 hours, and preferably from 0.5 hours to 12 hours.

As for the solvent that is used in the reaction, for example, N,N-dimethylformamide, N-methylpyrrolidone, isopropanol, ethanol, methanol, toluene, xylene, 1,4-dioxane, tetrahydrofuran or the like may be mentioned, and preferred examples include xylene, isopropanol and N-methylpyrrolidone. Furthermore, these solvents can also be used as mix-

[Chemical Formula 27]

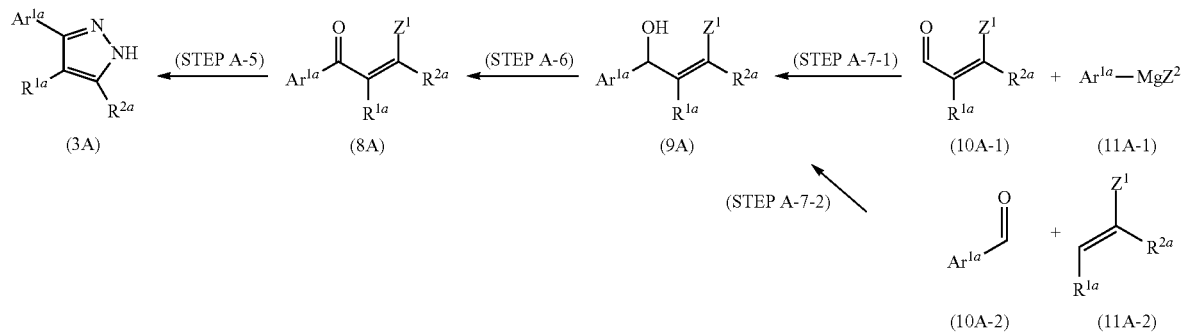

The compound represented by the formula (3A) can be produced by reacting a compound represented by formula (8A) [wherein $Ar^{1a}$, $R^{1a}$ and $R^{2a}$ have the same meanings as defined above, and $Z^1$ represents a fluorine atom or a chlorine atom] with hydrazine in the presence of a base and a copper catalyst. The subject reaction can be carried out according to a method described in the literature (see, for example, Org. Lett., 9, 525-528 (2007) or the like). As for hydrazine, either hydrated hydrazine or anhydrous hydrazine can be used, but preferably hydrated hydrazine is used. The amount of use of hydrazine may be ⅕ to 20 equivalents based on the compound represented by the formula (8A), and the amount of use is, for tures of two or more species. As for the reaction temperature, an appropriate temperature is usually selected from 0° C. to the reflux temperature of the solvent. The reaction time is not particularly limited, but for example, the reaction time may be usually from 0.2 hours to 24 hours, and preferably from 0.5 hours to 12 hours.

As for the compound represented by the formula (8A), for example, commercially available 2-fluorobenzophenone (manufactured by Tokyo Chemical Industry Co., Ltd.), 2,3'-difluorobenzophenone (manufactured by Apollo Chemical Company, LLC), 2,4'-difluorobenzophenone (manufactured by Tokyo Chemical Industry Co., Ltd.), 2,5-difluorobenzophenone (manufactured by Fluorochem, Ltd.), 2,6-difluorobenzophenone (manufactured by Acros Organics, Inc.), 2-fluoro-4-(trifluoromethyl)benzophenone (manufactured by Fluorochem, Ltd.), or the like may be used, or the compound can also be produced by subjecting a compound represented by formula (9A-1) [wherein $Ar^{1a}$, $R^{1a}$, $R^{2a}$ and $Z^1$ have the same meanings as defined above] to an oxidation reaction. The oxidation reaction may be, for example, a method of using the Dess-Martin Periodinane, the Swern oxidation method, an oxidation method using chromic acid, or the like. The subject reaction is carried out according to a known method, but for example, a method of producing the compound represented by the formula (8A) by subjecting the compound represented by the formula (9A-1) to the action of the Dess-Martin Periodinane in an organic solvent. The amount of use of the Dess-Martin Periodinane is, for example, ⅕ to 10 equivalents based on the compound represented by the formula (9A), and is preferably ½ equivalents to 3 equivalents. The solvent used in the reaction may be, for example, N,N-dimethylformamide, toluene, dichloromethane, chloroform, or the like, and dichloromethane may be mentioned as a preferred example. These solvents can also be used as mixtures of two or more kinds. The reaction can be carried out at a temperature of usually −20° C. to 60° C., and preferably 0° C. to 40° C. The reaction time is not particularly limited, but the reaction time is, for example, usually from 1 hour to 48 hours, and preferably from 2 hours to 24 hours.

The compound represented by the formula (9A) can also be produced by subjecting a compound represented by formula (11A-2) [wherein $R^{1a}$, $R^{2a}$ and $Z^1$ have the same meanings as defined above] sequentially to the action of lithium diisopropylamide and a compound represented by formula (10A-2) [wherein Aria has the same meaning as defined above], and then adding a proton source to stop the reaction. The amount of use of lithium diisopropylamide may be ½ to 10 equivalents based on the compound represented by the formula (9A-2), and is preferably 1 equivalent to 5 equivalents. The amount of use of the compound represented by the formula (9A-2) may be ½ to 10 equivalents based on the compound represented by the formula (9A-2), and is preferably 1 equivalent to 5 equivalents. As for the solvent used in the reaction, for example, toluene, 1,4-dioxane, tetrahydrofuran, diethyl ether or the like may be mentioned, and tetrahydrofuran may be mentioned as a preferred example. These solvents can also be used as mixtures of two or more kinds. The reaction can be carried out at a temperature of usually −80° C. to 60° C., and preferably −80° C. to 30° C. The reaction time is not particularly limited, but the reaction time is, for example, usually from 0.2 hours to 24 hours, and preferably from 0.5 hours to 12 hours. As for the proton source used to stop the reaction, water, an inorganic acid, an organic acid or the like can be used, and water is preferred. The amount of use of the proton source used to stop the reaction may be 1 equivalent to a large excess, based on the compound represented by the formula (9A-2). The temperature at the time of stopping the reaction may be usually −80° C. to 60° C.

As for the compound represented by the formula (9A-2), for example, commercially available N-methoxy-N-methylbenzylamide (manufactured by Sigma-Aldrich Corp.) and the like can be used.

As for the compound represented by the formula (9A-3), for example, commercially available 4-chloropyridine hydrochloride (manufactured by Tokyo Chemical Industry Co., Ltd.), 2,6-difluoropyridine (manufactured by Tokyo Chemical Industry Co., Ltd.), 2-chloro-6-fluoropyridine (Matrix Chemical LLC), and the like can be used.

The compound represented by the formula (9A-1) can be produced by reacting a compound represented by formula (10A-1) [wherein $R^{1a}$, $R^{2a}$ and $Z^1$ have the same meanings as defined above] with a commercially available Grignard reagent represented by formula (11A-1) [wherein $Ar^{1a}$ has the same meaning as defined above; and $Z^2$ represents a chlorine atom, a bromine atom or an iodine atom], and then adding a proton source to stop the reaction. The Grignard reagent represented by the formula (11A-1) may be phenylmagnesium bromide (manufactured by Tokyo Chemical Industry Co., Ltd.), p-tolylmagnesium bromide (manufactured by Sigma-Aldrich Corp.), or the like. The amount of use of the compound represented by the formula (11A-1) may be ½ to 10 equivalents based on the compound represented by the formula (IA-1), and the amount of use is preferably 1 equivalent to 5 equivalents. The solvent used in the reaction may be, for example, toluene, 1,4-dioxane, tetrahydrofuran, diethyl ether or the like, and tetrahydrofuran may be mentioned as a preferred example. These solvents can also be used as mixtures of two or more kinds. The reaction can be carried out at a temperature of usually −80° C. to 60° C., and preferably −20° C. to 40° C. The reaction time is not particularly limited, but the reaction time is, for example, usually from 0.2 hours to 24 hours, and preferably 0.5 hours to 12 hours. As for the proton source used to stop the reaction, water, an inorganic acid, an organic acid or the like can be used, and water is preferred. The amount of use of the proton source used to stop the reaction may be 1 equivalent to a large excess, based on the compound represented by the formula (11A-1). The temperature at the time of stopping the reaction may be usually −80° C. to 60° C.

As for the compound represented by the formula (10A-1), for example, commercially available 2-fluoro-4,5-dimethoxybenzaldehyde (manufactured by Tokyo Chemical Industry Co., Ltd.), 2-fluoro-4-methylbenzaldehyde (manufactured by Apollo Chemical Company LLC), and the like can be used.

The compound represented by the formula (9A) can also be produced by subjecting a compound represented by formula (11A-2) [wherein $R^{1a}$, $R^{2a}$ and $Z^1$ have the same meanings as defined above] sequentially to the action of lithium diisopropylamide and a compound represented by formula (10A-2) [wherein $Ar^{1a}$ has the same meaning as defined above], and then adding a proton source to stop the reaction. The amount of use of lithium diisopropylamide may be ½ to 10 equivalents based on the compound represented by the formula (11A-2), and is preferably 1 equivalent to 5 equivalents. The amount of use of the compound represented by the formula (10A-2) may be ½ to 10 equivalents based on the compound represented by the formula (11A-2), and is preferably 1 equivalent to 5 equivalents. As for the solvent used in the reaction, for example, toluene, 1,4-dioxane, tetrahydrofuran, diethyl ether or the like may be mentioned, and tetrahydrofuran may be mentioned as a preferred example. These solvents can also be used as mixtures of two or more kinds. The reaction can be carried out at a temperature of usually −80° C. to 60° C., and preferably −80° C. to 30° C. The reaction time is not particularly limited, but the reaction time is, for example, usually from 0.2 hours to 24 hours, and preferably from 0.5 hours to 12 hours. As for the proton source used to stop the reaction, water, an inorganic acid, an organic acid or the like can be used, and water is preferred. The amount of use of the proton source used to stop the reaction may be 1 equivalent to a large excess, based on the compound represented by the formula (11A-2). The temperature at the time of stopping the reaction may be usually −80° C. to 60° C.

As for the compound represented by the formula (10A-2), for example, commercially available benzaldehyde (manufactured by Tokyo Chemical Industry Co., Ltd.) or the like can be used.

As for the compound represented by the formula (11A-2), for example, commercially available 3-fluoroisonicotinaldehyde (manufactured by Sigma-Aldrich Corp.) or the like can be used.

Among the compounds represented by the formula (3), a compound represented by the formula (3B) [wherein $Ar^{1a}$, $R^{3a}$, $R^{4a}$ and n have the same meanings as defined above] in which $X^a$ is a nitrogen atom, and $R^{1a}$ and $R^{2a}$ together represent the formula ($Q^{6a}$), can be produced according to, for example, the retrosynthetic pathway of the following reaction pathway.

[Chemical Formula 28]

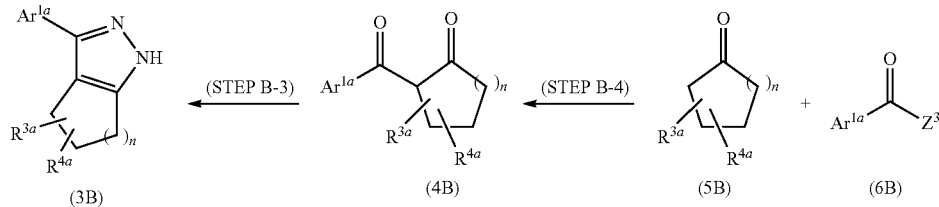

The compound represented by the formula (3B) can be produced by reacting a compound represented by formula (4B) [wherein $Ar^{1a}$, $R^{3a}$, $R^{4a}$ and n have the same meanings as defined above] with hydrazine. The subject reaction can be carried out according to the methods described in the literature (for example, J. Heterocycl. Chem., 18, 803-805 (1981)). As for hydrazine, either hydrated hydrazine or anhydrous hydrazine can be used, but hydrated hydrazine is preferred. The amount of use of hydrazine may be ⅕ to 20 equivalents based on the compound represented by the formula (4B), and the amount of use is, for example, ½ equivalents to 10 equivalents, and preferably 1 equivalent to 5 equivalents. However, the amount of use may be appropriately designed while taking into consideration of the purity of the compound represented by the formula (3B), yield, purification efficiency or the like. The solvent used in the reaction may be, for example, methanol, ethanol, isopropyl alcohol, 2-methyl-2-propanol, N,N-dimethylformamide, toluene, 1,4-dioxane, tetrahydrofuran, acetic acid or the like, and ethanol, isopropyl alcohol and acetic acid may be mentioned as preferred examples. These solvents can also be used as mixtures of two or more kinds. As for the reaction temperature, an appropriate temperature is selected usually from 0° C. to the reflux temperature of the solvent. The reaction time is not particularly limited, but the reaction time may be, for example, usually from 0.2 hours to 24 hours, and preferably from 0.5 hours to 12 hours.

As for the compound represented by the formula (4B), for example, commercially available 2-benzoylcyclohexanone (manufactured by Sigma-Aldrich Corp.) or the like may be used, or according to a known method (Tetrahedron Lett., 43, 2945-2948 (2002)), the compound can also be produced by allowing a compound represented by formula (5B) [wherein $R^{3a}$, $R^{4a}$ and n have the same meanings as defined above] and a compound represented by formula (6B) [wherein $Ar^{1a}$ has the same meaning as defined above, and $Z^3$ represents a fluorine atom, a chlorine atom, a bromine atom or an alkoxy group] to react in the presence of a base. In regard to the reaction between the compound represented by the formula (5B) and the compound represented by the formula (6B), the amount of use of the compound represented by the formula (6B) may be ⅕ to 20 equivalents based on the compound represented by the formula (5B), and the amount of use is, for example, ½ equivalents to 10 equivalents, and preferably 1 equivalent to 5 equivalents. However, the amount of use may be appropriately designed while taking into consideration of the purity of the compound represented by the formula (4B), yield, purification efficiency or the like. As for the base, for example, sodium hydride, potassium hydride, sodium ethoxide, potassium t-butoxide, lithium hexamethyldisilazane or the like may be used, and preferably, lithium hexamethyldisilazane is used. The amount of use of the base may be an equivalent amount to an excess amount based on the compound represented by the formula (5B), and the amount of use is, for example, 1 equivalent to 10 equivalents, and preferably 1 equivalent to 5 equivalents. As for the solvent used in the reaction, for example, N,N-dimethylformamide, N,N-dimethylacetamide, xylene, toluene, 1,4-dioxane, tetrahydrofuran or the like may be mentioned, and toluene may be a preferred example. These solvents can also be used as mixtures of two or more kinds. The reaction can be carried out at a temperature of usually 40° C. to 80° C., and preferably −20° C. to 40° C. The reaction time is not particularly limited, but the reaction time may be, for example, usually from 0.5 hours to 48 hours, and preferably from 1 hour to 24 hours.

As for the compound represented by the formula (5B), for example, commercially available cyclopentanone (manufactured by Tokyo Chemical Industry Co., Ltd.), cycloheptanone (manufactured by Tokyo Chemical Industry Co., Ltd.), cyclooctanone (manufactured by Tokyo Chemical Industry Co., Ltd.), 3-(trifluoromethyl), cyclohexanone (manufactured by Maybridge Co.) or the like can be used.

As for the compound represented by the formula (6B), for example, commercially available benzoyl chloride (manufactured by Tokyo Chemical Industry Co., Ltd.), p-methoxybenzoyl chloride (manufactured by Tokyo Chemical Industry Co., Ltd.) or the like can be used.

From the compounds represented by the formula (1) above, salts can be prepared. A method for producing salts is not specifically limited. For example, as a method for producing an acid addition salt, the compounds represented by the formula (1) are dissolved in alcohols such as methanol, ethanol and the like and added with one equivalent to several equivalents of an acid component to obtain acid addition salts. With respect to an acid component, any acid component, which corresponds to acid addition salts described below, can be used. Examples include a pharmaceutically acceptable mineral acid or organic acid such as hydrochloric acid, hydrobromic acid, sulfuric acid, hydrogen sulfuric acid, dihydrogen phosphate, hydrogen phosphate, citric acid, maleic acid, tartaric acid, fumaric acid, gluconic acid, methanesulfonic acid and the like. Further, as a method for producing a base addition salt, it can be carried out in the same manner as the method for producing an acid salt as described above, except that a base component is used instead of an acid component. With respect to a base component, any base component, which corresponds to base addition salts described below, can be used. Examples include a pharmaceutically acceptable base such as sodium hydroxide, potassium hydroxide, N-methyl-D-glucamine, N,N'-dibenzylethylenediamine, 2-aminoethanol, tris(hydroxymethyl)aminomethane, arginine, lysine and the like.

According to the present invention, the "compounds represented by the formula (1)" are understood as the compounds having the formula (1) in free form. Further, regarding salts thereof, the salts described below can be mentioned.

With respect to the salts of the compounds of the present invention, their type is not specifically limited. It can be any of an acid addition salt and a base addition salt. It can be also present in counter ion form in a molecule. In particular, when employed as an effective component of a pharmaceutical agent, pharmaceutically acceptable salts are particularly preferred. According to the present invention, when described in connection with the use as a pharmaceutical agent, the salts of the compounds of the present invention are generally understood as a pharmaceutically acceptable salt. Examples of an acid addition salt include hydrochloric acid salt, hydrobromic acid salt, sulfuric acid salt, hydrogen sulfuric acid salt, dihydrogen phosphoric acid salt, citric acid salt, maleic acid salt, tartaric acid salt, fumaric acid salt, gluconic acid salt, methanesulfonic acid salt, or an addition salt with optically active acid such as camphor sulfonic acid, mandelic acid or substituted mandelic acid. Examples of a base addition salt include a metal salt such as sodium salt, potassium salt and the like, and an addition salt with an organic base such as N-methyl-D-glucamine, N,N'-dibenzylethylenediamine, 2-aminoethanol, tris(hydroxymethyl)aminomethane, arginine or lysine, etc. However, salt types are not limited to these and it is obvious that a skilled person in the art can appropriately select them. Among them, a pharmaceutically acceptable salt is preferred.

The compounds of the present invention can be anhydrous form. Further, hydrates of the compounds of the present invention are also preferred.

Further, solvates of the compounds of the present invention are preferred, and non-solvates are also preferred.

Further, the compounds of the present invention can be either crystalline or non-crystalline. The crystals can be a monocrystal or a mixture including multiple types of crystalline form. Further, it also can be a mixture including both crystalline form and non-crystalline form.

More specifically, preferred examples include anhydrous and non-solvate form of the "compounds represented by the formula (1)" or a hydrate and/or a solvate thereof, or crystals thereof.

Still further, anhydrous and non-solvate form of the "salts of the compounds represented by the formula (1)" or a hydrate and/or a solvate thereof, and also anhydrous and non-solvate form of the salts or a hydrate and/or a solvate of the salts may also be acceptable.

When a prodrug is to be produced from the compounds of the present invention, in accordance with an ordinary method, a group which can from a prodrug is appropriately introduced to one or more groups selected from the hydroxy group and the amino group included in the compounds of the present invention by using a reagent for preparing a prodrug, e.g., corresponding halide compound, etc., and then the prodrug can be appropriately obtained by general separation and purification method. Further, a reagent for preparing a prodrug, like an alcohol or an amine, can be used to introduce a group which can appropriately form a prodrug with the carboxyl group of the compounds of the present invention according to an ordinary method. Still further, to obtain a prodrug, the protective group present on the compounds of the formula (2) can be utilized during the production process.

Prodrugs of the compounds of the present invention are not specifically limited and examples thereof include a compound in which a functional group, which can form a prodrug, is introduced to one or more groups selected from the hydroxy group, the amino group and the carboxyl group contained in the compounds of the present invention. As for a functional group which can form a prodrug with a hydroxy group or an amino group, an acyl group and an alkoxycarbonyl group can be exemplified. Preferred examples thereof include an acetyl group, a propionyl group, a methoxycarbonyl group, an ethoxycarbonyl group and the like. An ethoxycarbonyl group is particularly preferred. In addition, there is other embodiment in which an acetyl group is particularly preferred. In addition, there is other embodiment in which a propionyl group is more preferred. In addition, there is also other embodiment in which a methoxycarbonyl group is more preferred. As for a functional group which can form a prodrug with a carboxyl group, a methyl group, an ethyl group, n-propyl group, an isopropyl group, an n-butyl group, an isobutyl group, a s-butyl group, a t-butyl group, an amino group, a methylamino group, an ethylamino group, a dimethylamino group, or a diethylamino group can be exemplified. Preferred examples thereof include an ethyl group, an n-propyl group, an isopropyl group and the like. An ethyl group is more preferred. In addition, there is other embodiment in which an n-propyl is more preferred. In addition, there is also other embodiment in which an isopropyl group is preferred.

The compounds of the present invention may sometimes have an asymmetric carbon. Stereoconfiguration of such asymmetric carbon is not specifically limited, and it can be any of R configuration and S configuration, or a mixture including both of them. Any stereoisomers including optical isomers in pure form or a diastereomer derived from such asymmetric carbon, any mixture of stereoisomers, racemate and the like are all within the scope of the present invention.

The compounds of the present invention described above have a strong EP1 receptor inhibitory action as will be shown in Test Example 1 that will be described later, and are therefore useful as effective components of medicines.

The compounds of the present invention are an antagonist for EP1 receptor and can be applied for various disorders wherein EP1 receptor is involved. In addition, they are useful as an analgesic, a febricide, a pain reliever, or an agent for prophylaxis and/or treatment of symptoms of a lower urinary tract. In particular, among the symptoms of a lower urinary tract, they are effective for urine collection disorder, and especially useful as an agent for prophylaxis and/or treatment of a overactive bladder. Symptoms of a overactive bladder include frequency urinary, urinary urgency and urinary incontinence. Urinary urgency is exemplified as a preferred example. In addition, there is other aspect in which frequency urinary or urinary incontinence is preferred example. As for urinary incontinence, urge incontinence can be mentioned as a preferred example. The compounds of the present invention are also effective for these symptoms.

It has been known that PGE2 is produced in bladder smooth muscle or endothelium of a urinary tract (Brown, W W. et al., Am. J. Physiol., 239, p. F452-F458 (1980), Mitchell J A & Warner T D, Br. J. Pharmacol., 128, p. 1121-1132 (1999)). It has been also known that PGE2 can induce contraction of a human isolated urinary bladder piece (Palea, S., et al., Br. J. Pharmacol. 124 (1998) 865-872) or can regulate urinary reflection by acting on a capsaicin-sensitive sensory nerve (Maggi, C A., Pharmacol. Res. 25, p 13-20 (1992)). Further, it has been demonstrated that PGE2 is involved with occurrence of a overactive bladder as it was confirmed that PGE2 infusion into a urinary bladder caused decreased urethal closure pressure, contraction of a urinary bladder, and a strong urgency sensation (Schussler, B. Urol. Res., 18, p 349-352 (1990)).

On the other hand, it is known that EP1 antagonists increase the bladder volume of a normal rat (Maggi, C A., et al., Eur. J. Pharmacol. 152, p. 273-279 (1988)), that EP1 antagonists suppress overactivity of detrusor muscles (Yoshida M. et al., J. Urol. 163, suppl. 44, abstract 191, (2000)), and that the EP1 antagonists suppress the afferent nerve activity at the time of cystitis (Ikeda M., et al., Biomed Res. 27, p. 49-54 (2006)). It is also known that in EP1 receptor deficient mice, no influence on normal micturition can be seen, but the shortening of the interval of micturition due to the PGE2 in the bladder or lower urinary tract obstruction, does not occur (Schroder, A., et al., J. Urol., 172, p. 1166-1170 (2004)). It can be expected from the compound of the present invention that micturition disorders in the pathological condition can be ameliorated, and the compound is effective in the amelioration of lower urinary tract symptoms, the amelioration of overactive bladder, or the amelioration of symptoms such as frequency urinary, urinary urgency or urinary incontinence.

It can be confirmed that the compound of the present invention represented by the formula (1) is useful as an effective component of a medicine for the amelioration of the symptoms such as frequency urinary, urinary urgency or urinary incontinence, or for the prophylaxis and/or treatment of lower urinary tract symptoms, by any one of, or a combination of, the methods represented by Test Example 4, Test Example 5, Test Example 6, Test Example 7, Test Example 8 and Test Example 9 that will be described later.

It is shown that an EP1 receptor deficient mouse exhibits reduced sensitivity to pain (a decrease in the acetic acid-induced stretching behavior (Stock, J L., et al., J. Clin. Invest., 107, p. 325-331 (2000)), and that the EP1 antagonists are effective in a rat model of CCI (Kawahara H., et al., Anesth. Analg., 93, p. 1012-1017 (2001)). It is also shown that the compound has an analgesic action in a rat Freund's complete adjuvant model (Giblin, G M P., et al., Bioorg. Med. Chem. Lett., 17, p. 385-389 (2007)), and that the compound has an analgesic action in a rat model of postoperative algesia (Omote, K. et al., Anesth. Analg., 92, p. 233-238 (2001)). Thus, the EP1 antagonists are known to be effective in the amelioration of pain and/or neuropathic pain. It can be confirmed that the compound of the present invention is useful as an effective component of a medicine for the amelioration of pain, by performing oral administration, intravenous administration or intraperitoneal administration of the compound to a mouse, and examining the number of stretching after intraperitoneal administration of acetic acid (acetic acid rising method), or the like. Alternatively, the usefulness of the compound of the present invention can also be confirmed by performing oral administration, intravenous administration or intraperitoneal administration of the compound to rats which have had the skin and the fascias incised from the heels of a hindlimb toward the tiptoe, had the fascias and the skin sutured, and recovered in a cage; and then examining the threshold against various stimuli. The usefulness of the compound can also be confirmed by performing oral administration, intravenous administration or intraperitoneal administration of the compound to rats which have been administered with a solution of a killed tubercle bacillus (*M. TUBERCULOSIS* DES. H37 RA, DIFCO Laboratories) (adjuvant) subcutaneously at the left hindlimb footpad, and determining the escape behavior threshold with a Von Frey type apparatus for dolorimetric evaluation. Alternatively, the usefulness of the compound of the present invention against neuropathic pain can be confirmed by performing oral administration, intravenous administration or intraperitoneal administration to rats which have entangled ischiadic nerve, and examining the threshold against various stimuli.

It has been shown that the EP1 antagonists are effective against the renal disorders in streptozotocin (STZ)-induced diabetic rats (Makino H., et al., J. Am. Soc. Nephrol., 13, 1757-1765 (2002)), and are also effective against the renal disorders in SHRSP rats which constitute a naturally occurring hypertension model (Suganami, T., et al., Hypertension, 42, 1183-1190 (2003)). Thus, it is known that the EP1 antagonists are effective for ameliorating renal diseases. It can be confirmed that the compound of the present invention is useful as an effective component of a medicine for the prophylaxis and/or treatment of renal diseases, by performing oral administration, intravenous administration or intraperitoneal administration of the compound to SHRSP rats or STZ rats, and examining the amount of urinary protein excretion, histological changes of the kidney, or the like.

It has been shown that the EP1 antagonists are effective in a mouse skin cancer model (Tober, K L., et al., J. Invest. Dermatol., 126, p. 205-211 (2006)), that the antagonists are effective in a rat colon cancer model (Kawamori, T., et al., Anticancer Res., 21, p. 3865-3869 (2001); and Niho, N., et al., Cancer Sci., 96, p. 260-264 (2005)), that the antagonists are effective in a rat lung cancer model (Kawamori, T., et al., Carcinogenesis, 22, p. 2001-2004 (2001)), that the antagonists suppress the proliferation of glioma cells, and that the antagonists suppress the growth of tumor cells in mice (Matsuo, M., et al., J. Neurooncol., 66, 285-292 (2004)). Thus, it is known that the EP1 antagonists have high applicability to cancer regions. It can be confirmed that the compound of the present invention is useful as an effective component of a medicine for the treatment of skin cancer, for example, by subcutaneously administering the compound of the present invention to a mouse, and examining inflammation or the number of tumors in the skin induced by ultraviolet irradiation. Furthermore, it can be confirmed that the compound of the present invention is useful as an effective component of a medicine for the treatment of colon cancer, for example, by orally administering the compound of the present invention to a rat, and examining the number of colon aberrant crypt foci induced by azoxymethane, or the like. It can be confirmed that the compound of the present invention is useful as an effective component of a medicine for the treatment of lung cancer, for example, by orally administering the compound of the present invention to a rat, and performing a histological analysis of lung tumor induced by 2-amino-1-methyl-6-phenylimidazo[4,5-b]pyridine (PhIP), or the like.

It has been shown that the EP1 antagonists are effective in a mouse model of occlusion of middle cerebral artery (Kawano, T., et al., Nat. Med., 12, p. 225-22 (2006); and Ahmad, A S, et al., Toxicol. Sci., 89, p. 265-270 (2006)), and it is known that the EP1 antagonists are effective for the prophylaxis and/or treatment of cerebral infarction. It can be confirmed that the compound of the present invention is useful as an effective component of a medicine for the prophylaxis and/or treatment of cerebral infarction, by performing oral administration, intravenous administration or intraperitoneal administration to a mouse which has been subjected to middle cerebral artery embolization, and examining the histological analysis of brain (proportion of necrotic area, or the like) or the like.

It is shown that the EP1 antagonists suppress osteoclast cell formation in mice (Inoue H., et al., J. Endocrinol., 161, p. 231-236 (1999); and Tsujisawa, T. et al., J. Bone Miner. Res., 20, p. 15-22 (2006)), and it is known that the EP1 antagonists are effective in the amelioration of bone diseases. It can be confirmed that the compound of the present invention is useful as an effective component of a medicine for the prophylaxis and/or treatment of bone diseases, by adding the compound of the present invention to cultured bone marrow cells which have been stimulated with $1,25(OH)_2$ vitamin $D_3$, IL-1 or the like, and measuring the number of TRAP-positive cells to thereby examine the osteoclast cell formation.

It is known that since the EP1 antagonists are effective in a rat model of gastric mucosal injury (Hase S., et al., Life Sci., 74, p. 629-641 (2003)), the EP1 antagonists have applicability to the digestive organ region. It can be confirmed that the compound of the present invention is useful as an effective component of a medicine for the digestive organ region, by performing in advance oral administration, intravenous administration or intraperitoneal administration of the compound of the present invention to a rat, and then examining the histological changes of the mucosal membrane or the membrane permeability, in connection with the protective effects of the compound against gastric mucosal injury induced by administering histamine and PGE2.

The pharmaceutical agent of the present invention can be prepared as a pharmaceutical agent which includes the compounds of the present invention as an effective component. For example, when a compound administered as a prodrug or salt thereof is metabolized in a living body to generate the compounds of the formula (1) or pharmaceutically acceptable salts thereof, it is all within the scope of the pharmaceutical agent of the present invention.

Such derivatives that are useful as the compounds of the present invention have excellent safety (i.e., having favorable pharmacology regarding various toxicity and also safety) and pharmacokinetics of a drug, etc., and usefulness as an effective component for a pharmaceutical agent is confirmed.

Examples of safety test include the followings, but are not limited thereto. Cell toxicity test (test using HL60 cell or liver cell, etc.), Genetic Toxicity Test (Ames test, mouse lymphoma TK test, chromosome abnormality test, small nuclear test, etc.), skin sensitization test (Buehler method, GPMT method, APT method, LLNA test, etc.), skin photosensitization test (Adjuvant and Strip method, etc.), safety pharmacology test regarding cardiovascular system (telemetry method, APD method, hERG inhibition evaluation test), safety pharmacology test regarding central nervous system (FOB method, modified Irwin method, etc.), safety pharmacology test regarding respiratory system (measurement using an instrument for measuring respiratory function, measurement using an instrument for determining blood gas analysis, etc.), general toxicity test, reproduction and developmental toxicity test, etc.

In addition, regarding a test for pharmacokinetics of a drug, the followings are included, but not limited thereto. Inhibition or induction test regarding cytochrome P450 enzyme, cell permeation test (i.e., a test using CaCO-2 cells or MDCK cells, etc), drug-transporter ATPase assay, oral absorption test, blood concentration time profile test, metabolism test (stability test, metabolic molecular kinds test, reactivity test, etc.), solubility test (i.e., solubility test based on turbidity, etc.) and the like.

Usefulness of the derivatives that are useful as the compounds of the present invention as an effective component for a pharmaceutical agent can be determined based on a cell toxicity test, for example. Regarding a cell toxicity test, a method using various cultured cells like human pre-leukemia HL-60 cells, primarily-isolated cultured liver cells, neutrophil fraction prepared from human peripheral blood, etc. can be mentioned. Test can be carried out according to the method described below, but it is not limited thereto. Cells are prepared in suspension including $10^5$ to $10^7$ cells/ml. 0.01 mL to 1 mL suspension is aliquoted to a micro tube or a micro plate, etc. Then, a solution including the compounds dissolved therein is added thereto in an amount of $\frac{1}{100}$ to 1 times the cell suspension, followed by culturing in a cell culture medium having final concentration of the compounds at 0.001 μM to 1000 μM under the condition of 37° C., 5% $CO_2$ for 30 minutes to several days. Once the cell culture is completed, cell viability ratio is determined using MTT method or WST-1 method (Ishiyama, M., et al., In Vitro Toxicology, 8, p. 187, 1995), etc. By measuring cell toxicity expressed by the compounds of the present invention, their usefulness as an effective component of a pharmaceutical agent can be confirmed.

Usefulness of the derivatives that are useful as the compounds of the present invention as an effective component for a pharmaceutical agent can be determined based on a Genetic Toxicity Test, for example. Examples of Genetic Toxicity Test include Ames test, mouse lymphoma TK test, chromosome abnormality test, small nuclear test, etc. The Ames test is a method for determining reverse mutation by culturing designated cells such as *Salmonella* or *E. coli* on a culture dish including a chemical compound (see, II-1. Genetic Toxicity Test under "Guidelines for Genetic Toxicity Test", Pharmecuticals Examination, Vol. 1604, 1999). Further, the mouse lymphoma TK test is a test for determining a mutational property of a gene in which thymidine kinase gene of mouse lymphoma cell L5178Y is used as a target (see, II-3. Mouse Lymphoma TK Test under "Guidelines for Genetic Toxicity Test", Pharmecuticals Examination, Vol. 1604, 1999; Clive, D. et al., Mutat. Res., 31, pp. 17-29, 1975; Cole, J., et al., Mutat. Res., 111, pp. 371-386, 1983, etc.). Further, the chromosome abnormality test is a method in which mammalian cells are cultured in the presence of a compound and the cells are fixed, and the chromosome is stained and observed to determine any activity which may cause chromosomal abnormality (see, II-2. Chromosome Abnormality Test Using Cultured Mammalian Cells under "Guidelines for Genetic Toxicity Test", Pharmaceuticals Examination, Vol. 1604, 1999). Further, the small nucleus test is a method of determining an ability to form a small nucleus which is caused by chromosomal abnormality, and it includes a method in which rodents are used (i.e., in vivo test, II-4. Small Nucleus Test Using Rodents, under "Guidelines for Genetic Toxicity Test", Pharmaceuticals Examination, Vol. 1604, 1999; Hayashi, M. et al., Mutat. Res., 312, pp. 293-304, 1994; Hayashi, M. et al., Environ. Mol. Mutagen., 35, pp. 234-252, 2000) or cultured cells are used (i.e., in vitro test, Fenech, M. et al., Mutat. Res., 147, pp. 29-36, 1985; Miller, B., et al., Mutat. Res., 392, pp. 45-59, 1997), etc. By running one, two or more tests based on these methods, gene toxicity of the compounds of the present invention can be clearly identified so that their usefulness as an effective component of a pharmaceutical agent can be confirmed.

Usefulness of the derivatives that are useful as the compounds of the present invention as an effective component for a pharmaceutical agent can be determined based on a skin sensitization test, for example. Examples of skin sensitization test include Buehler method (Buehler, E. V. Arch. Dermatol., 91, pp. 171-177, 1965), GPMT method (i.e., Maximization method, Magnusson, B. et al., J. Invest. Dermatol., 52, pp. 268-276, 1969), APT method (i.e., Adjuvant and Patch method, Sato, Y. et al., Contact Dermatitis, 7, pp. 225-237, 1981), wherein a mormot is used for a skin sensitization test. Further, as a skin sensitization study wherein a mouse is used, there is LLNA method (Local Lymph Node Assay method, OECD Guideline for the testing of chemicals 429, skin sensitization 2002; Takeyoshi, M. et al., Toxicol. Lett., 119(3), pp. 203-8, 2001; Takeyoshi, M. et al., J. Appl. Toxicol., 25(2), pp. 129-34, 2005) and the like. By running one, two or more tests based on these methods, skin sensitization property of the compounds of the present invention can be clearly identified so that their usefulness as an effective component of a pharmaceutical agent can be confirmed.

Usefulness of the derivatives that are useful as the compounds of the present invention as an effective component for a pharmaceutical agent can be determined based on a skin photosensitization test, for example. Examples of skin photosensitization test include a test using a mormot (see, Guidelines for Non-clinical test of pharmaceuticals—Explanation, 2002, YAKUJI NIPPO LIMITED 2002, 1-9: Skin Photosensitization Test, etc.). Further, specific methods include adjuvant and strip method (Ichikawa, H. et al., J. Invest. Dermatol., 76, pp. 498-501, 1981), Harber method (Harber, L. C., Arch. Dermatol., 96, pp. 646-653, 1967), Horio method (Horio, T., J. Invest. Dermatol., 67, pp. 591-593, 1976), Jordan method (Jordan, W. P., Contact Dermatitis, 8, pp. 109-116, 1982), Kochever method (Kochever, I. E. et al., J. Invest. Dermatol., 73, pp. 144-146, 1979), Maurer method (Maurer, T. et al., Br. J. Dermatol., 63, pp. 593-605, 1980), Morikawa method (Morikawa, F. et al., "Sunlight and man", Tokyo Univ. Press, Tokyo, pp. 529-557, 1974), Vinson method (Vinson, L. J., J. Soc. Cosm. Chem., 17, pp. 123-130, 1966) and the like. By running one, two or more tests based on these methods, skin photosensitization property of the compounds of the present invention can be clearly identified so that their usefulness as an effective component of a pharmaceutical agent can be confirmed.

Usefulness of the derivatives that are useful as the compounds of the present invention as an effective component for a pharmaceutical agent can be determined by carrying out a safety pharmacology test regarding cardiovascular system. Examples of safety pharmacology test regarding cardiovascular system include a telemetry method (i.e., a method by which compound's effect on an electrocardiogram, heart rate, blood pressure, blood flow amount, and the like is determined under non-anesthetized condition (Shigeru Kanno, Hirokazu Tsubone, Yoshitaka Nakata eds., Electrocardiography, Echocardiography, Blood Pressure, and Pathology test of an Animal for Basic and Clinical Medicine, 2003, published by Maruzen)), APD method (i.e., a method for measuring action potential duration of a myocardial cell, (Muraki, K. et al., A M. J. Physiol., 269, H524-532, 1995; Ducic, I. et al., J. Cardiovasc. Pharmacol., 30(1), pp. 42-54, 1997)), measurement of hERG inhibition (patch clamp method (Chachin, M. et al., Nippon Yakugaku Zasshi, 119, pp. 345-351, 2002), Binding assay method (Gilbert, J. D. et al., J. Pharm. Tox. Methods, 50, pp. 187-199, 2004), $Rb^+$ efflux assay method (Cheng, C. S. et al., Drug Develop. Indust. Pharm., 28, pp. 177-191, 2002), Membrane potential assay method (Dorn, A. et al., J. Biomol. Screen., 10, pp. 339-347, 2005) etc.) etc. By running one, two or more tests based on these methods, effect of the compounds of the present invention on a cardiovascular system can be clearly identified so that their usefulness as an effective component of a pharmaceutical agent can be confirmed.

Usefulness of the derivatives that are useful as the compounds of the present invention as an effective component for a pharmaceutical agent can be determined by carrying out a safety pharmacology test regarding a central nervous system. Examples of safety pharmacology test regarding a central nervous system include FOB method (i.e., a method for evaluating overall function, Mattson, J. L. et al., J. American College of Technology 15 (3), pp. 239-254, 1996), modified Irwin method (i.e., a method for evaluating general symptoms and behavioral characteristics (Irwin, S. Comprehensive Observational Assessment (Berl.) 13, pp. 222-257, 1968)), etc. By running one, two or more tests based on these methods, effect of the compounds of the present invention on a central nervous system can be clearly identified so that their usefulness as an effective component of a pharmaceutical agent can be confirmed.

Usefulness of the derivatives that are useful as the compounds of the present invention as an effective component for a pharmaceutical agent can be determined by carrying out a safety pharmacology test regarding a respiratory system, for example. Examples of safety pharmacology test regarding a respiratory system include a measurement using an instrument for measuring respiratory function (i.e., a method which measures breathing number, amount of air per single breathing, amount of breathing air per minute or hour, (Drorbaugh, J. E. et al., Pediatrics, 16, pp. 81-87, 1955; Epstein, M. A. et al., Respir. Physiol., 32, pp. 105-120, 1978), or a measurement using a blood gas analyzer (i.e., a method which measures blood gas, hemoglobin oxygen saturation, etc., Matsuo, S. Medicina, 40, pp. 188, 2003), etc. By running one, two or more tests based on these methods, effect of the compounds of the present invention on a respiratory system can be clearly identified so that their usefulness as an effective component of a pharmaceutical agent can be confirmed.

Usefulness of the derivatives that are useful as the compounds of the present invention as an effective component for a pharmaceutical agent can be determined by carrying out a general toxicity test. Specifically, according to a general toxicity test, a compound which is either dissolved or suspended in an appropriate solvent is orally administered or intravenously administered of a single time or multiple times (for several days) to rodents such as rat, mouse, and the like or non-rodents such as monkey, dog and the like as a test animal, and then animal's general state or any change in clinical chemistry or tissue in terms of pathology, etc. is determined. By identifying general toxicity of a compound based on this method, usefulness of the compounds of the present invention as an effective component for a pharmaceutical agent can be confirmed.

Usefulness of the derivatives that are useful as the compounds of the present invention as an effective component for a pharmaceutical agent can be determined by carrying out a reproduction and developmental toxicity test. The test is to determine any adverse drug reaction caused by a compound on sexual reproduction process by using rodents such as rat, mouse, and the like or non-rodents such as monkey, dog and the like (Guidelines for Non-clinical test of pharmaceuticals—Explanation, 2002, YAKUJI NIPPO LIMITED 2002, 1-6: Reproduction and developmental toxicity Test, etc.). With respect to a reproduction and developmental toxicity test, a test relating to an early embryo genesis from fertilization to implantation, a test relating to development before and after birth and an activity of a mother, a test relating to development of an embryo and a fetus (see, [3] Reproduction and developmental toxicity Test under "Guidelines for Toxicity Test for Pharmaceuticals", Pharmaceuticals Examination, Vol. 1834, 2000), etc. can be mentioned. By identifying reproduction and developmental toxicity of the compounds of the present invention based on this method, usefulness of a compound as an effective component for a pharmaceutical agent can be confirmed.

Usefulness of the derivatives that are useful as the compounds of the present invention as an effective component for a pharmaceutical agent can be determined by carrying out an inhibition or induction test of cytochrome P450 enzyme (Gomez-Lechon, M. J. et al., Curr. Drug Metab. 5(5), pp. 443-462, 2004). In an inhibition or induction test regarding cytochrome P450 enzyme, examples of the test include a method of determining in vitro an inhibitory effect of a compound on an enzyme activity by using cytochrome P450 enzyme of each molecular kinds that is either purified from a cell or prepared using a genetic recombinant, or a microsome as a human P450 expression system (Miller, V. P. et al., Ann. N.Y. Acad. Sci., 919, pp. 26-32, 2000), a method of determining expression of cytochrome P450 enzyme for each molecular kinds or variation in enzyme activity by using a human liver microsome or cell homogenate (Hengstler, J. G. et al., Drug Metab. Rev., 32, pp. 81-118, 2000), a method of examining compound's activity of inducing the enzyme by extracting the RNA from human liver cells that have been exposed to the compound and comparing the amount of mRNA expression with that of a control (Kato, M. et al., Drug Metab. Pharmacokinet., 20(4), pp. 236-243, 2005), etc. By running one or two or more tests based on these methods, effect of the compounds of the present invention on induction or inhibition of cytochrome P450 enzyme can be clearly identified so that their usefulness as an effective component of a pharmaceutical agent can be confirmed.

Usefulness of the derivatives that are useful as the compounds of the present invention as an effective component for a pharmaceutical agent can be determined by carrying out a cell permeation test, for example. Examples of the test include a method of determining compound's permeability against cell membrane under in vitro cell culture system by using CaCO-2, for example (Delie, F. et al., Crit. Rev. Ther. Drug Carrier Syst., 14, pp. 221-286, 1997; Yamashita, S. et al., Eur. J. Pham. Sci., 10, pp. 195-204, 2000; Ingels, F. M. et al., J. Pham. Sci., 92, pp. 1545-1558, 2003), or a method of determining compound's permeability against cell membrane under in vitro cell culture system by using MDCK cell (Irvine, J. D. et al., J. Pham. Sci., 88, pp. 28-33, 1999) etc. By running one, two or more tests based on these methods, the compounds' permeability against cell membrane can be clearly identified so that their usefulness as an effective component of a pharmaceutical agent can be confirmed.

Usefulness of the derivatives that are useful as the compounds of the present invention as an effective component for a pharmaceutical agent can be determined by carrying out a drug transporter ATPase assay using ATP-Binding Cassette (ABC) transporter, for example. Examples of the assay include a method of determining whether or not a compound is a substrate for P-gp by using P-glycoprotein (P-gp) baculovirus expression system (Germann, U. A., Methods Enzymol., 292, pp. 427-41, 1998), etc. Further, determination can be also carried out based on a transport assay using oocytes obtained from *Xenopus laevis*, as a solute carrier (SLC) transporter. With respect to transport assay, oocytes, which express OATP2, can be used to confirm whether or not the compound is a substrate for OATP2 (Tamai I. et al., Pharm Res. 2001 September; 18(9): 1262-1269). By identifying the compounds' activity on ABC transporter or SLC transporter based on this method, usefulness of the compounds of the present invention as an effective component for a pharmaceutical agent can be confirmed.

Usefulness of the derivatives that are useful as the compounds of the present invention as an effective component for a pharmaceutical agent can be determined by carrying out oral absorptivity test, or example. The oral absorptivity test is exemplified as a remarkably preferred test for determining a usefulness of the present compound. Examples of the assay include a method of determining blood transfer property of a compound after oral administration using LC-MS/MS method by preparing a certain amount of a compound dissolved or suspended in a solvent, orally administering it to a rodent, a monkey or a dog and measuring blood concentration of the compound over time (Harada Kenichi et al., eds. "Newest aspects in mass spectrometry for biological sciences", 2002, Kodansha Scientific, etc.). By identifying compound's oral absorptivity based on this method, usefulness of the compounds of the present invention as an effective component for a pharmaceutical agent can be confirmed.

Usefulness of the derivatives that are useful as the compounds of the present invention as an effective component for a pharmaceutical agent can be determined by carrying out a blood concentration time profile test. The blood concentration time profile test is exemplified as a remarkably preferred test for determining a usefulness of the present compound. Examples of the test include a method of determining blood concentration profile of a compound using LC-MS/MS method by orally or parenterally (e.g., intravenous, intramuscular, intraperitoneal, subcutaneous, or trans-dermal administration, or administration into an eye or via nose, etc.) administering the compound to a rodent, a monkey or a dog and measuring blood concentration of the compound over time (Harada Kenichi et al., eds. "Newest aspects in mass spectrometry for biological sciences", 2002, Kodansha Scientific, etc.). By identifying compound's blood concentration time profile based on this method, usefulness of the compounds of the present invention as an effective component for a pharmaceutical agent can be confirmed.

Usefulness of the derivatives that are useful as the compounds of the present invention as an effective component for a pharmaceutical agent can be determined by carrying out a metabolism test, for example. The metabolism test is exemplified as a remarkably preferred test for determining a usefulness of the present compound. Examples of the test include a method of determining stability in blood (i.e., a method by which in vivo metabolism clearance of a compound is calculated by measuring its metabolism rate in a liver microsome of a humor other animal; Shou, W. Z. et al., J. Mass Spectrom., 40(10), pp. 1347-1356, 2005; L1, C. et al., Drug Metab. Dispos., 34(6), 901-905, 2006), a metabolite molecular kinds test, a reactive metabolite testing method, etc. By running one, two or more tests based on these methods, the compounds' metabolic profile can be clearly identified so that their usefulness as an effective component of a pharmaceutical agent can be confirmed.

Usefulness of the derivatives that are useful as the compounds of the present invention as an effective component for a pharmaceutical agent can be determined by carrying out a dissolution test, for example. Examples of the test include a method of determining solubility based on turbidity (Lipinski, C. A. et al., Adv. Drug Deliv. Rev., 23, pp. 3-26, 1997; Bevan, C. D. et al., Anal. Chem., 72, pp. 1781-1787, 2000), etc. By identifying compound's dissolution property based on this method, usefulness of the compounds of the present invention as an effective component for a pharmaceutical agent can be confirmed.

Usefulness of the derivatives that are useful as the compounds of the present invention as an effective component for a pharmaceutical agent can be determined by examining problems associated with an upper gastrointestinal tract disorder or a kidney dysfunction, etc., for example. With respect to a pharmacological test for an upper gastrointestinal tract, compound's effect on gastric mucosal membrane using a fasted rat model having damaged gastric mucosal membrane can be mentioned. As for a pharmacological test for kidney function, a method of measuring renal blood flow amount and glomerular filtration rate [Physiology, 18$^{th}$ ed. Bunkodo, 1986, Chapter 17] can be mentioned. By running one, two or more tests based on these methods, the compounds' effect on an upper gastrointestinal tract or a kidney function can be clearly identified so that their usefulness as an effective component of a pharmaceutical agent can be confirmed.

In regard to the medicine of the present invention, a mixture of the compound of the present invention may be used directly, but it is preferred to prepare a pharmaceutical composition by adding one or two or more pharmaceutically acceptable carriers to a mixture of one or two or more compounds of the present invention, and to administer the composition. The type of the pharmaceutically acceptable carriers is not particularly limited, but for example, an excipient, a binder, a disintegrant, a gliding agent, additives or the like may be mentioned. Examples of the excipient include D-mannitol and the like. Examples of the binder include carboxymethylcellulose and the like. Examples of the disintegrant include cornstarch and the like. Examples of the gliding agent include glycerin and the like. Examples of the additives include paraoxybenzoic acid esters and the like. Furthermore, the additives also include surfactants such as polyoxyethylenesorbitan monooleate (tween 80) or HC60.

When the pharmaceutical agent of the present invention is administered to a human, it can be orally administered in form a tablet, powder, a granule, a capsule, a sugar-coated tablet, a liquid or syrup, etc. Further, it can be also administered via parenteral route in form including an injection solution, a linger's solution, a suppository, a trans-dermal or absorbing agent, etc.

Administration period of the pharmaceutical agent of the present invention is not specifically limited. However, when it is administered under the purpose of treatment, a period during which clinical sign of a disorder is found can be taken as a time period for the administration. In general, the administration is continued from several weeks to one year. However, depending on symptoms, it can be further administered, or can be continuously administered even after recovery from clinical symptoms. In addition, even when no clinical signs are observed, it can be administered for a prophylactic purpose based on clinician's judgment. Dosage of the pharmaceutical agent of the present invention is not specifically limited. For example, it can be generally in an effective component of 0.01 to 2000 mg per day for an adult, a single or divided in several portions. Administration frequency can be from once a month to everyday. Preferably, it is once a week to three times a week, or five times a week, or can be administered everyday. Single time dosage, administration period, and administration frequency, etc. may suitably be either increased or decreased according to age, body weight, overall health of a subject, or disorder to be treated and severeness of the disorder.

Combining the compounds of the present invention with other pharmaceutical agents and using the combination within the limit that advantageous effect such as obtainment of a desired pharmaceutical effect at maximum level and/or reduced adverse drug reaction also fall within the scope of the present invention. Examples of a pharmaceutical agent which can be used in combination of the compounds of the present invention to supplement or enhance the prophylactic and/or therapeutic activity of the compounds of the present invention for a overactive bladder include an anti-cholinergic agent, an $\alpha 1$ inhibitor, an agonist for $\beta 3$ receptor, an antagonist for neurokinin receptor, a calcium channel opener, an antagonist for P2X3 receptor, a blocker for serotonin 1A receptor, a blocker for NMDA receptor, an agent for inhibiting synthesis of prostaglandin, imipramine hydrochloride, flavoxate hydrochloride, capsaicin, resiniferatoxin, botulinum toxin, an anti-diuretic agent and the like.

The anti-cholinergic agent that is used for the present invention is an antagonist for muscarinic receptor, and for example, the antagonistic agent for muscarinic receptor that is descried in the literature (Yakugaku Zasshi, 126, p 199-206 (2006)) is preferred. Specifically, oxybutynin, propiverine, tolterodine, solifenacin and imidafenacin can be mentioned as a preferred example. Among these, propiverine, tolterodine or solifenacin is particularly preferred.

The $\alpha 1$ inhibitor used for the present invention is an inhibitor for adrenaline $\alpha 1$ receptor and examples include the inhibitor for adrenaline $\alpha 1$ receptor that is disclosed in the literature (Yakugaku Zasshi, 126, p 199-206 (2006)). Specific examples include prazosin, terazosin, tamsulosin, naftopidil, alfuzosin, doxazosin, or silodosin. Among these, tamsulosin, naftopidil, or silodosin is particularly preferred.

Administration time for the above-described agents for combination use is not specifically limited. The pharmaceutical agent of the present invention and the agents for combination use can be administered to a subject either simultaneously or with a time interval. Dose of the agents for combination use can be similar to those that are clinically used. It can be appropriately selected according to a subject to be administered, an administration route, a disorder to be treated, and type of a combination of the pharmaceutical agent of the present invention and the agents for combination use.

The administration form of the agents for combination use is not specifically limited as long as the pharmaceutical agent of the present invention and the agents for combination use may be presented as a combination at the time of administration. Such administration form includes, for example 1) administering a single formulation that is obtained by the formulating the compounds of the present invention as an effective component of the pharmaceutical agent of the present invention together with the agents for combination use, 2) administering simultaneously two kinds of the formulations that are obtained by separate formulation of the pharmaceutical agent of the present invention and the agents for combination use via the same administration route, 3) administering with time interval two kinds of the formulations that are obtained by separate formulation of the pharmaceutical agent of the present invention and the agents for combination use via the same administration route, 4) administering simultaneously two kinds of the formulations that are obtained by separate formulation of the pharmaceutical agent of the present invention and the agents for combination use via different administration routes, and 5) administering with time interval two kinds of the formulations that are obtained by separate formulation of the pharmaceutical agent of the present invention and the agents for combination use via different administration routes (for example, the pharmaceutical agent of the present invention is administered first followed by the administration of the agents for combination use, and vice versa) and the like.

The mixing ratio between the pharmaceutical agent of the present invention and the agents for combination use can be appropriately selected according to a subject to be administered, an administration route, a disorder to be treated, and the like.

EXAMPLE

Hereinafter, the present invention will be described in more detail in view of the Examples. However, scope of the present invention is not limited to them.

Regarding the Examples described below, various analyses were carried out according to the following descriptions, unless otherwise specified.

For thin layer chromatography (TLC), TLC plate manufactured by Merck Co., Germany was used (Precoated Silica Gel 60 F254). After development using chloroform:methanol (1:0-1:1), or hexane:ethyl acetate (1:0-0:1), UV ray (254 nm or 365 nm) irradiation was carried out, followed by chromogenic reaction using iodine vapor, p-anisic aldehyde solution, phosphorous molybdenum acid (ethanol solution), ninhydrin, or dinitrophenyl hydrazine hydrochloride solution for identification. For drying of an organic solvent, anhydrous magnesium sulfate or anhydrous sodium sulfate was used. For column chromatography, multiflap YFLC (manufactured by Yamazen) was used and either Hi-Flash Column (40 μm; manufactured by Yamazen) series or Purif Pack-Si series (manufactured by MORITE) was used as a column. For flash column chromatography, silica gel 60N (globule form, neutral, 40-100 μm, manufactured by Kanto Chemical Co., Inc.) was used. For preparative thin layer chromatography (hereinafter, abbreviated as "PTLC"), one or multiple PLC plates of silica gel 60 F254 (20×20 cm, layer thickness 2 mm, manufactured by Merck Co.) were used depending on the amount of a sample. For HPLC purification, LC-10A system (manufactured by Shimadzu Corporation) was used in conjunction with Develosil C-30-UG-5 column (manufactured by NOMURA CHEMICAL CO., LTD). As an elution solution, water-acetonitrile solution including 0.1% acetic acid was used. For the HPLC purification, a target compound was obtained by removing the solvent via freeze drying, unless otherwise specified. For nuclear magnetic resonance (NMR) spectrum measurement, AL-300 (FT-NMR, manufactured by JEOL Co.) was used. As a solvent, deuterated chloroform was used, unless otherwise specified. For measurement of chemical shift, tetramethylsilane (TMS) was employed as an internal standard. The chemical shift value was expressed in δ (ppm). In addition, a coupling constant was expressed in J (Hz).

As for "LCMS", liquid chromatography mass analysis spectrum (LC-MS) was used to obtain mass spectrum. For the analysis, three apparatuses (A), (B) and (C) described below were used separately.

(A) As a mass spectrometer, ZMD type mass spectrometer (manufactured by Micromass, England) was used and ionization was carried out based on an electrospray method (ESI) for the measurement. The liquid chromatography instrument used was Waters 600 LC system, manufactured by Waters Company. As a separation column, Develosil C30-UG-5 (50×4.6 mm, manufactured by NOMURA CHEMICAL CO., LTD) was used.

(B) As a mass spectrometer, Platform-LC type mass spectrometer (manufactured by Micromass, England) was used and ionization was carried out based on an electrospray method (ESI) for the measurement. The liquid chromatography instrument manufactured by GILSON, France was used. As a separation column, Develosil C30-UG-5 (50×4.6 mm, manufactured by NOMURA CHEMICAL CO., LTD) was used.

(C) As a mass spectrometer, Quadrupole type mass spectrometer, i.e., HPLC/SQD system (manufactured by Waters Company) was used and ionization was carried out based on an electrospray method (ESI) for the measurement. The liquid chromatography instrument used was Acquity Ultra Performance LC system, manufactured by Waters Company. As a separation column, ACQUITY HPLC BEH (C18 2.1×50 mm 1.7 μm, manufactured by Waters Company) was used.

With respect to the Examples and the Reference examples in which specific descriptions are given for LC condition, the measurements were carried out by using any one of the above-described apparatuses and in accordance with the following solvent condition. In addition, "m/z" indicates mass spectrum data (both M+H and M−H are described).

LC condition 1: (A-1)
Apparatus used: (A)
Flow rate: 2 ml/min
Solvent: Solution A=water including 0.1% (v/v) acetic acid, Solution B=acetonitrile including 0.1% (v/v) acetic acid
From 0 minute to 5 minutes: Linear gradient from [Solution A 95%+Solution B 5% (v/v)] to [Solution A 2%+Solution B 98% (v/v)]
From 5 minutes to 6 minutes: Maintain at [Solution A 2%+Solution B 98% (v/v)]
From 6 minutes to 7.5 minutes: Maintain at [Solution A 95%+Solution B 5% (v/v)]
LC condition: (B-1)
Apparatus used: (B)
Flow rate: 2 ml/min
Solvent: Solution A water including 0.1% (v/v) acetic acid, Solution B=acetonitrile including 0.1% (v/v) acetic acid
From 0 minute to 5 minutes: Linear gradient from [Solution A 95%+Solution B 5% (v/v)] to [Solution A 0%+Solution B 100% (v/v)]
From 5 minutes to 9 minutes: Maintain at [Solution A 0%+Solution B 100% (v/v)]
From 9 minutes to 10 minutes: Maintain at [Solution A 95%+Solution B 5% (v/v)]
LC condition: (C-1)
Apparatus used: (C)
Flow rate: 0.6 ml/min
Solvent: Liquid A=water, containing 0.1% (v/v) acetic acid, liquid B=acetonitrile, containing 0.1% (v/v) acetic acid
From 0 minute to 2 minutes: Linear gradient from [liquid A 95%+liquid B 5% (v/v)] to [liquid A 10%+liquid B 90% (v/v)]
From 2 minutes to 2.5 minutes: Linear gradient from [liquid A 10%+liquid B 90% (v/v)] to [liquid A 2%+liquid B 98% (v/v)]
From 2.5 minutes to 2.6 minutes: Linear gradient from [liquid A 2%+liquid B 5% (v/v)] to [liquid A 95%+liquid B 5% (v/v)]
From 2.6 minutes to 3.2 minutes: Maintained at [liquid A 95%+liquid B 5% (v/v)]
LC condition: (A-2)
Apparatus used: (A)
Flow rate: 2 ml/min
Solvent: Solution A=water including 0.1% (v/v) acetic acid, Solution B=acetonitrile including 0.1% (v/v) acetic acid
From 0 minutes to 5 minutes: Linear gradient from [Solution A 50%+Solution B 50% (v/v)] to [Solution A 2%+Solution B 98% (v/v)]
From 5 minutes to 6 minutes: Maintain at [Solution A 2%+Solution B 98% (v/v)]

From 6 minutes to 7.5 minutes: Maintain at [Solution A 50%+Solution B 50% (v/v)]
LC conditions: (C-2)
Apparatus used: (C)
Flow rate: 0.6 ml/min
Solvent: Liquid A=water, containing 0.1% (v/v) acetic acid, liquid B=acetonitrile, containing 0.1% (v/v) acetic acid
From 0 minute to 2 minutes: Linear gradient from [liquid A 70%+liquid B 30% (v/v)] to [liquid A 10%+liquid B 90% (v/v)]
From 2 minutes to 2.5 minutes: Linear gradient from [liquid A 10%+liquid B 90% (v/v)] to [liquid A 2%+liquid B 98% (v/v)]
From 2.5 minutes to 2.6 minutes: Linear gradient from [liquid A 2%+liquid B 98% (v/v)] to [liquid A 70%+liquid B 30% (v/v)]
From 2.5 minutes to 3.2 minutes: Maintained at [liquid A 70%+liquid B 30% (v/v)]
LC conditions: (C-3)
Apparatus used: (C)
Flow rate: 0.6 ml/min
Solvent: Liquid A=water, containing 0.1% (v/v) acetic acid, liquid B=acetonitrile, containing 0.1% (v/v) acetic acid
From 0 minute to 2 minutes: Linear gradient from [liquid A 50%+liquid B 50% (v/v)] to [liquid A 10%+liquid B 90% (v/v)]
From 2 minutes to 2.5 minutes: Linear gradient from [liquid A 10%+liquid B 90% (v/v)] to [liquid A 2%+liquid B 98% (v/v)]
From 2.5 minutes to 2.6 minutes: Linear gradient from [liquid A 2%+liquid B 98% (v/v)] to [liquid A 50%+liquid B 50% (v/v)]
From 2.5 minutes to 3.2 minutes: Maintained at [liquid A 50%+liquid B 50% (v/v)]

Reference Example 1

(2-Fluoro-5-methoxyphenyl)(phenyl)methanol

Phenylmagnesium bromide (1.6 mL, 1.0 M tetrahydrofuran solution, manufactured by Kanto Chemical Co., Inc.) was added to a solution of 2-Fluoro-5-methoxybenzaldehyde (500 mg, manufactured by Tokyo Chemical Industry Co., Ltd.) in tetrahydrofuran (16 mL, manufactured by Wako Pure Chemical Industries, Ltd.) at 0° C., and the mixture was stirred overnight at room temperature. Water (10 mL) was added to the reaction solution, and the mixture was extracted with ethyl acetate (3×20 mL), washed with brine (20 mL) and dried (MgSO$_4$). The solvent was then evaporated. The resulting residue was purified by silica gel column chromatography (hexane:ethyl acetate=9:1), to give 480 mg of the title compound. LC-MS: HPLC retention time 3.90 minutes, m/z 233 (M+H), condition B-1.

Reference Example 2

(2-fluoro-5-methoxyphenyl)(phenyl)methanone

The Dess-Martin Periodinane (548 mg, manufactured by Alfa Aesar GmbH & Co. KG) was added to a solution of the compound of Reference Example 1 (100 mg) in dichloromethane (910 μL, manufactured by Kanto Chemical Co., Inc.), and the mixture was stirred overnight at room temperature. A saturated aqueous solution of sodium thiosulfate (10 mL) and a saturated aqueous solution of sodium hydrogen carbonate (10 mL) were added to the reaction solution, and the mixture was extracted with chloroform (3×20 mL), washed with brine (20 mL), and dried (MgSO$_4$). The solvent was then evaporated. The resulting residue was purified by silica gel column chromatography (hexane:ethyl acetate=4:1), to give 40 mg of the title compound. LC-MS: HPLC retention time 4.87 minutes, m/z 231 (M+H), condition B-1.

Reference Example 3

6-Methoxy-3-phenyl-1H-indazole

To a solution of the compound of Reference Example 2 (40 mg) in xylenes (5 mL, manufactured by Kokusan Chemical Co., Ltd.), hydrazine hydrate (40 mg, manufactured by Tokyo Chemical Industry Co., Ltd.), copper(II) oxide (1.4 mg, manufactured by Kanto Chemical Co., Inc.) and potassium carbonate (24 mg, manufactured by Kokusan Chemical Co., Ltd.) were added, and the mixture was heated overnight at 150° C. The reaction solution was cooled to room temperature, and water (10 mL) was added thereto. The mixture was extracted with ethyl acetate (3×20 mL), washed with brine (20 mL), and dried (MgSO$_4$). The solvent was then evaporated. The resulting residue was purified by silica gel column chromatography (hexane:ethyl acetate=4:1), to give 27 mg of the title compound. LC-MS: HPLC retention time 4.87 minutes, m/z 225 (M+H), condition B-1.

Reference Example 4

3-Bromo-1-(tetrahydro-2H-pyran-2-yl)-1H-indazole

To a solution of 3-bromo-1H-indazole (500 mg) synthesized according to a method of the literature (V> Auwers, et al., J. Prakt. Chem., 1924, 314) in toluene (25 mL, manufactured by Wako Pure Chemical Industries, Ltd.), 3,4-dihydro-2H-pyrane (640 mg, manufactured by Tokyo Chemical Industry Co., Ltd.) and p-toluenesulfonic acid monohydrate (10 mg, manufactured by Wako Pure Chemical Industries, Ltd.) were added, and the mixture was heated for one hour at 80° C. The reaction solution was cooled to room temperature, and then a saturated aqueous solution of sodium hydrogen carbonate (10 mL) was added thereto. The mixture was extracted with ethyl acetate (3×20 mL), washed with brine (40 mL), and dried (MgSO$_4$), and the solvent was evaporated. The resulting residue was purified by silica gel column chromatography (hexane:ethyl acetate=9:1), to give 570 mg of the title compound. LC-MS: HPLC retention time 4.93 minutes, m/z 281 (M+H), condition B-1.

Reference Example 5

3-{1-(Tetrahydro-2H-pyran-2-yl)-1H-indazol-3-yl}phenol

To a solution of the compound of Reference Example 4 (200 mg) in N,N-dimethylformamide (7 mL, manufactured by Kanto Chemical Co., Inc.), potassium phosphate (302 mg, manufactured by Wako Pure Chemical Industries, Ltd.), tri-o-tolylphosphine (217 mg, manufactured by Kanto Chemical Co., Inc.), bis(dibenzylideneacetone)palladium (65 mg, Sigma-Aldrich Corp.), and (3-hydroxyphenyl)boronic acid (294 mg, manufactured by Combi-Blocks, Inc.) were added, and the mixture was heated for 12 hours at 80° C. The reaction solution was cooled to room temperature, and then water (20 mL) was added thereto. The mixture was stirred for one hour at the same temperature, and then the mixture was extracted with ethyl acetate (3×20 mL), washed with brine (20 mL), and dried (MgSO$_4$). The solvent was then evaporated. The resulting residue was purified by silica gel column chromatography (hexane:ethyl acetate=4:1), to give 204 mg of the title compound. LC-MS: HPLC retention time 4.44 minutes, m/z 295 (M+H), condition B-1.

Reference Example 6

3-(1H-indazol-3-yl)phenol

2 M hydrochloric acid (0.5 mL, manufactured by Wako Pure Chemical Industries, Ltd.) was added to a solution of the compound of Reference Example 5 (204 mg) in methanol (7 mL, manufactured by Wako Pure Chemical Industries, Ltd.), and the mixture was stirred overnight at room temperature. A 2 M aqueous solution of sodium hydroxide (0.5 mL, manufactured by Kanto Chemical Co., Inc.) was added to the reaction solution to neutralize the reaction solution, and then the resultant mixture was extracted with ethyl acetate (3×10 mL), washed with brine (10 mL), and dried ($MgSO_4$). The solvent was then evaporated, to give 141 mg of the title compound. LC-MS: HPLC retention time 3.89 minutes, m/z 211 (M+H), condition B-1.

Reference Example 7 t-butyl 3-iodo-1H-indazole-1-carboxylate

To a solution of 3-iodo-1H-indazole (986 mg) synthesized according to the literature (C. Vallerie, et al., Tetrahedron Lett., 2000, 41, 4363-4366) in dichloromethane (20 mL, manufactured by Kanto Chemical Co., Inc.), a dicarboxylic acid di-t-butyl ester (1.76 g, manufactured by Wako Pure Chemical Industries, Ltd.), triethylamine (818 μL, manufactured by Wako Pure Chemical Industries, Ltd.) and dimethylaminopyridine (247 mg, manufactured by Tokyo Chemical Industry Co., Ltd.) were added, and the mixture was stirred for one hour at room temperature. Water (20 mL) was added to the reaction solution, and the mixture was extracted with chloroform (3×20 mL), washed with brine (40 mL), and dried ($MgSO_4$). The solvent was then evaporated. The resulting residue was purified by silica gel column chromatography (hexane:ethyl acetate=9:1), to give 1.33 g of the title compound. LC-MS: HPLC retention time 2.16 minutes, m/z 344 (M), condition C-1.

Reference Example 8 t-butyl 3-{4-(trifluoromethyl)phenyl}-1H-indazole-1-carboxylate

To a solution of the compound of Reference Example 7 (40 mg) in 1,4-dioxane (500 μL, manufactured by Kanto Chemical Co., Inc.), potassium phosphate (26 mg, manufactured by Wako Pure Chemical Industries, Ltd.), tricyclohexylphosphine-tetrafluoroborate (17 mg, manufactured by Sigma-Aldrich Corp.), palladium acetate (21 mg, manufactured by Kanto Chemical Co., Inc.) and p-(trifluoromethyl)phenylboronic acid (26 mg, manufactured by Wako Pure Chemical Industries, Ltd.) were added, and the mixture was heated for 3 hours at 100° C. The reaction solution was cooled to room temperature, and then water (20 mL) was added thereto. The mixture was extracted with ethyl acetate (3×20 mL), washed with brine (20 mL), and dried ($MgSO_4$), and then the solvent was evaporated, to give 41 mg of the title compound. LC-MS: HPLC retention time 5.89 minutes, m/z 363 (M+H), condition B-1.

Reference Example 9

3-{4-(trifluoromethyl)Phenyl}-1H-indazole

Concentrated hydrochloric acid (0.5 mL, manufactured by Kanto Chemical Co., Inc.) was added to a solution of the compound of Reference Example 8 (41 mg) in methanol (500 μL, manufactured by Kanto Chemical Co., Inc.), and the mixture was stirred for 3 hours at room temperature. Subsequently, aqueous ammonia (1 mL, manufactured by Kanto Chemical Co., Inc.) was added to the reaction solution to neutralize the reaction solution, and then the mixture was extracted with chloroform (3×10 mL), washed with brine (10 mL), and dried ($MgSO_4$). The solvent was then evaporated, to give 39.2 mg of the title compound. LC-MS: HPLC retention time 4.53 minutes, m/z 263 (M+H), condition B-1.

Reference Example 10

3-Cyclopentenyl-1H-indazole

To a solution of the compound of Reference Example 7 (40 mg) in N,N-dimethylformamide (500 μL, manufactured by Kanto Chemical Co., Inc.), potassium phosphate (145 mg, manufactured by Wako Pure Chemical Industries, Ltd.), tri-o-tolylphosphine (21 mg, manufactured by Kanto Chemical Co., Inc.), bis(dibenzylideneacetone)palladium (12 mg, manufactured by Sigma-Aldrich Corp.), and cyclopenteneboronic acid (30 mg, manufactured by Combi-Blocks, Inc.) were added, and the mixture was heated overnight at 110° C. The reaction solution was cooled to room temperature, and then water (1 mL) was added thereto. The mixture was stirred for one hour at room temperature, and then the mixture was extracted with ethyl acetate (3×2 mL), washed with brine (10 mL), and dried ($MgSO_4$). The solvent was then evaporated. The resulting residue was purified by silica gel column chromatography (hexane:ethyl acetate=4:1), to give 15.4 mg of the title compound. LC-MS: HPLC retention time 4.16 minutes, m/z 185 (M+H), condition B-1.

Reference Example 11 t-butyl-3-{4-(hydroxymethyl)phenyl}-1H-indazole-1-carboxylate

To a solution of the compound of Reference Example 7 (41.7 mg) in 1,4-dioxane (500 μL, manufactured by Kanto Chemical Co., Inc.), potassium phosphate (49 mg, manufactured by Wako Pure Chemical Industries, Ltd.), tricyclohexylphosphine-tetrafluoroborate (16.9 mg, manufactured by Sigma-Aldrich Corp.), palladium acetate (5.2 mg, manufactured by Kanto Chemical Co., Inc.), and 4-t-butoxymethylphenylboronic acid (29.5 mg, manufactured by Frontier Scientific, Inc.) were added, and the mixture was heated for 3 hours at 100° C. The reaction solution was cooled to room temperature, and then water (20 mL) was added thereto. The mixture was extracted with ethyl acetate (3×20 mL), washed with brine (20 mL), and dried ($MgSO_4$). The solvent was then evaporated, to give 34.5 mg of the title compound. LC-MS: HPLC retention time 2.34 minutes, m/z 325 (M+H), condition C-2.

Reference Example 12 t-butyl 3-(6-methoxypyridyl-3-yl)-1H-indazole-1-carboxylate

To a solution of the compound of Reference Example 7 (40 mg) in N,N-dimethylformamide (500 μL, manufactured by Kanto Chemical Co., Inc.), potassium phosphate (21 mg, manufactured by Wako Pure Chemical Industries, Ltd.), tri-o-tolylphosphine (7 mg, manufactured by Kanto Chemical Co., Inc.), bis(dibenzylideneacetone)palladium (11 mg, manufactured by Sigma-Aldrich Corp.), and 2-methoxy-5-pyridineboronic acid (21 mg, manufactured by Wako Pure Chemical Industries, Ltd.) were added, and the mixture was heated overnight at 120° C. The reaction solution was cooled to room temperature, and then water (1 mL) was added thereto. The mixture was extracted with ethyl acetate (3×2 mL), washed with brine (10 mL), and dried ($MgSO_4$), and then the solvent was evaporated. The resulting residue was purified by silica gel column chromatography (hexane:ethyl acetate=2:1), to give 16.3 mg of the title compound. LC-MS: HPLC retention time 5.10 minutes, m/z 326 (M+H), condition B-1.

Reference Example 13 t-butyl 3-(piperidyl-1-yl)-1H-indazole-1-carboxylate

To a solution of the compound of Reference Example 7 (160 mg) in 1,4-dioxane (500 μL, manufactured by Kanto Chemical Co., Inc.), cesium carbonate (303 mg, manufactured by Wako Pure Chemical Industries, Ltd.), XANTPHOS (108 mg, manufactured by Strem Chemicals, Inc.), palladium acetate (21 mg, manufactured by Kanto Chemical Co., Inc.), and piperidine (48 mg, manufactured by Sigma-Aldrich Corp.) were added, and the mixture was heated overnight at 90° C. The reaction solution was cooled to room temperature, and then water (1 mL) was added thereto. The mixture was extracted with ethyl acetate (3×2 mL), washed with brine (10 mL), and dried ($MgSO_4$), and then the solvent was evaporated. The resulting residue was purified by silica gel column chromatography (hexane:ethyl acetate=4:1), to give 56.8 mg of the title compound. LC-MS: HPLC retention time 2.11 minutes, m/z 302 (M+H), condition C-1.

Reference Example 14

6-(t-butyldiphenylsiloxy)-1H-indazole

Imidazole (3.0 g, manufactured by Kanto Chemical Co., Inc.) and t-butylchlorodiphenylsilane (12.1 g, manufactured by Tokyo Chemical Industry Co., Ltd.) were added to a solution of 1H-indazol-6-ol (3.0 g) synthesized according to the literature (L. F. Fieser, J. Am. Chem. Soc., 1926, 48, 1097-1107) in N,N-dimethylformamide (100 mL, manufactured by Kanto Chemical Co., Inc.), and the mixture was stirred for 3 hours at room temperature. Water (200 mL) was added to the reaction solution, and the mixture was extracted with diethyl ether (3×200 mL), washed with brine (400 mL), and dried ($MgSO_4$). The solvent was then evaporated. The resulting residue was purified by silica gel column chromatography (hexane:ethyl acetate=10:1), to give 7.3 g of the title compound. LC-MS: HPLC retention time 2.05 minutes, m/z 373 (M+H), condition C-1.

Reference Example 15

6-(t-butyldiphenylsiloxy)-3-iodo-1H-indazole t-butoxypotassium (5.5 g, manufactured by Wako Pure Chemical Industries, Ltd.) and iodine (12.4 g, manufactured by Kanto Chemical Co., Inc.) were added to a solution of the compound of Reference Example 14 (7.3 g) in tetrahydrofuran (200 mL, manufactured by Wako Pure Chemical Industries, Ltd.) at 0° C., and the mixture was stirred overnight at the same temperature. Water (200 mL) was added to the reaction solution, and the mixture was extracted with ethyl acetate (3×200 mL), washed with 1 M sodium hydroxide (400 mL, manufactured by Kanto Chemical Co., Inc.), and dried ($MgSO_4$). The solvent was then evaporated. The resulting residue was purified by silica gel column chromatography (hexane:ethyl acetate=10:1), to give 10.7 g of the title compound. LC-MS: HPLC retention time 2.37 minutes, m/z 499 (M+H), condition C-1.

Reference Example 16 t-butyl 6-(t-butyldiphenylsiloxy)-3-iodo-1H-indazole-1-carboxylate

To a solution of the compound of Reference Example 15 (10.7 g) in dichloromethane (200 mL, manufactured by Kanto Chemical Co., Inc.), dicarboxylic acid di-t-butyl ester (4.67 g, manufactured by Wako Pure Chemical Industries, Ltd.), triethylamine (2.16 mL, manufactured by Wako Pure Chemical Industries, Ltd.), and dimethylaminopyridine (2.61 g, manufactured by Tokyo Chemical Industry Co., Ltd.) were added, and the mixture was stirred for one hour at room temperature. Water (200 mL) was added to the reaction solution, and the mixture was extracted with ethyl acetate (3×200 mL), washed with brine (400 mL), and dried ($MgSO_4$). The solvent was then evaporated. The resulting residue was purified by silica gel column chromatography (hexane:ethyl acetate=9:1), to give 12.3 g of the title compound. LC-MS: HPLC retention time 2.47 minutes, m/z 599 (M+H), condition C-1.

Reference Example 17

6-Trifluoromethyl-3-iodo-1H-indazole

Potassium hydroxide (73 mg, manufactured by Wako Pure Chemical Industries, Ltd.) and iodine (330 mg, manufactured by Kanto Chemical Co., Inc.) were added to a solution of 6-(trifluoromethyl)-1H-indazole (121 mg) synthesized according to the literature (Shoji, et al., Tetrahedron Lett., 2004, 45, 1769-1772) in N,N-dimethylformamide (6.5 mL, manufactured by Kanto Chemical Co., Inc.), and the mixture was stirred for 3 hours at room temperature. An aqueous solution of sodium thiosulfate (20 mL) was added to the reaction solution, and the mixture was extracted with ethyl acetate (3×20 mL), washed with brine (40 mL), and dried ($MgSO_4$). The solvent was then evaporated. The resulting residue was purified by silica gel column chromatography (hexane:ethyl acetate=9:1), to give 169 mg of the title compound. LC-MS: HPLC retention time 4.46 minutes, m/z 313 (M+H), condition B-1.

Reference Example 18 t-butyl 6-trifluoromethyl-3-iodo-1H-indazole-1-carboxylate

To a solution of the compound of Reference Example 17 (169 mg) in dichloromethane (5.4 mL, manufactured by Kanto Chemical Co., Inc.), dicarboxylic acid di-t-butyl ester (237 mg, manufactured by Wako Pure Chemical Industries, Ltd.), triethylamine (0.11 mL, manufactured by Wako Pure Chemical Industries, Ltd.) and dimethylaminopyridine (33 mg, manufactured by Tokyo Chemical Industry Co., Ltd.) were added, and the mixture was stirred for one hour at room temperature. Water (20 mL) was added to the reaction solution, and the mixture was extracted with chloroform (3×20 mL), washed with brine (40 mL), and dried (MgSO$_4$). The solvent was then evaporated. The resulting residue was purified by silica gel column chromatography (hexane:ethyl acetate=7:3), to give 231 mg of the title compound. LC-MS: HPLC retention time 5.00 minutes, m/z 413 (M+H), condition B-1.

Reference Example 19 t-butyl 6-hydroxy-3-phenyl-1H-indazole-1-carboxylate

To a solution of the compound of Reference Example 16 (4.0 g) in N,N-dimethylformamide (30 mL, manufactured by Kanto Chemical Co., Inc.), potassium phosphate (2.84 g, manufactured by Wako Pure Chemical Industries, Ltd.), tri-o-tolylphosphine (1.01 g, manufactured by Kanto Chemical Co., Inc.), bis(dibenzylideneacetone)palladium (612 mg, manufactured by Sigma-Aldrich Corp.), and phenylboronic acid (1.63 g, manufactured by Sigma-Aldrich Corp.) were added, and the mixture was heated overnight at 80° C. The reaction solution was cooled to room temperature, and then water (20 mL) was added thereto. The mixture was stirred for one hour at room temperature, and then the mixture was extracted with ethyl acetate (3×20 mL), washed with brine (20 mL), and dried (MgSO$_4$). The solvent was then evaporated. The resulting residue was purified by silica gel column chromatography (hexane:ethyl acetate=6:1), to give 643 mg of the title compound. LC-MS: HPLC retention time 4.70 minutes, m/z 311 (M+H), condition B-1.

Reference Example 20

6-Hydroxy-3-phenyl-1H-indazole

Trifluoroacetic acid (2.36 mL, manufactured by Wako Pure Chemical Industries, Ltd.) was added to a solution of the compound of Reference Example 19 (643 mg) in dichloromethane (20 mL, manufactured by Wako Pure Chemical Industries, Ltd.), and the mixture was stirred for 3 hours at room temperature. A saturated aqueous solution of sodium hydrogen carbonate (50 mL) was added to the reaction solution, and the mixture was stirred for one hour at the same temperature. Subsequently, the mixture was extracted with ethyl acetate (3×50 mL), washed with brine (100 mL), and dried (MgSO$_4$), and then the solvent was evaporated, to give 420 mg of the title compound. LC-MS: HPLC retention time 3.32 minutes, m/z 211 (M+H), condition B-1.

Reference Example 21

3-Phenyl-6-trifluoromethanesulfonyloxy-1H-indazole

N-phenyltrifluoromethanesulfonimide (204 mg, manufactured by Sigma-Aldrich Corp.) was added to a solution of the compound of Reference Example 20 (100 mg) in dichloromethane (3 mL, manufactured by Kanto Chemical Co., Inc.), and the mixture was heated overnight at room temperature. The reaction solution was cooled to room temperature, and then water (1 mL) was added thereto. The mixture was extracted with ethyl acetate (3×2 mL), washed with brine (10 mL), and dried (MgSO$_4$), and then the solvent was evaporated, to give 182 mg of the title compound. LC-MS: HPLC retention time 4.97 minutes, m/z 343 (M+H), condition B-1.

Reference Example 22

3,6-Diphenyl-1H-indazole

To a solution of the compound of Reference Example 21 (40 mg) in 1,4-dioxane (500 µL, manufactured by Kanto Chemical Co., Inc.), potassium phosphate (50 mg, manufactured by Wako Pure Chemical Industries, Ltd.), tricylcohexylphosphine-tetrafluoroborate (17 mg, manufactured by Sigma-Aldrich Corp.), palladium acetate (5 mg, manufactured by Kanto Chemical Co., Inc.), and phenylboronic acid (17 mg, manufactured by Sigma-Aldrich Corp.) were added, and the mixture was heated for 3 hours at 100° C. The reaction solution was cooled to room temperature, and then water (20 mL) was added thereto. The mixture was ethyl acetate (3×20 mL), washed with brine (20 mL), and dried (MgSO$_4$), and then the solvent was evaporated. The resulting residue was purified by silica gel column chromatography (hexane:ethyl acetate=4:1), to give 29.2 mg of the title compound. LC-MS: HPLC retention time 1.96 minutes, m/z 271 (M+H), condition C-1.

Reference Example 23

3-Iodo-6-nitro-1H-indazole

Iodine (2.14 g, manufactured by Kanto Chemical Co., Inc.) and potassium hydroxide (475 mg, manufactured by Wako Pure Chemical Industries, Ltd.) were added to a solution of 6-nitro-1H-indazole (690 mg, manufactured by Wako Pure Chemical Industries, Ltd.) in N,N-dimethylformamide (20 mL, manufactured by Kanto Chemical Co., Inc.), and the mixture was stirred for one hour at room temperature. A saturated aqueous solution of sodium thiosulfate (20 mL) was added to the reaction solution, and the mixture was extracted with chloroform (3×20 mL), washed with brine (40 mL), and dried (MgSO$_4$). The solvent was then evaporated. The resulting residue was purified by silica gel column chromatography (chloroform:methanol=9:1), to give 1.04 g of the title compound. LC-MS: HPLC retention time 0.54 minutes, m/z 290 (M+H), condition C-3.

Reference Example 24

6-Nitro-3-phenyl-1H-indazole

To a solution of the compound of Reference Example 23 (200 mg) in N,N-dimethylformamide (3.5 mL, manufactured by Kanto Chemical Co., Inc.), potassium phosphate (247 mg, manufactured by Wako Pure Chemical Industries, Ltd.), tri-o-tolylphosphine (217 mg, manufactured by Kanto Chemical Co., Inc.), bis(dibenzylideneacetone)palladium (65 mg, manufactured by Sigma-Aldrich Corp.), and phenylboronic acid (85 mg, manufactured by Sigma-Aldrich Corp.) were added, and the mixture was heated for 3 hours at 100° C. The reaction solution was cooled to room temperature, and then water (10 mL) was added thereto. The mixture was stirred for one hour at room temperature, and then the mixture was extracted with ethyl acetate (3×10 mL), washed with brine (20 mL), and dried (MgSO$_4$). The solvent was then evaporated, to give 65 mg of the title compound. LC-MS: HPLC retention time 1.63 minutes, m/z 240 (M+H), condition C-1.

Reference Example 25

3-Phenyl-1,4,5,6,7,8-hexahydrocyclohepta[c]pyrazole

Lithium hexamethyldisilazane (10 mL, 1.6 M tetrahyfuran solution, manufactured by Sigma-Aldrich Corp.) was added to a solution of cycloheptanone (561 mg, manufactured by Tokyo Chemical Industry Co., Ltd.) in toluene (10 mL, manufactured by Kanto Chemical Co., Inc.) at 0° C., and the mixture was stirred for one minute. Benzoyl chloride (90 µL, manufactured by Wako Pure Chemical Industries, Ltd.) was then added thereto at the same temperature, and the mixture was stirred for one hour. Subsequently, acetic acid (5 mL, manufactured by Wako Pure Chemical Industries, Ltd.) and hydrazine monohydrate (1 mL, manufactured by Tokyo Chemical Industry Co, Ltd.) were added to the reaction solution, and the mixture was stirred for 3 hours. A saturated aqueous solution of sodium carbonate (30 mL) was added to the reaction solution, and the mixture was extracted with (3×20 mL), washed with brine (40 mL), and dried (MgSO$_4$). The solvent was then evaporated. The resulting residue was purified by silica gel column chromatography (hexane:ethyl acetate=9:1), to give 230 mg of the title compound. LC-MS: HPLC retention time 1.57 minutes, m/z 213 (M+H), condition C-1.

Reference Example 26

{2-Chloro-6-(trifluoromethyl)pyridin-3-yl}(phenyl)methanol

Lithium diisopropylamide (3.7 mL, 1.8 M tetrahydrofuran solution, manufactured by Tokyo Chemical Industry Co., Ltd.) was added to a solution of 2-chloro-6-(trifluoromethyl) pyridine (1.0 g, manufactured by Matrix Chemical LLC) in tetrahydrofuran (55 mL, manufactured by Kanto Chemical Co., Inc.) at −78° C., and the mixture was stirred for 30 minutes at the same temperature. Then, benzaldehyde (1.17 g, manufactured by Kokusan Chemical Co., Ltd.) was added thereto at −78° C., and the mixture was stirred overnight while gradually raising the temperature to room temperature. Water (50 mL) was added to the reaction solution, and the mixture was extracted with ethyl acetate (3×10 mL), washed with brine (20 mL), and dried (MgSO$_4$). The solvent was then evaporated. The resulting residue was purified by silica gel column chromatography (chloroform:methanol=9:1), to give 1.58 g of the title compound. LC-MS: HPLC retention time 1.68 minutes, m/z 288 (M+H), condition C-1.

Reference Example 27

{2-Chloro-6-(trifluoromethyl)pyridin-3-yl}(phenyl)methanone

The Dess-Martin Periodinane (1.25 g, manufactured by Alfa Aesar GmbH & Co. KG) was added to a solution of the compound of Reference Example 26 (500 mg) in dichloromethane (25 mL, manufactured by Kanto Chemical Co., Inc.), and the mixture was stirred for one hour at room temperature. A saturated aqueous solution of sodium thiosulfate (20 mL) and a saturated aqueous solution of sodium hydrogen carbonate (20 mL) were added to the reaction solution, and the mixture was extracted with chloroform (3×20 mL), washed with brine (40 mL), and dried (MgSO$_4$). The solvent was then evaporated. The resulting residue was purified by silica gel column chromatography (chloroform:methanol=9:1), to give 853 mg of the title compound. LC-MS: HPLC retention time 1.46 minutes, m/z 286 (M+H), condition C-1.

Reference Example 28

6-(Trifluoromethyl)-3-phenyl-1H-pyrazolo[3,4-b]pyridine

Hydrazine monohydrate (479 mg, manufactured by Tokyo Chemical Industry Co., Ltd.) was added to a solution of the compound of Reference Example 27 (853 mg) in ethanol (30 mL, manufactured by Wako Pure Chemical Industries, Ltd.), and the mixture was stirred for 12 hours at 100° C. The reaction solution was cooled to room temperature, and then water (20 mL) was added thereto. The mixture was extracted with ethyl acetate (3×20 mL), washed with brine (20 mL), and dried (MgSO$_4$), and then the solvent was evaporated. The resulting residue was purified by silica gel column chromatography (hexane:ethyl acetate=1:1), to give 316 mg of the title compound. LC-MS: HPLC retention time 1.27 minutes, m/z 264 (M+H), condition C-1.

Example 1

Ethyl 2-(3-phenyl-1H-indazol-1-yl)thiazole-4-carboxylate

To a solution of 3-phenyl-1H-indazole (689 mg) synthesized according to the literature (T. Edward C., et al., Tetrahedron, 1991, 47, 9599-9620) in mesitylene (5 mL, manufactured by Kanto Chemical Co., Inc.), potassium phosphate (2.38 g, manufactured by Wako Pure Chemical Industries, Ltd.), (1S,2S)-(+)-N,N-dimethylcyclohexane-1,2-diamine (50 mg, manufactured by Tokyo Chemical Co., Ltd.), copper iodide (34 mg, manufactured by Kanto Chemical Co., Inc.), and ethyl 2-bromo-4-thiazolecarboxylate (840 mg) synthesized according to the literature (T. R. Kelly, et al., J. Org. Chem., 1996, 61, 4623-4633) were added, and the mixture was heated overnight at 180° C. The reaction solution was cooled to room temperature, and then water (20 mL) was added thereto. Ethyl acetate was extracted (3×20 mL), washed with brine (20 mL), and dried (MgSO$_4$), and then the solvent was evaporated. The resulting residue was purified by silica gel column chromatography (hexane:ethyl acetate=9:1), to give 579 mg of the title compound. LC-MS: HPLC retention time 6.80 minutes, m/z 350 (M+H), condition B-1.

Example 2

2-(3-Phenyl-1H-indazol-1-yl)thiazole-4-carboxylic acid

A 5 M aqueous solution of sodium hydroxide (10 mL, manufactured by Kanto Chemical Co., Inc.) was added to a solution of the compound of Example 1 (579 mg) in ethanol (10 mL, manufactured by Wako Pure Chemical Industries, Ltd.), and the mixture was stirred for 3 hours at room temperature. 5 M hydrochloric acid (10 mL, manufactured by Kanto Chemical Co., Inc.) was added to the mixture to neutralize the mixture, and then the mixture was extracted with ethyl acetate (3×10 mL), washed with brine (10 mL), and dried (MgSO$_4$). The solvent was then evaporated, to give 477 mg of the title compound. LC-MS: HPLC retention time 5.31 minutes, m/z 322 (M+H), condition A-1.

Example 3

Ethyl 5-(4-methyl-3,5-diphenyl-1H-pyrazol-1-yl)thiophene-2-carboxylate

To a solution of 3-phenyl-1H-indazole (50 mg) synthesized according to the literature (T. Edward C., et al., Tetrahedron, 1991, 47, 9599-9620) in N,N-dimethylacetamide (500 µL, manufactured by Kanto Chemical Co., Inc.), potassium phosphate (85 mg, manufactured by Wako Pure Chemical Industries, Ltd.), (1S,2S)-(+)-N,N-dimethylcyclohexane-1,2-diamine (5 mg, manufactured by Tokyo Chemical Industry Co., Ltd.), copper iodide (4 mg, manufactured by Kanto Chemical Co., Inc.), and ethyl 5-bromothiophene-2-carboxylate (45 mg, manufactured by Alfa Aesar GmbH & Co. KG) were added, and the mixture was irradiated with microwave irradiation for 45 minutes at 185° C. The reaction solution was cooled to room temperature, and then water (1 mL) was added thereto. The mixture was extracted with ethyl acetate (3×2 mL), washed with brine (5 mL), and dried ($MgSO_4$), and then the mixture was evaporated. The resulting residue was purified by silica gel column chromatography (hexane:ethyl acetate 85:15), to give 50 mg of the title compound. LC-MS: HPLC retention time 6.52 minutes, m/z 349 (M+H), condition A-1.

Example 4

Ethyl 2-(6-amino-3-phenyl-1H-indazol-1-yl)thiazole-4-carboxylate

10% Palladium-carbon (18 mg, manufactured by Merck Chemicals, Ltd.) was added to a solution of ethyl 2-(6-nitro-3-phenyl-1H-indazol-1-yl)thiazole-4-carboxylate (234 mg), which had been synthesized from the compound of Reference Example 24 according to the method of Example 3, in methanol (20 mL manufactured by Wako Pure Chemical Industries, Ltd.) at room temperature, and the mixture was stirred overnight in a hydrogen atmosphere. After completion of the reaction, the 10% palladium-carbon was removed by filtration, and the solvent was evaporated. The resulting residue was purified by silica gel column chromatography (hexane:ethyl acetate=6:4), to give 39.1 mg of the title compound. LC-MS: HPLC retention time 1.95 minutes, m/z 365 (M+H), condition C-1.

Example 5

Ethyl 2-{6-(benzylamino)-3-phenyl-1H-indazol-1-yl}thiazole-4-carboxylate

To a solution of the compound of Example 4 (10 mg) in dichloromethane (350 μL, manufactured by Kanto Chemical Co., Inc.), acetic acid (10 μL, manufactured by Wako Pure Chemical Industries, Ltd.), benzaldehyde (4 mg, manufactured by Nacalai Tesque, Inc.) and sodium triacetoxyborohydride (17.7 mg, manufactured by Sigma-Aldrich Corp.) were added, and the mixture was stirred overnight at room temperature. Water (1 mL) was added to the reaction solution, and the mixture was extracted with ethyl acetate (3×2 mL), washed with brine (10 mL), and dried ($MgSO_4$). The solvent was then evaporated. The resulting residue was purified by silica gel column chromatography (hexane:ethyl acetate=9:1), to give 2.4 mg of the title compound. LC-MS: HPLC retention time 5.83 minutes, m/z 519 (M+H), condition B-1.

Example 6

Ethyl 2-{6-(cyclopentyloxy)-3-phenyl-1H-indazol-1-yl}thiazole-4-carboxylate

Sodium hydride (added with 40% mineral oil, 13.5 mg, manufactured by Kanto Chemical Co., Inc.) was added to a solution of ethyl 2-(6-hydroxy-3-phenyl-1H-indazol-1-yl)thiazole-4-carboxylate (20 mg), which had been synthesized from the compound of Reference Example 20 according to the method of Example 3, in N,N-dimethylformamide (1 mL, manufactured by Kanto Chemical Co., Inc.) under ice cooling, and the mixture was stirred for 5 minutes at the same temperature. Subsequently, bromocyclopentane (269 mg, manufactured by Kanto Chemical Co., Inc.) was added, and the mixture was stirred overnight at room temperature. Water (10 mL) was added to the reaction solution, and the mixture was extracted with diethyl ether (3×10 mL), washed with brine (10 mL), and dried ($MgSO_4$). The solvent was then evaporated. The resulting residue was purified by silica gel column chromatography (hexane:ethyl acetate=7:1), to give 6.9 mg of the title compound. LC-MS: HPLC retention time 2.13 minutes, m/z 434 (M+H), condition C-1.

Example 7

2-{(3-phenyl-1H-indazol-1-yl)methyl}thiazole-4-carboxylic acid

Sodium hydride (added with 40% mineral oil, 9 mg, manufactured by Kanto Chemical Co., Inc.) was added to a solution of 3-phenyl-1H-indazole (40 mg), which had been synthesized according to the literature (T. Edward, C., et al., Tetrahedron, 1991, 47, 9599-9620), in N,N-dimethylformamide (1 mL, manufactured by Kanto Chemical Co., Inc.) under ice cooling, and the mixture was stirred for 5 minutes at the same temperature. Subsequently, ethyl 2-bromomethylthiazole-4-carboxylate (51 mg) synthesized according to the method of the literature (K. Benno, et al., Leibigs. Ann. Chem., 1981, 4, 623-632) was added thereto, and the mixture was stirred overnight at room temperature. Water (1 mL) was added to the reaction solution, and the mixture was extracted with ethyl acetate (3×2 mL), washed with brine (10 mL), and dried ($MgSO_4$). The solvent was then evaporated. The resulting residue was purified by PTLC (hexane:ethyl acetate=2:1), to give 7.2 mg of the title compound. LC-MS: HPLC retention time 4.08 minutes, m/z 336 (M+H), condition A-1.

Example 8

Ethyl 2-[{3-phenyl-6-(trifluoromethyl)-1H-indazol-1-yl}methyl]thiazole-4-carboxylate Sodium hydride (added with 40% mineral oil, 20 mg, manufacture by Kanto Chemical Co., Inc.) was added to a solution of 3-phenyl-6-(trifluoromethyl)-1H-indazole (40 mg), which had been synthesized in Reference Example 18 according to the methods of Reference Examples 8 and 9, in N,N-dimethylformamide (1 mL, manufactured by Kanto Chemical Co., Inc.) under ice cooling, and the mixture was stirred for 5 minutes at the same temperature. Subsequently, ethyl 2-bromomethylthiazole-4-carboxylate (114 mg) synthesized according to the method of the literature (K. Benno, et al., Liebigs. Ann. Chem., 1981, 4, 623-632) was added thereto, and the mixture was stirred overnight at room temperature. Water (1 mL) was added to the reaction solution, and the mixture was extracted with ethyl acetate (3×2 mL), washed with brine (10 mL), and dried ($MgSO_4$). The solvent was then evaporated. The resulting residue was purified by silica gel column chromatography (hexane:ethyl acetate=5:1), to give 7.2 mg of the title compound. LC-MS: HPLC retention time 1.41 minutes, m/z 404 (M+H), condition C-1.

Examples 9 to 106

The production of the compounds of Examples 9 to 106 will be described below. The details of the Examples 9 to 106 will be described in Table 1. The meanings of the symbols in Table 1 are as follows.

"Exp.": Example No., "Str.": Example compound, "S.M.1", "S.M.2" and "S.M.3": starting material for the production of the corresponding Example compound. The symbols in the columns of "S.M.1", "S.M.2" and "S.M.3" represent the following starting materials. "IM.1": ethyl 2-bromo-4-thiazolcarboxylate (produced according to the method described in J. Org. Chem., 61, 4623-4633 (1996)), "IM.2":

3-phenylindole (Produced according to the method described in J. Heterocycl. Chem., 37, 1281-1288 (2000)), "IM.3": 3-phenyl-1H-pyrazolo[3,4-b]pyridine (produced according to the method described in Can. J. Chem., 66, 420-428 (1988)). Furthermore, if the starting material is the compound described in the Examples or Reference Examples in the present specification, the starting materials are indicated as the Example Nos. or Reference Example Nos. thereof (in the case of the Example No., indicated as "Exp. (Example No.)", and in the case of the Reference Example No., indicated as "Ref. (Reference Example No.)." For example, "Ref.2" indicates the compound of Reference Example 2). In the case of a commercially available reagent, the compound indicates the commercially available reagent corresponding to the symbol described in the column of "Reagent" in the Table 2. If one or two starting materials have been used, only the relevant starting materials are indicated.

"Synth.1" and "Synth.2": methods for production of the corresponding Example compounds. The symbols in the columns of "Synth.1" and "Synth.2" indicate the following production methods. "A" indicates the production method described in Reference Example 1; "B" indicates the production method described in Reference Example 2; "C" indicates the production method described in Reference Example 3; "D" indicates the production method described in Reference Example 5; "E" indicates the production method described in Reference Example 6; "F" indicates the production method described in Reference Example 8; "G" indicates the production method described in Reference Example 9; "H" indicates the production method described in Reference Example 10; "I" indicates the production method described in Reference Example 11; "J" indicates the production method described in Reference Example 12; "K" indicates the production method described in Reference Example 13; "L" indicates the production method described in Reference Example 25; "a" indicates the production method described in Example 1; "b" indicates the production method described in Example 2; "c" indicates the production method described in Example 3; "d" indicates the production method described in Example 5; "e" indicates the production method described in Example 6; "f" indicates the production method described in Example 7; and "g" indicates the production method described in Example 8. The symbols indicate the compound that can be synthesized according to the corresponding Examples.

In regard to the Example compounds in the Table 1, an intermediate can be produced by the production method described in "Synth.1", using the starting materials described in "S.M.1" and "S.M.2", and the Example compound can be produced by the production method described in "Synth.2" using the intermediate and the starting materials described in "S.M.3". If one or two starting materials are used, only the relevant starting materials are indicated. Furthermore, if the production methods corresponding to "Synth.1" and "Synth.2" are unnecessary, indication may be given in only one column.

"LCMS": Indicates the data of liquid chromatograph mass analysis spectrum (m/z). Specifically, the data consist of "method,", "R.T." and "MS";

"method": LCMS conditions. Indication of the conditions as "A-1" implies that the previously mentioned "LCMS" apparatus and the conditions (A-1) are used. Similarly, indication of the conditions as "B-1" implies that the previously mentioned "LCMS" apparatus and the conditions (B-1) are used. Similarly, indication of the conditions as "C-1" implies that the previously mentioned "LCMS" apparatus and the conditions (C-1) are used. Similarly, indication of the conditions as "A-2" implies that the previously mentioned "LCMS" apparatus and the conditions (A-2) are used. Indication of the conditions as "C-2" implies that the previously mentioned "LCMS" apparatus and the conditions (C-2) are used;

"R.T.": Retention time (minutes) in LCMS;

"MS": indicates the data of mass spectrum (indicated together with M+H or M−H) (however, the indication of "N.D." implies that no molecular ion peak could be detected).

The meanings of the symbols in Table 2 are as follows.

"Reagent": symbol corresponding to the reagents used in the columns of "S.M.1", "S.M.2" and "S.M.3" in the Table 1, "Structure": structure of the reagent, "Supl.": manufacturer of the reagent used. The manufacturer of the reagent used may be indicated by the following abbreviations. Tokyo Chemical Industry Co., Ltd.: "TCI", Sigma-Aldrich Corp.: "Ald", Apollo Chemical Co.: "Apollo", Kanto Chemical Co., Inc.: "KANTO", Wako Pure Chemical Industries, Ltd.: "WAKO", Lancaster Chemical Corp.: "LANC", Maybridge Co.: "MAYB", Acros Organics, Inc.: "Acros", Alfa Aesar GmbH & Co. KG: "AAesar", Boron Molecular Pty., Ltd.: "BMol", Combi-Blocks, Inc.: "Comb", FluoroChem, Ltd.: "Fchem", and Frontier Scientific, Inc.: "Front".

The abbreviations in the sentences and in the tables have the following meanings. n: normal, i: iso, s: secondary, t: tertiary, Me: methyl, Et: ethyl, Pr: propyl, Bu: butyl, Ph: phenyl, Bn: benzyl, Py: pyridyl, CHO: formyl, COOH: carboxyl, $NO_2$: nitro, $NH_2$: amino, $CF_3$: trifluoromethyl, F: fluoro, Cl: chloro, Br: bromo, I: iodo, OMe: methoxy, OH, hydroxy, THF: tetrahydrofuran.

The number given before each substituent represents the position of substitution. The number given together with a hyphen before the abbreviation of an aromatic ring represents the position of substitution of the aromatic ring.

TABLE 1

| Exp. | Str. | S.M.1 | S.M.2 | Synth.1 | S.M.3 | Synth.2 | method | R.T. | MS |
|---|---|---|---|---|---|---|---|---|---|
| 9 | 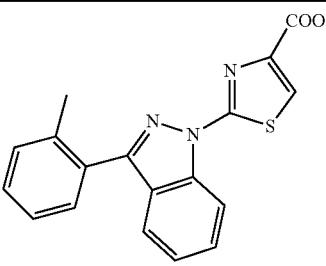 | Ref.4 | Ba1 | D, E | IM.1 | a, b | A-1 | 5.75 | 336 (M + H) |

TABLE 1-continued
| Exp. | Str. | S.M.1 | S.M.2 | Synth.1 | S.M.3 | Synth.2 | LC-MS method | R.T. | MS |
|---|---|---|---|---|---|---|---|---|---|
| 10 | 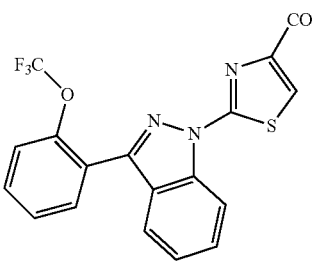 | Ref.7 | Ba2 | F, G | IM.1 | a, b | C-1 | 1.83 | 406 (M + H) |
| 11 | 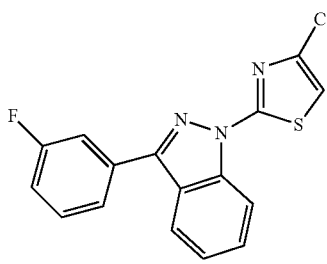 | FKet1 | — | C | IM.1 | a, b | B-1 | 5.15 | 340 (M + H) |
| 12 | 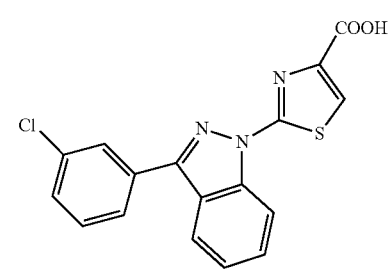 | Ref.7 | Ba3 | F, G | IM.1 | a, b | C-1 | 1.94 | 356 (M + H) |
| 13 | 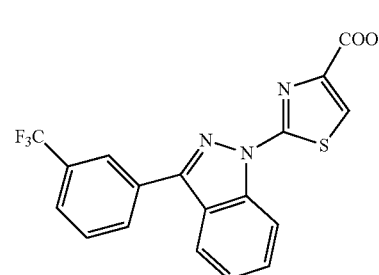 | Ref.7 | Ba4 | F, G | IM.1 | a, b | C-1 | 1.91 | 390 (M + H) |
| 14 | 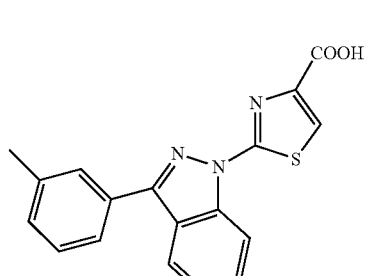 | Ref.7 | Ba5 | F, G | IM.1 | a, b | C-1 | 1.88 | 336 (M + H) |

TABLE 1-continued

| Exp. | Str. | S.M.1 | S.M.2 | Synth.1 | S.M.3 | Synth.2 | LC-MS method | R.T. | MS |
|---|---|---|---|---|---|---|---|---|---|
| 15 | | Ref.7 | Ba6 | F, G | IM.1 | a, b | C-1 | 2.07 | 398 (M + H) |
| 16 | | Ref.6 | — | — | IM.1 | a, b | A-1 | 4.17 | 338 (M + H) |
| 17 | | Ref.7 | Ba7 | I, G | IM.1 | a, b | C-1 | 1.31 | 352 (M + H) |
| 18 | | Ref.7 | Ba8 | F, G | IM.1 | a, b | C-1 | 1.73 | 352 (M + H) |
| 19 | | Ref.7 | Ba9 | F, G | IM.1 | a, b | C-1 | 1.96 | 406 (M + H) |

TABLE 1-continued

| | | | | | | | LC-MS | | |
|---|---|---|---|---|---|---|---|---|---|
| Exp. | Str. | S.M.1 | S.M.2 | Synth.1 | S.M.3 | Synth.2 | method | R.T. | MS |
| 20 | | Ref.7 | Ba10 | F, G | IM.1 | a, b | C-1 | 1.56 | 364 (M + H) |
| 21 | | Ref.7 | Ba11 | F, G | IM.1 | a, b | C-1 | 1.58 | 347 (M + H) |
| 22 | | FKet2 | — | C | IM.1 | a, b | C-1 | 0.89 | 340 (M + H) |
| 23 | | Ref.7 | Ba12 | F, G | IM.1 | a, b | C-1 | 1.95 | 356 (M + H) |
| 24 | | Ref.9 | — | — | IM.1 | a, b | B-1 | 5.75 | 390 (M + H) |

TABLE 1-continued

| Exp. | Str. | S.M.1 | S.M.2 | Synth.1 | S.M.3 | Synth.2 | LC-MS method | R.T. | MS |
|---|---|---|---|---|---|---|---|---|---|
| 25 | | Ref.4 | Ba13 | D, E | IM.1 | a, b | A-1 | 5.30 | 352 (M + H) |
| 26 | | Ref.7 | Ba14 | F, G | IM.1 | a, b | C-1 | 1.96 | 406 (M + H) |
| 27 | | Ref.7 | Ba15 | F, G | IM.1 | a, b | C-1 | 2.04 | 414 (M + H) |
| 28 | | Ref.11 | — | G | IM.1 | a, b | C-1 | 1.26 | 352 (M + H) |
| 29 | | Ref.7 | Ba16 | F, G | IM.1 | a, b | C-1 | 1.67 | 366 (M + H) |

TABLE 1-continued

| Exp. | Str. | S.M.1 | S.M.2 | Synth.1 | S.M.3 | Synth.2 | LC-MS method | R.T. | MS |
|---|---|---|---|---|---|---|---|---|---|
| 30 | | Ref.4 | Ba17 | D, E | IM.1 | a, b | A-1 | 5.02 | 336 (M + H) |
| 31 | | Ref.7 | Ba18 | F, G | IM.1 | a, b | C-1 | 1.93 | 348 (M + H) |
| 32 | | Ref.7 | Ba19 | F, G | IM.1 | a, b | C-1 | 2.17 | 378 (M + H) |
| 33 | | Ref.7 | Ba20 | F, G | IM.1 | a, b | C-1 | 2.09 | 398 (M + H) |
| 34 | | Ref.7 | Ba21 | F, G | IM.1 | a, b | C-1 | 1.87 | 368 (M + H) |

TABLE 1-continued

| Exp. | Str. | S.M.1 | S.M.2 | Synth.1 | S.M.3 | Synth.2 | LC-MS method | R.T. | MS |
|---|---|---|---|---|---|---|---|---|---|
| 35 | | Ref.7 | Ba22 | F, G | IM.1 | a, b | C-1 | 1.17 | 384 (M + H) |
| 36 | | Ref.7 | Ba23 | F, G | IM.1 | a, b | C-1 | 1.55 | 364 (M + H) |
| 37 | | Ref.7 | Ba24 | F, G | IM.1 | a, b | C-1 | 1.86 | 426 (M + H) |
| 38 | | Ref.7 | Ba25 | J, G | IM.1 | a, b | C-1 | 1.83 | 365 (M + H) |
| 39 | | Ref.7 | Ba26 | F, G | IM.1 | a, b | C-2 | 0.96 | 358 (M + H) |

TABLE 1-continued

| Exp. | Str. | S.M.1 | S.M.2 | Synth.1 | S.M.3 | Synth.2 | LC-MS method | R.T. | MS |
|---|---|---|---|---|---|---|---|---|---|
| 40 | | Ref.7 | Ba27 | F, G | IM.1 | a, b | C-2 | 1.02 | 358 (M + H) |
| 41 | | Ref.7 | Ba28 | F, G | IM.1 | a, b | C-2 | 1.02 | 374 (M + H) |
| 42 | | Ref.7 | Ba29 | F, G | IM.1 | a, b | C-2 | 1.47 | 389 (M + H) |
| 43 | | Ref.7 | Ba30 | F, G | IM.1 | a, b | C-2 | 1.26 | 389 (M + H) |
| 44 | | Ref.7 | Ba31 | F, G | IM.1 | a, b | C-2 | 1.59 | 389 (M + H) |

TABLE 1-continued

| Exp. | Str. | S.M.1 | S.M.2 | Synth.1 | S.M.3 | Synth.2 | LC-MS method | R.T. | MS |
|---|---|---|---|---|---|---|---|---|---|
| 45 | | Ref.7 | Ba32 | F, G | IM.1 | a, b | C-2 | 1.23 | 424 (M + H) |
| 46 | | Ref.7 | Ba33 | F, G | IM.1 | a, b | C-2 | 0.98 | 354 (M + H) |
| 47 | | Ref.7 | Ba34 | F, G | IM.1 | a, b | C-2 | 0.97 | 370 (M + H) |
| 48 | | Ref.7 | Ba35 | F, G | IM.1 | a, b | C-2 | 0.95 | 386 (M + H) |
| 49 | | Ref.7 | Ba36 | F, G | IM.1 | a, b | C-2 | 0.96 | 386 (M + H) |

TABLE 1-continued
| Exp. | Str. | S.M.1 | S.M.2 | Synth.1 | S.M.3 | Synth.2 | LC-MS method | R.T. | MS |
|---|---|---|---|---|---|---|---|---|---|
| 50 | 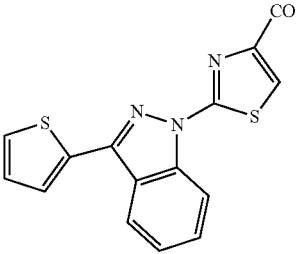 | Ref.7 | Ba37 | J, G | IM.1 | a, b | C-1 | 1.69 | 328 (M + H) |
| 51 | 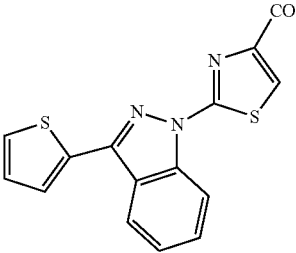 | Ref.7 | Ba38 | F, G | IM.1 | a, b | C-1 | 1.69 | 328 (M + H) |
| 52 | 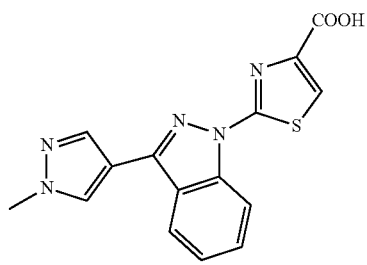 | Ref.7 | Ba39 | F, G | IM.1 | a, b | C-1 | 1.19 | 326 (M + H) |
| 53 | 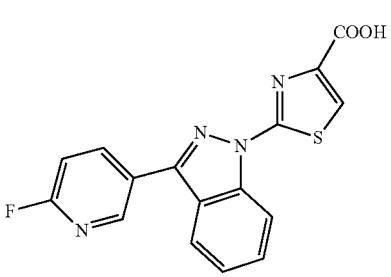 | Ref.7 | Ba40 | J, G | IM.1 | a, b | C-1 | 1.49 | 341 (M + H) |
| 54 | 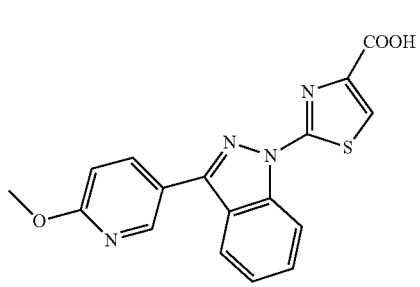 | Ref. 12 | — | G | IM.1 | a, b | C-1 | 1.62 | 353 (M + H) |

TABLE 1-continued
| Exp. | Str. | S.M.1 | S.M.2 | Synth.1 | S.M.3 | Synth.2 | LC-MS method | R.T. | MS |
|---|---|---|---|---|---|---|---|---|---|
| 55 | 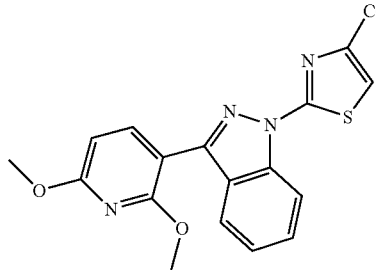 | Ref.7 | Ba41 | J, G | IM.1 | a, b | C-1 | 1.79 | 383 (M + H) |
| 56 | 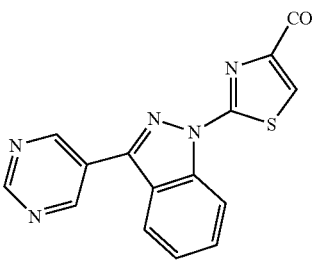 | Ref.7 | Ba42 | J, G | IM.1 | a, b | C-1 | 0.27 | 324 (M + H) |
| 57 | 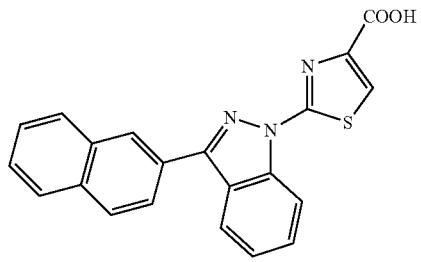 | Ref.7 | Ba43 | F, G | IM.1 | a, b | C-1 | 1.99 | 372 (M + H) |
| 58 | 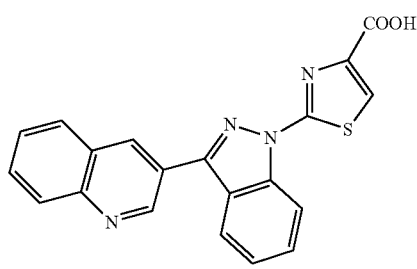 | Ref.7 | Ba44 | J, G | IM.1 | a, b | C-1 | 1.57 | 373 (M + H) |
| 59 | 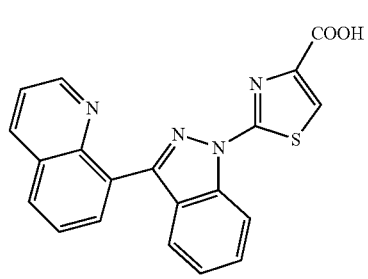 | Ref.7 | Ba45 | J, G | IM.1 | a, b | C-1 | 1.53 | 373 (M + H) |

TABLE 1-continued
| Exp. | Str. | S.M.1 | S.M.2 | Synth.1 | S.M.3 | Synth.2 | LC-MS method | R.T. | MS |
|---|---|---|---|---|---|---|---|---|---|
| 60 | 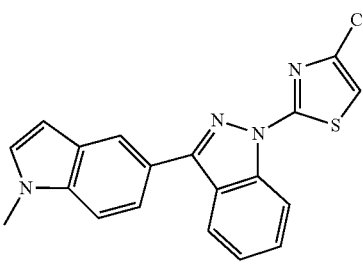 | Ref.7 | Ba46 | J, G | IM.1 | a, b | C-1 | 1.74 | 375 (M + H) |
| 61 | 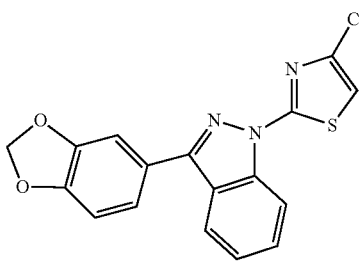 | Ref.7 | Ba47 | F, G | IM.1 | a, b | C-1 | 1.66 | 366 (M + H) |
| 62 | 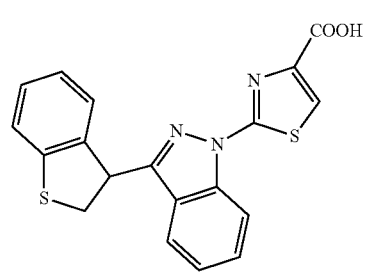 | Ref.7 | Ba48 | F, G | IM.1 | a, b | C-1 | 1.94 | 378 (M + H) |
| 63 | 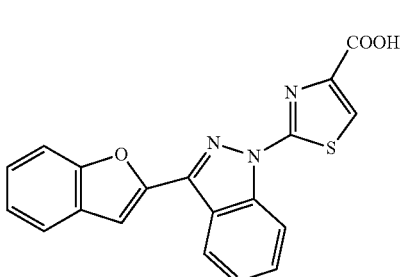 | Ref.7 | Ba49 | J, G | IM.1 | a, b | C-1 | 1.88 | 362 (M + H) |
| 64 | 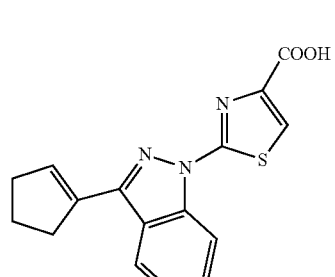 | Ref.10 | — | — | IM.1 | a, b | B-1 | 5.04 | 312 (M + H) |

TABLE 1-continued

|  |  |  |  |  |  |  | LC-MS | | |
| --- | --- | --- | --- | --- | --- | --- | --- | --- | --- |
| Exp. | Str. | S.M.1 | S.M.2 | Synth.1 | S.M.3 | Synth.2 | method | R.T. | MS |
| 65 | | Ref.7 | Ba50 | F, G | IM.1 | a, b | C-1 | 2.02 | 326 (M + H) |
| 66 | | Ref.7 | Ba51 | F, G | IM.1 | a, b | C-1 | 1.22 | 328 (M + H) |
| 67 | | Ref.7 | Am1 | K, G | IM.1 | a, b | C-1 | 1.87 | 329 (M + H) |
| 68 | | Ref.13 | — | G | IM.1 | a, b | C-1 | 1.56 | 329 (M + H) |
| 69 | | Ref.7 | Am2 | K, G | IM.1 | a, b | C-1 | 1.74 | 343 (M + H) |

TABLE 1-continued

| Exp. | Str. | S.M.1 | S.M.2 | Synth.1 | S.M.3 | Synth.2 | LC-MS method | R.T. | MS |
|---|---|---|---|---|---|---|---|---|---|
| 70 | | Ref.7 | Am3 | K, G | IM.1 | a, b | C-1 | 1.66 | 359 (M + H) |
| 71 | | Ref.7 | Am4 | K, G | IM.1 | a, b | C-1 | 1.22 | 407 (M + H) |
| 72 | | FKet3 | — | C | IM.1 | a, b | C-1 | 0.97 | 340 (M + H) |
| 73 | | FKet4 | — | C | IM.1 | a, b | B-1 | 5.32 | 340 (M + H) |
| 74 | | FKet5 | — | C | IM.1 | a, b | C-1 | 1.19 | 390 (M + H) |

TABLE 1-continued

| Exp. | Str. | S.M.1 | S.M.2 | Synth.1 | S.M.3 | Synth.2 | LC-MS method | R.T. | MS |
|---|---|---|---|---|---|---|---|---|---|
| 75 | (3-phenyl-5-methoxy-indazol-1-yl thiazole-4-COOH) | Ref.3 | — | — | IM.1 | a, b | C-1 | 0.86 | 352 (M + H) |
| 76 | (3-phenyl-6-fluoro-indazol-1-yl thiazole-4-COOH) | FKet6 | — | C | IM.1 | a, b | C-1 | 0.91 | 340 (M + H) |
| 77 | (3-phenyl-6-CF3-indazol-1-yl thiazole-4-COOH) | FKet7 | — | C | IM.1 | a, b | C-1 | 1.14 | 390 (M + H) |
| 78 | (3-phenyl-6-phenyl-indazol-1-yl thiazole-4-COOH) | Ref.22 | — | — | IM.1 | a, b | B-1 | 6.45 | 398 (M + H) |
| 79 | (3-phenyl-7-OH-indazol-1-yl thiazole-4-COOEt) | Ref.20 | — | — | IM.1 | a | B-1 | 5.77 | 366 (M + H) |

TABLE 1-continued

| Exp. | Str. | S.M.1 | S.M.2 | Synth.1 | S.M.3 | Synth.2 | LC-MS method | R.T. | MS |
|---|---|---|---|---|---|---|---|---|---|
| 80 | (3-phenyl-6-hydroxy-indazol-1-yl thiazole-4-carboxylic acid) | Exp.79 | — | — | — | b | B-1 | 4.69 | 338 (M + H) |
| 81 | (3-phenyl-6-methoxy-indazol-1-yl thiazole-4-carboxylic acid) | Exp.79 | — | — | Ah1 | e, b | B-1 | 5.47 | 352 (M + H) |
| 82 | (3-phenyl-6-ethoxy-indazol-1-yl thiazole-4-carboxylic acid) | Exp.79 | — | — | Ah2 | e, b | C-1 | 1.92 | 366 (M + H) |
| 83 | (3-phenyl-6-propoxy-indazol-1-yl thiazole-4-carboxylic acid) | Exp.79 | — | — | Ah3 | e, b | C-1 | 2.10 | 379 (M + H) |
| 84 | (3-phenyl-6-isopropoxy-indazol-1-yl thiazole-4-carboxylic acid) | Exp.79 | — | — | Ah4 | e, b | B-1 | 5.98 | 380 (M + H) |

TABLE 1-continued

| Exp. | Str. | S.M.1 | S.M.2 | Synth.1 | S.M.3 | Synth.2 | LC-MS method | R.T. | MS |
|---|---|---|---|---|---|---|---|---|---|
| 85 | | Exp.79 | — | — | Ah5 | e, b | B-1 | 6.27 | 394 (M + H) |
| 86 | | Exp.79 | — | — | Ah6 | e, b | B-1 | 6.35 | 394 (M + H) |
| 87 | | Exp.6 | — | — | — | b | C-1 | 2.21 | 406 (M + H) |
| 88 | | Exp.79 | — | — | Ah7 | e, b | C-1 | 1.73 | 429 (M + H) |

TABLE 1-continued

| Exp. | Str. | S.M.1 | S.M.2 | Synth.1 | S.M.3 | Synth.2 | LC-MS method | R.T. | MS |
|---|---|---|---|---|---|---|---|---|---|
| 89 | | Exp.79 | — | — | Ah8 | e, b | C-1 | 2.15 | 428 (M + H) |
| 90 | | Exp.79 | — | — | Ah9 | e, b | C-1 | 2.28 | 512 (M + H) |
| 91 | | Exp.4 | — | — | — | b | C-1 | 1.34 | 337 (M + H) |
| 92 | | Exp.5 | — | — | — | b | C-1 | 1.70 | 382 (M + H) |

TABLE 1-continued

| Exp. | Str. | S.M.1 | S.M.2 | Synth.1 | S.M.3 | Synth.2 | LC-MS method | R.T. | MS |
|---|---|---|---|---|---|---|---|---|---|
| 93 | (structure) | Ad1 | — | A, B, C | IM.1 | a, b | C-1 | 1.70 | 382 (M + H) |
| 94 | (structure) | Exp.3 | — | — | — | b | B-1 | 5.24 | 321 (M + H) |
| 95 | (structure) | IM.2 | — | — | IM.1 | a, b | A-1 | 5.04 | 321 (M + H) |
| 96 | (structure) | IM.3 | — | — | IM.1 | a, b | A-1 | 4.44 | 323 (M + H) |
| 97 | (structure) | Ad2 | — | A, B, C | IM.1 | a, b | B-1 | 4.30 | 323 (M + H) |

TABLE 1-continued

| Exp. | Str. | S.M.1 | S.M.2 | Synth.1 | S.M.3 | Synth.2 | LC-MS method | R.T. | MS |
|---|---|---|---|---|---|---|---|---|---|
| 98 | | Ket1 | — | L | IM.1 | a, b | C-1 | 1.77 | 312 (M + H) |
| 99 | | Ket2 | — | L | IM.1 | a, b | C-1 | 1.89 | 326 (M + H) |
| 100 | | Ref.25 | — | — | IM.1 | a, b | C-1 | 1.94 | 340 (M + H) |
| 101 | | Ket3 | — | L | IM.1 | a, b | C-1 | 1.85 | 354 (M + H) |
| 102 | | Ket4 | — | L | IM.1 | a, b | C-1 | 1.94 | 394 (M + H) |

TABLE 1-continued

| Exp. | Str. | S.M.1 | S.M.2 | Synth.1 | S.M.3 | Synth.2 | LC-MS method | R.T. | MS |
|---|---|---|---|---|---|---|---|---|---|
| 103 | (structure) | Ket4 | — | L | IM.1 | a, b | C-1 | 1.79 | 394 (M + H) |
| 104 | (structure) | Exp.8 | — | — | — | b | C-1 | 1.78 | 404 (M + H) |
| 105 | (structure) | Ref.18 | Ba15 | J, G | IM.1 | a, b | C-1 | 2.04 | 396 (M + H) |
| 106 | (structure) | Ref.28 | — | — | IM.1 | a, b | C-1 | 1.68 | 391 (M + H) |

TABLE 2

| Reagent | Structure | Supl. |
|---|---|---|
| Ba1 | (2-methylphenylboronic acid) | Ald |
| Ba2 | (2-trifluoromethoxyphenylboronic acid) | WAKO |
| Ba3 | (3-chlorophenylboronic acid) | Ald |
| Ba4 | (3-trifluoromethylphenylboronic acid) | WAKO |

TABLE 2-continued

| Reagent | Structure | Supl. |
|---|---|---|
| Ba5 | 3-methylphenylboronic acid | Ald |
| Ba6 | biphenyl-3-ylboronic acid | Ald |
| Ba7 | 3-((tert-butoxy)methyl)phenylboronic acid | Front |
| Ba8 | 3-methoxyphenylboronic acid | Ald |
| Ba9 | 3-(trifluoromethoxy)phenylboronic acid | WAKO |
| Ba10 | 3-acetylphenylboronic acid | Ald |
| Ba11 | 3-cyanophenylboronic acid | Comb |
| Ba12 | 4-chlorophenylboronic acid | Ald |
| Ba13 | 4-methoxyphenylboronic acid | WAKO |
| Ba14 | 4-(trifluoromethoxy)phenylboronic acid | Ald |
| Ba15 | 4-phenoxyphenylboronic acid | Ald |
| Ba16 | 4-(methoxymethyl)phenylboronic acid | Front |
| Ba17 | 4-methylphenylboronic acid | Ald |
| Ba18 | 4-vinylphenylboronic acid | TCI |
| Ba19 | 4-tert-butylphenylboronic acid | LANC |
| Ba20 | biphenyl-4-ylboronic acid | LANC |
| Ba21 | 4-(methylthio)phenylboronic acid | Ald |
| Ba22 | 4-(methylsulfinyl)phenylboronic acid | LANC |

TABLE 2-continued

| Reagent | Structure | Supl. |
|---|---|---|
| Ba23 | 4-acetylphenylboronic acid | WAKO |
| Ba24 | 4-benzoylphenylboronic acid | WAKO |
| Ba25 | 4-(dimethylamino)phenylboronic acid | Ald |
| Ba26 | 3,4-difluorophenylboronic acid | Ald |
| Ba27 | 3,5-difluorophenylboronic acid | Ald |
| Ba28 | 3-chloro-4-fluorophenylboronic acid | Ald |
| Ba29 | 3,4-dichlorophenylboronic acid | Ald |
| Ba30 | 2,4-dichlorophenylboronic acid | TCI |
| Ba31 | 3,5-dichlorophenylboronic acid | WAKO |
| Ba32 | 2-chloro-4-(trifluoromethyl)phenylboronic acid | WAKO |
| Ba33 | 4-fluoro-2-methylphenylboronic acid | WAKO |
| Ba34 | 3-fluoro-4-methoxyphenylboronic acid | Ald |
| Ba35 | 3-chloro-4-methoxyphenylboronic acid | Ald |
| Ba36 | 4-chloro-2-methoxyphenylboronic acid | Ald |
| Ba37 | thiophene-2-boronic acid | MAYB |
| Ba38 | thiophene-3-boronic acid | LANC |

TABLE 2-continued
| Reagent | Structure | Supl. |
|---|---|---|
| Ba39 | 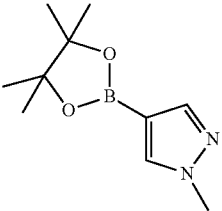 | BMol |
| Ba40 | 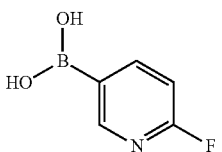 | Ald |
| Ba41 | 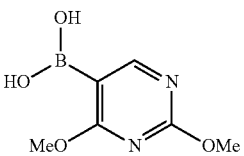 | BMol |
| Ba42 | 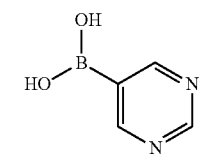 | Front |
| Ba43 | 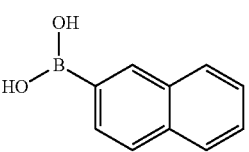 | TCI |
| Ba44 | 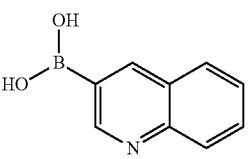 | WAKO |
| Ba45 | 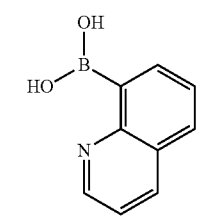 | Front |
| Ba46 | 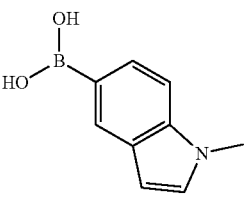 | WAKO |
| Ba47 | 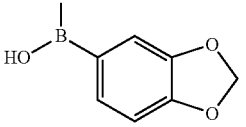 | Ald |
| Ba48 | 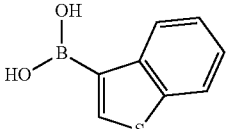 | Ald |
| Ba49 | 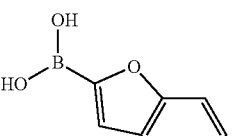 | LANC |
| Ba50 | 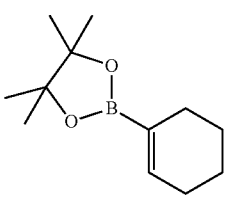 | WAKO |
| Ba51 | 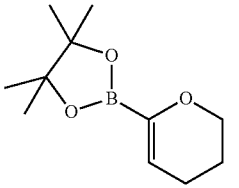 | Front |
| Am1 | 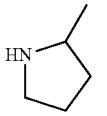 | Ald |
| Am2 | 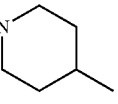 | Acros |
| Am3 | 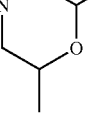 | Ald |
| Am4 | 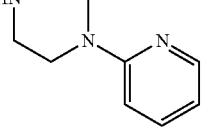 | TCI |
| FKet1 | 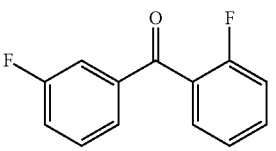 | Apollo |

TABLE 2-continued

| Reagent | Structure | Supl. |
|---|---|---|
| FKet2 | 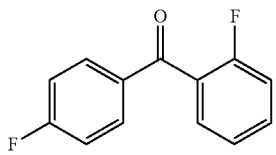 | TCI |
| FKet3 | 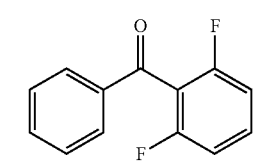 | Acros |
| FKet4 | 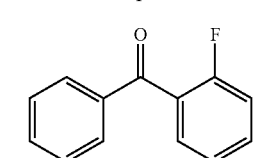 | Fchem |
| FKet5 | 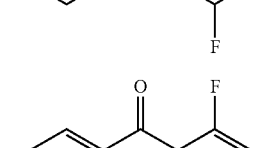 | Fchem |
| FKet6 | 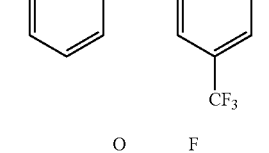 | Acros |
| FKet7 | 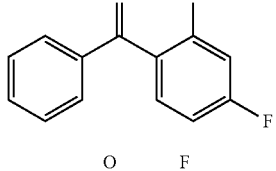 | Fchem |
| Ah1 | Me—I | TCI |
| Ah2 | 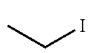 | KANTO |
| Ah3 | 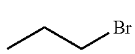 | TCI |
| Ah4 | 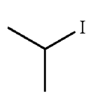 | TCI |
| Ah5 | 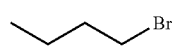 | TCI |
| Ah6 | 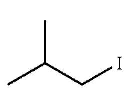 | TCI |
| Ah7 | 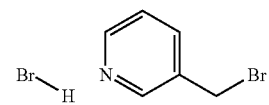 | Ald |

TABLE 2-continued

| Reagent | Structure | Supl. |
|---|---|---|
| Ah8 | 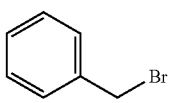 | Ald |
| Ah9 | 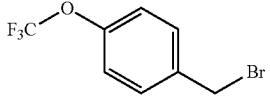 | TCI |
| Ad1 | 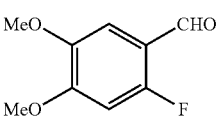 | TCI |
| Ad2 | 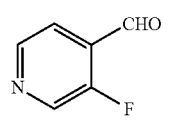 | Ald |
| Ket1 | 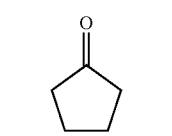 | TCI |
| Ket2 | 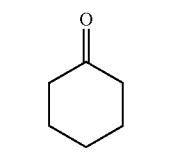 | TCI |
| Ket3 | 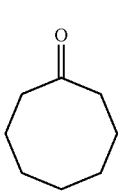 | TCI |
| Ket4 | 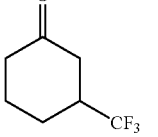 | MAYB |

Reference Example 29

3-Phenyl-1H-pyrazolo[4,3-c]pyridine

A 2 M aqueous solution of sodium hydroxide (20 mL, manufactured by Kanto Chemical Co., Inc.) was added to a solution of 4-chloropyridine hydrochloride (3.18 g) in tetrahydrofuran (20 mL, manufactured by Kanto Chemical Co., Inc.) to neutralize the solution, and then the mixture was extracted with ethyl acetate (3×50 mL), washed with brine mL), and dried (MgSO$_4$). The solvent was then evaporated to give 4-chloropyridine. 4-Chloropyridine was added dropwise to a solution of lithium diisopropylamide (23% solution in tetrahydrofuran/ethylbenzene/heptane, 14.1 mL, manufactured by Sigma-Aldrich Corp.) in tetrahydrofuran (40 mL, manufactured by Kanto Chemical Co., Inc.) at −78° C., and the mixture was stirred for 30 minutes. Subsequently, N-methoxy-N-methylbenzamide (3.55 mL, manufactured by Sigma-Aldrich Corp.) was further added to the mixture at the same temperature, and while the temperature was gradually raised to room temperature, the mixture was stirred overnight. A saturated aqueous solution of ammonium chloride (50 mL) was added to the reaction solution, and the mixture was extracted with ethyl acetate (3×50 mL), washed with brine (50 mL), and dried ($MgSO_4$). The solvent was then evaporated, isopropanol (20 mL, manufactured by Kanto Chemical Co., Inc.) and hydrazine hydrate (5.0 mL, manufactured by Tokyo Chemical Industry Co., Ltd.) were added to the obtained residue, and the mixture was stirred for one hour at room temperature. A saturated aqueous solution of ammonium chloride (30 mL) was added to the reaction solution, and the mixture was extracted with ethyl acetate (3×30 mL), washed with brine (50 mL), and dried ($MgSO_4$). The solvent was then evaporated, and a saturated aqueous solution of ammonium chloride (50 mL) was added to the reaction solution. The mixture was extracted with ethyl acetate (3×50 mL), washed with brine (50 mL), and dried ($MgSO_4$), and then the solvent was evaporated. The resulting residue was purified by silica gel column chromatography (hexane:ethyl acetate=2:1), to give 4.1 g of the title compound. LC-MS: HPLC retention time 0.64 minutes, m/z (M+H) 232, condition C-1.

Reference Example 30

(2,6-Difluoropyridin-3-yl)(phenyl)methanone

To a solution of 2,6-difluoropyridine (1.0 g, manufactured by Tokyo Chemical Industry Co., Ltd.) in tetrahydrofuran (40 mL, manufactured by Kanto Chemical Co., Inc.), lithium diisopropylamide (23% solution in tetrahydrofuran/ethylbenzene/heptane, 5.79 mL, manufactured by Sigma-Aldrich Corp.) was added dropwise at −78° C., and the mixture was stirred for 30 minutes. Subsequently, N-methoxy-N-methylbenzamide (1.46 mL, manufactured by Sigma-Aldrich Corp.) was further added at the same temperature, and while the temperature was gradually raised to room temperature, the mixture was stirred overnight. A saturated aqueous solution of ammonium chloride (30 mL) was added to the reaction solution, and the mixture was extracted with ethyl acetate (3×30 mL), washed with brine (30 mL), and dried ($MgSO_4$). The solvent was then evaporated, to give 1.90 g of the title compound. LC-MS: HPLC retention time 1.63 minutes, m/z (M−F+OMe) 232, condition C-1.

Reference Example 31

6-(3-Methylbutan-2-ylthio)-3-phenyl-1H-pyrazolo[3,4-b]pyridine

3-Methyl-2-butanethiol (238 mg, manufactured by Wako Pure Chemical Industries, Ltd.) was added to a solution of the Reference Example 30 (100 mg) in N-methylpyrrolidone (4.5 mL, manufactured by Kanto Chemical Co., Inc.), and the mixture was stirred for one hour at room temperature. Subsequently, hydrazine hydrate (73 μL, manufactured by Tokyo Chemical Industry Co., Ltd.) was added thereto, and the mixture was stirred overnight at the same temperature. Water (5 mL) was added to the reaction solution, and the mixture was extracted with chloroform (3×10 mL), washed with brine (10 mL), and dried ($MgSO_4$). The solvent was then evaporated, to give 6.0 mg of the title compound. LC-MS: HPLC retention time 2.12 minutes, m/z (M+H) 298, condition C-1.

Reference Example 32

6-(Azetidin-1-yl)-3-phenyl-1H-pyrazolo[3,4-b]pyridine

Azetidine (130 mg, manufactured by Sigma-Aldrich Corp.) was added to a solution of the Reference Example 30 (100 mg) in N-methylpyrrolidone (4.5 mL, manufactured by Kanto Chemical Co., Inc.), and the mixture was stirred for one hour at room temperature. Subsequently, hydrazine hydrate (73 μL, manufactured by Tokyo Chemical Industry Co., Ltd.) was added thereto, and the mixture was stirred overnight at the same temperature. Water (5 mL) was added to the reaction solution, and the mixture was extracted with chloroform (3×10 mL), washed with brine (10 mL), and dried ($MgSO_4$). The solvent was then evaporated, to give 90 mg of the title compound. LC-MS: HPLC retention time 1.22 minutes, m/z (M+H) 251, condition C-1.

Reference Example 33

6-Chloro-3-phenyl-1H-pyrazolo[3,4-b]pyridine

To a solution of 2-chloro-6-fluoropyridine (1.0 g, manufactured by Matrix Chemical LLC) in tetrahydrofuran (40 mL, manufactured by Kanto Chemical Co., Inc.), lithium diisopropylamide (23% solution in tetrahydrofuran/ethylbenzene/heptane, 5.07 mL, manufactured by Sigma-Aldrich Corp.) was added dropwise at −78° C., and the mixture was stirred for 30 minutes. Subsequently, N-methoxy-N-methylbenzamide (1.27 mL, manufactured by Sigma-Aldrich Corp.) was added thereto at the same temperature, and while the temperature was gradually raised to room temperature, the mixture was stirred overnight. A saturated aqueous solution of ammonium chloride (30 mL) was added to the reaction solution, and the mixture was extracted with ethyl acetate (3×30 mL), washed with brine (30 mL), and dried ($MgSO_4$). The solvent was then evaporated, and isopropanol (20 mL, manufactured by Kanto Chemical Co., Inc.) and hydrazine hydrate (1.22 mL, manufactured by Tokyo Chemical Industry Co., Ltd.) were added to the obtained residue. The mixture was heated and stirred for 12 hours at 80° C. The mixture was cooled to room temperature, and then hexane (10 mL) was added to the reaction solution. The solvent was evaporated, to give 180 mg of the title compound. LC-MS: HPLC retention time 1.53 minutes, m/z (M+H) 230, condition C-1.

Reference Example 34

3-(3-Phenyl-1H-pyrazolo[3,4-b]pyridin-6-ylthio)phenol 3-(Tertiary-butyldimethylsiloxy)thiophenol (548 mg, manufactured by Lancaster Chemical Corp.) was added to a solution of the Reference Example 30 (100 mg) in N-methylpyrrolidone (4.5 mL, manufactured by Kanto Chemical Co., Inc.), and the mixture was stirred for one hour at room temperature. Subsequently, hydrazine hydrate (73 μL, manufactured by Tokyo Chemical Industry Co., Ltd.) was added thereto, and the mixture was stirred overnight at the same temperature. Water (5 mL) was added to the reaction solution, and the mixture was extracted with chloroform (3×10 mL), washed with brine (10 mL), and dried ($MgSO_4$). The solvent was then evaporated, to give 62.3 mg of the title compound. LC-MS: HPLC retention time 1.51 minutes, m/z (M+H) 320, condition C-1.

Example 107

Ethyl 2-(3-phenyl-6-propionamide-1H-indazol-1-yl)thiazole-4-carboxylate

To a solution of the Example 4 (30 mg) in dichloromethane (350 μL, manufactured by Wako Pure Chemical Industries, Ltd.), triethylamine (35 μL, manufactured by Wako Pure Chemical Industries, Ltd.) and propionic acid chloride (20 μL, manufactured by Tokyo Chemical Industry Co., Ltd.) were added, and the mixture was stirred overnight. Water (10 mL) was added to the reaction solution, and the mixture was extracted with ethyl acetate (3×10 mL), washed with brine (10 mL), and dried (MgSO$_4$). The solvent was then evaporated. The resulting residue was purified by silica gel column chromatography (hexane:ethyl acetate=9:1), to give 35.1 mg of the title compound. LC-MS: HPLC retention time 2.04 minutes, m/z 420 (M+H), condition C-1.

Example 108

Ethyl 2-[6-{2-(dimethylamino)acetamide}-3-phenyl-1H-indazol-1-yl]thiazole-4-carboxylate Dimethylaminoacetyl chloride (20 μL, manufactured by Lancaster Chemical Corp.) was added to a solution of the Example 4 (20 mg) in pyridine (350 μL, manufactured by Kanto Chemical Co., Inc.), and the mixture was stirred overnight at room temperature. Water (10 mL) was added to the reaction solution, and the mixture was extracted with ethyl acetate (3×10 mL), washed with brine (10 mL), and dried (MgSO$_4$). The solvent was then evaporated. The resulting residue was purified by silica gel column chromatography (hexane:ethyl acetate=9:1), to give 18.7 mg of the title compound. LC-MS: HPLC retention time 0.80 minutes, m/z 450 (M+H), condition C-1.

Example 109

Ethyl 2-(3-phenyl-6-pivalamide-1H-indazol-1-yl)thiazole-4-carboxylate

To a solution of pivalic acid (17 mg, manufactured by Tokyo Chemical Industry Co., Ltd.) in dimethylformamide (350 μL, manufactured by Kanto Chemical Co., Inc.), 1-hydroxybenzotriazole hydrate (22 mg, manufactured by Kokusan Chemical Co., Ltd.) and 1-ethyl-3-(3-dimethylaminopropyl)-carbodiimide hydrochloride (32 mg, manufactured by Kokusan Chemical Co., Ltd.) were added at room temperature, and then a solution of the Example 4 (20 mg) in dimethylformamide (800 μL, manufactured by Kanto Chemical Co., Inc.), and triethylamine (28.1 μL) were added thereto. The mixture was stirred overnight. Saturated sodium hydrogen carbonate (500 mL) was added to the reaction solution, and then the mixture was extracted with ethyl acetate (3×5 mL), washed with brine (10 mL), and dried (MgSO$_4$). The solvent was then evaporated. The resulting residue was purified by silica gel column chromatography (hexane:ethyl acetate=9:1), to give 24 mg of the title compound. LC-MS: HPLC retention time 1.98 minutes, m/z 449 (M+H), condition C-1.

Example 110

Ethyl 2-{6-(methylsulfonamide)-3-phenyl-1H-indazol-1-yl}thiazole-4-carboxylate

To a solution of the Example 4 (30 mg) in dichloromethane (800 μL, manufactured by Wako Pure Chemical Industries, Ltd.), triethylamine (35 μL, manufactured by Wako Pure Chemical Industries, Ltd.) and methanesulfonic acid chloride (28 μL, manufactured by Tokyo Chemical Industry Co., Ltd.) were added, and the mixture was stirred overnight at room temperature. Water (10 mL) was added to the reaction solution, and the mixture was extracted with ethyl acetate (3×10 mL), washed with brine (10 mL), and dried (MgSO$_4$). The solvent was then evaporated. The resulting residue was purified by silica gel column chromatography (hexane:ethyl acetate=9:1), to give 37 mg of the title compound. LC-MS: HPLC retention time 1.98 minutes, m/z 442 (M+H), condition C-1.

Example 111

Ethyl 2-{6-(cyclopropanesulfonamide)-3-phenyl-1H-indazol-1-yl}thiazole-4-carboxylate Cyclopropanesulfonyl chloride (20 μL, manufactured by Matrix Chemical LLC) was added to a solution of the Example 4 (20 mg) in pyridine (350 μL, manufactured by Kanto Chemical Co., Inc.), and the mixture was stirred overnight at room temperature. Water (10 mL) was added to the reaction solution, and the mixture was extracted with ethyl acetate (3×10 mL), washed with brine (10 mL), and dried (MgSO$_4$). The solvent was then evaporated. The resulting residue was purified by silica gel column chromatography (hexane:ethyl acetate=9:1), to give 27.5 mg of the title compound. LC-MS: HPLC retention time 1.74 minutes, m/z 469 (M+H), condition C-1.

Example 112

Ethyl 2-{6-(methylamino)-3-phenyl-1H-indazol-1-yl}thiazole-4-carboxylate

Example 113

Ethyl 2-{6-(dimethylamino)-3-phenyl-1H-indazol-1-yl}thiazole-4-carboxylate

A 36% aqueous solution of formaldehyde (33 mg, manufactured by Kanto Chemical Co., Inc.) was added to a solution of the Example 4 (45 mg) in dichloroethane (350 μL, manufactured by Kanto Chemical Co., Inc.), and the mixture was stirred for one hour at room temperature. The solvent of the reaction solution was evaporated, and then dichloroethane (350 μL, manufactured by Kanto Chemical Co., Inc.), acetic acid (100 μL, manufactured by Wako Pure Chemical Industries, Ltd.), and sodium triacetoxyborohydride (89 mg, manufactured by Sigma-Aldrich Corp.) were added to the reaction solution. The mixture was stirred overnight at room temperature. Water (10 mL) was added to the reaction solution, and the mixture was extracted with ethyl acetate (3×10 mL), washed with brine (10 mL), and dried (MgSO$_4$). The solvent was then evaporated. The resulting residue was purified by silica gel column chromatography (hexane:ethyl acetate=9:1), to give 3.1 mg of a monomethyl form as a more polar compound and 6.1 mg of a dimethyl form as a less polar compound. Monomethyl form (Example 112): LC-MS: HPLC retention time 1.90 minutes, m/z (M+H) 379, condition C-1. Dimethyl form (Example 113): LC-MS: HPLC retention time 2.20 minutes, m/z (M+H) 393, condition C-1.

Example 114

Ethyl 2-(6-iodo-3-phenyl-1H-indazol-1-yl)thiazole-4-carboxylate

To a solution of the Example 4 (20 mg) in acetonitrile (550 μL, manufactured by Wako Pure Chemical Industries, Ltd.), t-butyl nitrite (26 μL, manufactured by Acros Organics, Inc.) and iodine (42 mg, manufactured by Kanto Chemical Co., Inc.) were added at room temperature, and the mixture was heated to reflux for 2 hours. The reaction solution was cooled to room temperature, and then water (5 mL) was added. The mixture was extracted with ethyl acetate (3×10 mL), washed with brine (10 mL), and dried ($MgSO_4$), and then the solvent was evaporated. The resulting residue was purified by silica gel column chromatography (hexane:ethyl acetate=9:1), to give 37.2 mg of the title compound. LC-MS: HPLC retention time 2.50 minutes, m/z (M+H) 475, condition C-1.

Example 115

Ethyl (E)-2-{3-phenyl-6-(prop-1-enyl)-1H-indazol-1-yl}thiazole-4-carboxylate

To a solution of the Example 114 (30 mg) in dimethylformamide (500 μL, manufactured by Kanto Chemical Co., Inc.), tetrakis(triphenylphosphine)palladium (29 mg, manufactured by Tokyo Chemical Industry Co., Ltd.), trans-1-propen-1-ylboronic acid (16 mg, manufactured by Sigma-Aldrich Corp.), and a 2 M aqueous solution of sodium carbonate (20 μL) were added, and the mixture was stirred overnight at 100° C. Water (400 μL) was added to the reaction solution, and then the mixture was extracted with ethyl acetate (3×5 mL), washed with brine (10 mL), and dried ($MgSO_4$). The solvent was then evaporated. The resulting residue was purified by silica gel column chromatography (hexane:ethyl acetate=9:1), to give 16.8 mg of the title compound. LC-MS: HPLC retention time 2.39 minutes, m/z (M+H) 390, condition C-1.

Example 116

Ethyl 2-(3-phenyl-6-vinyl-1H-indazol-1-yl)thiazole-4-carboxylate

To a solution of the Example 114 (45 mg) in dioxane (500 μL, manufactured by Kanto Chemical Co., Inc.), tetrakis(triphenylphosphine)palladium (22 mg, manufactured by Tokyo Chemical Industry Co., Ltd.) and tributylvinyltin (33 mg, manufactured by Sigma-Aldrich Corp.) were added, and the mixture was stirred overnight at 100° C. Water (400 μL) was added to the reaction solution, and then the mixture was extracted with ethyl acetate (3×5 mL), washed with brine (10 mL), and dried ($MgSO_4$). The solvent was then evaporated. The resulting residue was purified by silica gel column chromatography (hexane:ethyl acetate=9:1), to give 16.8 mg of the title compound. LC-MS: HPLC retention time 2.25 minutes, m/z (M+H) 376, condition C-1.

Example 117

2-(6-Ethoxy-3-phenyl-1H-pyrazolo[3,4-b]pyridin-1-yl)thiazole-4-carboxylic acid

To an ethanol (2 mL, manufactured by Wako Pure Chemical Industries, Ltd.) solution of ethyl 2-(6-chloro-3-phenyl-1H-pyrazolo[3,4-b]pyridin-1-yl)thiazole-4-carboxylate (33 mg), which had been synthesized from the compound of Reference Example 33 according to the method of Example 3, 5 M sodium hydroxide (500 μL, manufactured by Kanto Chemical Co., Inc.) was added, and the mixture was stirred for one hour at room temperature. 5 M hydrochloric acid (500 μL, manufactured by Kanto Chemical Co., Inc.) was added to neutralize the mixture, and then the mixture was extracted with chloroform (3×3 mL), washed with brine (3 mL), and dried ($MgSO_4$). The solvent was then evaporated, to give 17.6 mg of the title compound. LC-MS: HPLC retention time 1.38 minutes, m/z (M+H) 367, condition C-1.

Example 118

2-(6-Cyano-3-phenyl-1H-indazol-1-yl)thiazole-4-carboxylic acid

Example 119

2-(6-Carboxy-3-phenyl-1H-indazol-1-yl)thiazole-4-carboxylic acid

To an ethanol (2 mL, manufactured by Wako Pure Chemical Industries, Ltd.) solution of ethyl 2-(6-cyano-3-phenyl-1H-indazol-1-yl)thiazole-4-carboxylate (86.5 mg), which had been synthesized from 4-cyano-2-fluorobenzaldehyde (manufactured by Apollo Chemical Company LLC) according to the methods of Reference Examples 1, 2 and 3 and Example 3, 5 M sodium hydroxide (500 μL, manufactured by Kanto Chemical Co., Inc.) was added, and the mixture was stirred for one hour at room temperature. 5 M hydrochloric acid (500 μL, manufactured by Kanto Chemical Co., Inc.) was added to neutralize the mixture, and then the mixture was extracted with chloroform (3×3 mL), washed with brine (3 mL), and dried ($MgSO_4$). The solvent was then evaporated. The resulting residue was purified by preparative thin layer chromatography (hexane:ethyl acetate=2:1), to give 3.1 mg of a cyano form as a more polar compound and 6.1 mg of a carboxy form as a less polar compound. Cyano form (Example 118): LC-MS: HPLC retention time 1.36 minutes, m/z (M+H) 347, condition C-1. Carboxy form (Example 119): LC-MS: HPLC retention time 0.96 minutes, m/z (M+H) 366, condition C-1.

Examples 120 to 179

The production of the compounds of Examples 120 to 179 will be described below. The details of the Examples 120 to 179 are indicated in Table 3. The meanings of the symbols in Table 3 are as follows.

"Exp.": Example No., "Str.": Example compound, "S.M.1", "S.M.2" and "S.M.3": starting material for the production of the corresponding Example compound. The symbols in the columns of "S.M.1", "S.M.2" and "S.M.3" represent the following starting materials. "IM.1": ethyl 2-bromo-4-thiazolecarboxylate (produced according to the method described in J. Org. Chem., 61, 4623-4633 (1996)). Furthermore, if the starting material is the compound described in the Examples or Reference Examples in the present specification, the starting materials are indicated as the Example Nos. or Reference Example Nos. thereof (in the case of the Example No., indicated as "Exp. (Example No.)", and in the case of the Reference Example No., indicated as "Ref. (Reference Example No.)." For example, "Ref.2" indicates the compound of Reference Example 2). In the case of a commercially available reagent, the compound indicates the commercially available reagent corresponding to the symbol described in the column of "Reagent" in the Table 4. If one or two starting materials have been used, only the relevant starting materials are indicated.

"Synth.1" and "Synth.2": methods for production of the corresponding Example compounds. The symbols in the columns of "Synth.1" and "Synth.2" indicate the following production methods. "A" indicates the production method described in Reference Example 1; "B" indicates the production method described in Reference Example 2; "C" indicates the production method described in Reference Example 3; "M" indicates the production method described in Reference Example 31; "N" indicates the production method described in Reference Example 32; "a" indicates the production method described in Example 1; "b" indicates the production method described in Example 2; "e" indicates the production method described in Example 6; "h" indicates the production method described in Example 107; "i" indicates the production method described in Example 108; "j" indicates the production method described in Example 109; "k" indicates the production method described in Example 110; "l" indicates the production method described in Example 111; "m" indicates the production method described in Example 113; and "n" indicates the production method described in Example 114. The symbols indicate the compound that can be synthesized according to the corresponding Examples.

In regard to the Example compounds in the Table 3, an intermediate can be produced by the production method described in "Synth.1", using the starting materials described in "S.M.1" and "S.M.2", and the Example compound can be produced by the production method described in "Synth.2" using the intermediate and the starting materials described in "S.M.3". If one or two starting materials are used, only the relevant starting materials are indicated. Furthermore, if the production methods corresponding to "Synth.1" and "Synth.2" are unnecessary, indication may be given in only one column.

"LCMS": Indicates the data of liquid chromatograph mass analysis spectrum (m/z). Specifically, the data consist of "method,", "R.T." and "MS";

"method": LCMS conditions. Indication of the conditions as "A-1" implies that the previously mentioned "LCMS" apparatus and the conditions (A-1) are used. Similarly, indication of the conditions as "B-1" implies that the previously mentioned "LCMS" apparatus and the conditions (B-1) are used. Similarly, indication of the conditions as "C-1" implies that the previously mentioned "LCMS" apparatus and the conditions (C-1) are used. Similarly, indication of the conditions as "A-2" implies that the previously mentioned "LCMS" apparatus and the conditions (A-2) are used. Indication of the conditions as "C-2" implies that the previously mentioned "LCMS" apparatus and the conditions (C-2) are used;

"R.T.": Retention time (minutes) in LCMS;

"MS": indicates the data of mass spectrum (indicated together with M+H or M−H) (however, the indication of "N.D." implies that no molecular ion peak could be detected).

The meanings of the symbols in Table 4 are as follows.

"Reagent": symbol corresponding to the reagents used in the columns of "S.M.1", "S.M.2" and "S.M.3" in the Table 3, "Structure": structure of the reagent, "Supl.": manufacturer of the reagent used. The manufacturer of the reagent used may be indicated by the following abbreviations. Tokyo Chemical Industry Co., Ltd.: "TCI", Sigma-Aldrich Corp.: "Ald", Apollo Chemical Co.: "Apollo", Kanto Chemical Co., Inc.: "KANTO", Wako Pure Chemical Industries, Ltd.: "WAKO", Lancaster Chemical Corp.: "LANC", Maybridge Co.: "MAYB", Acros Organics, Inc.: "Acros", Alfa Aesar GmbH & Co. KG: "AAesar", FluoroChem, Ltd.: "Fchem", Oakwood Products, Inc.: "Oakw", ART Chemicals Co.: "ART", and Bionet, Inc.: "Bion".

The abbreviations in the sentences and in the tables have the following meanings. n: normal, i: iso, s: secondary, t: tertiary, Me: methyl, Et: ethyl, Pr: propyl, Bu: butyl, Ph: phenyl, Bn: benzyl, Py: pyridyl, CHO: formyl, COOH: carboxyl, $NO_2$: nitro, $NH_2$: amino, $CF_3$: trifluoromethyl, F: fluoro, Cl: chloro, Br: bromo, I: iodo, OMe: methoxy, OH, hydroxy, THF: tetrahydrofuran.

The number given before each substituent represents the position of substitution. The number given together with a hyphen before the abbreviation of an aromatic ring represents the position of substitution of the aromatic ring.

TABLE 3

| Exp. | Str. | S.M.1 | S.M.2 | Synth.1 | S.M.3 | Synth.2 | LC-MS method | R.T. | MS |
|---|---|---|---|---|---|---|---|---|---|
| 120 | 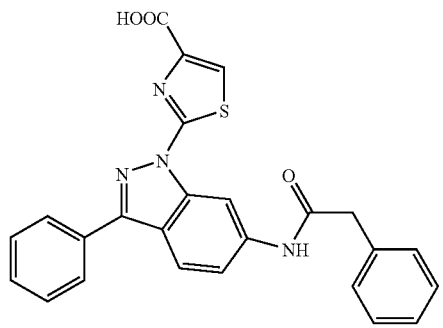 | Exp4 | — | — | Ac1 | h, b | C-1 | 1.84 | 455 (M + H) |

TABLE 3-continued

| Exp. | Str. | S.M.1 | S.M.2 | Synth.1 | S.M.3 | Synth.2 | LC-MS method | R.T. | MS |
|---|---|---|---|---|---|---|---|---|---|
| 121 | | Exp4 | — | — | Ac2 | h, b | C-1 | 1.74 | 407 (M + H) |
| 122 | | Exp4 | — | — | Ac3 | h, b | C-1 | 1.55 | 379 (M + H) |
| 123 | | Exp107 | — | — | Ac4 | b | C-1 | 1.26 | 393 (M + H) |
| 124 | | Exp4 | — | — | Ac5 | h, b | C-1 | 1.61 | 442 (M + H) |
| 125 | | Exp4 | — | — | Ac6 | h, b | C-1 | 2.04 | 435 (M + H) |

TABLE 3-continued

| Exp. | Str. | S.M.1 | S.M.2 | Synth.1 | S.M.3 | Synth.2 | LC-MS method | R.T. | MS |
|---|---|---|---|---|---|---|---|---|---|
| 126 | | Exp108 | — | — | Ac7 | b | C-1 | 1.15 | 469 (M + H) |
| 127 | | Exp4 | — | — | Ac8 | i, b | C-1 | 1.91 | 447 (M + H) |
| 128 | | Exp4 | — | — | Ac9 | i, b | C-1 | 1.90 | 445 (M + H) |
| 129 | | Exp4 | — | — | Ac10 | i, b | C-1 | 1.93 | 433 (M + H) |
| 130 | | Exp4 | — | — | Ca1 | j, b | C-1 | 1.43 | 445 (M + H) |

TABLE 3-continued

| Exp. | Str. | S.M.1 | S.M.2 | Synth.1 | S.M.3 | Synth.2 | LC-MS method | R.T. | MS |
|---|---|---|---|---|---|---|---|---|---|
| 131 | | Exp4 | — | — | Ca2 | j, b | C-1 | 1.86 | 433 (M + H) |
| 132 | | Exp4 | — | — | Ca3 | j, b | C-1 | 1.72 | 445 (M + H) |
| 133 | | Exp4 | — | — | Ca4 | j, b | C-1 | 2.14 | 499 (M + H) |
| 134 | | Exp109 | — | — | Ca5 | b | C-1 | 1.84 | 421 (M + H) |
| 135 | | Exp4 | — | — | Ca6 | j, b | C-1 | 1.70 | 405 (M + H) |

TABLE 3-continued

| Exp. | Str. | S.M.1 | S.M.2 | Synth.1 | S.M.3 | Synth.2 | LC-MS method | R.T. | MS |
|---|---|---|---|---|---|---|---|---|---|
| 136 | | Exp4 | — | — | Ca7 | j, b | C-1 | 1.83 | 445 (M + H) |
| 137 | | Exp4 | — | — | Sc1 | k, b | C-1 | 1.67 | 429 (M + H) |
| 138 | | Exp4 | — | — | Sc2 | k, b | C-1 | 1.76 | 443 (M + H) |
| 139 | | Exp4 | — | — | Sc3 | k, b | C-1 | 1.87 | 456 (M + H) |
| 140 | | Exp110 | — | — | Sc8 | k, b | C-1 | 1.16 | 415 (M + H) |

TABLE 3-continued

| Exp. | Str. | S.M.1 | S.M.2 | Synth.1 | S.M.3 | Synth.2 | LC-MS method | R.T. | MS |
|---|---|---|---|---|---|---|---|---|---|
| 141 | | Exp111 | — | — | Sc9 | l, b | C-1 | 1.75 | 443 (M + H) |
| 142 | | Exp4 | — | — | Sc10 | l, b | C-1 | 1.84 | 457 (M + H) |
| 143 | | Exp4 | — | — | Sc11 | l, b | C-1 | 1.70 | 441 (M + H) |
| 144 | | Exp4 | — | — | Sc12 | l, b | C-1 | 1.96 | 483 (M + H) |
| 145 | | Exp4 | — | — | Ad3 | e, b | C-1 | 2.00 | 445 (M + H) |

TABLE 3-continued
| Exp. | Str. | S.M.1 | S.M.2 | Synth.1 | S.M.3 | Synth.2 | LC-MS method | R.T. | MS |
|---|---|---|---|---|---|---|---|---|---|
| 146 | 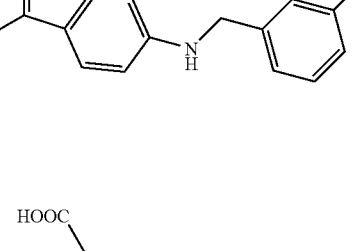 | Exp4 | — | — | Ad4 | e, b | C-1 | 1.99 | 445 (M + H) |
| 147 | 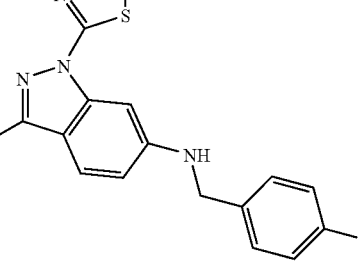 | Exp4 | — | — | Ad5 | e, b | C-1 | 1.99 | 445 (M + H) |
| 148 | 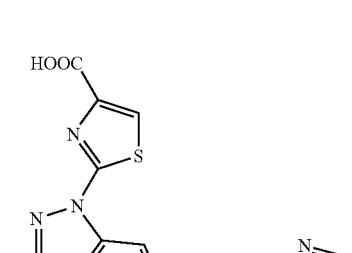 | Exp4 | — | — | Ad6 | e, b | C-1 | 1.52 | 428 (M + H) |
| 149 | 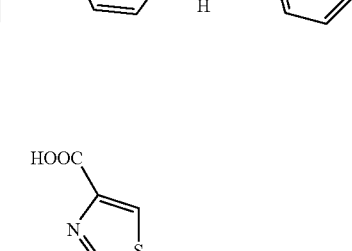 | Exp4 | — | — | Ad7 | e, b | C-1 | 1.41 | 428 (M + H) |

TABLE 3-continued
| Exp. | Str. | S.M.1 | S.M.2 | Synth.1 | S.M.3 | Synth.2 | LC-MS method | R.T. | MS |
|---|---|---|---|---|---|---|---|---|---|
| 150 | 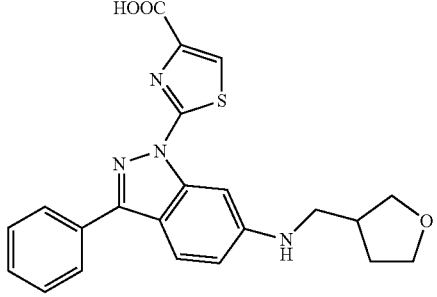 | Exp4 | — | — | Ad8 | e, b | C-1 | 1.78 | 421 (M + H) |
| 151 | 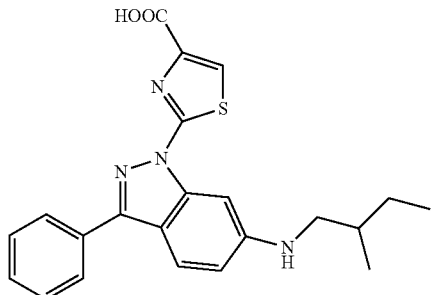 | Exp4 | — | — | Ad9 | e, b | C-1 | 2.15 | 407 (M + H) |
| 152 | 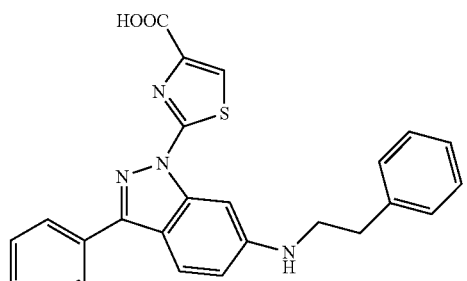 | Exp4 | — | — | Ad10 | e, b | C-1 | 2.10 | 441 (M + H) |
| 153 | 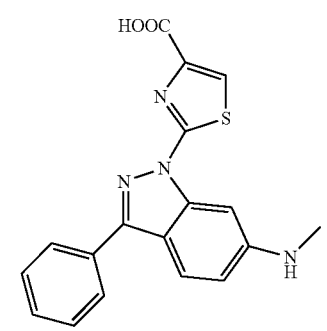 | Exp112 | — | — | — | b | C-1 | 1.34 | 351 (M + H) |
| 154 | 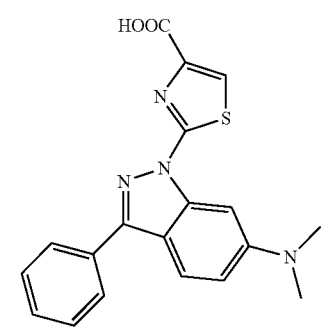 | Exp113 | — | — | — | b | C-1 | 1.59 | 365 (M + H) |

TABLE 3-continued

| Exp. | Str. | S.M.1 | S.M.2 | Synth.1 | S.M.3 | Synth.2 | LC-MS method | R.T. | MS |
|---|---|---|---|---|---|---|---|---|---|
| 155 | (3-phenyl-6-methyl-1H-indazol-1-yl thiazole-4-carboxylic acid) | Ad11 | — | A, B, C | I.M.1 | a, b | C-1 | 1.91 | 336 (M + H) |
| 156 | (3-phenyl-6-chloro-1H-indazol-1-yl thiazole-4-carboxylic acid) | Exp4 | — | — | Ha1 | m, b | C-1 | 1.96 | 356 (M + H) |
| 157 | (3-phenyl-6-bromo-1H-indazol-1-yl thiazole-4-carboxylic acid) | Exp4 | — | — | Ha2 | m, b | C-1 | 1.99 | 401 (M + H) |
| 158 | (3-phenyl-6-iodo-1H-indazol-1-yl thiazole-4-carboxylic acid) | Exp113 | — | — | — | b | C-1 | 2.05 | 448 (M + H) |

TABLE 3-continued

| Exp. | Str. | S.M.1 | S.M.2 | Synth.1 | S.M.3 | Synth.2 | LC-MS method | R.T. | MS |
|---|---|---|---|---|---|---|---|---|---|
| 159 | | Exp114 | — | — | — | b | C-1 | 1.83 | 362 (M + H) |
| 160 | | Exp113 | — | — | Ba52 | n, b | C-1 | 1.84 | 362 (M + H) |
| 161 | | Exp113 | — | — | Ba53 | n, b | C-1 | 1.25 | 377 (M + H) |
| 162 | | Exp115 | — | — | — | b | C-1 | 1.66 | 348 (M + H) |

TABLE 3-continued

| Exp. | Str. | S.M.1 | S.M.2 | Synth.1 | S.M.3 | Synth.2 | LC-MS method | R.T. | MS |
|---|---|---|---|---|---|---|---|---|---|
| 163 | | Ref29 | — | — | — | a, b | C-1 | 0.70 | 323 (M + H) |
| 164 | | PP1 | — | — | — | a, b | C-1 | 1.67 | 391 (M + H) |
| 165 | | Ref30 | Th3 | M | — | a, b | C-1 | 1.50 | 383 (M + H) |
| 166 | | Ref31 | — | — | — | a, b | C-1 | 1.95 | 425 (M + H) |

TABLE 3-continued
| Exp. | Str. | S.M.1 | S.M.2 | Synth.1 | S.M.3 | Synth.2 | LC-MS method | R.T. | MS |
|---|---|---|---|---|---|---|---|---|---|
| 167 | 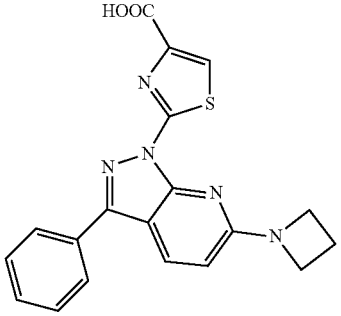 | Ref32 | — | — | — | a, b | C-1 | 1.31 | 378 (M + H) |
| 168 | 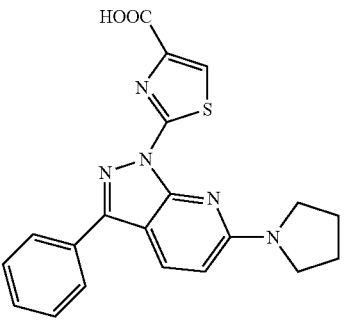 | Ref30 | Am5 | N | — | a, b | C-1 | 1.49 | 392 (M + H) |
| 169 | 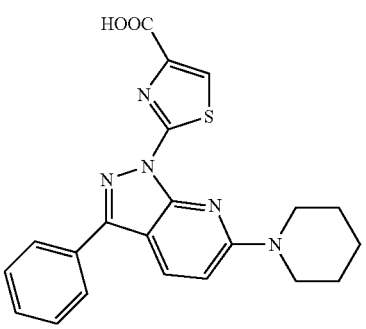 | Ref30 | Am6 | N | — | a, b | C-1 | 1.59 | 406 (M + H) |
| 170 | 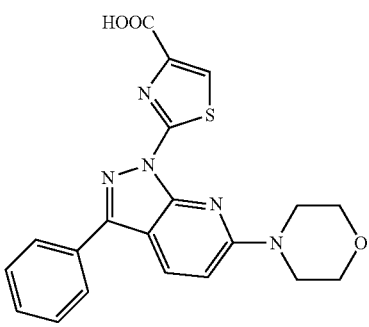 | Ref30 | Am7 | N | — | a, b | C-1 | 1.03 | 408 (M + H) |

TABLE 3-continued
| Exp. | Str. | S.M.1 | S.M.2 | Synth.1 | S.M.3 | Synth.2 | LC-MS method | R.T. | MS |
|---|---|---|---|---|---|---|---|---|---|
| 171 | 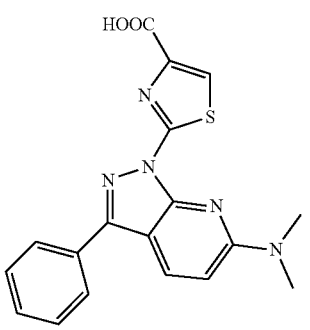 | Ref30 | Am8 | N | — | a, b | C-1 | 1.22 | 366 (M + H) |
| 172 | 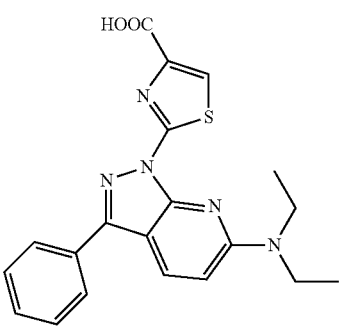 | Ref30 | Am9 | N | — | a, b | C-1 | 1.51 | 394 (M + H) |
| 173 | 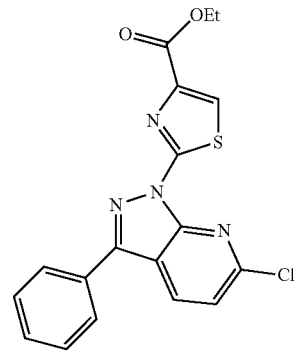 | Ref33 | — | — | — | a | C-1 | 1.67 | 385 |
| 174 | 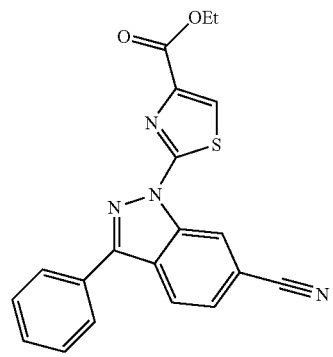 | Ad12 | — | A, B, C | I.M.1 | a | C-1 | 2.18 | 364 (M + H) |

TABLE 3-continued

| Exp. | Str. | S.M.1 | S.M.2 | Synth.1 | S.M.3 | Synth.2 | LC-MS method | R.T. | MS |
|---|---|---|---|---|---|---|---|---|---|
| 175 | | Ref31 | Th2 | N | I.M.1 | a, b | C-1 | 1.60 | 449 (M + H) |
| 176 | | Ref31 | Th3 | N | I.M.1 | a, b | C-1 | 1.72 | 445 (M + H) |
| 177 | | Ref31 | Th4 | N | I.M.1 | a, b | C-1 | 1.90 | 515 (M + H) |
| 178 | | Ref34 | — | — | I.M.1 | a, b | C-1 | 1.32 | 447 (M + H) |

TABLE 3-continued
| Exp. | Str. | S.M.1 | S.M.2 | Synth.1 | S.M.3 | Synth.2 | LC-MS method | R.T. | MS |
|---|---|---|---|---|---|---|---|---|---|
| 179 | 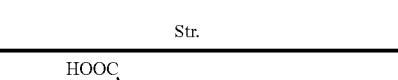 | Ref31 | Th5 | N | I.M.1 | a, b | C-1 | 1.85 | 499 (M + H) |
TABLE 4
| Reagent | Compd. Name | Supl. |
|---|---|---|
| Ch1 | 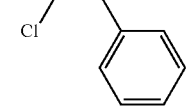 | TCI |
| Ch2 | | TCI |
| Ch3 | | WAKO |
| Ch4 | | TCI |
| Ch5 | | LANC |
| Ch6 | | LANC |
| Ch7 | | TCI |
| Ch8 | | TCI |
| Ch9 | | TCI |
| Ca1 | | Mayb |
| Ca2 | | TCI |
| Ca3 | | Fchem |
| Ca4 | | TCI |
| Ca5 | | TCI |
| Ca6 | | Oakw |
| Sc1 | | TCI |

TABLE 4-continued

| Reagent | Compd. Name | Supl. |
|---|---|---|
| Sc2 | propanesulfonyl chloride | Ald |
| Sc3 | isobutanesulfonyl chloride | Ald |
| Sc4 | isopropanesulfonyl chloride | Ald |
| Sc5 | sec-butanesulfonyl chloride | Oakw |
| Sc6 | cyclohexanesulfonyl chloride | Apollo |
| Ad3 | 2-fluorobenzaldehyde | TCI |
| Ad4 | 3-fluorobenzaldehyde | WAKO |
| Ad5 | 4-fluorobenzaldehyde | TCI |
| Ad6 | pyridine-2-carbaldehyde | TCI |
| Ad7 | pyridine-3-carbaldehyde | TCI |
| Ad8 | tetrahydrofuran-3-carbaldehyde | Ald |
| Ad9 | 2-methylbutyraldehyde | TCI |
| Ad10 | phenylacetaldehyde | KANTO |
| Ad11 | 4-methyl-2-fluorobenzaldehyde | Apollo |
| Ad12 | 4-cyano-2-fluorobenzaldehyde | Apollo |
| Ha1 | CuCl$_2$ | KANTO |
| Ha2 | CuBr$_2$ | KANTO |
| Ba52 | cis-propenylboronic acid | Ald |
| Ba53 | (E)-3-acetoxypropenylboronic acid | Aaesar |
| Am5 | pyrrolidine | KANTO |
| Am6 | piperidine | Ald |
| Am7 | morpholine | Ald |
| Am8 | dimethylamine | Ald |
| Am9 | diethylamine | TCI |
| PP1 | 3-phenyl-6-(trifluoromethyl)-1H-pyrazolo[4,3-b]pyridine | Bion |
| Th1 | ethanethiol | Ald |
| Th2 | 2-fluorobenzenethiol | Fchem |

TABLE 4-continued

| Reagent | Compd. Name | Supl. |
|---|---|---|
| Th3 | C6H5-CH2-SH (benzyl mercaptan) | TCI |
| Th4 | F3CO-C6H4-SH (4-(trifluoromethoxy)benzenethiol) | Fchem |
| Th5 | F3C-C6H4-SH (3-(trifluoromethyl)benzenethiol) | LANC |

Test Example 1

Measurement of an Antagonist Activity by Using Cells Expressing Human EP1 Receptor In order to investigate the EP1 receptor antagonist activity of the compounds of the present invention, a reporter activity was measured by using HEK293 cells in which human EP1 receptor has been stably expressed.

(1) Measurement Method

As a result of searching Refseq Database for prostaglandin E receptor, genetic information of human EP1 (NM_000955) receptor was obtained. Based on this sequence information, human EP1 receptor gene was cloned by PCR using human cDNA as a template and by an ordinary method to give human EP1 receptor. Then, HEK293 in which the receptor is stably expressed was established, together with a reporter gene (SRE-Luciferase) in which serum responsible element (SRE) is added at the upstream region of firefly luciferase gene. The resulting cells were seeded to a 96 well plate ($5 \times 10^4$ cells/well) and cultured for one day. To the plate, PGE2 (200 nM, final concentration 10 nM) and the test compound (in an amount of ½₀, 20× of the final concentration) were added to initiate the reaction. After allowing the reaction to proceed at 37° C. for 6 hours, the medium was aspirated off, added with a luminescent agent and the reporter activity was measured.

(2) Measurement Result

The test compounds, which had been tested, were expressed as "Exp. example number" using the example number. Same expression system is used below.

The representative compounds of the present invention showed an excellent antagonist activity during the antagonist activity measurement test using the cells expressing human EP1 receptor.

Some test compounds (test compound Nos.: Exp.2, Exp.9, Exp.11, Exp.22, Exp.23, Exp.25, Exp.65, Exp.68, Exp.76, Exp.77, Exp.81, Exp.91, Exp.92, Exp.95, Exp.99, Exp.102, Exp.104, Exp.105, and Exp.106) have an $IC_{50}$ value of 0.02 µM or less in the measurement of antagonist activity using human EP1 receptor expressing cells. Furthermore, other test compounds (test compound Nos.: Exp.7, Exp.16, Exp.24, Exp. 51, Exp.64, Exp.69, Exp.73 and Exp.97) have an $IC_{50}$ value of 0.1 to 0.02 µM in the measurement of antagonist activity using human EP1 receptor expressing cells. Still other test compounds test compound Nos.: Exp.72, Exp.80, Exp.94 and Exp.96) have an $IC_{50}$ value of 0.5 to 0.1 µM in the measurement of antagonist activity using human EP1 receptor expressing cells.

Some test compounds (test compound Nos.: Exp.119, Exp.154, Exp.155, Exp. 156, Exp. 157, Exp. 158, Exp. 159, Exp. 160, Exp. 162, and Exp.164) have an $IC_{50}$ value of 0.02 µM or less in the measurement of antagonist activity using human EP1 receptor expressing cells. Furthermore, other test compounds (test compound Nos.: Exp.116, Exp. 118, Exp. 126, Exp. 148, Exp. 152, Exp. 153, Exp. 167, Exp. 175, Exp. 178, and Exp.179) have an $IC_{50}$ value of 0.1 to 0.02 µM in the measurement of antagonist activity using human EP1 receptor expressing cells. Still other test compounds test compounds (test compound Nos.: Exp.122, Exp. 130, Exp. 131, Exp. 133, Exp. 135, Exp. 141, Exp. 142, Exp. 145, Exp. 146, Exp. 147, Exp. 149, Exp. 150, Exp. 151, Exp. 161, Exp. 165, Exp. 166, Exp. 176, and Exp.177) have an $IC_{50}$ value of 0.5 to 0.1 µM in the measurement of antagonist activity using human EP1 receptor expressing cells.

Test Example 2

Measurement of an Antagonist Activity by Using Cells Expressing Human EP1 Receptor In order to investigate the EP1 receptor antagonist activity of the compounds of the present invention, intracellular $Ca^{2+}$ was measured by using HEK293 cells in which human EP1 receptor has been stably expressed.

(1) Measurement Method

Cells expressing human EP1 receptor were suspended in an assay buffer to the concentration of $5 \times 10^6$ cells/ml, added with Puronic F-127 (final concentration 0.2%), and Fura 2-AM (final concentration 5 uM), followed by incubation at 37° C. for 30 minutes. After washing twice with the assay buffer, the cells were again suspended in the assay buffer to $1 \times 10^6$ cells/60 ul, and then transferred to a 96 well UV plate ($1 \times 10^6$ cells/60 ul/well). Thereafter, by using a fluorescent chemical screening system (FDSS4000, Hamamatsu Photonics K.K.), intracellular $Ca^{2+}$ concentration was measured after adding 20 ul of each of the test compounds and PGE2 (5× of the final concentration for both). $Ca^{2+}$ concentration was measured by determining fluorescence intensity after irradiation with two excitation wavelengths, i.e., 340 and 380 nm.

Furthermore, EP1 antagonist activity was calculated as a ratio (%) of inhibiting increase in intracellular $Ca^{2+}$ concentration by PGE2 (10 nM).

Assay buffer: 20 mM HEPES/KOH (pH 7.4), 115 mM NaCl, 5.4 mM KCl, 0.8 mM $MgCl_2$, 0.8 mM $CaCl_2$, 13.8 mM D-glucose, 0.1% BSA (2) Measurement Result The representative compounds of the present invention showed an excellent antagonist activity during the intracellular $Ca^{2+}$ assay.

Some test compounds (test compound Nos.: Exp.2, Exp.77, Exp.105 and Exp.106) have an $IC_{50}$ value of 0.1 µM or less in the intracellular $Ca^{2+}$ assay. Furthermore, other test compounds (test compound Nos.: Exp.9, Exp.16, Exp.25, Exp.81 and Exp.95) have an $IC_{50}$ value of 0.3 to 0.1 µM in the intracellular $Ca^{2+}$. Still other test compounds (test compound Nos.: Exp.65 and Exp.76) have an $IC_{50}$ value of 1.0 to 0.3 µM in the intracellular $Ca^{2+}$ assay.

Test Example 3

Receptor Binding Test Using Cells Expressing Human EP1 Receptor

Inhibitory activity of the test compounds on binding of [$^3$H]PGE2 in HEK293 cells stably expressing human EP1 receptor was measured.

(1) Measurement Method

HEK293 cells, which stably express human EP1 receptor, were established by using the gene for human EP1 receptor, and then a membrane fraction was prepared therefrom. Thus-prepared membrane fraction was incubated at 30° C. for 90 minutes with a reaction solution (200 μL/well) which includes the test compound and [$^3$H]PGE2. Upon the completion of the reaction, the reaction solution was aspirated off under reduced pressure, and the [$^3$H]PGE2 bound to the membrane fraction was trapped by using Unifilter Plateg CF/C (manufactured by Packard) and the bound radioactivity was counted with a liquid scintillator.

Kd value was obtained from a Scatchard plot. Non-specific binding was obtained from the binding in the presence of an excess amount (10 μM) of non-labeled PGE2. For the measurement of an inhibitory activity of the test compound on [$^3$H]PGE2 binding, [$^3$H]PGE2 (1 nM) and various concentrations of the test compound were added. Meanwhile, for all of the reactions, the buffer as described below was used.

Buffer; 10 mM MES/NaOH (pH 6.0), 10 mM $MgCl_2$, 1 mM EDTA, 0.1% BSA

Dissociation constant of the compounds, i.e., Ki, was obtained according to the following equation. In this regard, [C] indicates the concentration of [$^3$H]PGE2 that was used for binding inhibition test (1 nM for the present test).

$$Ki=IC50/(1+[C]/Kd).$$

(2) Measurement Result

The representative compounds of the present invention showed an excellent activity during the [$^3$H]PGE2 binding inhibition test.

Some test compounds (test compound Nos.: Exp.2, Exp.77, Exp.81, Exp.105 and Exp.106) have a Ki value of 0.1 μM or less in the measurement of [$^3$H]PGE2 binding inhibitory activity.

Test Example 4

Activity of Relaxing Rat Bladder Smooth Muscle

An activity of relaxing rat bladder smooth muscle can be determined with reference to the method established by Maggi, et al. (Eur. J. Pharmacol. 152, p. 273-279 (1988)). Specifically, a smooth muscle specimen is prepared from a bladder isolated from a male SD rat, and isometric contracting power is measured in an organ bath. After the contraction with $3\times10^{-7}$M PGE2, the compound to be tested is dissolved in DMSO and added to the organ bath with final concentration of $10^{-8}$M to $10^{-5}$M. As a result, a relaxing activity of the compound can be determined.

Test Example 5

Micturition Interval Prolongation in an Anesthetized rat—I

Activity of prolonging micturition interval in an anesthetized rat can be determined with reference to the method established by Maggi, et al. (Eur. J. Pharmacol. 145, p. 105-112 (1988)). Specifically, a female SD rat is anesthetized with urethane and fixed in a supine position, and a catheter is inserted through an external urethral opening. Using a three-way stopcock, it is connected to a pressure transducer and a syringe pump. While infusing physiological saline including 100 μM PGE2 to the bladder at constant rate, cystometrogram is recorded. After confirming stabilized micturition interval, micturition threshold pressure and maximal voiding pressure, a solvent or the compound to be tested is administered to the left femoral vein so that an activity of prolonging micturition interval can be determined as an efficacy of the drug compound.

Test Example 6

Micturition Interval Prolongation in an Anesthetized Rat—II

Activity of prolonging micturition interval in an anesthetized rat was determined with reference to the method established by Maggi, et al. (Eur. J. Pharmacol. 145, p. 105-112 (1988)). Specifically, a female SD rat was anesthetized with urethane and fixed in a supine position, and a catheter was inserted through an external urethral opening. Using a three-way stopcock, it was connected to a pressure transducer and a syringe pump. While infusing physiological saline including 0.2% acetic acid to the bladder at constant rate, cystometrogram was recorded. After confirming stabilized micturition interval, micturition threshold pressure and maximal voiding pressure, a solvent or the compound to be tested was administered to the left femoral vein and an activity of prolonging micturition interval was determined as an efficacy of the drug compound. Each group included five animals. As a result, it was found that the representative compounds of the present invention have an excellent efficacy of prolonging micturition interval. Results are summarized in Table 3.

TABLE 3

| Test compound No. | Voiding interval-extending action |
|---|---|
| Exp. 2 | 30.0% |

Test Example 7

Micturition Interval Prolonging Activity in an Awakening Rat

Micturition interval prolonging activity in an awakening rat can be determined with reference to the method established by Shinozaki et al. (Biomed. Res. 26(1), p. 29-33 (2005)). Specifically, a rat bladder was exposed under anesthetization using halothane. To the vertex region of the bladder a catheter was inserted while the other end was taken out from the abdominal cavity and connected to a pressure transducer and an infusion pump. A catheter is also inserted to a jugular vein of the animal. The rat was put into a restraining cage and after awakened from the anesthetization, physiological saline was infused to the bladder via the bladder catheter and cystometrogram (hereinafter, abbreviated as "CMG") was continuously recorded. Two to three hours later, the bladder infusion solution was replaced with physiological saline including 0.2% acetic acid and CMG recording was further carried out. One to two hours after the replacement of the infusion solution, a solvent or the compound to be tested was administered to the jugular vein and an activity of prolonging micturition interval by administration of acetic acid was determined as an efficacy of the drug compound.

Test Example 8

Frequency Urinary Measurement in a Rat (Awaken State)

Frequency urinary of a rat can be measured with reference to the method by Oka et al. (Jpn. J. Pharmacol. 87, p. 27-33

(2001)). Specifically, a rat is placed in a metabolic cage and discharged urine is continuously collected and weighed. Each different weight of urine can be regarded as frequency urinary and also variation in total weight can be regarded as total weight of discharged urine. In this regard, it was known, for example, that frequent micturition can be caused by intraperitoneal administration of cyclophosphamide (Lecci et al., Br. J. Pharmacol. 130, p. 331-338 (2000)), spinal cord injury (Kamo et al., Am. J. Physiol. Renal Physiol. 287, p. F434-F441 (2004)) or cerebral infarction by ligation of middle cerebral artery (Yokoyama et al., J. Urol., 174, p. 2032-2036 (2005)). To the frequent micturition model established accordingly, a solvent or a test compound is orally administered and a therapeutic effect of the compound can be determined in view of the decreased frequency urinary.

Test Example 9

Therapeutic Effect on Symptoms of Bladder Irritation and Overactive Bladder Caused by Lower Urinary Tract Obstruction Urinary tract obstruction (BOO) model can be established with reference to the method of Malmgren et al. (J. Urol. 137, p. 1291-1294 (1987)). After six weeks, the bladder of a BOO model rat is exposed under anesthetization. To the vertex region of the bladder a catheter was inserted while the other end was taken out from the backside of a cervical region. A catheter is also inserted to a jugular vein. Two days later, the rat is placed in a restraining cage, and physiological saline was infused via the bladder catheter and cystometrogram was continuously recorded. A solvent or the test compound is intravenously infused and reduced number of non-voiding contraction (NVC) having almost no micturition is determined as an efficacy of the drug compound.

Test Example 10

By using a frequent micturition rat model in which frequent micturition is induced by infusion of prostaglandin E2 to a bladder (Takeda et al., Neurourol. Urodyn. 21, p. 558-565 (2002)), or infusion of ATP to a bladder (Atiemo et al. Urology 65, p. 622-626 (2005)), a therapeutic effect of a drug compound can be determined by following an increase in frequency urinary or an increase in infusion amount (bladder volume) in accordance with intravenous administration of a test compound during cystometry measurement. In addition, by following a decrease in frequency urinary after administering a test compound during the test for measuring frequency urinary, a therapeutic effect of a drug compound can be determined.

Test Example 11

Evaluation of an Analgesic Action in a Sciatic Nerve Ligation Model (Bennet Model)

Analgesic action in a sciatic nerve ligation rat model (Bennet model) can be determined with reference to the method of Kawahara et al. (Anesth. Analg. 93, p. 1012-1017 (2001)).
[Model Establishment]
A male SD rat (200 to 250 g, Charles River Corporation, Japan) was anesthetized with sodium pentobarbital (50 mg/kg, i. p.), and being laid on its stomach, an incision is made right above the right femur. From the center femur region, biceps femoris is peeled off and a sciatic nerve is exposed (about 5 mm) while being careful not to damage it. Using 4-0 braid silk thread (Nescosuture), in the center femur region, ligation is made at four positions at 1 mm interval from the peripheral side. For the ligation, neither surgical knot nor square knot is made. Only a single knot is made and the knot is gradually tightened to the level at which the hind leg can be slightly moved. Then, the muscular membrane and the skin are sewn. For a sham operation group, procedures are taken until the exposure of sciatic nerve and then muscular membrane and the skin are sewn.
[Measurement Method for Thermal Stimulation Test]
Measurement is carried out by using BASILE Planter Test (UGO BASILE 7370). To a right hind leg of an unconstrained rat, intrusive thermal stimulation is applied and a time spent until the escape behavior is made (response latency) is measured. Specifically, a rat is placed in a box for measurement and acclimated for about 5 minutes. Next, a movable I.R. (infrared) generator is placed under a glass plate and I.R. irradiation is adjusted to be focused on the inside of six balls close to the sole of right foot of the rat. It is important to confirm that a close contact is made between the glass plate and hind foot. Subsequently, after starting thermal stimulation, response latency for the escape behavior, i.e., flinching of the leg, is measured. When escape behavior occurs, the switch is automatically turned off and the response time is counted.
[Measurement Method for Pressure Stimulation Test]
Measurement is carried out by using an analgesy meter for pressure stimulation test (UGO BASILE 7200). Specifically, the right leg of a rat is placed between a supporting board and a pressurizing needle and pressure is applied at constant rate of 16 g/s. When the rat feels pain and draws its leg responding to the pain, a pedal switch is stopped and the measurement value is recorded.
[Evaluation Schedule]
First, thermal stimulation test and pressure stimulation test are performed before an operation. Seven days after the operation, a solvent or the test compound is administered once via an oral, an intravenous, an intraperitoneal or a subcutaneous route. 1, 2 and 24 hours after the administration, the same procedure is carried out. For the continuous oral administration group, a solvent or the test compound is administered one day after the operation, once a day for seven days. 1, 2 and 24 hours after the $7^{th}$-day administration, the thermal stimulation test and pressure stimulation test are carried out.

Test Example 12

Evaluation of Analgesic Action in a Freund's Complete Adjuvant Rat Model

An analgesic action in a Freund's complete adjuvant rat model can be investigated with reference to the method of Giblin et al. (Bioorg. Med. Chem. Lett. 17, p. 385-389 (2007)).
[Model Establishment]
A male SD rat (150 to 200 g, Charles River Corporation, Japan) was anesthetized with sodium pentobarbital (50 mg/kg, i. p.). Inactivated tuberculosis bacteria (M. TUBERCULOSIS DES. H37 RA, DIFCO Laboratories) which is suspended in fluid paraffin (10.0 mg/mL concentration) is injected subcutaneously to the sole of left hind foot of the rat (0.05 mL volume).
[Measurement Method for Pain Stimulation Test]
Measurement is carried out by using Von Frey type apparatus for pain test (UGO BASILE 37400). A rat is placed a plastic cage with wire bottom and maintained in an unconstrained state. For acclimation, the rat is placed to the cage at least 20 minutes before the test. A filament, which provides pressure stimulation, is adjusted to be focused on the inside of six balls close to the sole of left foot of the rat. A constant amount of pressure stimulation is vertically applied. It is determined whether or not the rat exhibits an escape behavior responding to the pressure stimulation. Thereafter, threshold value for the escape behavior is obtained.

[Evaluation Schedule]

First, one day before establishing a model, the pain stimulation test is carried out. In addition, having the model establishment day as Day 0, the pain stimulation test is carried out on Day 1, 3, 7, 9, 11, and 13. On Day 13 after model establishment, a solvent or the test compound is administered once via an oral, an intravenous, an intraperitoneal or a subcutaneous route and then the pain stimulation test is carried out until two hours after the administration. In case of a continuous administration, from Day 13 of the model establishment, a solvent or the test compound is administered twice per day for five days via an oral, an intravenous, an intraperitoneal or a subcutaneous route (administration frequency and administration period are not limited to these). From Day 14 after the model establishment, a pain stimulation test is carried out every day before the administration of a solvent or the test compound and it is continued 24 hours after the day of the termination of the administration.

Test Example 13

Evaluation of an Analgesic Action in a Rat Model of Postoperative Pain

An analgesic action in a rat model of postoperative pain can be determined in view of the method presented by Omote et al. (Anesth Analg. 92, p. 233-8 (2001)).

[Model Establishment]

A male SD rat (250 to 300 g, SLC Corporation, Japan) was anesthetized with 3% isofluran. To avoid any infection, the sole of right hind foot was sterilized with povidone iodine and penicillin-G (30,000 U, Benzylpenicillin; Sigma-Aldrich Company) was injected intramuscularly to the triceps. Skin and fascia are cut from the region which is 0.5 cm apart from the heel to the tip of paw of a right hind limb of the rat (i.e., 1 cm long). After the incision, the skin and fascia are sewn together by using 5-0 nylon thread and the rat is put into a cage for recovery.

[Measurement Method for Pain Stimulation Test]

Measurement is carried out by using Von Frey type apparatus for pain test (UGO BASILE 37400). A rat is placed a plastic cage with wire bottom and maintained in an unconstrained state. For acclimation, the rat is placed to the cage at least 20 minutes before the test. A filament, which provides pressure stimulation, is adjusted to be focused on the inside of six balls close to the sole of left foot of the rat. A constant amount of pressure stimulation is vertically applied. It is then determined whether or not the rat exhibits an escape behavior responding to the pressure stimulation. Thereafter, threshold value for the escape behavior is obtained.

[Administration of a Solvent and a Test Compound]

A rat is anesthetized with 1.5% isofluran. To the sole of the animal which received an operation, a solvent or the test compound is injected while being careful to avoid any leakage. Two and twenty-four hours after the operation, the solvent or the test compound is administered twice, respectively.

[Evaluation Schedule]

First, before the operation, the pain stimulation test is carried out to obtain a control value. Two and twenty-four hours after the operation but before the administration, the pain stimulation test was carried out and significant reduction in threshold value compared to the control value as a baseline is confirmed. Then, 15, 30, 45, 60, 90 or 120 minutes after each administration, the pain stimulation test is carried out and an analgesic effect of the test compound compared to the baseline value is obtained.

Test Example 14

Action of Extending Interval of Micturition in Rat in Wakefulness II

SD rats (Charles River Laboratories Japan, Inc., male) were employed as experimental animals. Each rat was put under anesthesia by inhalation of 2% isoflurane (laughing gas:oxygen=7:3), and then was fixed in the supine position. Anesthesia was maintained by the inhalation of 2% isoflurane. The abdominal part was incised along the midline, and the urinary bladder was exposed from the intraperitoneal cavity. The vertex vesicae part was subjected to a small incision, and a polyethylene tube (PE-50: Becton Dickinson and Company) was inserted into the bladder and fixed. The other end of the catheter was subcutaneously directed to the dorsal side, the catheter was fixed to the abdominal wall, and then the incision was sutured. The catheter directed to the dorsal side was connected to a Siebel, and the middle part was protected with a stainless steel spring. At the same time, a catheter used for the administration into the jugular vein was inserted, and the catheter was subcutaneously directed to the dorsal side, and was likewise passed through the spring. On the day after the next day of the surgery, 0.3% acetic acid was injected into the bladder through the catheter placed in the bladder, for 30 minutes at a rate of 4.0 mL/hr, and thus cystitis was induced. Thereafter, while physiological saline warmed to 37° C. was injected to the other end of the tube inserted into the bladder through one branch of a three-way stopcock at a rate of 3.0 mL/hr, the internal pressure of the bladder was continuously recorded from another branch using a pressure amplifier through a pressure transducer. The excreted urine was cumulatively accumulated in a vessel on a digital balance, and the weight change was simultaneously measured. After it was confirmed that the micturition pattern was stabilized, the compound of the present invention was intravenously administered through the catheter placed in the jugular vein, and measurement was made for 60 minutes. The value obtained before the administration was taken from an average value of the values measured for 30 minutes before the administration, and the value obtained after the administration was taken from an average value of the values measured for 60 minutes immediately after the administration. The number of cases was three animals. As a result, the representative compound of the present invention, for example, the Example 77, was recognized to have a micturition interval extension of 30% or more and an increase in the amount of micturition.

The invention claimed is:
1. A compound represented by the following formula (1):

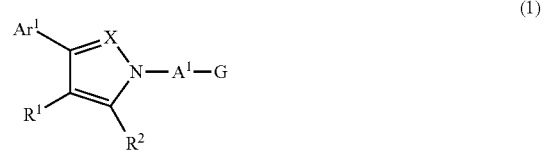

wherein in the formula (1), $Ar^1$ represents an aryl group which may be substituted, a saturated cyclic hydrocarbyl group which may be substituted, or a saturated heterocyclic group which may be substituted;

X represents a nitrogen atom;

$R^1$ and $R^2$ together represent any of the formulas ($Q^1$) to ($Q^6$):

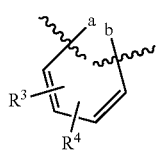

($Q^1$)

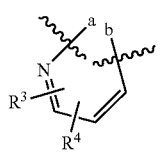

($Q^2$)

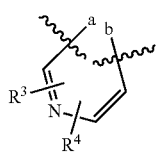

($Q^3$)

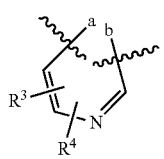

($Q^4$)

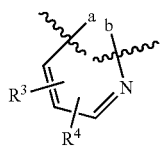

($Q^5$)

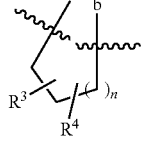

($Q^6$)

wherein in the formulas ($Q^1$) to ($Q^6$), $R^3$ and $R^4$, which may be identical or different, each independently represents any of a hydrogen atom, a halogen atom, an alkyl group which may be substituted, an alkenyl group which may be substituted, an alkynyl group which may be substituted, an aryl group which may be substituted, an aralkyl group which may be substituted, a hydroxy group, an alkoxy group which may be substituted, an aryloxy group which may be substituted, an alkylthio group, an acyl group, an acyloxy group, an alkylsulfinyl group, an alkylsulfonyl group, an alkylcarbamoyl group, —N($R^{Q1}$)($R^{Q2}$) {wherein $R^{Q1}$ and $R^{Q2}$ may be identical or different, and each independently represents a hydrogen atom, an alkyl group which may be substituted, or an aryl group which may be substituted; or $R^{Q1}$ and $R^{Q2}$ together form a 3- to 7-membered ring to represent a cyclic amine in the form of N($R^{Q1}$)($R^{Q2}$)}, an acylamino group, an acyl(alkyl)amino group, an alkylsulfonylamino group, an alkylsulfonyl(alkyl)amino group, a carboxyl group, —CON($R^{Q3}$)($R^{Q4}$) {wherein $R^{Q3}$ and $R^{Q4}$ may be identical or different, and each independently represents a hydrogen atom, an alkyl group which may be substituted, or an aryl group which may be substituted; or $R^{Q3}$ and $R^{Q4}$ ether form a 3- to 7-membered ring to represent a cyclic amine in the form of N($R^{Q3}$)($R^{Q4}$)}, and —COOR$^{Q5}$ {wherein $R^{Q5}$ represents an alkyl group which may be substituted};

n represents an integer from 1 to 4; and $R^1$ and $R^2$ represent that they are bonded to each of the formulas ($Q^1$) to ($Q^6$) at the position of a and the position of b, respectively;

$A^1$ represents a single bond, an alkylene group which may be substituted, or an alkenylene group which may be substituted;

G represents any of the formulas ($G^1$), ($G^2$), or ($G^3$):

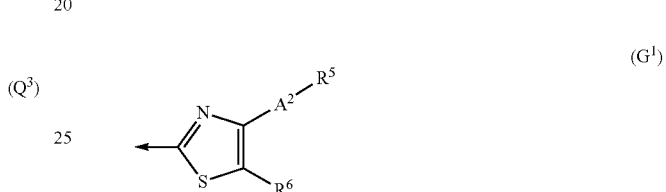

($G^1$)

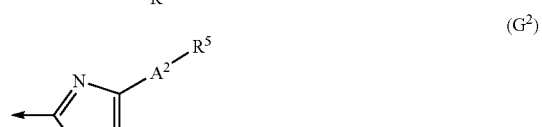

($G^2$)

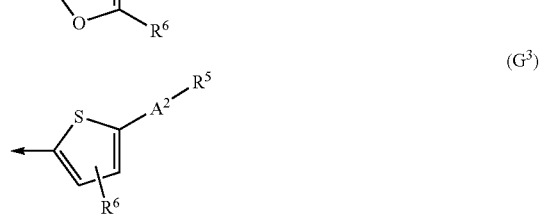

($G^3$)

wherein in the formulas ($G^1$), ($G^2$), and ($G^3$), $A^2$ represents a single bond, an alkylene group which may be substituted, or an alkenylene group which may be substituted; $R^5$ represents a carboxyl group, —CON($R^{51}$)($R^{52}$) {wherein $R^{51}$ and $R^{52}$ may be identical or different, and each independently represents a hydrogen atom, an alkyl group which may be substituted, or an aryl group which may be substituted; or $R^{51}$ and $R^{52}$ together form a 3- to 7-membered ring to represent a cyclic amine in the form of N($R^{51}$)($R^{52}$)}, —COOR$^{53}$ {wherein $R^{53}$ represents an alkyl group which may be substituted}, or a tetrazol-5-yl group; and $R^6$ represents a hydrogen atom or an alkyl group which may be substituted, or a salt thereof.

2. The compound or the salt thereof according to claim 1, wherein $R^5$ is a carboxyl group.

3. The compound or the salt thereof according to claim 1, wherein $A^2$ is a single bond.

4. The compound or the salt thereof according to claim 1, wherein $A^1$ is a single bond, or a methylene group which may be substituted with a lower alkyl group.

5. The compound or the salt thereof according to claim 1, wherein $A^1$ is a single bond.

6. The compound or the salt thereof according to claim 1, wherein $A^1$ is a methylene group which may be substituted with a lower alkyl group.

7. The compound or the salt thereof according to claim 1, wherein $R^1$ and $R^2$ together represent the formula (Q1).

8. The compound or the salt thereof according to claim 1, wherein $R^1$ and $R^2$ together represent the formula ($Q^6$).

9. The compound or the salt thereof according to claim 1, wherein $R^3$ and $R^4$ are groups that are each independently selected from the group consisting of a hydrogen atom, a halogen atom, an alkyl group which may be substituted, a hydroxy group, an alkoxy group which may be substituted, and —N($R^{Q1}$)($R^{Q2}$) [wherein $R^{Q1}$ and $R^{Q2}$ may be identical or different, and each independently represents a hydrogen atom, an alkyl group which may be substituted, or an aryl group which may be substituted; or $R^{Q1}$ and $R^{Q2}$ together form a 3- to 7-membered ring to represent a cyclic amine in the form of N($R^{Q1}$)($R^{Q2}$)].

10. The compound or the salt thereof according to claim 1, wherein $Ar^1$ is an aryl group which may be substituted.

11. The compound or the salt thereof according to claim 1, wherein $Ar^1$ is a phenyl group which may be substituted.

12. The compound or the salt thereof according to claim 1, wherein $Ar^1$ is a phenyl group which may be substituted with one or plural groups that are each independently selected from the group consisting of a halogen atom, an alkyl group which may be substituted, a hydroxy group, and an alkoxy group which may be substituted.

13. The compound or the salt thereof according to claim 1, wherein $Ar^1$ is a saturated heterocyclic group which may be substituted.

14. A compound selected from the group consisting of:

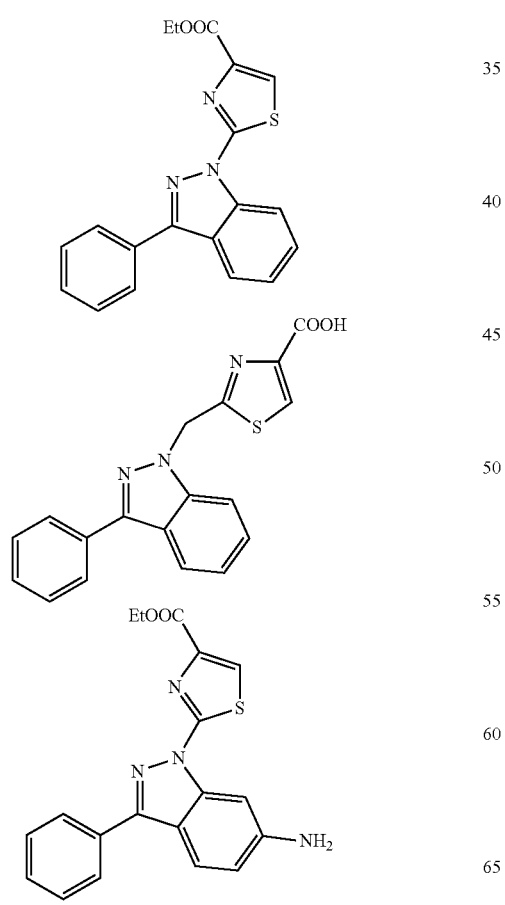

-continued

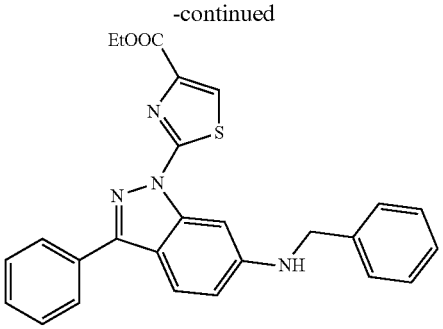

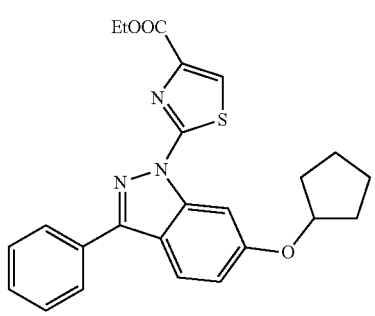

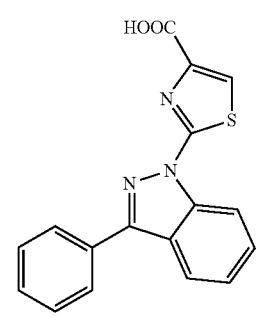

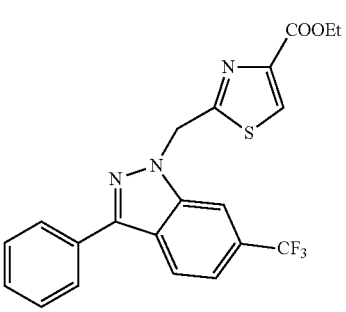

181
-continued
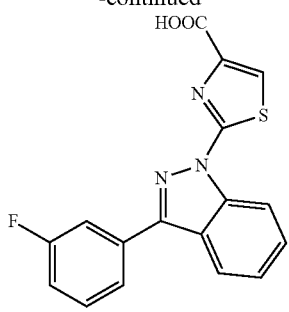
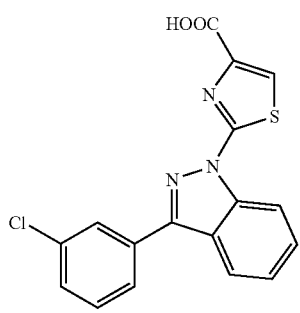
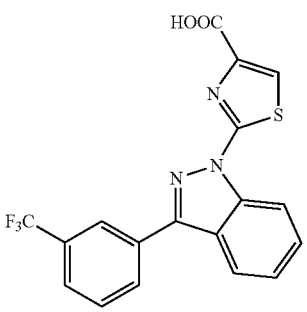
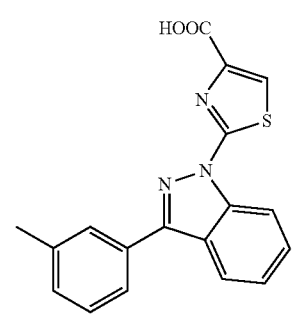
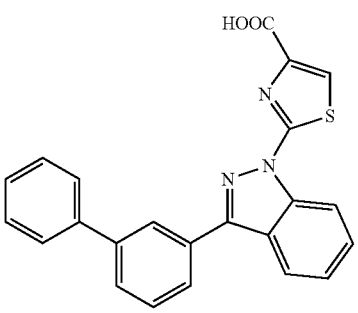
182
-continued
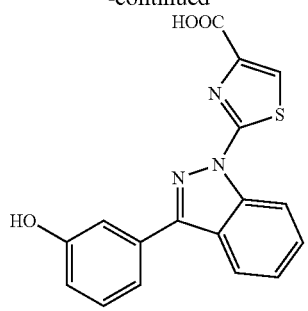
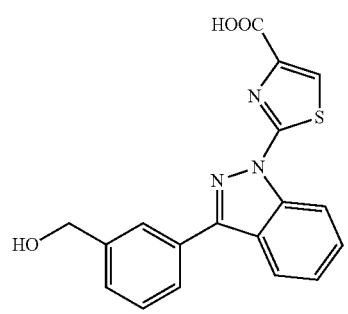
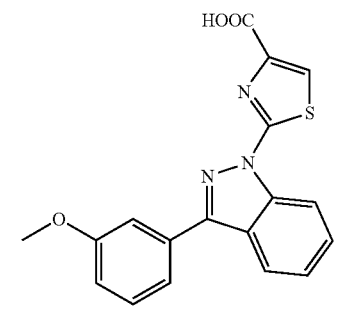
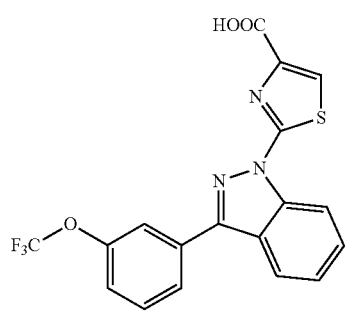
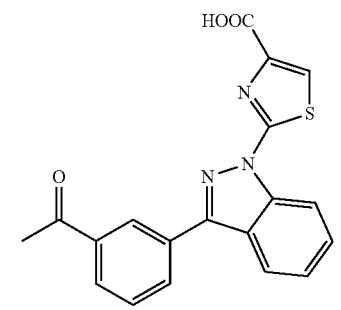

-continued
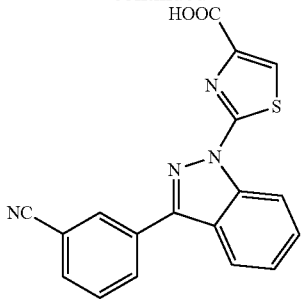
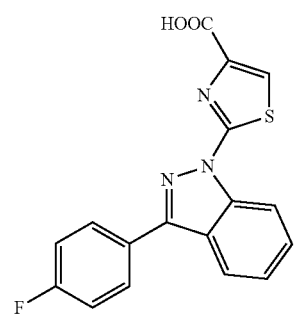
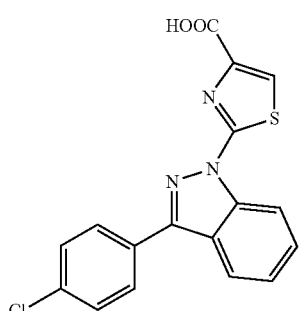
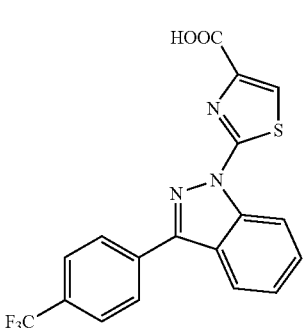
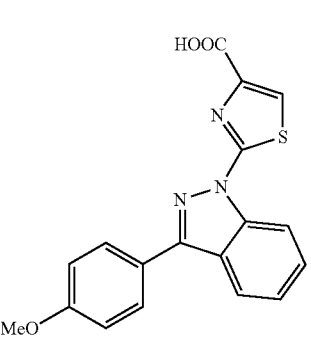
-continued
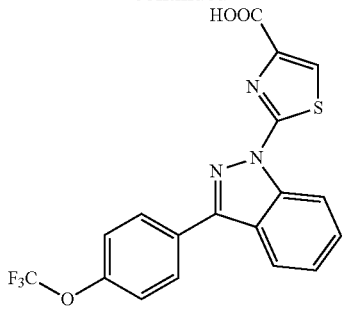
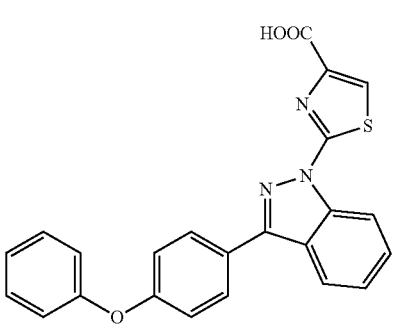
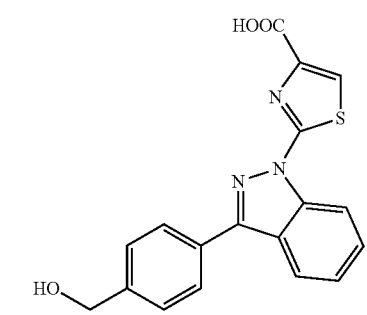
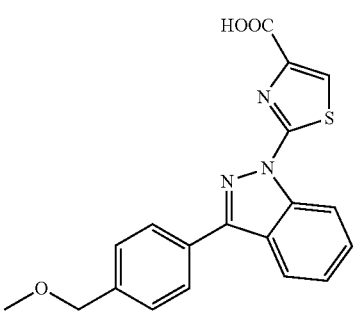
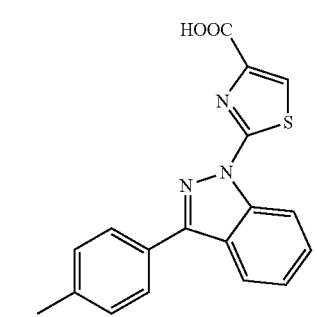

185
-continued
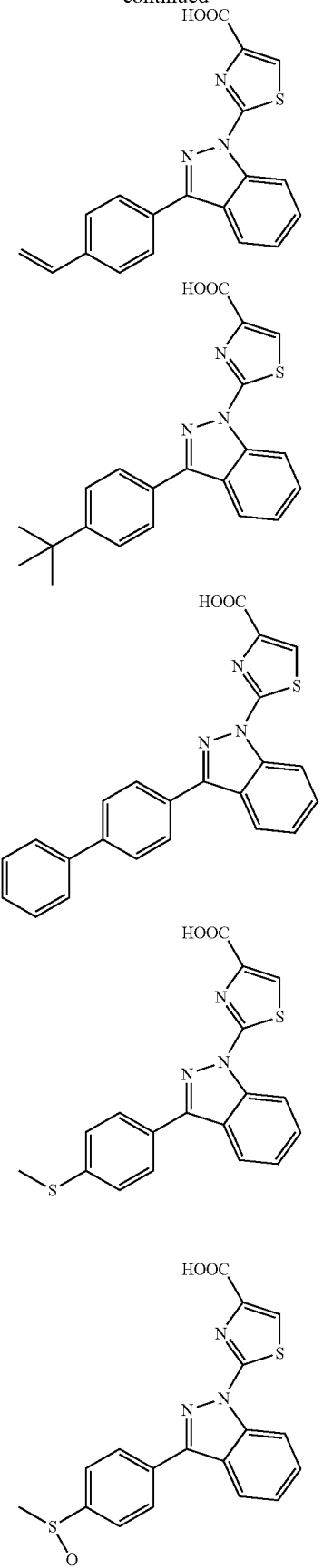
186
-continued
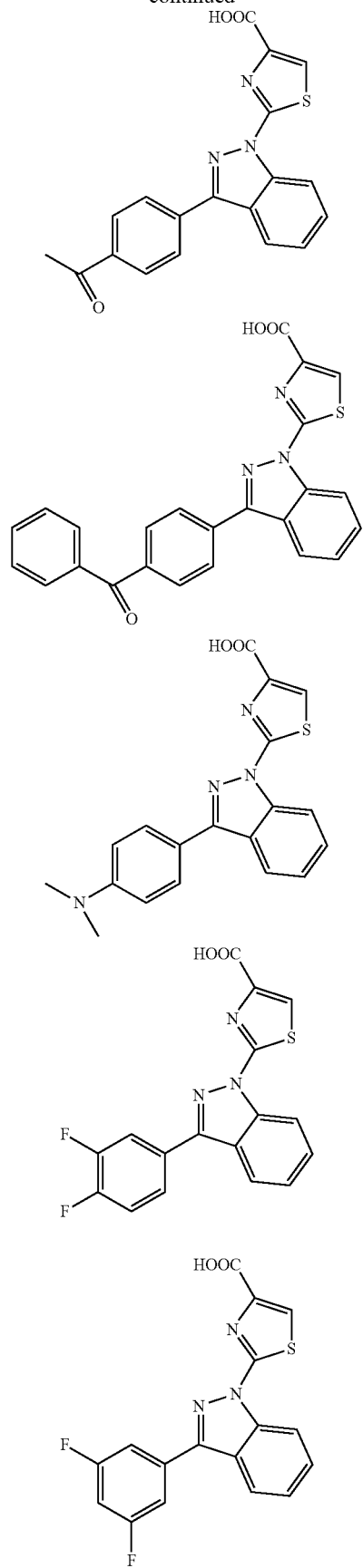

187
-continued
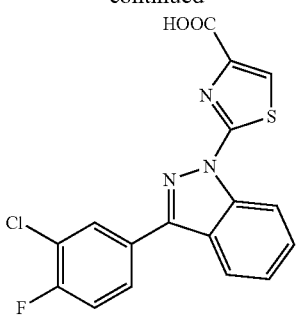
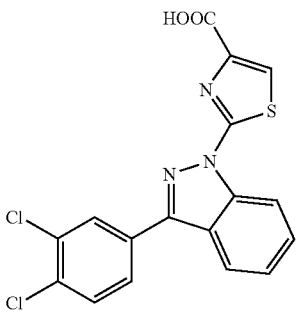
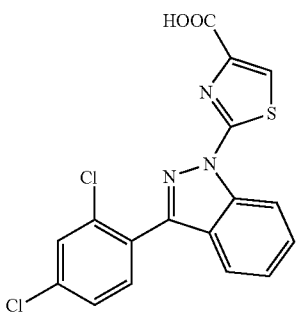
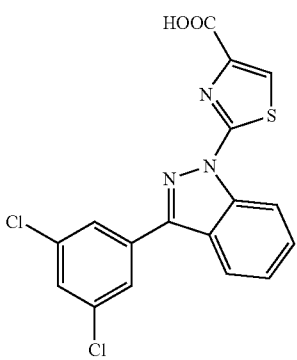
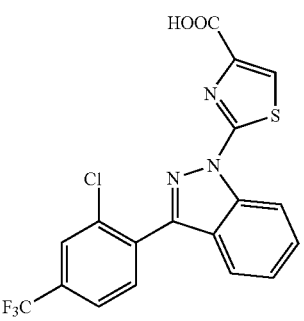
188
-continued
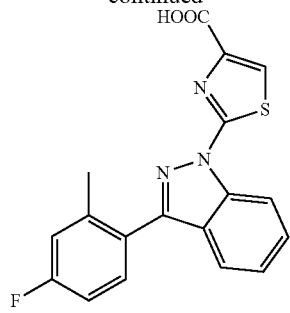
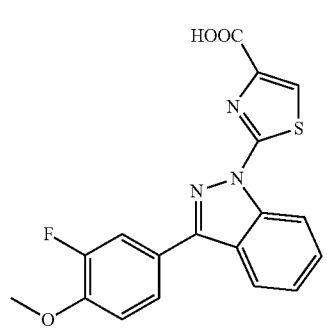
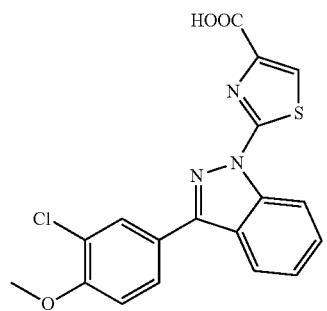
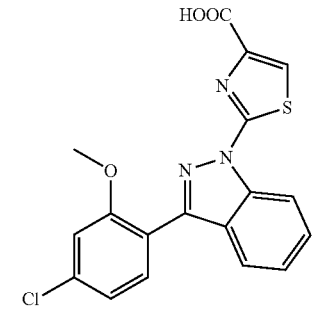
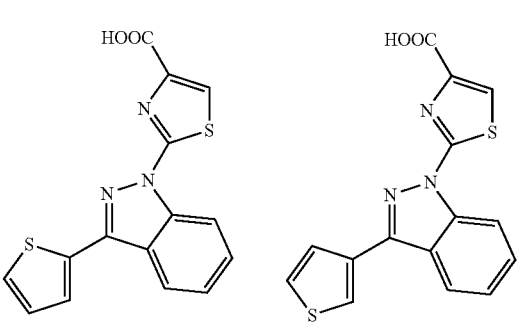

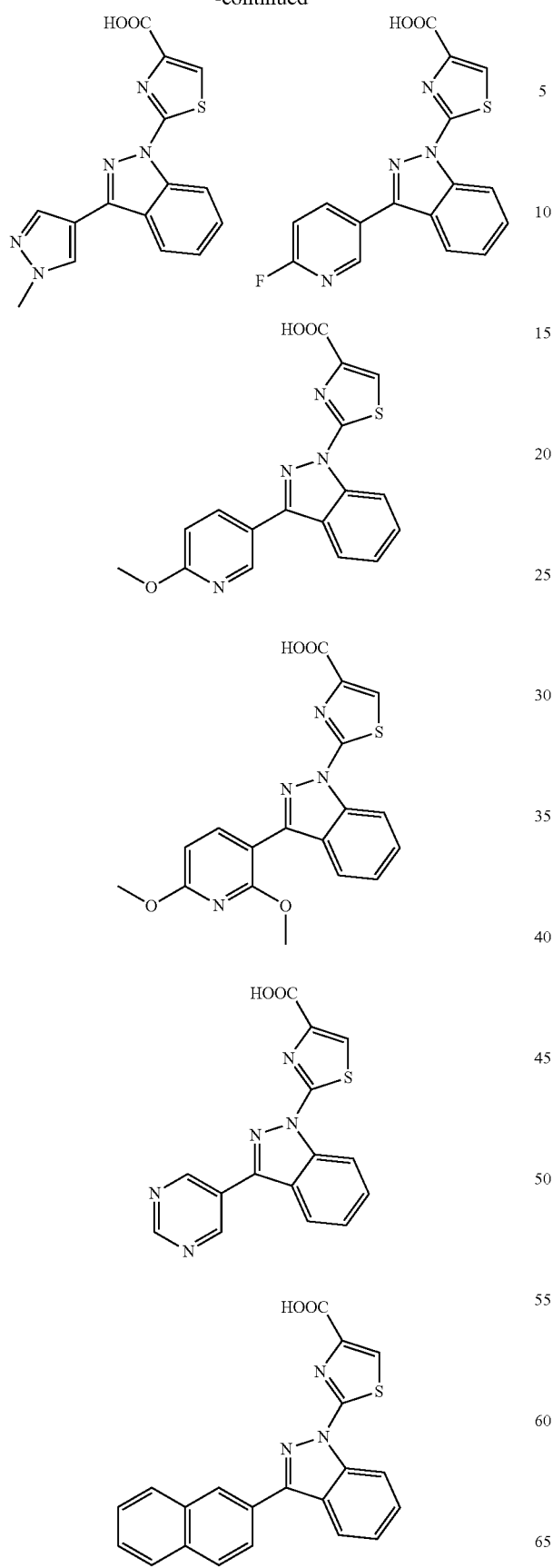
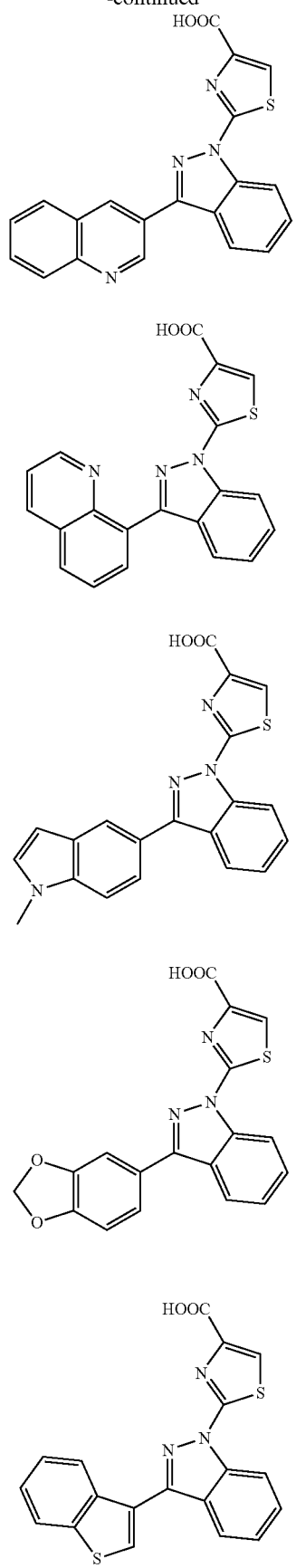

191
-continued
192
-continued
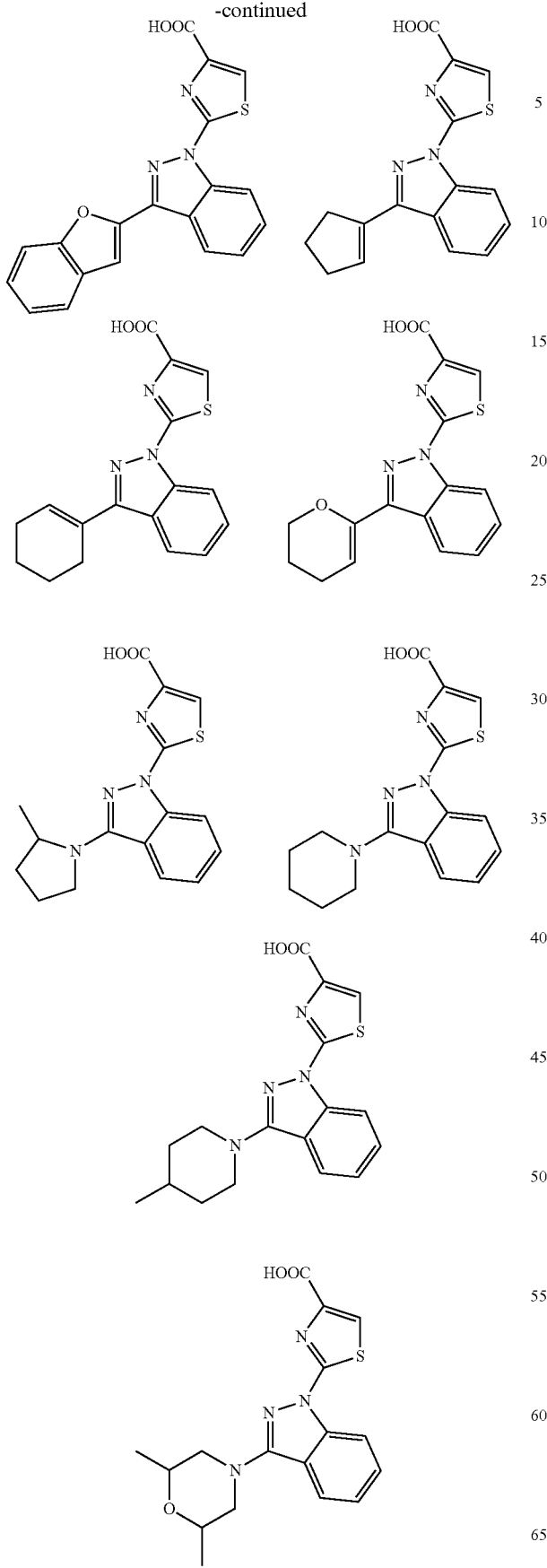
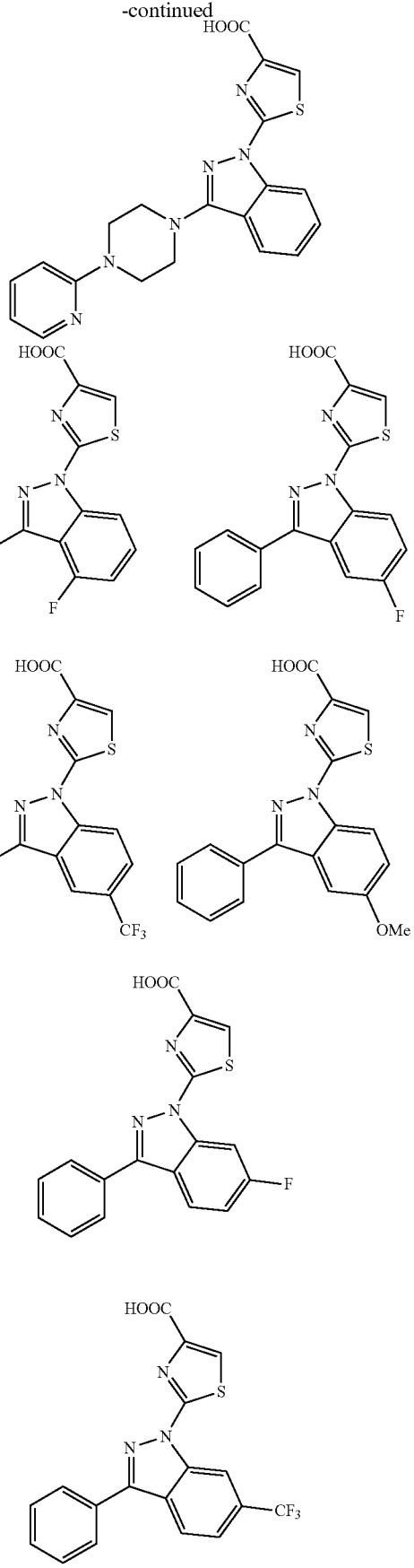

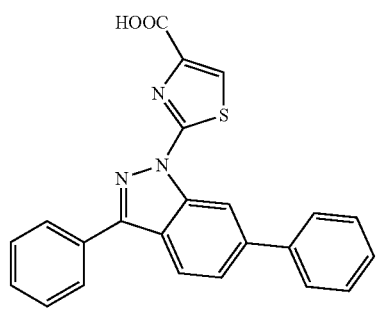
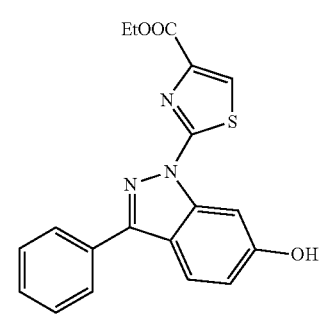
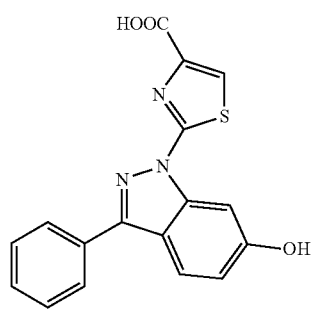
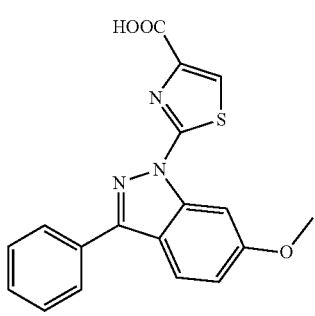
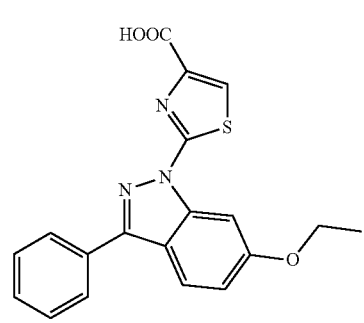
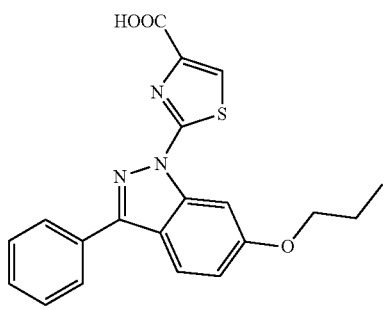
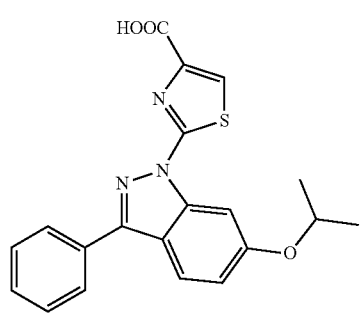
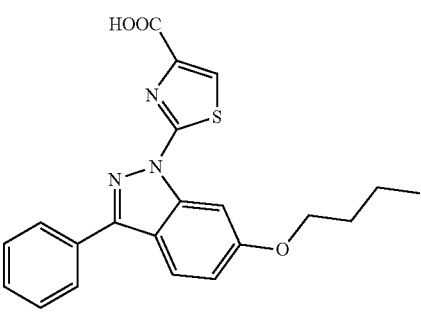
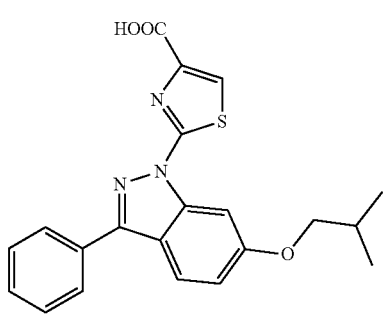
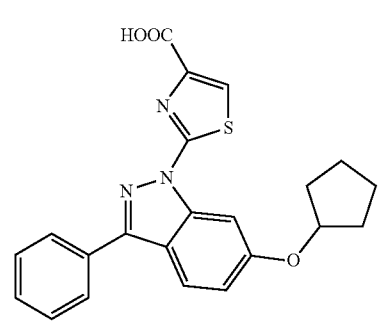

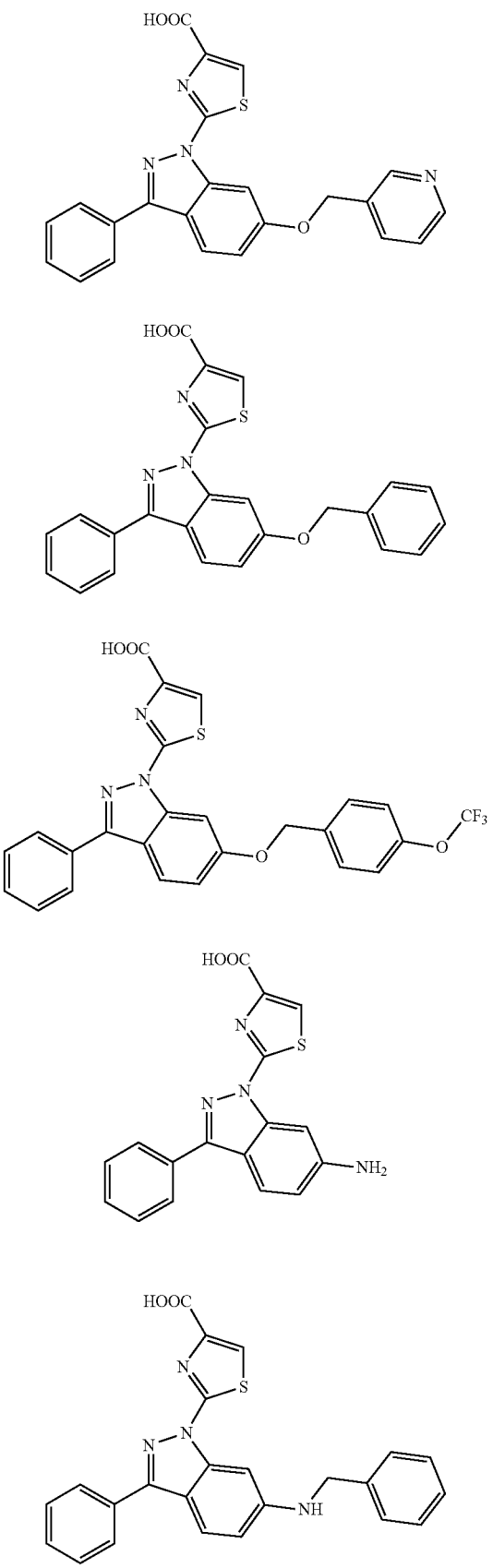
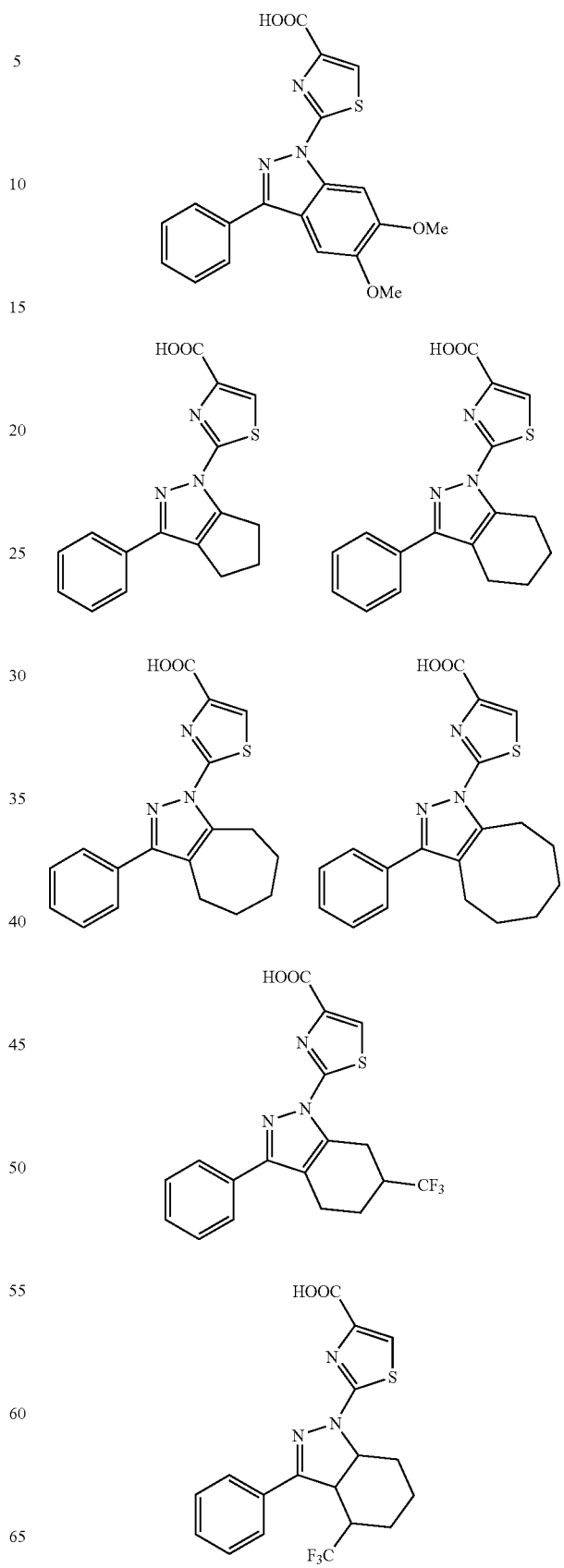

197
-continued
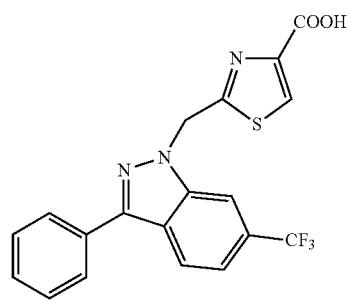
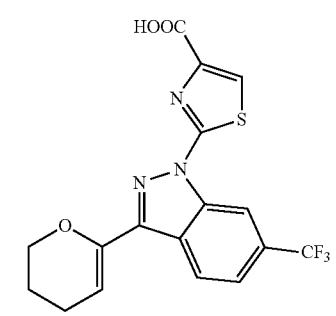
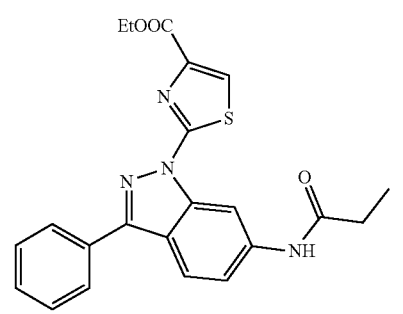
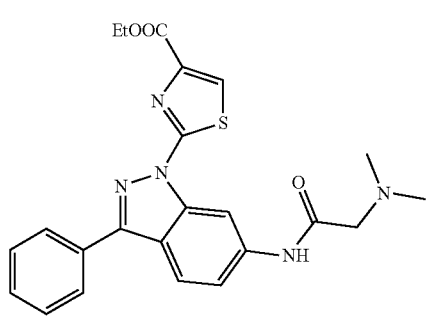
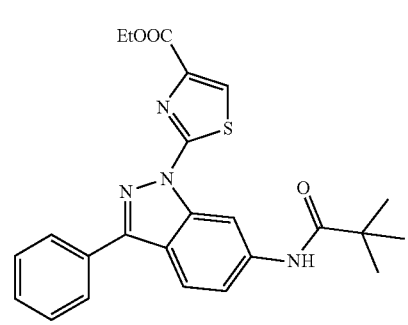
198
-continued
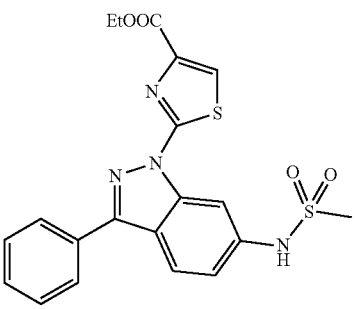
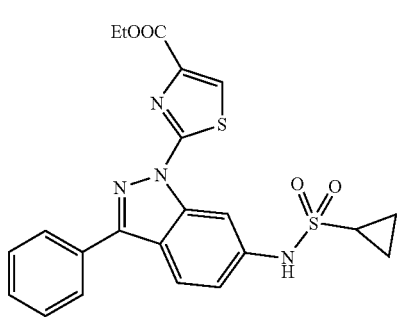
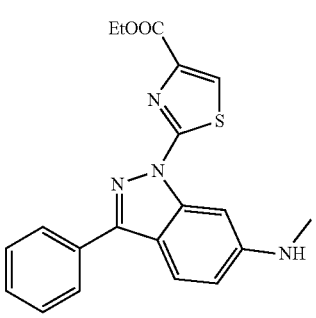
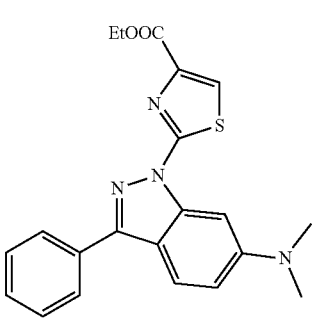
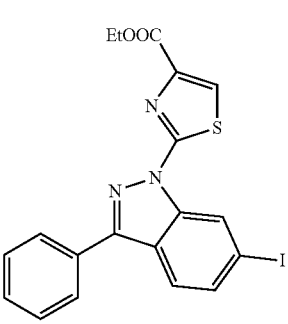

199
-continued
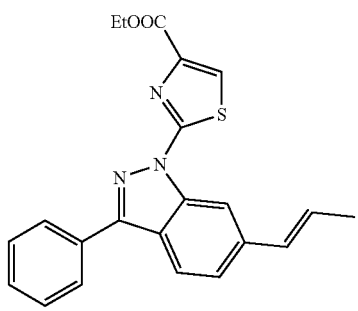
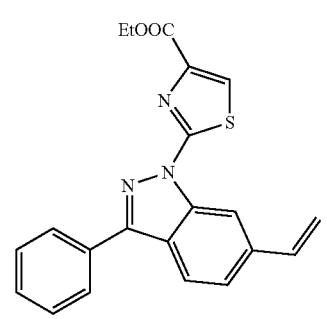
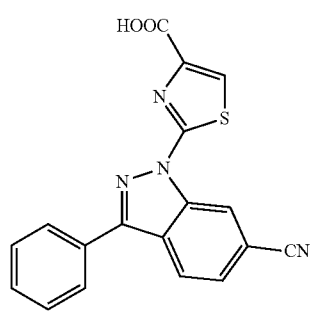
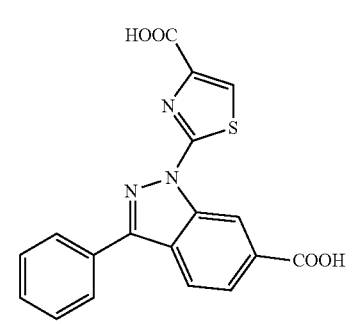
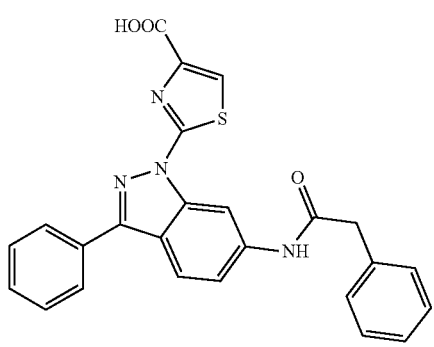
200
-continued
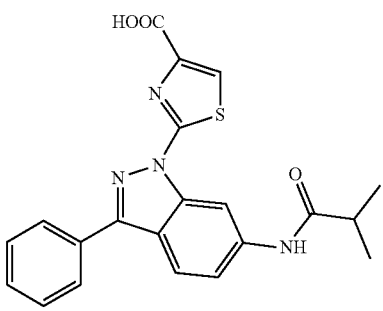
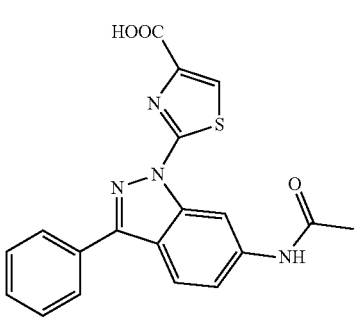
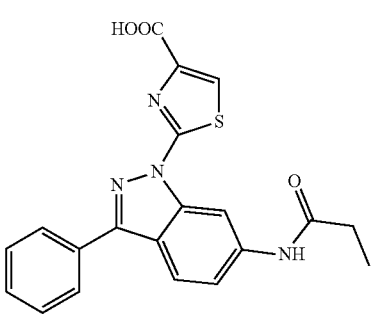
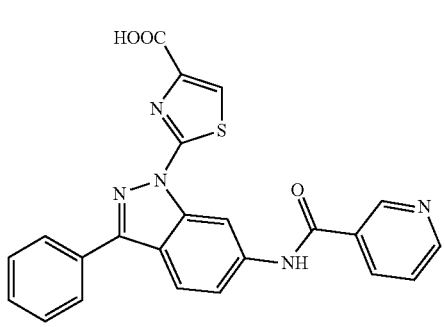
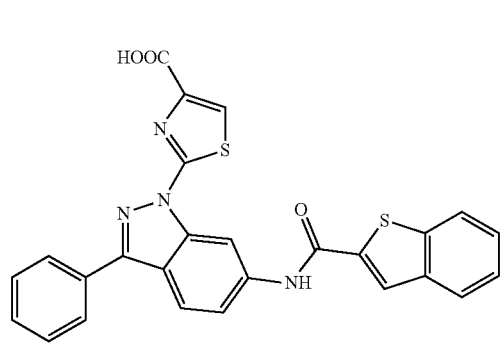

201
-continued
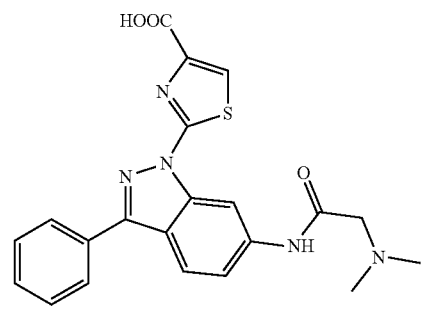
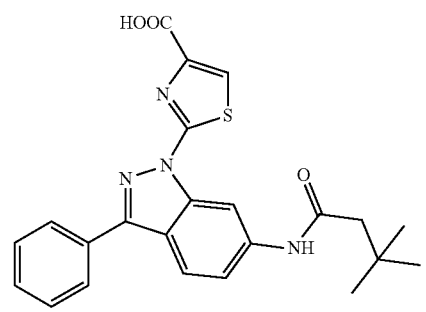
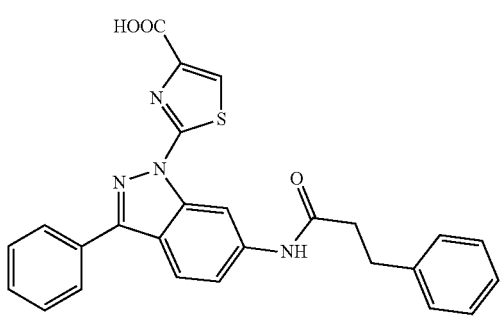
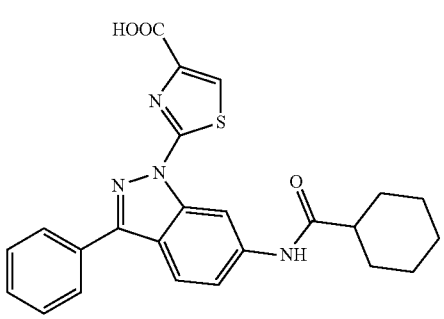
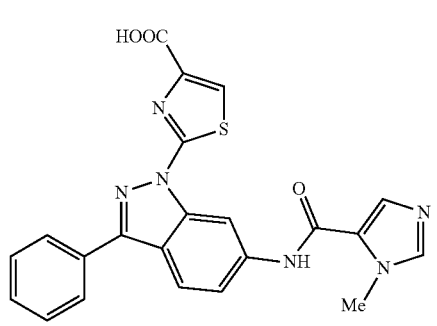
202
-continued
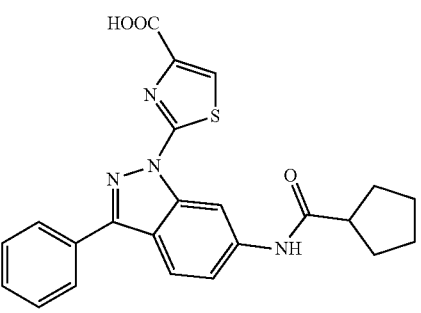
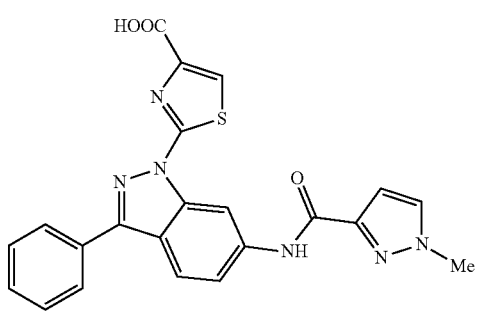
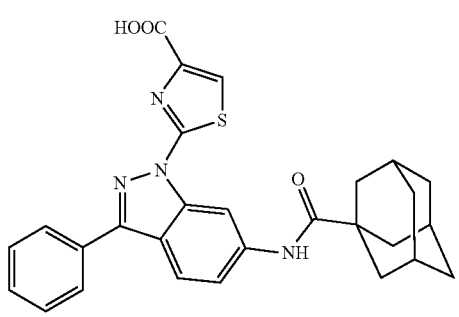
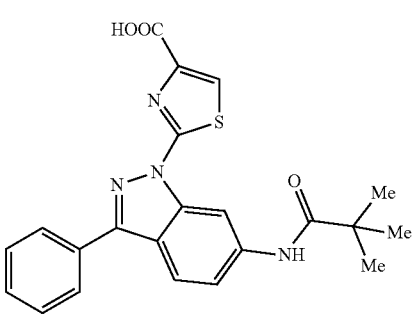
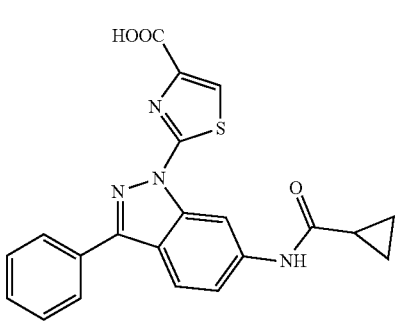

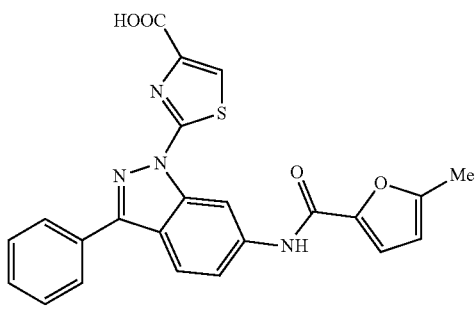
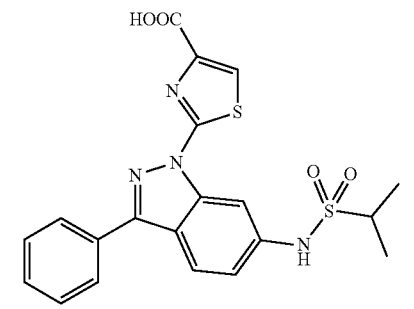
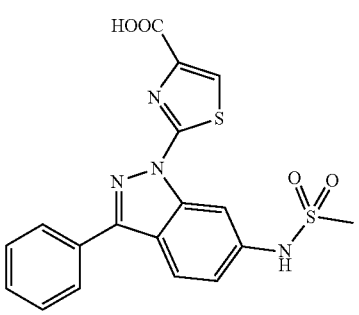
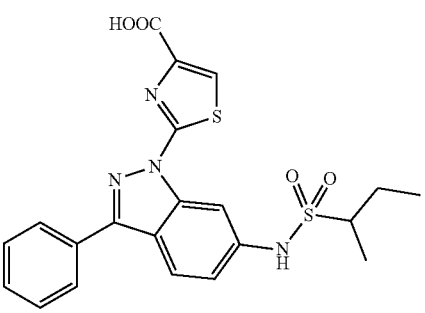
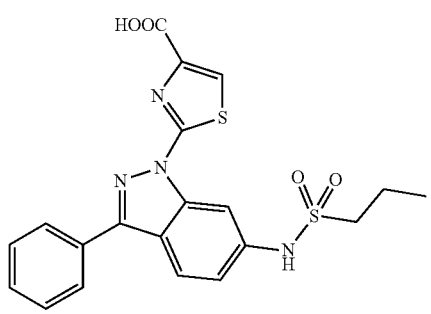
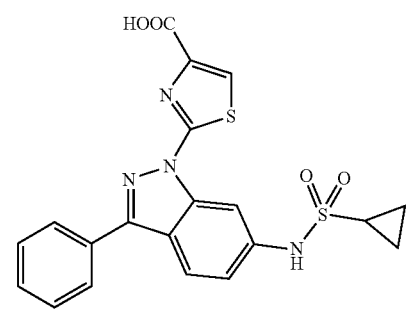
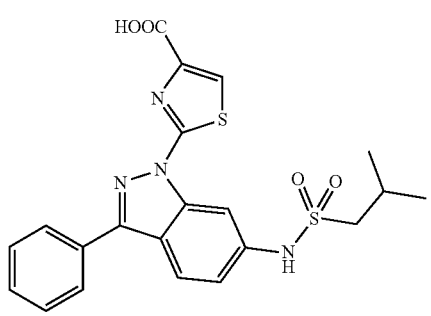
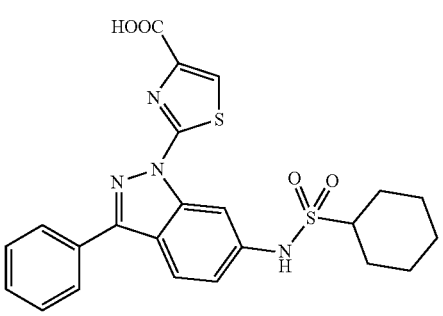
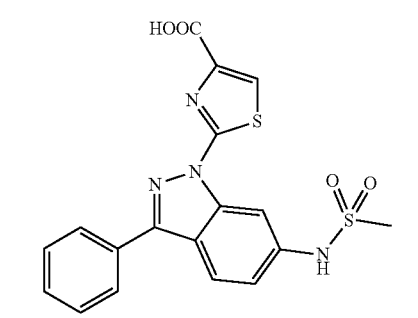
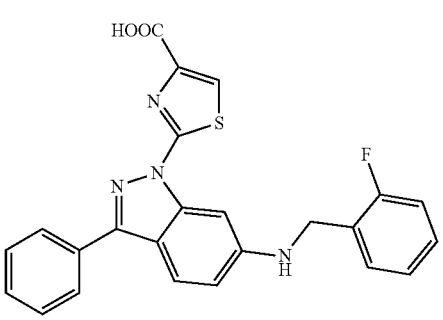

205
-continued
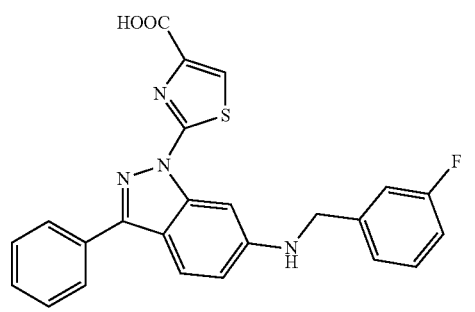
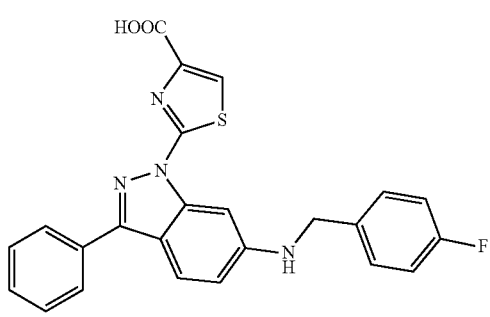
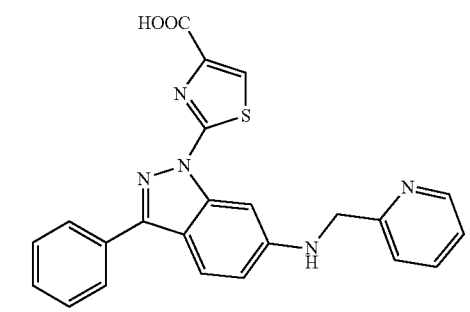
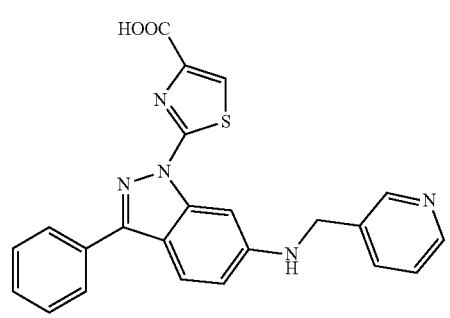
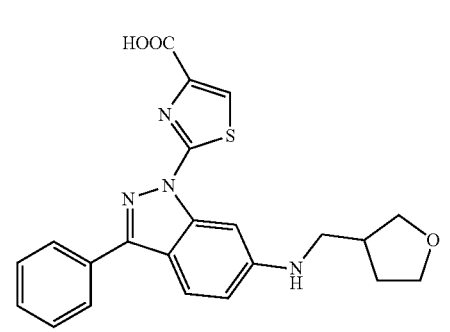
206
-continued
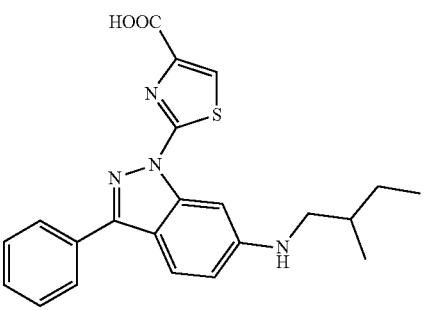
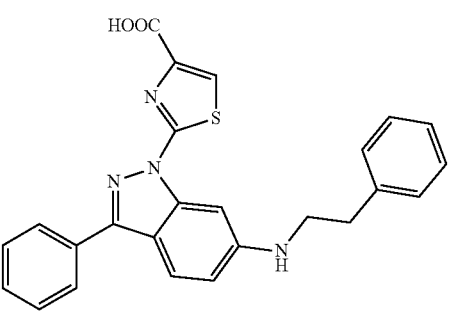
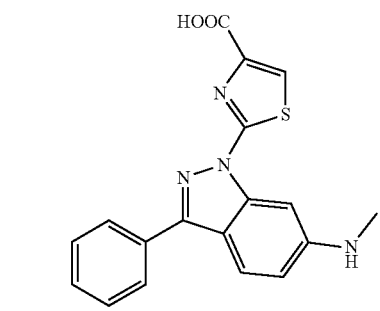
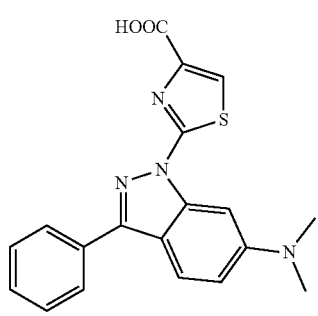
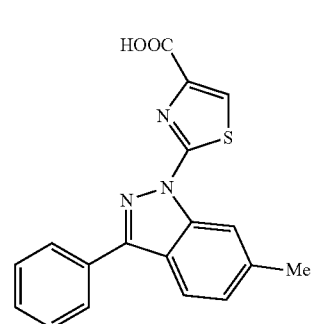

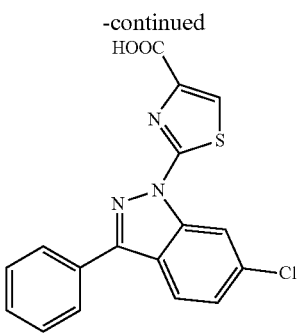
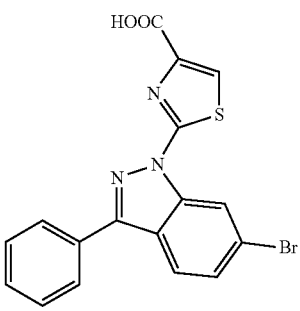
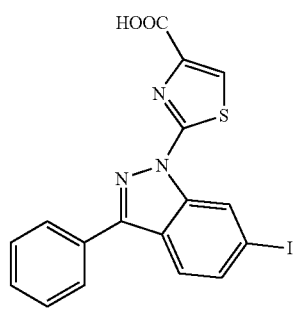
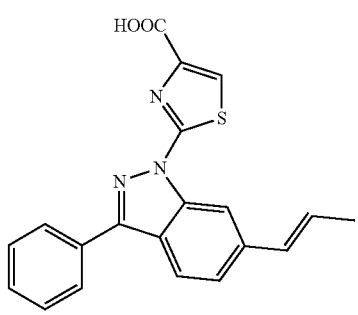
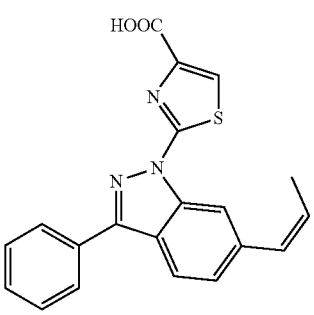
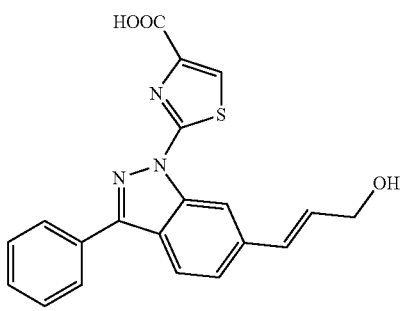
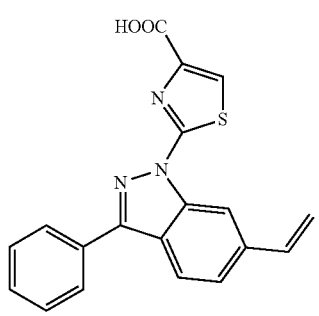
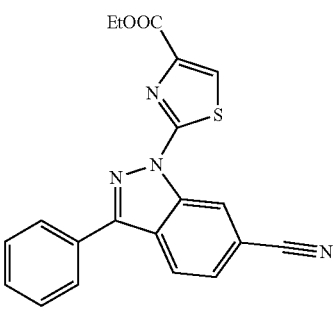
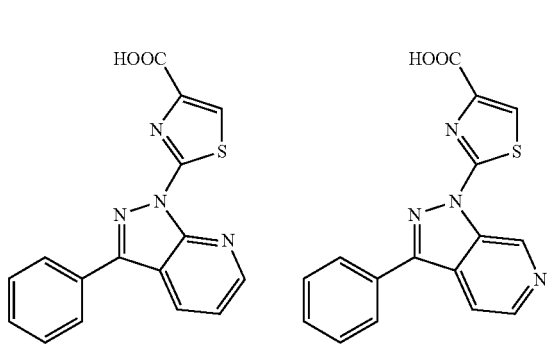
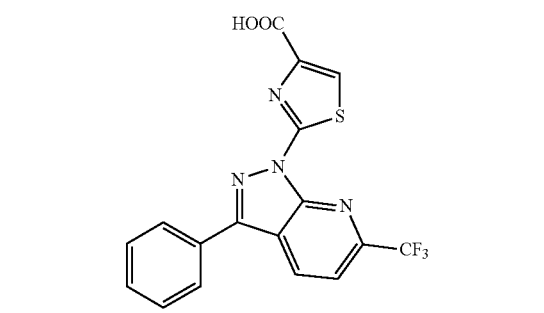

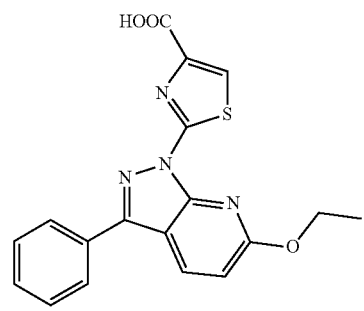
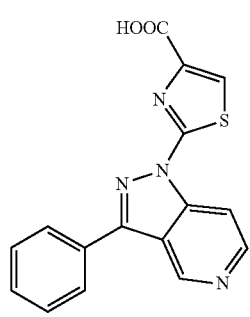
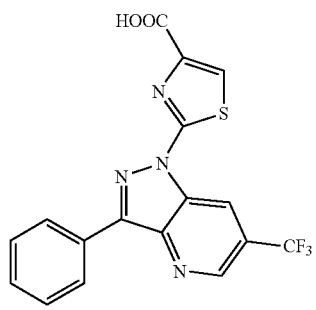
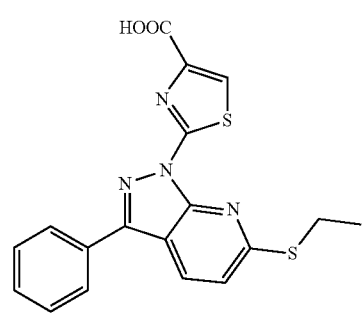
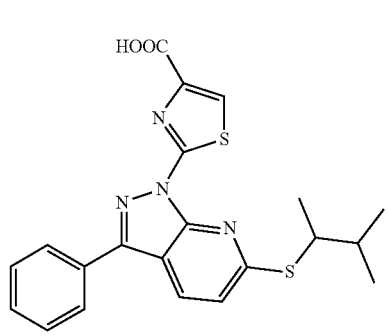
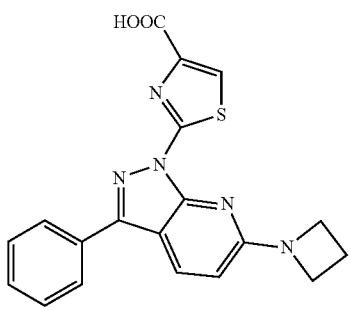
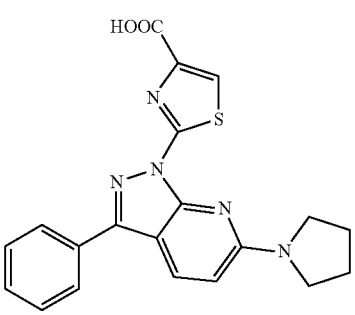
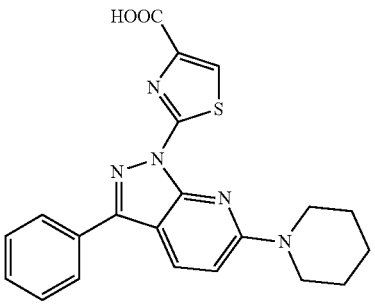
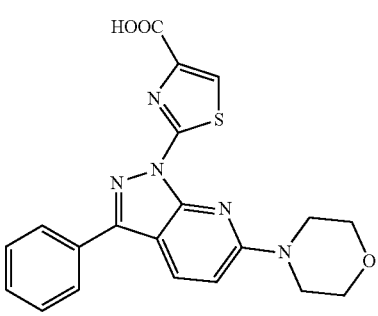
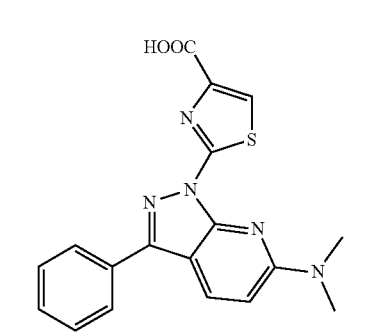

-continued
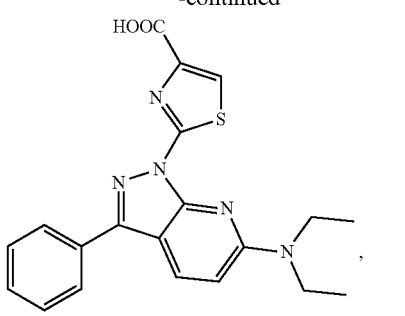
, and
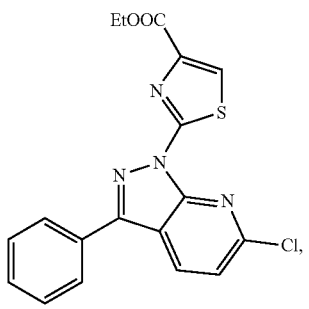
or a salt thereof.
15. A compound selected from the group consisting of:
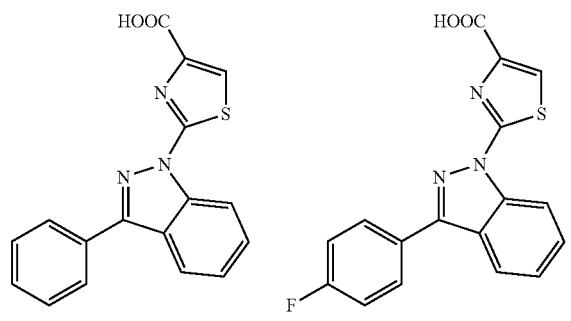
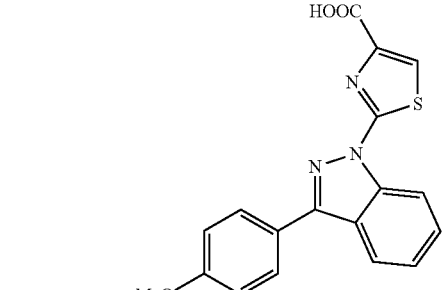
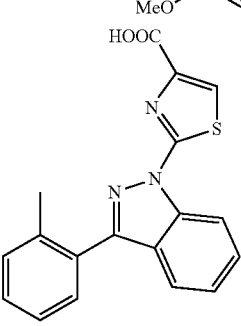 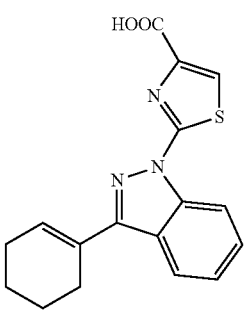
-continued
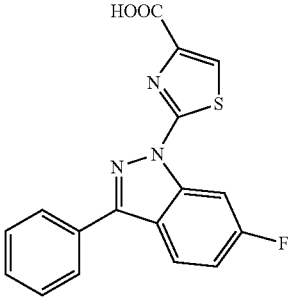
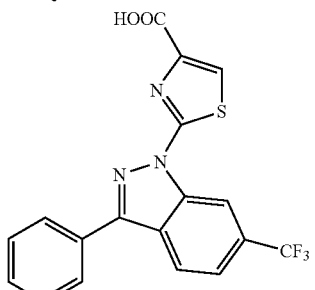
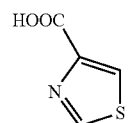
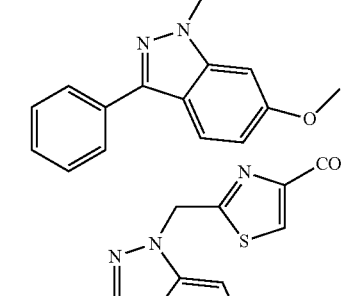
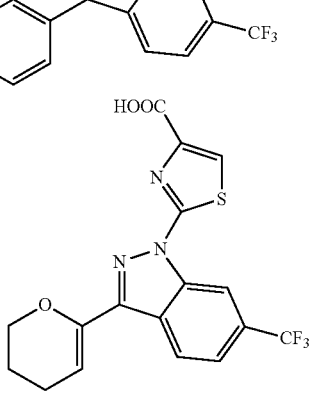
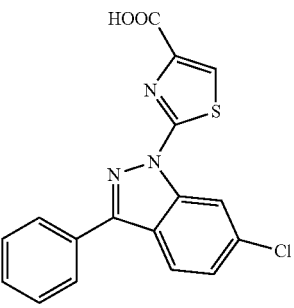

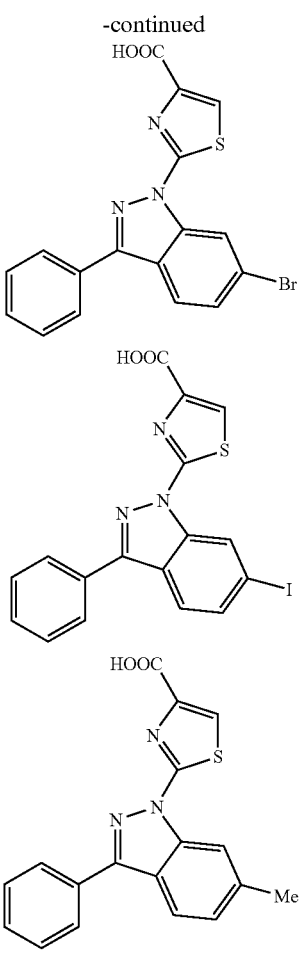

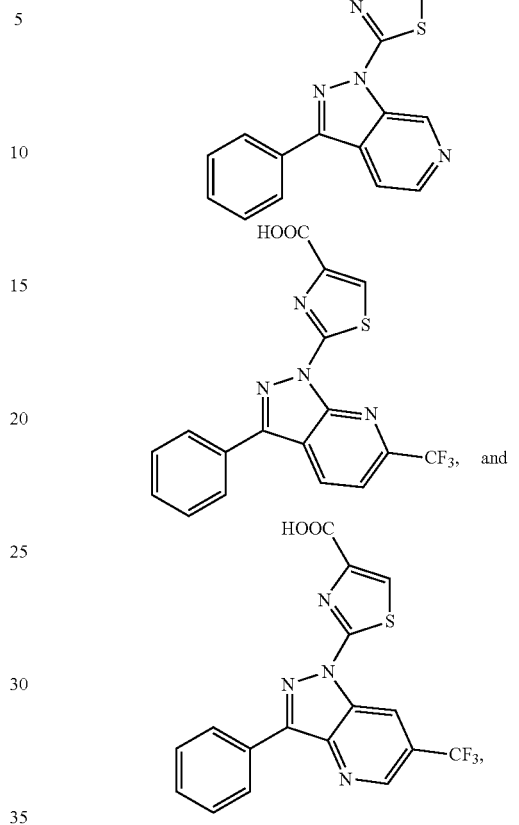

or a salt thereof.

16. The compound or the salt thereof according to claim 1, wherein G is formula ($G^1$).

17. The compound or the salt thereof according to claim 1, wherein $R^1$ and $R^2$ together represent the formula ($Q^1$), ($Q^4$), ($Q^5$), or ($Q^6$).

18. The compound or the salt thereof according to claim 1, wherein $R^1$ and $R^2$ together represent the formula ($Q^4$) or (Q5).

19. A pharmaceutical composition comprising the compound according to any one of claims 1, 2, 3-6, 7, 8-13, 14, 15, or 16-18, or a pharmaceutically acceptable salt thereof, and at least one pharmaceutically acceptable carrier.

20. A method of making a pharmaceutical composition for treating overactive bladder comprising formulating the compound according to any one of claims 1, 2, 3-6, 7, 8-12, 14, 15, or 16-18, or a pharmaceutically acceptable salt thereof, with at least one pharmaceutically acceptable carrier.

21. A method for treating overactive bladder in a mammal, the method comprising administering to a mammal in need thereof the compound according to any one of claims 1, 2, 3-6, 7, 8-13, 14, 15, or 16-18, or a pharmaceutically acceptable salt thereof, in an amount effective to treat overactive bladder.

* * * * *